US010584120B1

(12) United States Patent
Chen et al.

(10) Patent No.: US 10,584,120 B1
(45) Date of Patent: Mar. 10, 2020

(54) BENZIMIDAZOLE COMPOUNDS AND USE THEREOF FOR TREATING ALZHEIMER'S DISEASE OR HUNTINGTON'S DISEASE

(71) Applicants: National Health Research Institutes, Miaoli County (TW); Academia Sinica, Taipei (TW)

(72) Inventors: Chih-Hao Chen, Taipei (TW); Chuan Shih, Carmel, IN (US); Chiung-Tong Chen, Taipei (TW); Hwei-Jiung Wang, Taipei (TW); Kai-Fa Huang, New Taipei (TW)

(73) Assignees: National Health Research Institutes, Miaoli County (TW); Academia Sinica, Taipei (TW)

( * ) Notice: Subject to any disclaimer, the term of this patent is extended or adjusted under 35 U.S.C. 154(b) by 0 days.

(21) Appl. No.: 16/552,554

(22) Filed: Aug. 27, 2019

Related U.S. Application Data

(60) Provisional application No. 62/725,421, filed on Aug. 31, 2018.

(51) Int. Cl.

| | |
|---|---|
| ***C07D 417/14*** | (2006.01) |
| ***C07D 403/14*** | (2006.01) |
| ***C07D 413/14*** | (2006.01) |
| ***A61P 25/28*** | (2006.01) |
| ***C07D 409/14*** | (2006.01) |
| ***A61K 45/06*** | (2006.01) |

(52) U.S. Cl.
CPC ............ *C07D 417/14* (2013.01); *A61P 25/28* (2018.01); *C07D 403/14* (2013.01); *C07D 413/14* (2013.01); *A61K 45/06* (2013.01); *C07D 409/14* (2013.01)

(58) Field of Classification Search
CPC .. C07D 417/14; C07D 403/14; C07D 413/14; C07D 409/14; A61P 25/28; A61K 45/06
USPC .......................................................... 514/360
See application file for complete search history.

(56) References Cited

U.S. PATENT DOCUMENTS

| | | | |
|---|---|---|---|
| 8,486,940 | B2 | 7/2013 | Heiser et al. |
| 9,650,362 | B2 | 5/2017 | Heiser et al. |
| 2008/0221086 | A1 | 9/2008 | Thormann et al. |
| 2008/0286231 | A1 | 11/2008 | Buchholz et al. |
| 2011/0224254 | A1 | 9/2011 | Heiser et al. |
| 2016/0039795 | A1 | 2/2016 | Heiser et al. |

FOREIGN PATENT DOCUMENTS

WO WO-2010/026212 A1 3/2010

OTHER PUBLICATIONS

Jimenez-Sanchez et al "siRNA Screen Identifies QPCT as a Druggable Target for Huntington's Disease" Nature Chemical Biology vol. 11, pp. 347-357, 2015.

*Primary Examiner* — Kristin A Vajda
(74) *Attorney, Agent, or Firm* — Cesari and KcKenna, LLP

(57) ABSTRACT

Benzimidazole compounds of formula (I), shown below, are disclosed. The compounds are potent human glutaminyl cyclase inhibitors. Also disclosed is a pharmaceutical composition containing one of these compounds and a pharmaceutical acceptable carrier, as well as a method of treating Alzheimer's disease or Huntington's disease by administering to a subject in need thereof an effective amount of such a compound.

(I)

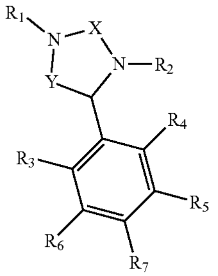

24 Claims, No Drawings

BENZIMIDAZOLE COMPOUNDS AND USE THEREOF FOR TREATING ALZHEIMER'S DISEASE OR HUNTINGTON'S DISEASE

CROSS-REFERENCE TO RELATED APPLICATIONS

The present application claims the priority of Provisional Application No. 62/725,421 filed on Aug. 31, 2018. The content of this prior application is hereby incorporated by reference in its entirety.

BACKGROUND

Alzheimer's disease (AD) and Huntington's disease (HD) are both incurable degenerative brain diseases.

More specifically, AD is the most common form of dementia and HD, on the other hand, causes uncontrolled movements of the arms, legs, head, face, and upper body. HD also causes a decline in thinking and reasoning skills, including memory, concentration, judgement, and ability to plan and organize.

Both AD and HD are caused by aberrant aggregation of proteins or peptide. Indeed, AD is triggered by a malfunction of aggregated mutant β-amyloid peptide (Aβ) and HD arises from a toxic function of aggregated mutant huntingtin protein (HTT).

Human glutaminyl cyclase (QC) catalyzes cyclization of N-terminal residues of glutamine or glutamate to form pyroglutamate (pGlu) on Aβ and HTT. The pGlu-modified Aβ and pGlu-modified HTT thus formed are aggregative, neurotoxic, and resistant to proteolysis. They can initiate pathological cascades, resulting in development of AD or HD.

Inhibition of human QC has been found to diminish aggregation of both Aβ and HTT in cultured macrophage cells and in *Drosophila* and mouse models. See J. Pharmacol. Exp. Ther. 2017, 362, 119-130; J. Med. Chem. 2017, 60, 2573-2590; Nat. Med. 2008, 14(10), 1106-1111; and Nat. Chem. Bio. 2015, 11, 347-354.

As such, human QC is an emerging drug target for the treatment of AD or HD.

Currently, only a few drug candidates that inhibit QC are in clinical trials for treating AD or HD. There is a need to develop new QC inhibitors.

Earlier studies have shown that QC is a zinc-dependent enzyme. As such, compounds capable of chelating zinc at active sites of QC, e.g., benzimidazole compounds, are potential QC inhibitors.

SUMMARY

Certain benzimidazole compounds have been found to be QC inhibitors. Unexpectedly, the compounds demonstrate high potency in inhibiting QC and, as such, can be used for treating AD or HD.

In one aspect, this invention relates to the benzimidazole compounds of formula (I) below:

(I)

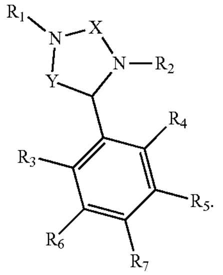

X and Y, independently, are $CH_2$ or C═O; $R_1$ is H or $C_{1-6}$ alkyl; $R_2$ is a moiety containing a phenyl ring fused to a 5-membered heteroaryl ring (e.g.,

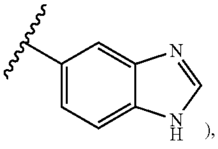 [SMILES: *c1ccc2[nH]cnc2c1]

), being linked to N through the phenyl ring; $R_3$, $R_4$, $R_5$, $R_6$, and $R_7$, independently, are H, halo (e.g., F, Cl, Br, or I), nitro, cyano, amino, OH, $CF_3$, $C_{1-6}$ alkoxyl, $C_{1-6}$ alkyl, $C_{2-6}$ alkenyl, $C_{2-6}$ alkynyl, $C_{3-10}$ cycloalkyl, heterocycloalkyl, aryl, or heteroaryl that is optionally substituted by one or more substituents selected from halo (e.g., F, Cl, Br, or I), nitro, cyano, amino, OH, $CF_3$, —COOH, —$COOC_{1-6}$ alkyl, $C_{1-6}$ alkoxyl, $C_{1-6}$ alkyl, $C_{2-6}$ alkenyl, $C_{2-6}$ alkynyl, $C_{3-10}$ cycloalkyl, heterocycloalkyl, aryl, and heteroaryl, wherein at least one of $R_3$, $R_4$, $R_5$, $R_6$, and $R_7$ is heteroaryl and wherein each of $C_{1-6}$ alkoxyl, $C_{1-6}$ alkyl, $C_{2-6}$ alkenyl, $C_{2-6}$ alkynyl, $C_{3-10}$ cycloalkyl, heterocycloalkyl, aryl, and heteroaryl, second or third occurrence, is optionally substituted with halo (e.g., F, Cl, Br, or I), nitro, cyano, amino, OH, $CF_3$, $C_{1-6}$ alkoxyl, $C_{1-6}$ alkyl, $C_{2-6}$ alkenyl, $C_{2-6}$ alkynyl, $C_{3-10}$ cycloalkyl, heterocycloalkyl, aryl, or heteroaryl.

Examples of heteroaryl assigned to $R_7$ include

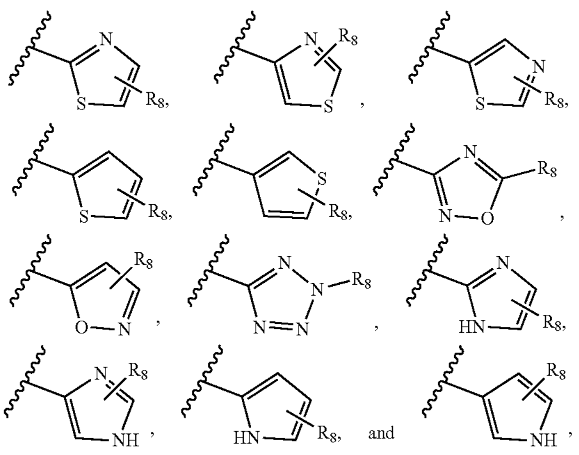

in which $R_8$ is H, halo (e.g., F, Cl, Br, or I), nitro, cyano, amino, OH, $CF_3$, —COOH, —$COOC_{1-6}$ alkyl, $C_{1-6}$ alkoxyl, $C_{1-6}$ alkyl, $C_{2-6}$ alkenyl, $C_{2-6}$ alkynyl, $C_{3-10}$ cycloalkyl, heterocycloalkyl, aryl, or heteroaryl, each of $C_{1-6}$ alkoxyl, $C_{1-6}$ alkyl, $C_{2-6}$ alkenyl, $C_{2-6}$ alkynyl, $C_{3-10}$ cycloalkyl, heterocycloalkyl, aryl, and heteroaryl being optionally substituted with halo (e.g., F, Cl, Br, or I), nitro, cyano, amino, OH, $CF_3$, $C_{1-6}$ alkoxyl, $C_{1-6}$ alkyl, $C_{2-6}$ alkenyl, $C_{2-6}$ alkynyl, $C_{3-10}$ cycloalkyl, heterocycloalkyl, aryl, or heteroaryl.
Among specific assignments to $R_7$ are
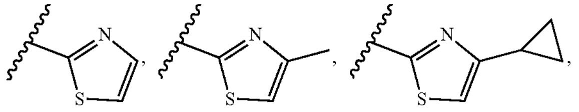
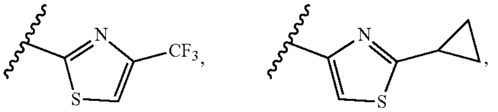
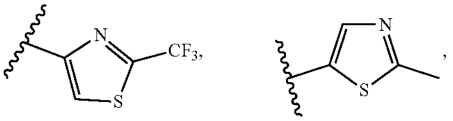
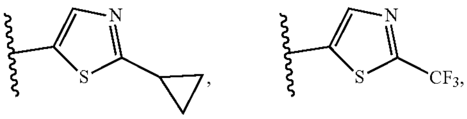
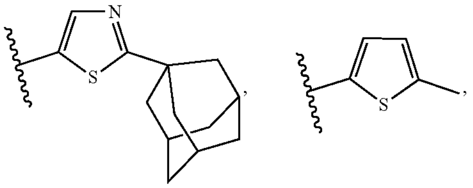
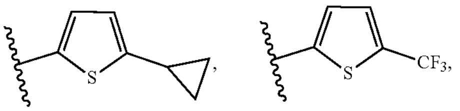
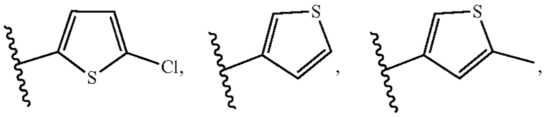
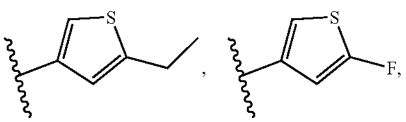
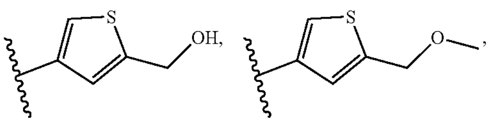
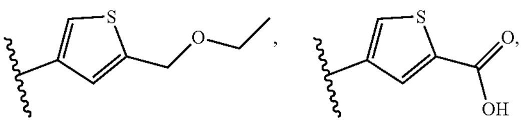
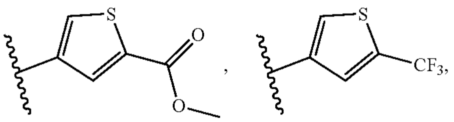
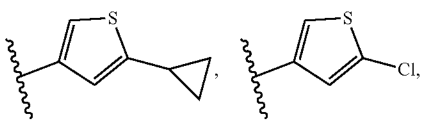
-continued
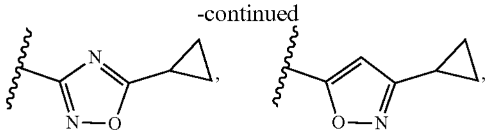
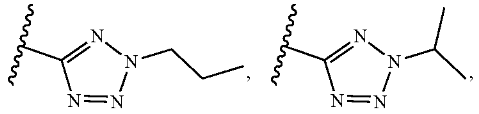
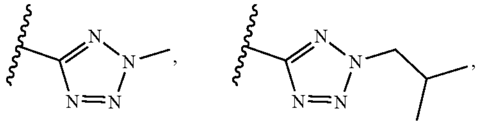
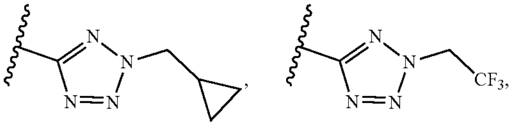
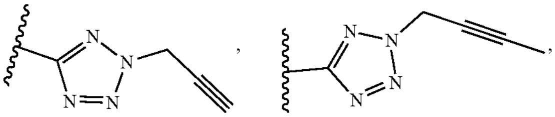
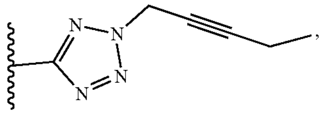
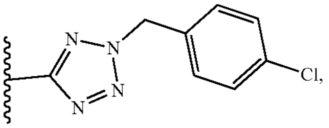
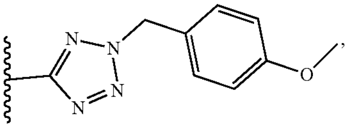
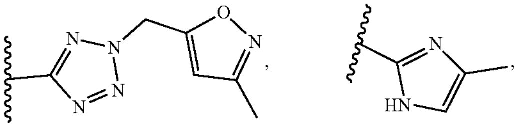
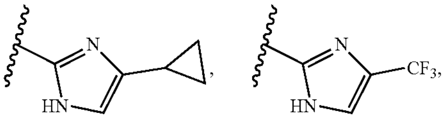
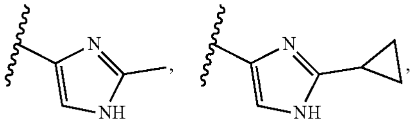
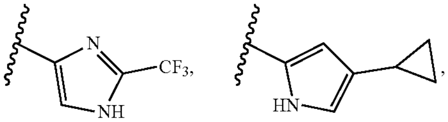
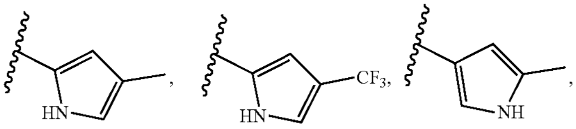
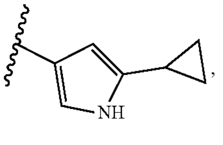
and
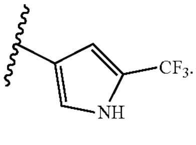

Among specific assignments to $R_8$ are H, F, Cl, $CH_3$, $CF_3$, ethyl, n-propyl,

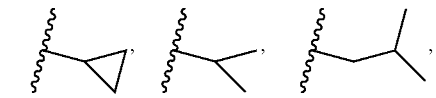

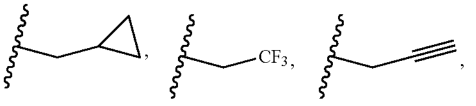

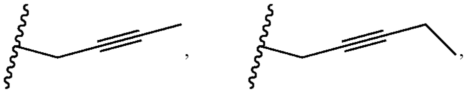

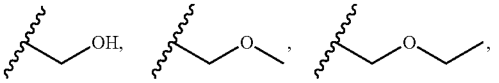

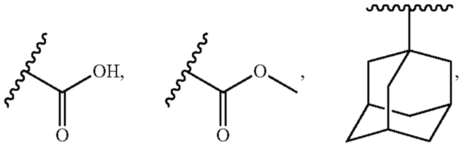

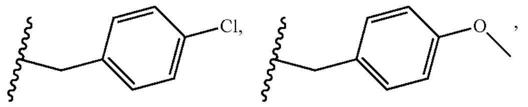 and

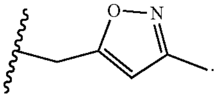

The above-described compounds can be classified into two subsets. In one subset, Y is $CH_2$ and, in the other subset, Y is C═O. Preferred compounds in each subset feature that $R_1$ is H; X is C═O; $R_2$ is

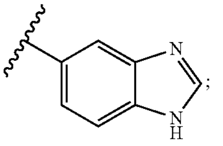 [SMILES: *c1ccc2[nH]cnc2c1]

$R_3$, $R_4$, $R_5$, and $R_6$, independently, are H or F; $R_7$ is

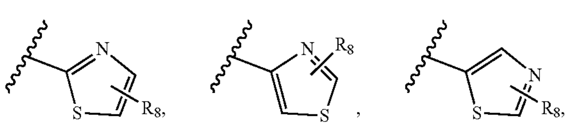

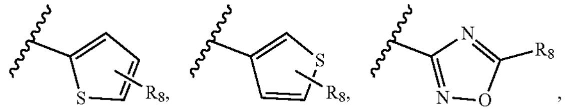

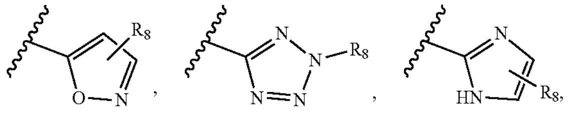

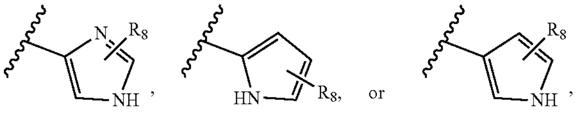

in which the assignments to $R_8$ are set forth in the preceding paragraph. In particularly preferred compounds, the assignments to $R_7$ are also set forth in the preceding paragraph.

The term "alkyl" herein refers to a saturated, linear, or branched hydrocarbon moiety, e.g., —$CH_3$ or —$CH(CH_3)_2$. The term "alkoxy" refers to an —O($C_{1-6}$ alkyl) radical, e.g., —$OCH_3$ and —$OCH(CH_3)_2$. The term "alkenyl" refers to a linear or branched hydrocarbon moiety that contains at least one double bond, e.g., —CH═CH—$CH_3$. The term "alkynyl" refers to a linear or branched hydrocarbon moiety that contains at least one triple bond, e.g., —C≡C—$CH_3$. The term "cycloalkyl" refers to a saturated mono-, di-, or tri-cyclic hydrocarbon moiety, e.g., cyclohexyl. The term "heterocycloalkyl" refers to a saturated mono-, di-, or tri-cyclic moiety having at least one ring heteroatom (e.g., N, O, and S), e.g., 4-tetrahydropyranyl. The term "aryl" refers to a hydrocarbon moiety having one or more aromatic rings. Examples of aryl include phenyl, phenylene, naphthyl, naphthylene, pyrenyl, anthryl, and phenanthryl. The term "heteroaryl" refers to a moiety having one or more aromatic rings that contain at least one heteroatom (e.g., N, O, and S). Examples of heteroaryl include furyl, furylene, fluorenyl, pyrrolyl, thienyl, oxazolyl, imidazolyl, thiazolyl, pyridyl, pyrimidinyl, quinazolinyl, quinolyl, isoquinolyl, and indolyl. The term "amino" refers to a radical of —$NH_2$, —NH($C_{1-6}$alkyl), or —N($C_{1-6}$ alkyl)$_2$, e.g., —NHCH3 and —$NHCH(CH_3)_2$.

Alkoxy, Alkyl, alkenyl, alkynyl, cycloalkyl, heterocycloalkyl, aryl, and heteroaryl mentioned herein include both substituted and unsubstituted moieties, unless specified otherwise. Substituents on alkoxy, alkyl, alkenyl, alkynyl, cycloalkyl, heterocycloalkyl, aryl, and heteroaryl include, but are not limited to, halo, nitro, cyano, amino, OH, $CF_3$, —COOH, —$COOC_{1-6}$ alkyl, $C_{1-6}$ alkoxyl, $C_{1-6}$ alkyl, $C_{2-6}$ alkenyl, $C_{2-6}$ alkynyl, $C_{3-10}$ cycloalkyl, heterocycloalkyl, aryl, or heteroaryl.

The compounds described above include the compounds themselves, as well as their salts, prodrugs, stereoisomers, and tautomers, if applicable. A salt, for example, can be formed between an anion and a positively charged group (e.g., amino) on a compound of formula (I). Suitable anions include chloride, bromide, iodide, sulfate, nitrate, phosphate, citrate, methanesulfonate, trifluoroacetate, acetate, malate, tosylate, tartrate, fumurate, glutamate, glucuronate, lactate, glutarate, and maleate. Likewise, a salt can also be formed between a cation and a negatively charged group (e.g., carboxylate) on a compound of formula (I). Suitable cations include sodium ion, potassium ion, magnesium ion, calcium ion, and an ammonium cation such as tetramethylammonium ion. The compounds also include those salts containing quaternary nitrogen atoms. Examples of prodrugs include esters and other pharmaceutically acceptable derivatives, which, upon administration to a subject, are capable of providing active compounds. Stereoisomers of the compounds of formula (I) can include cis and trans isomers, optical isomers such as (R) and (S) enantiomers, diastereomers, geometric isomers, rotational isomers, atropisomers, conformational isomers, and mixtures thereof. Tautomers of the compounds include those exhibiting more than one type of isomerism.

In another aspect, this invention relates to a pharmaceutical composition containing a compound of formula (I) and a pharmaceutical acceptable carrier.

The carrier in the pharmaceutical composition must be "acceptable" in the sense that it is compatible with the active ingredient of the composition (and preferably, capable of stabilizing the active ingredient) and not deleterious to the subject to be treated. Examples of carriers include colloidal silicon oxide, magnesium stearate, cellulose, sodium lauryl sulfate, and D&C Yellow 10.

Also within the scope of this invention is a method of treating AD or HD. The method includes administering to a subject in need thereof an effective amount of a compound of formula (I).

The term "treating" refers to application or administration of the compound or its salt, prodrug, stereoisomer, or tautomer to a subject with the purpose to confer a therapeutic effect, i.e., to cure, relieve, alter, affect, ameliorate, or prevent AD or HD, the symptom of AD or HD, or the predisposition toward AD or HD.

"An effective amount" is the amount of the compound or its salt, prodrug, stereoisomer, or tautomer, which is required to confer the desired effect on the subject. Effective amounts vary, as recognized by those skilled in the art, depending on route of administration, excipient usage, and the possibility of co-usage with other therapeutic treatments such as use of other active agents.

A composition having a compound of formula (I) or its salt, prodrug, stereoisomer, or tautomer can be administered parenterally or orally. The term "parenteral" as used herein refers to subcutaneous, intracutaneous, intravenous, intraperitoneal, intramuscular, intraarticular, intraarterial, intrasynovial, intrasternal, intrathecal, intralesional, or intracranial injection, as well as any suitable infusion technique.

A composition for oral administration can be any orally acceptable dosage form, e.g., capsules, tablets, emulsions and aqueous suspensions, dispersions, and solutions. In the case of tablets, commonly used carriers include, among others, lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with an emulsifying or suspending agent. If desired, a sweetening, flavoring, or coloring agent can be added.

The details of one or more embodiments of the invention are set forth in the description below. Other features, objects, and advantages of the invention will be apparent from the description and from the claims.

DETAILED DESCRIPTION

Disclosed in detail hereinafter are the benzimidazole compounds of formula (I) shown above.

Compounds of this invention that have chiral centers may exist as stereoisomers. Stereoisomers of the compounds of formula (I) can include cis and trans isomers, optical isomers such as (R) and (S) enantiomers, diastereomers, geometric isomers, rotational isomers, atropisomers, conformational isomers, and tautomers of the compounds, including compounds exhibiting more than one type of isomerism; and mixtures thereof (such as racemates and diastereomers). All such isomeric forms are contemplated. In addition, the compounds of formula (I) in the present invention may exhibit the phenomena of tautomerism.

Of note, the compounds of formula (I) can have an enantiomeric excess of 90% or higher (e.g., ≥95% and ≥99%).

117 exemplary compounds of formula (I) are shown in Table 1 below:

TABLE 1

| | |
|---|---|
| 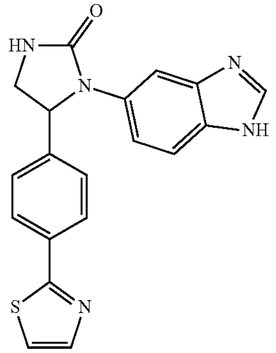 [SMILES: O=C1NCC(c2ccc(-c3nccs3)cc2)N1c1ccc2[nH]cnc2c1] | 1 |
| 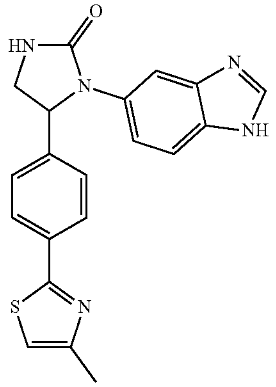 [SMILES: Cc1csc(-c2ccc(C3CNC(=O)N3c3ccc4[nH]cnc4c3)cc2)n1] | 2 |
| 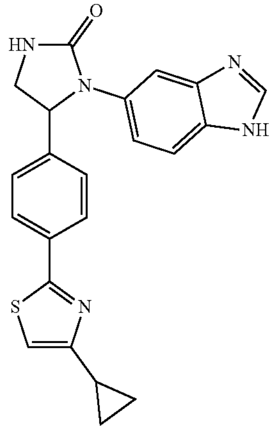 [SMILES: O=C1NCC(c2ccc(-c3nc(C4CC4)cs3)cc2)N1c1ccc2[nH]cnc2c1] | 3 |
| 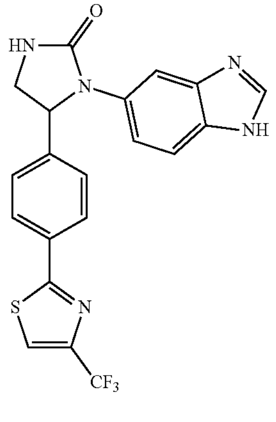 [SMILES: O=C1NCC(c2ccc(-c3nc(C(F)(F)F)cs3)cc2)N1c1ccc2[nH]cnc2c1] | 4 |

TABLE 1-continued
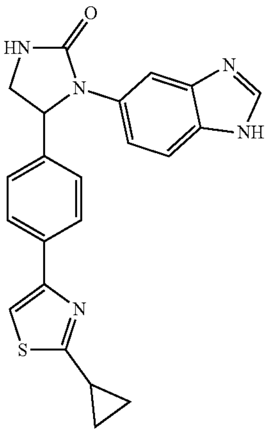 [SMILES: O=C1NCC(c2ccc(-c3csc(C4CC4)n3)cc2)N1c1ccc2[nH]cnc2c1]
5
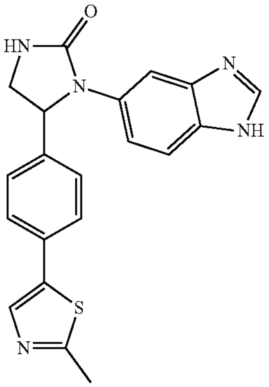 [SMILES: Cc1ncc(-c2ccc(C3CNC(=O)N3c3ccc4[nH]cnc4c3)cc2)s1]
6
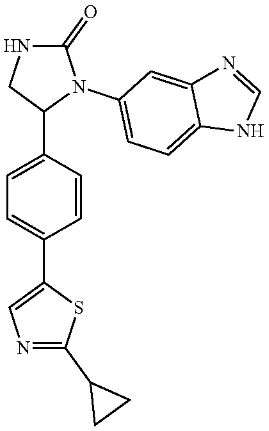 [SMILES: O=C1NCC(c2ccc(-c3cnc(C4CC4)s3)cc2)N1c1ccc2[nH]cnc2c1]
7
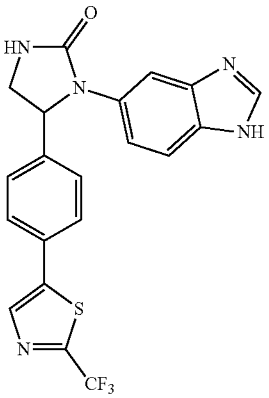
8
TABLE 1-continued
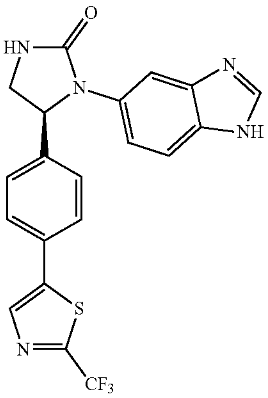 [SMILES: O=C1NC[C@H](c2ccc(-c3cnc(C(F)(F)F)s3)cc2)N1c1ccc2[nH]cnc2c1]
9
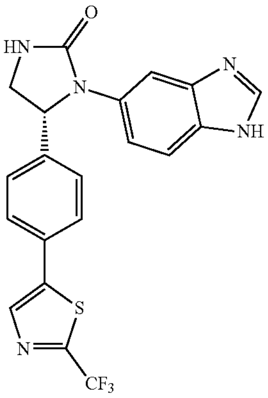 [SMILES: O=C1NC[C@@H](c2ccc(-c3cnc(C(F)(F)F)s3)cc2)N1c1ccc2[nH]cnc2c1]
10
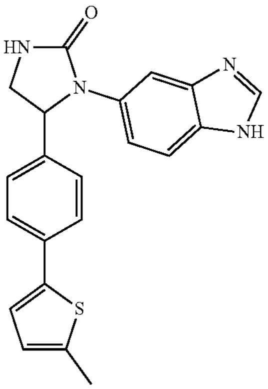 [SMILES: Cc1ccc(-c2ccc(C3CNC(=O)N3c3ccc4[nH]cnc4c3)cc2)s1]
11
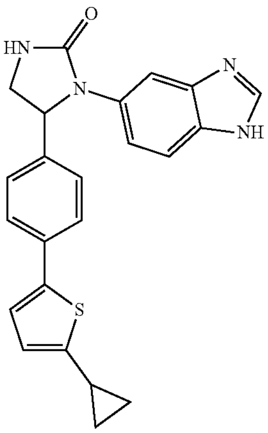 [SMILES: O=C1NCC(c2ccc(-c3ccc(C4CC4)s3)cc2)N1c1ccc2[nH]cnc2c1]
12

TABLE 1-continued
13
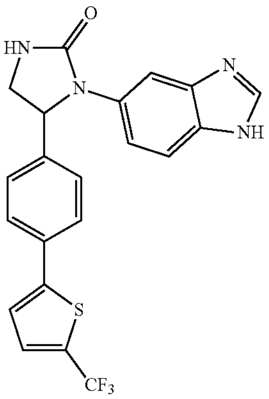
14
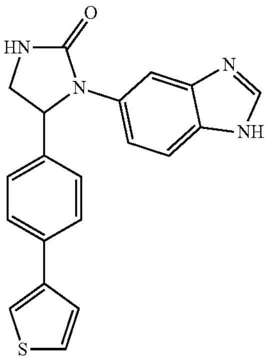 [SMILES: O=C1NCC(c2ccc(-c3ccsc3)cc2)N1c1ccc2[nH]cnc2c1]
15
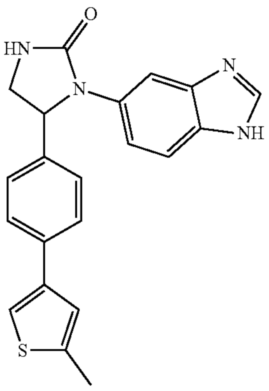 [SMILES: Cc1cc(-c2ccc(C3CNC(=O)N3c3ccc4[nH]cnc4c3)cc2)cs1]
16
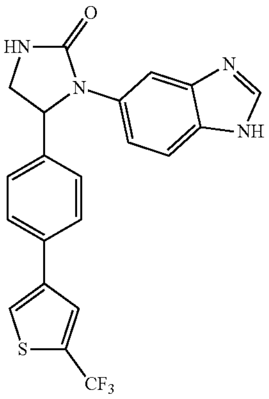
TABLE 1-continued
17
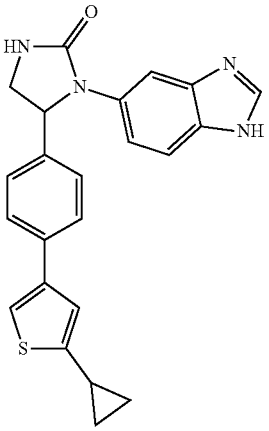 [SMILES: O=C1NCC(c2ccc(-c3csc(C4CC4)c3)cc2)N1c1ccc2[nH]cnc2c1]
18
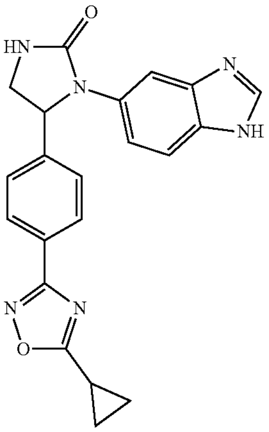 [SMILES: O=C1NCC(c2ccc(-c3noc(C4CC4)n3)cc2)N1c1ccc2[nH]cnc2c1]
19
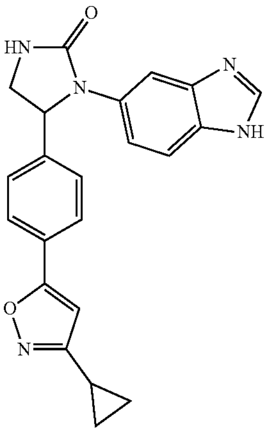 [SMILES: O=C1NCC(c2ccc(-c3cc(C4CC4)no3)cc2)N1c1ccc2[nH]cnc2c1]
20
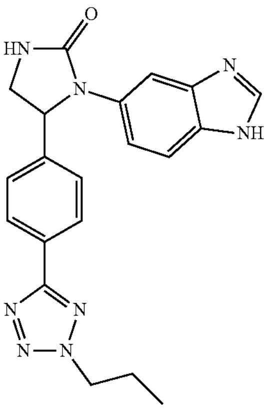 [SMILES: CCCn1nnc(-c2ccc(C3CNC(=O)N3c3ccc4[nH]cnc4c3)cc2)n1]

TABLE 1-continued
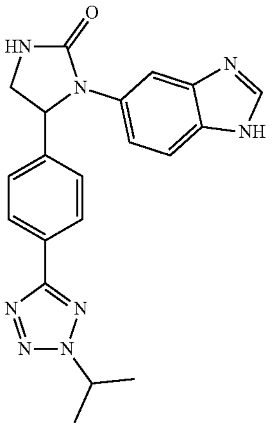 [SMILES: CC(C)n1nnc(-c2ccc(C3CNC(=O)N3c3ccc4[nH]cnc4c3)cc2)n1]
21
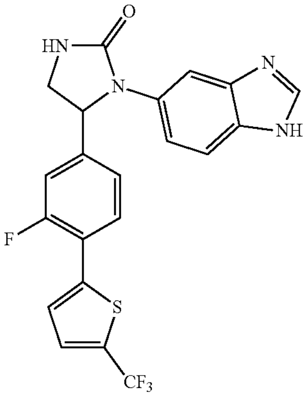 [SMILES: O=C1NCC(c2ccc(-c3ccc(C(F)(F)F)s3)c(F)c2)N1c1ccc2[nH]cnc2c1]
22
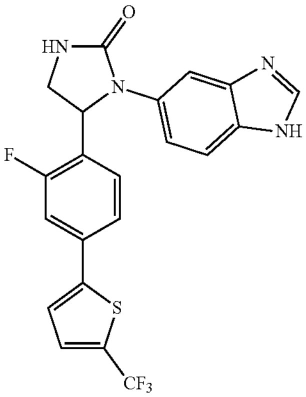 [SMILES: O=C1NCC(c2ccc(-c3ccc(C(F)(F)F)s3)cc2F)N1c1ccc2[nH]cnc2c1]
23
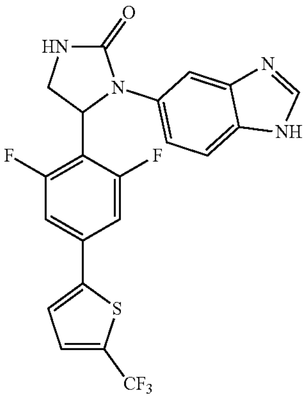 [SMILES: O=C1NCC(c2c(F)cc(-c3ccc(C(F)(F)F)s3)cc2F)N1c1ccc2[nH]cnc2c1]
24
TABLE 1-continued
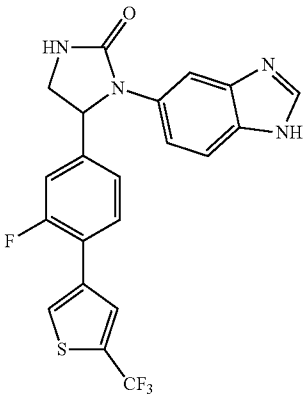 [SMILES: O=C1NCC(c2ccc(-c3csc(C(F)(F)F)c3)c(F)c2)N1c1ccc2[nH]cnc2c1]
25
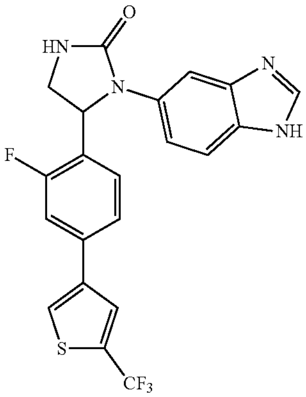 [SMILES: O=C1NCC(c2ccc(-c3csc(C(F)(F)F)c3)cc2F)N1c1ccc2[nH]cnc2c1]
26
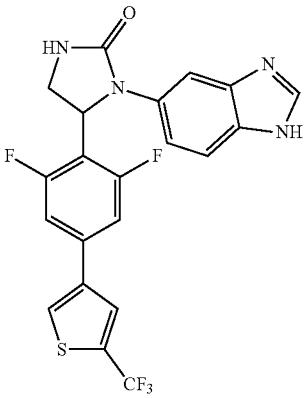 [SMILES: O=C1NCC(c2c(F)cc(-c3csc(C(F)(F)F)c3)cc2F)N1c1ccc2[nH]cnc2c1]
27
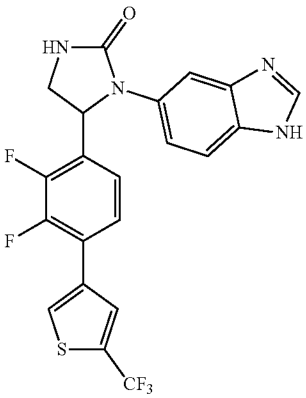 [SMILES: O=C1NCC(c2ccc(-c3csc(C(F)(F)F)c3)c(F)c2F)N1c1ccc2[nH]cnc2c1]
28

TABLE 1-continued
29
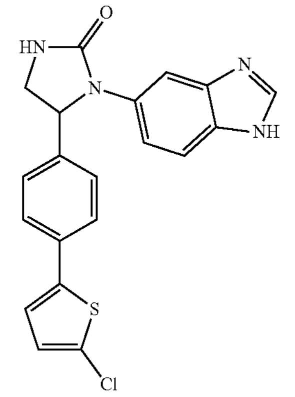 [SMILES: O=C1NCC(c2ccc(-c3ccc(Cl)s3)cc2)N1c1ccc2[nH]cnc2c1]
30
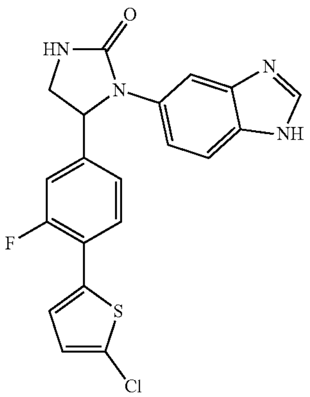 [SMILES: O=C1NCC(c2ccc(-c3ccc(Cl)s3)c(F)c2)N1c1ccc2[nH]cnc2c1]
31
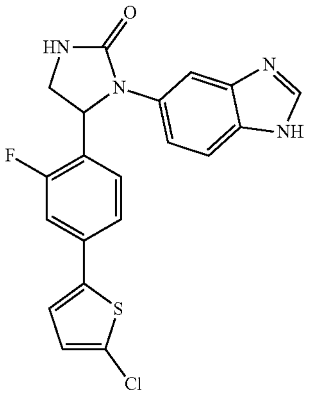 [SMILES: O=C1NCC(c2ccc(-c3ccc(Cl)s3)cc2F)N1c1ccc2[nH]cnc2c1]
32
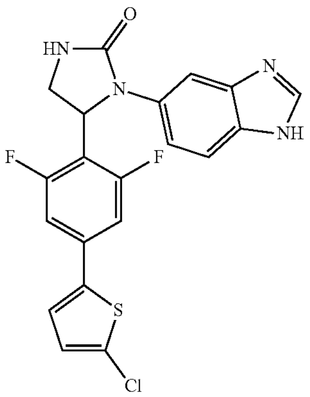 [SMILES: O=C1NCC(c2c(F)cc(-c3ccc(Cl)s3)cc2F)N1c1ccc2[nH]cnc2c1]
TABLE 1-continued
33
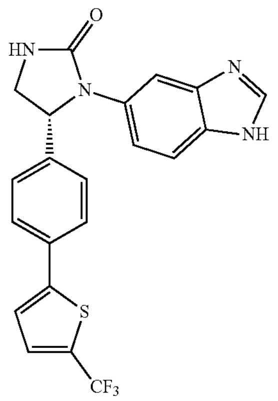
34
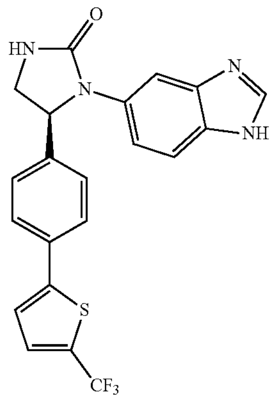
35
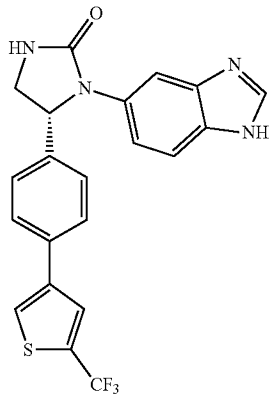 [SMILES: O=C1NC[C@@H](c2ccc(-c3csc(C(F)(F)F)c3)cc2)N1c1ccc2[nH]cnc2c1]
36
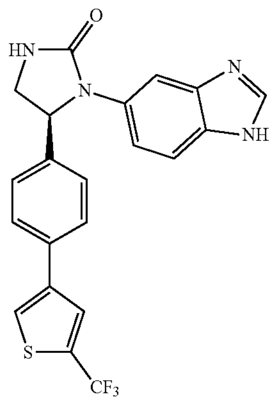 [SMILES: O=C1NC[C@H](c2ccc(-c3csc(C(F)(F)F)c3)cc2)N1c1ccc2[nH]cnc2c1]

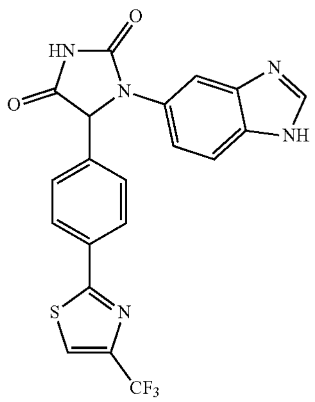 [SMILES: O=C1NC(=O)N(c2ccc3[nH]cnc3c2)C1c1ccc(-c2nc(C(F)(F)F)cs2)cc1]
37
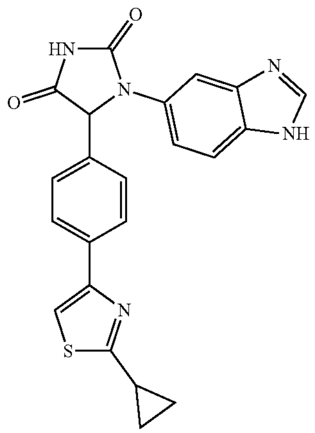 [SMILES: O=C1NC(=O)N(c2ccc3[nH]cnc3c2)C1c1ccc(-c2csc(C3CC3)n2)cc1]
38
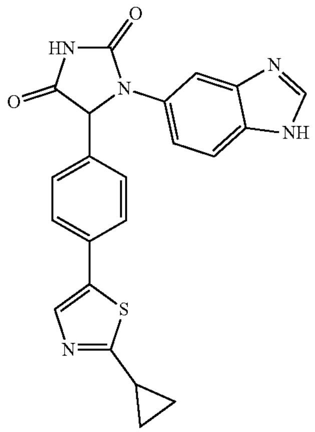 [SMILES: O=C1NC(=O)N(c2ccc3[nH]cnc3c2)C1c1ccc(-c2cnc(C3CC3)s2)cc1]
39
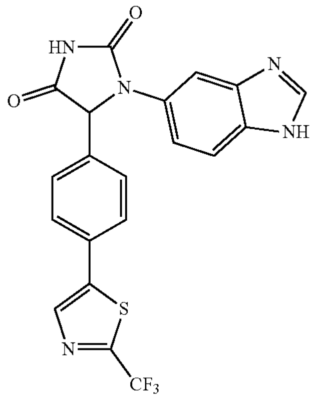 [SMILES: O=C1NC(=O)N(c2ccc3[nH]cnc3c2)C1c1ccc(-c2cnc(C(F)(F)F)s2)cc1]
40
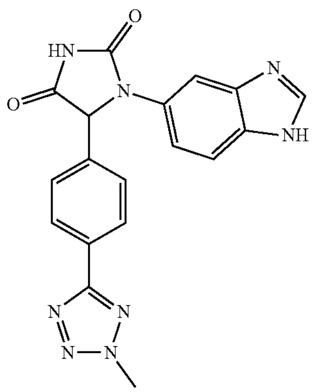 [SMILES: Cn1nnc(-c2ccc(C3C(=O)NC(=O)N3c3ccc4[nH]cnc4c3)cc2)n1]
41
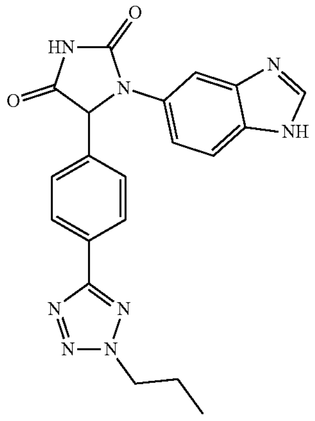 [SMILES: CCCn1nnc(-c2ccc(C3C(=O)NC(=O)N3c3ccc4[nH]cnc4c3)cc2)n1]
42
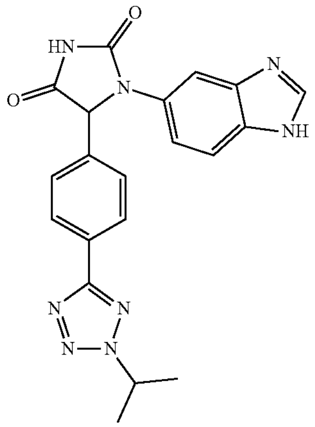 [SMILES: CC(C)n1nnc(-c2ccc(C3C(=O)NC(=O)N3c3ccc4[nH]cnc4c3)cc2)n1]
43
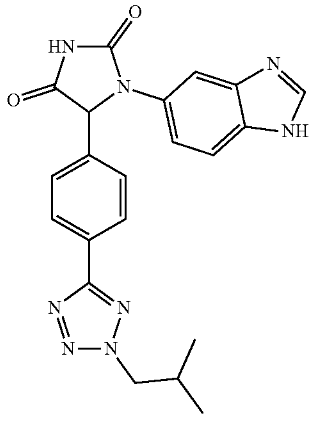 [SMILES: CC(C)Cn1nnc(-c2ccc(C3C(=O)NC(=O)N3c3ccc4[nH]cnc4c3)cc2)n1]
44

TABLE 1-continued
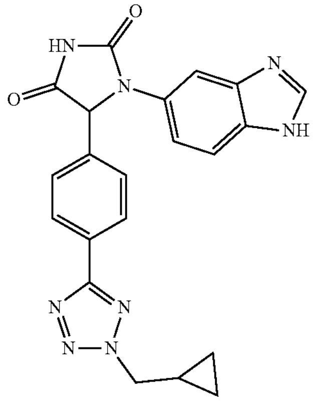 [SMILES: O=C1NC(=O)N(c2ccc3[nH]cnc3c2)C1c1ccc(-c2nnn(CC3CC3)n2)cc1]
45
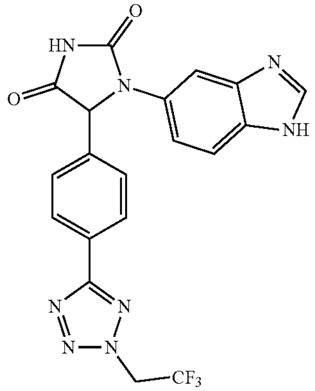 [SMILES: O=C1NC(=O)N(c2ccc3[nH]cnc3c2)C1c1ccc(-c2nnn(CC(F)(F)F)n2)cc1]
46
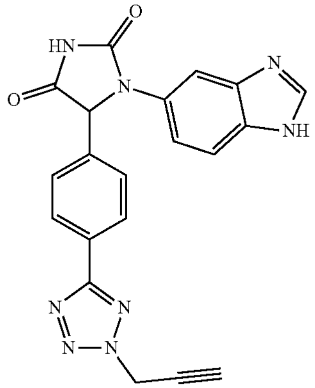 [SMILES: C#CCn1nnc(-c2ccc(C3C(=O)NC(=O)N3c3ccc4[nH]cnc4c3)cc2)n1]
47
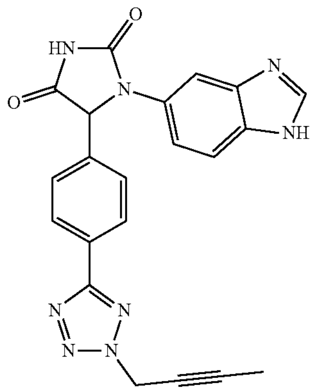 [SMILES: CC#CCn1nnc(-c2ccc(C3C(=O)NC(=O)N3c3ccc4[nH]cnc4c3)cc2)n1]
48
TABLE 1-continued
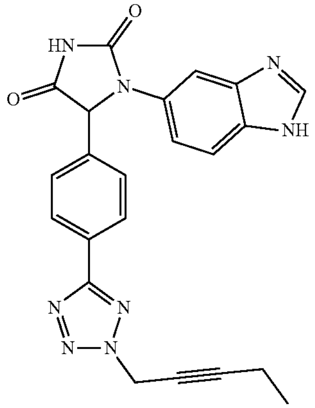 [SMILES: CCC#CCn1nnc(-c2ccc(C3C(=O)NC(=O)N3c3ccc4[nH]cnc4c3)cc2)n1]
49
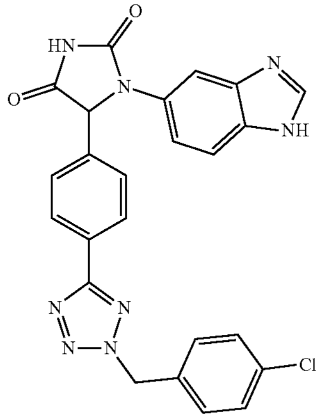 [SMILES: O=C1NC(=O)N(c2ccc3[nH]cnc3c2)C1c1ccc(-c2nnn(Cc3ccc(Cl)cc3)n2)cc1]
50
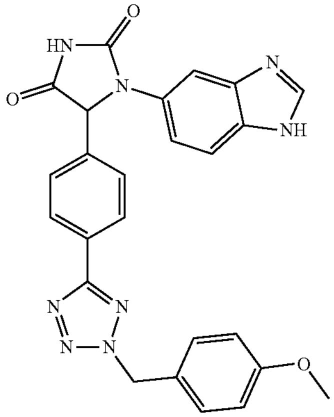 [SMILES: COc1ccc(Cn2nnc(-c3ccc(C4C(=O)NC(=O)N4c4ccc5[nH]cnc5c4)cc3)n2)cc1]
51
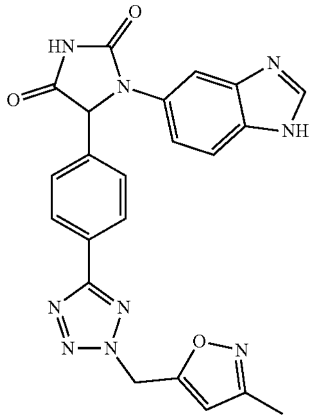 [SMILES: Cc1cc(Cn2nnc(-c3ccc(C4C(=O)NC(=O)N4c4ccc5[nH]cnc5c4)cc3)n2)on1]
52

TABLE 1-continued
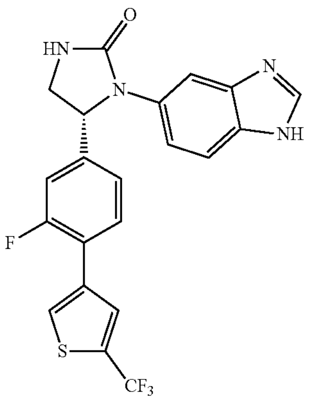 [SMILES: O=C1NC[C@@H](c2ccc(-c3csc(C(F)(F)F)c3)c(F)c2)N1c1ccc2[nH]cnc2c1]
53
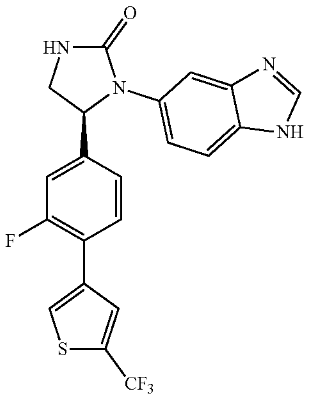 [SMILES: O=C1NC[C@H](c2ccc(-c3csc(C(F)(F)F)c3)c(F)c2)N1c1ccc2[nH]cnc2c1]
54
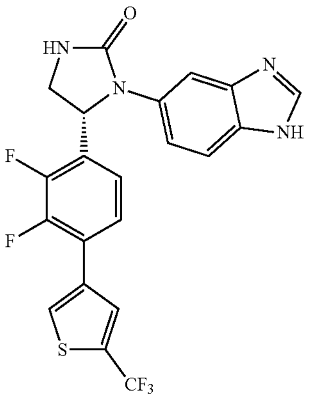 [SMILES: O=C1NC[C@@H](c2ccc(-c3csc(C(F)(F)F)c3)c(F)c2F)N1c1ccc2[nH]cnc2c1]
55
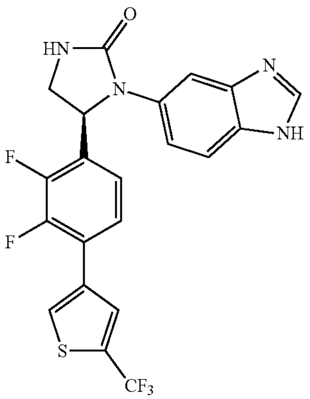 [SMILES: O=C1NC[C@H](c2ccc(-c3csc(C(F)(F)F)c3)c(F)c2F)N1c1ccc2[nH]cnc2c1]
56
TABLE 1-continued
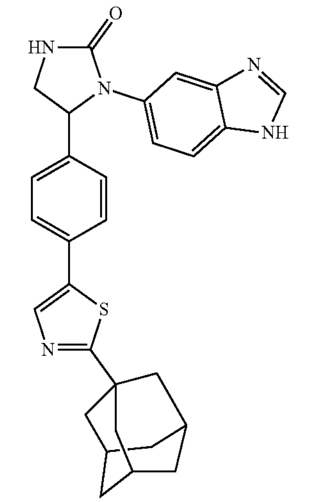 [SMILES: O=C1NCC(c2ccc(-c3cnc(C45CC6CC(CC(C6)C4)C5)s3)cc2)N1c1ccc2[nH]cnc2c1]
57
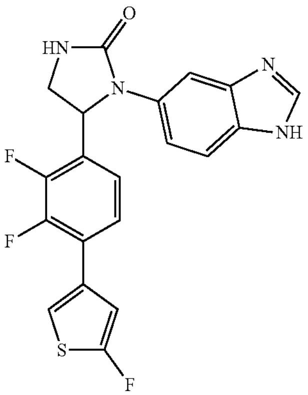 [SMILES: O=C1NCC(c2ccc(-c3csc(F)c3)c(F)c2F)N1c1ccc2[nH]cnc2c1]
58
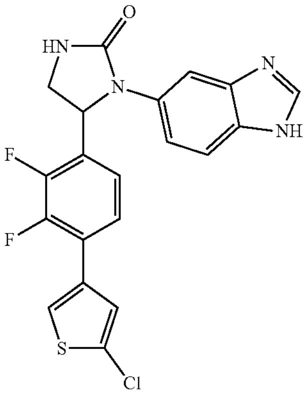 [SMILES: O=C1NCC(c2ccc(-c3csc(Cl)c3)c(F)c2F)N1c1ccc2[nH]cnc2c1]
59
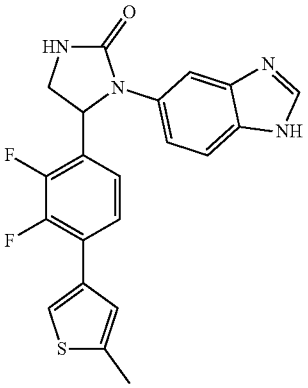 [SMILES: Cc1cc(-c2ccc(C3CNC(=O)N3c3ccc4[nH]cnc4c3)c(F)c2F)cs1]
60

TABLE 1-continued
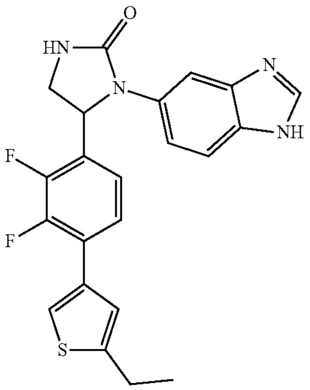 [SMILES: CCc1cc(-c2ccc(C3CNC(=O)N3c3ccc4[nH]cnc4c3)c(F)c2F)cs1]
61
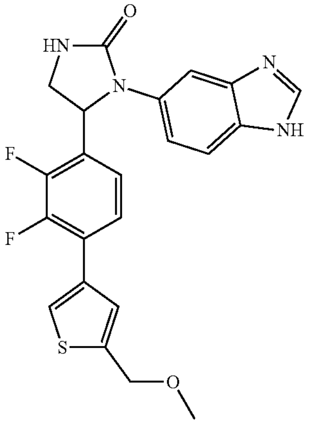 [SMILES: COCc1cc(-c2ccc(C3CNC(=O)N3c3ccc4[nH]cnc4c3)c(F)c2F)cs1]
62
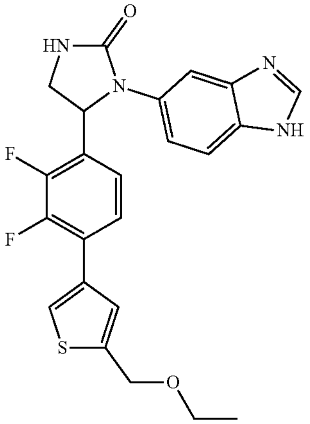 [SMILES: CCOCc1cc(-c2ccc(C3CNC(=O)N3c3ccc4[nH]cnc4c3)c(F)c2F)cs1]
63
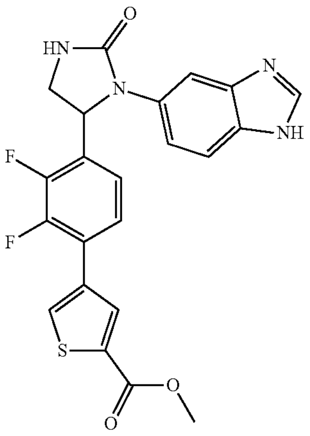 [SMILES: COC(=O)c1cc(-c2ccc(C3CNC(=O)N3c3ccc4[nH]cnc4c3)c(F)c2F)cs1]
64
TABLE 1-continued
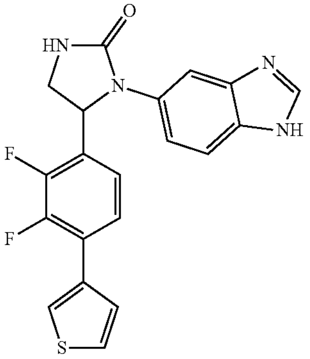 [SMILES: O=C1NCC(c2ccc(-c3ccsc3)c(F)c2F)N1c1ccc2[nH]cnc2c1]
65
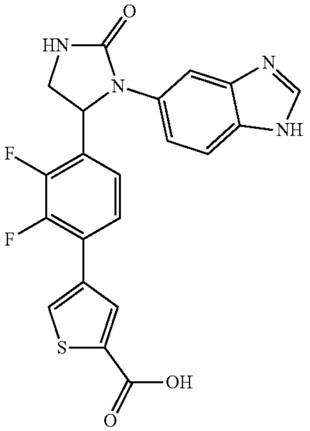 [SMILES: O=C(O)c1cc(-c2ccc(C3CNC(=O)N3c3ccc4[nH]cnc4c3)c(F)c2F)cs1]
66
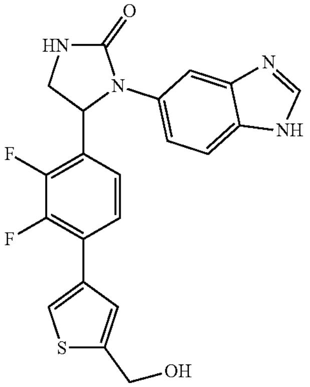 [SMILES: O=C1NCC(c2ccc(-c3csc(CO)c3)c(F)c2F)N1c1ccc2[nH]cnc2c1]
67
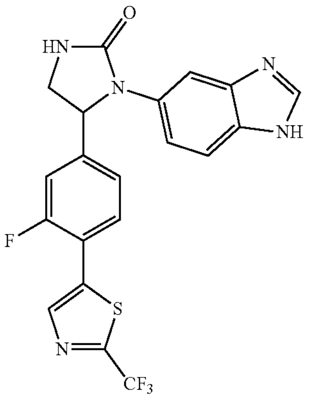 [SMILES: O=C1NCC(c2ccc(-c3cnc(C(F)(F)F)s3)c(F)c2)N1c1ccc2[nH]cnc2c1]
68

TABLE 1-continued
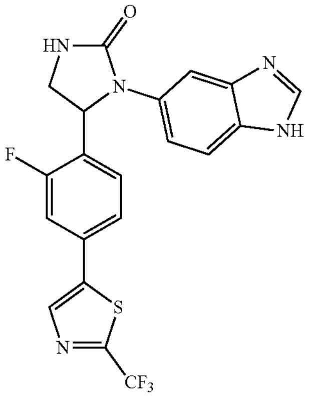 [SMILES: O=C1NCC(c2ccc(-c3cnc(C(F)(F)F)s3)cc2F)N1c1ccc2[nH]cnc2c1]
69
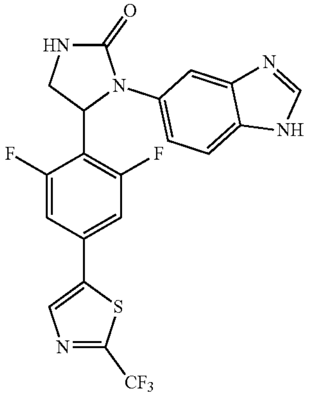 [SMILES: O=C1NCC(c2c(F)cc(-c3cnc(C(F)(F)F)s3)cc2F)N1c1ccc2[nH]cnc2c1]
70
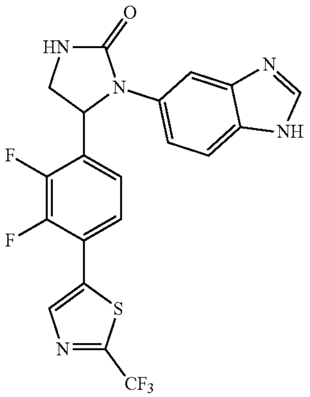 [SMILES: O=C1NCC(c2ccc(-c3cnc(C(F)(F)F)s3)c(F)c2F)N1c1ccc2[nH]cnc2c1]
71
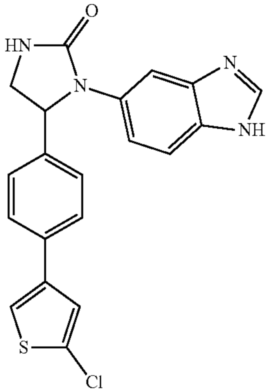 [SMILES: O=C1NCC(c2ccc(-c3csc(Cl)c3)cc2)N1c1ccc2[nH]cnc2c1]
72
TABLE 1-continued
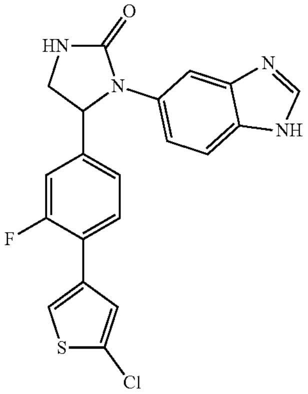 [SMILES: O=C1NCC(c2ccc(-c3csc(Cl)c3)c(F)c2)N1c1ccc2[nH]cnc2c1]
73
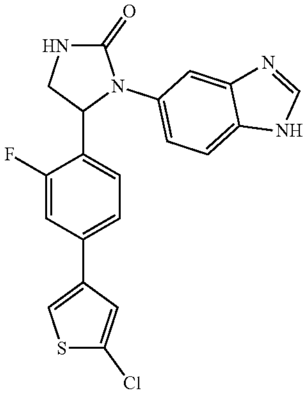 [SMILES: O=C1NCC(c2ccc(-c3csc(Cl)c3)cc2F)N1c1ccc2[nH]cnc2c1]
74
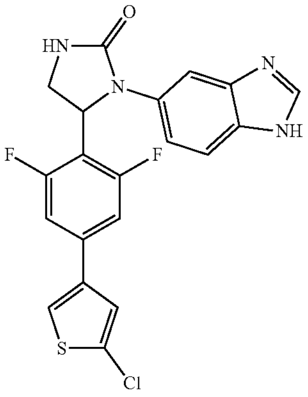 [SMILES: O=C1NCC(c2c(F)cc(-c3csc(Cl)c3)cc2F)N1c1ccc2[nH]cnc2c1]
75
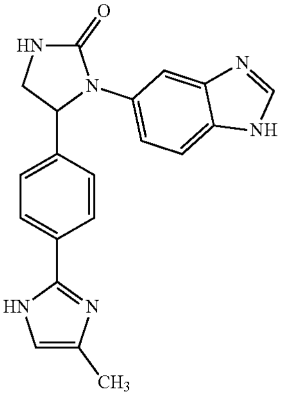 [SMILES: Cc1c[nH]c(-c2ccc(C3CNC(=O)N3c3ccc4[nH]cnc4c3)cc2)n1]
76

TABLE 1-continued
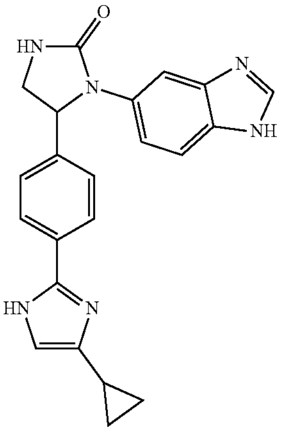 [SMILES: O=C1NCC(c2ccc(-c3nc(C4CC4)c[nH]3)cc2)N1c1ccc2[nH]cnc2c1]
77
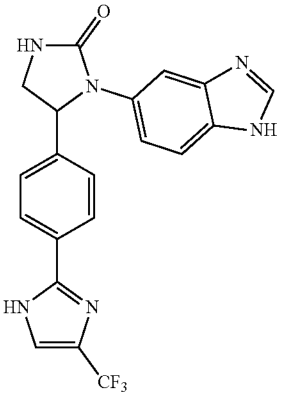
78
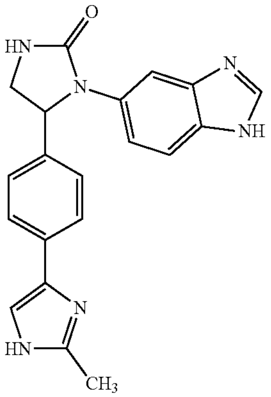
79
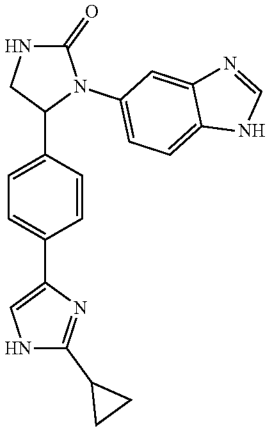
80
TABLE 1-continued
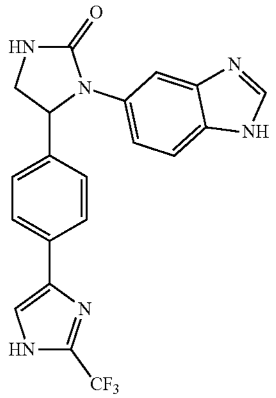
81
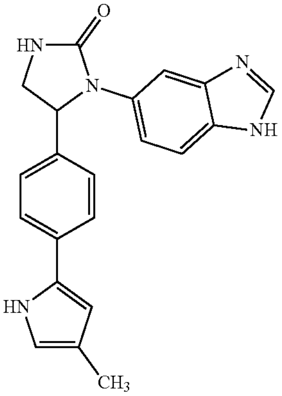
82
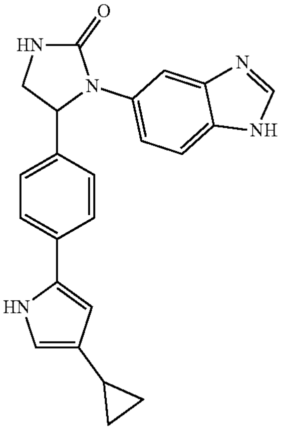 [SMILES: O=C1NCC(c2ccc(-c3cc(C4CC4)c[nH]3)cc2)N1c1ccc2[nH]cnc2c1]
83
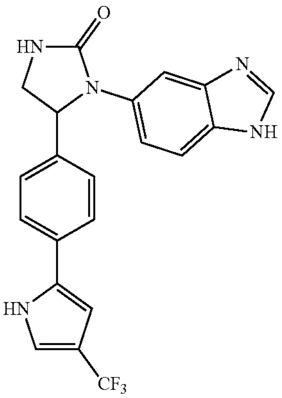 [SMILES: O=C1NCC(c2ccc(-c3cc(C(F)(F)F)c[nH]3)cc2)N1c1ccc2[nH]cnc2c1]
84

TABLE 1-continued
85
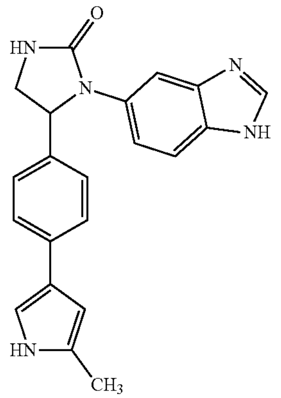
86
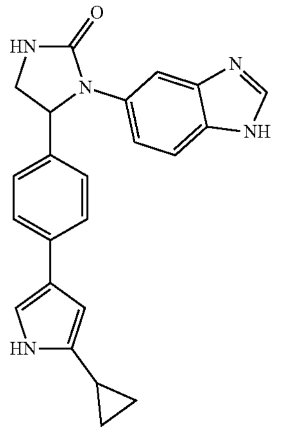 [SMILES: O=C1NCC(c2ccc(-c3c[nH]c(C4CC4)c3)cc2)N1c1ccc2[nH]cnc2c1]
87
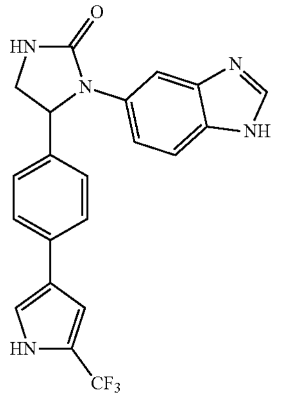
88
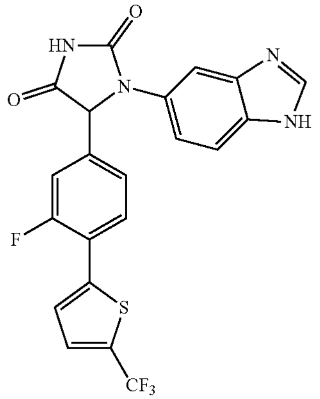 [SMILES: O=C1NC(=O)N(c2ccc3[nH]cnc3c2)C1c1ccc(-c2ccc(C(F)(F)F)s2)c(F)c1]
TABLE 1-continued
89
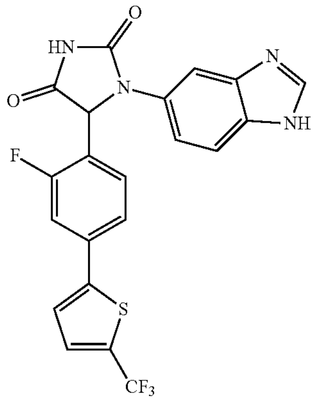 [SMILES: O=C1NC(=O)N(c2ccc3[nH]cnc3c2)C1c1ccc(-c2ccc(C(F)(F)F)s2)cc1F]
90
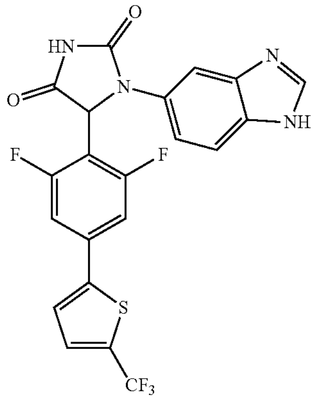 [SMILES: O=C1NC(=O)N(c2ccc3[nH]cnc3c2)C1c1c(F)cc(-c2ccc(C(F)(F)F)s2)cc1F]
91
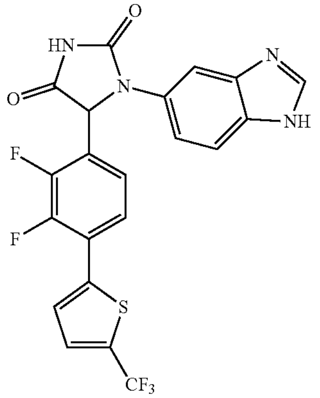 [SMILES: O=C1NC(=O)N(c2ccc3[nH]cnc3c2)C1c1ccc(-c2ccc(C(F)(F)F)s2)c(F)c1F]
92
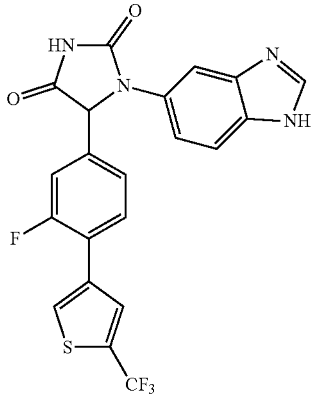 [SMILES: O=C1NC(=O)N(c2ccc3[nH]cnc3c2)C1c1ccc(-c2csc(C(F)(F)F)c2)c(F)c1]

TABLE 1-continued
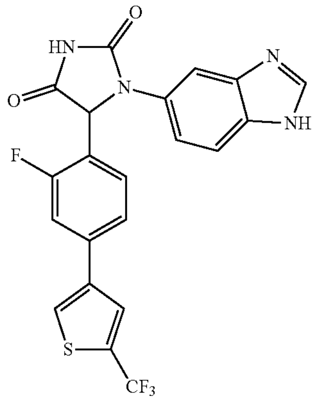
93
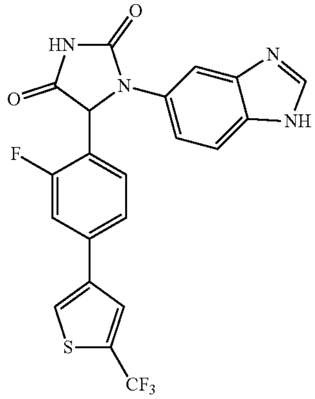 [SMILES: O=C1NC(=O)N(c2ccc3[nH]cnc3c2)C1c1ccc(-c2csc(C(F)(F)F)c2)cc1F]
94
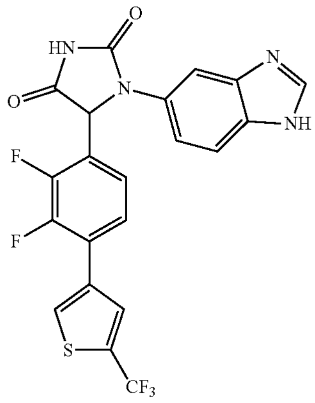 [SMILES: O=C1NC(=O)N(c2ccc3[nH]cnc3c2)C1c1ccc(-c2csc(C(F)(F)F)c2)c(F)c1F]
95
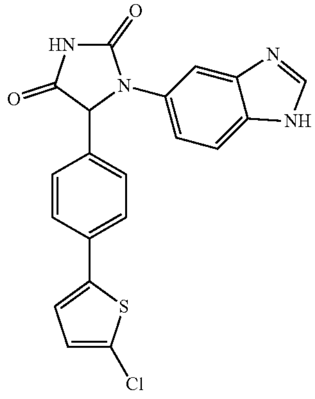 [SMILES: O=C1NC(=O)N(c2ccc3[nH]cnc3c2)C1c1ccc(-c2ccc(Cl)s2)cc1]
96
TABLE 1-continued
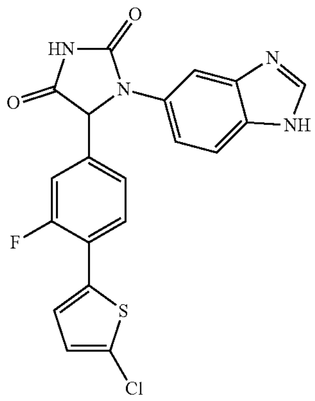 [SMILES: O=C1NC(=O)N(c2ccc3[nH]cnc3c2)C1c1ccc(-c2ccc(Cl)s2)c(F)c1]
97
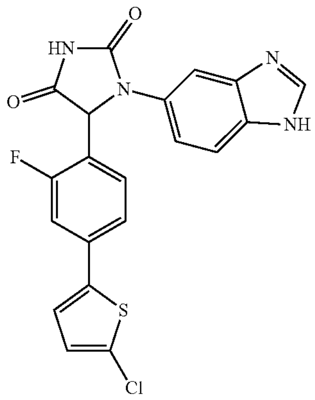 [SMILES: O=C1NC(=O)N(c2ccc3[nH]cnc3c2)C1c1ccc(-c2ccc(Cl)s2)cc1F]
98
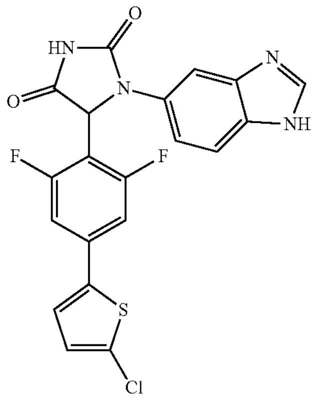 [SMILES: O=C1NC(=O)N(c2ccc3[nH]cnc3c2)C1c1c(F)cc(-c2ccc(Cl)s2)cc1F]
99
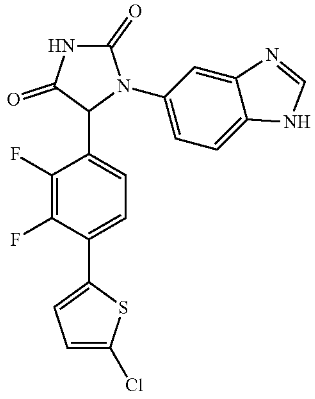 [SMILES: O=C1NC(=O)N(c2ccc3[nH]cnc3c2)C1c1ccc(-c2ccc(Cl)s2)c(F)c1F]
100

TABLE 1-continued
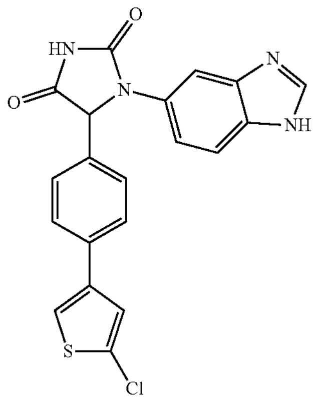 [SMILES: O=C1NC(=O)N(c2ccc3[nH]cnc3c2)C1c1ccc(-c2csc(Cl)c2)cc1]
101
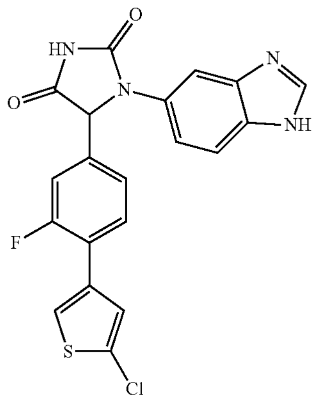 [SMILES: O=C1NC(=O)N(c2ccc3[nH]cnc3c2)C1c1ccc(-c2csc(Cl)c2)c(F)c1]
102
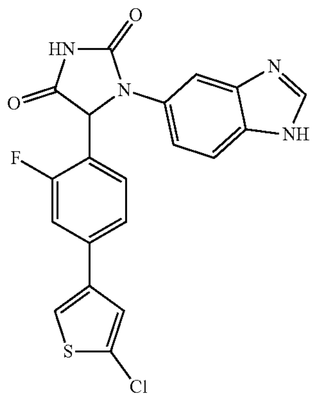 [SMILES: O=C1NC(=O)N(c2ccc3[nH]cnc3c2)C1c1ccc(-c2csc(Cl)c2)cc1F]
103
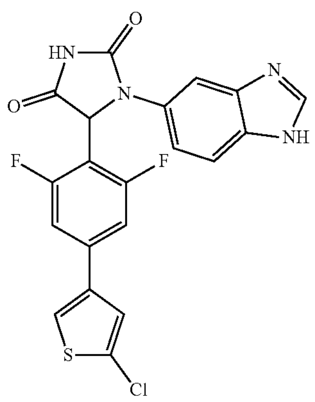 [SMILES: O=C1NC(=O)N(c2ccc3[nH]cnc3c2)C1c1c(F)cc(-c2csc(Cl)c2)cc1F]
104
TABLE 1-continued
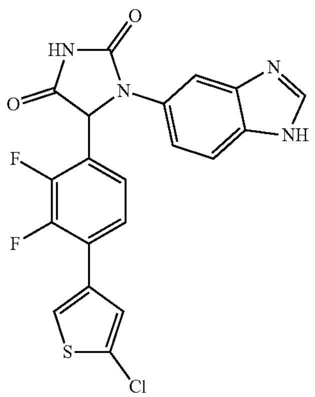 [SMILES: O=C1NC(=O)N(c2ccc3[nH]cnc3c2)C1c1ccc(-c2csc(Cl)c2)c(F)c1F]
105
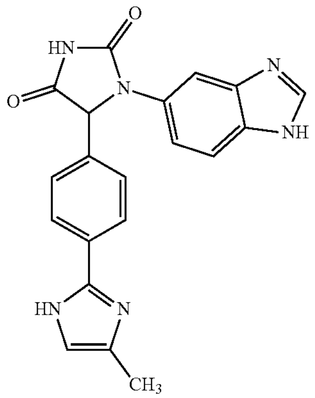 [SMILES: Cc1c[nH]c(-c2ccc(C3C(=O)NC(=O)N3c3ccc4[nH]cnc4c3)cc2)n1]
106
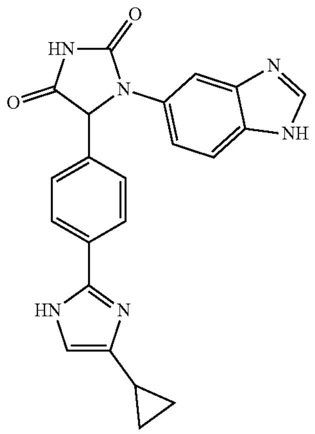 [SMILES: O=C1NC(=O)N(c2ccc3[nH]cnc3c2)C1c1ccc(-c2nc(C3CC3)c[nH]2)cc1]
107
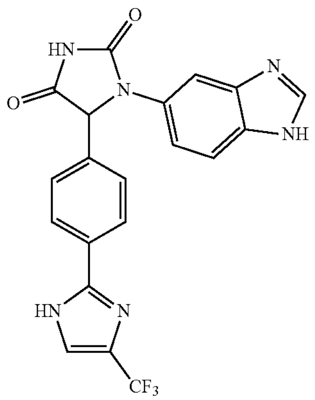 [SMILES: O=C1NC(=O)N(c2ccc3[nH]cnc3c2)C1c1ccc(-c2nc(C(F)(F)F)c[nH]2)cc1]
108

TABLE 1-continued
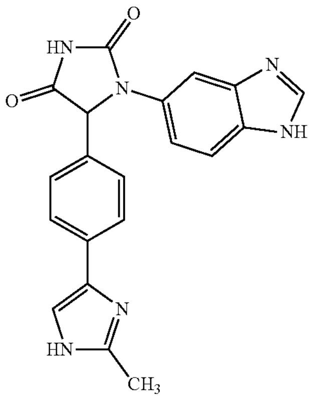 [SMILES: Cc1nc(-c2ccc(C3C(=O)NC(=O)N3c3ccc4[nH]cnc4c3)cc2)c[nH]1]
109
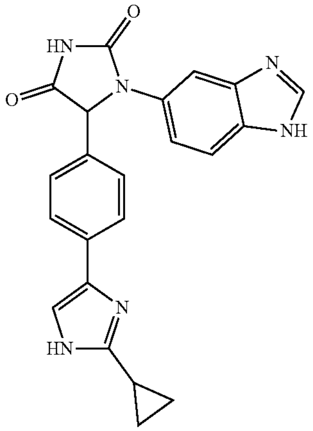 [SMILES: O=C1NC(=O)N(c2ccc3[nH]cnc3c2)C1c1ccc(-c2c[nH]c(C3CC3)n2)cc1]
110
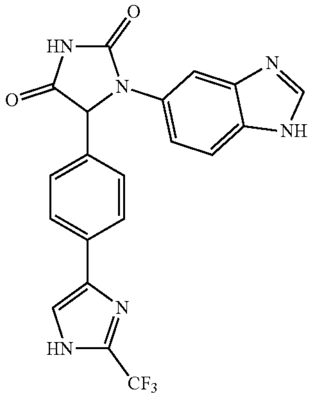 [SMILES: O=C1NC(=O)N(c2ccc3[nH]cnc3c2)C1c1ccc(-c2c[nH]c(C(F)(F)F)n2)cc1]
111
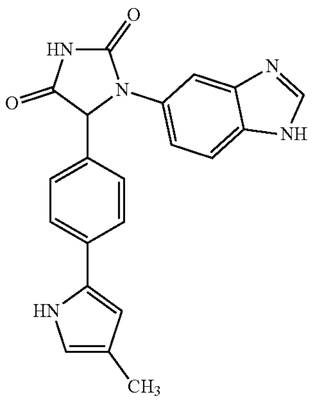 [SMILES: Cc1c[nH]c(-c2ccc(C3C(=O)NC(=O)N3c3ccc4[nH]cnc4c3)cc2)c1]
112
TABLE 1-continued
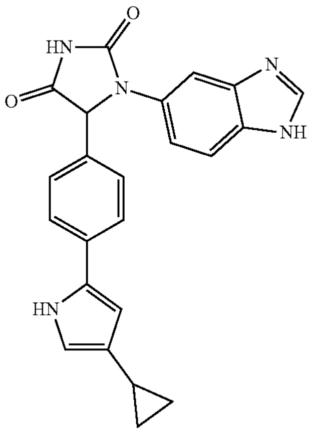 [SMILES: O=C1NC(=O)N(c2ccc3[nH]cnc3c2)C1c1ccc(-c2cc(C3CC3)c[nH]2)cc1]
113
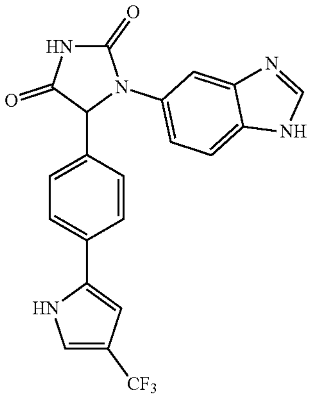 [SMILES: O=C1NC(=O)N(c2ccc3[nH]cnc3c2)C1c1ccc(-c2cc(C(F)(F)F)c[nH]2)cc1]
114
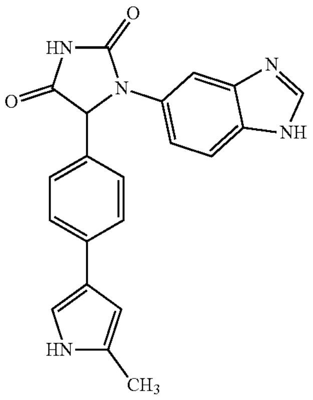 [SMILES: Cc1cc(-c2ccc(C3C(=O)NC(=O)N3c3ccc4[nH]cnc4c3)cc2)c[nH]1]
115
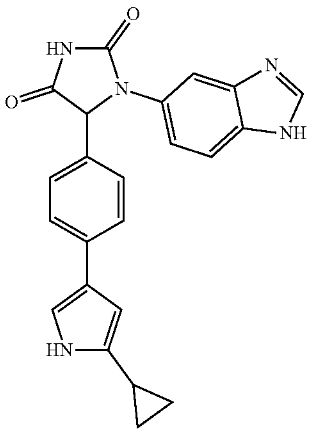 [SMILES: O=C1NC(=O)N(c2ccc3[nH]cnc3c2)C1c1ccc(-c2c[nH]c(C3CC3)c2)cc1]
116

TABLE 1-continued

| | |
|---|---|
| 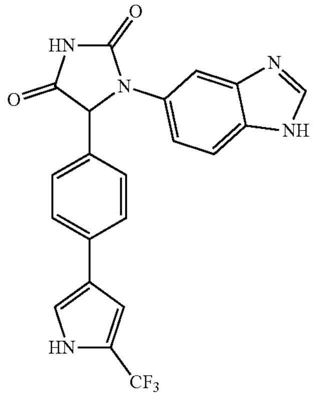 [SMILES: O=C1NC(=O)N(c2ccc3[nH]cnc3c2)C1c1ccc(-c2c[nH]c(C(F)(F)F)c2)cc1] | 117 |

Among the 117 compounds listed above, Compounds 9 and 10 are the two enantiomers of Compound 8; Compounds 33 and 34 are the two enantiomers of Compound 13; Compounds 35 and 36 are the two enantiomers of Compound 16; Compounds 53 and 54 are the two enantiomers of Compound 25; and Compounds 55 and 56 are the two enantiomers of Compound 28.

Compounds 9, 34, 36, 54, and 56 are preferred.

Methods for synthesizing the compounds of formula (I) are well known in the field. Note that the procedures for preparing as many as 67 compounds, i.e., Compounds 1-67, are set forth in EXAMPLE 1 below.

The compounds thus prepared can be initially screened using in vitro assays for their potency in inhibiting the activity of glutaminyl cyclase (QC). The in vitro assays are set forth in EXAMPLE 2 below. Further, the prepared compounds can be subsequently evaluated using in vivo assays. The in vivo assays are set forth in EXAMPLE 3 below. The selected compounds can be further tested to verify their efficacy in treating AD or HD. Based on the results, appropriate dosage ranges and administration routes can be investigated and determined.

All reagents and solvents were purchased from commercial suppliers and used without further purification unless otherwise noted. All anhydrous reactions were performed under a nitrogen atmosphere using dry solvents. All reactions were monitored by thin layer chromatography using Merck Silica gel 60 $F_{254}$ glass-backed plate. Column chromatography was performed by Merck silica gel 60 (0.040-0.063 mm, 230-400 mesh). Purity of the final compounds was determined on a Hitachi 2000 series HPLC system with a reverse phase $C_{18}$ column (Agilent ZORBAX Eclipse XDB-C18 5 μm, 4.6 mm×150 mm), operating at 25° C. Mobile phase A was acetonitrile. Mobile phase B was 10 mM $NH_4OAc$ aqueous solution containing 0.1% formic acid. The gradient system started from A/B (10%/90%) at 0 min to A/B (90%/10%) at 45 min. The flow rate of the mobile phase was 0.5 mL/min, and the injection volume of the sample was 5 μL. Peaks were detected at 254 nm. The purity of all tested compounds is >95%. LC/MS data were measured on an Agilent MSD-1100 ESI-MS/MS System. All tested compounds were detected at UV 254 nm unless otherwise stated. $^1$H NMR spectra were measured by Varian Mercury-300 and Varian Mercury-400 spectrometers, and the chemical shifts (6) were reported in parts per million (ppm) relative to the resonance of the solvent peak. Multiplicities are reported with the following abbreviations: s (singlet), d (doublet), t (triplet), q (quartet), quin (quintet), m (multiplet), or br (broad).

Without further elaboration, it is believed that one skilled in the art can, based on the above description, utilize the present invention to its fullest extent. The specific embodiments described in EXAMPLES 1-3 below are, therefore, to be construed as merely illustrative, and not limitative of the remainder of the disclosure in any way whatsoever. All publications cited herein are incorporated by reference.

Example 1: Preparation and Characterization of Compounds

Compounds 1-67 were prepared by Synthetic Methods 1-18 respectively shown in Schemes 1-18 below.

Synthetic Method 1

Compounds 1-4, each having a 1,3-thiazol-2-yl ring, were prepared according to the synthetic procedures shown in Scheme 1 below. (4-Formylphenyl)boronic acid 118 was coupled with 2-bromothiazole derivatives 119a-d under a Suzuki-coupling condition to afford 4-(1,3-thiazol-2-yl)benzaldehyde derivatives 120a-d. The core structure of imidazolidinone ring was built in the following three steps. TMSCN was added to a solution of benzaldehydes 120a-d and 1H-benzimidazol-5-amine 121 in acetic acid. The reaction mixture was stirred at room temperature for 2 hours and then worked up to yield amino acetonitriles 122a-d, which were hydrogenated using Raney Nickel catalyst in acetic acid at 5~10° C. to afford diamines 123a-d. In the final step, 1,1'-carbonyldiimidazole (CDI) was added to a solution of diamines 123a-d in THF and then stirred at 75° C. for 18 hours. Compounds 1-4 were obtained after purification by column chromatography.

Scheme 1

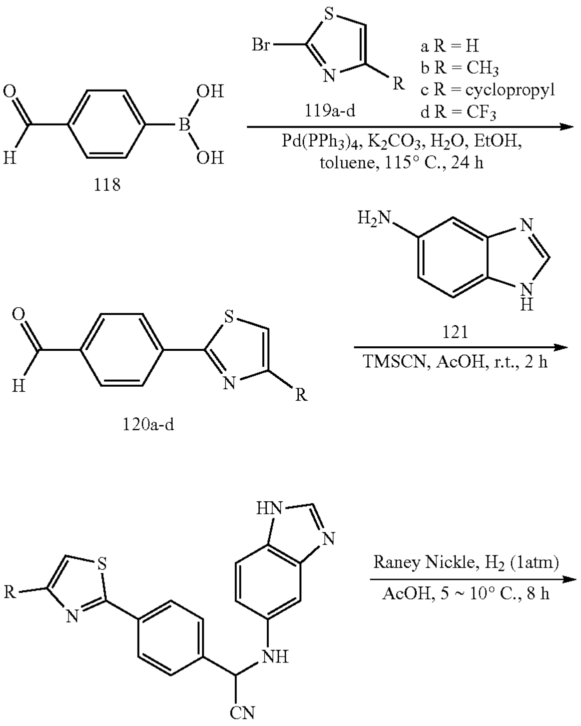

118

119a-d 120a-d

121

122a-d

-continued

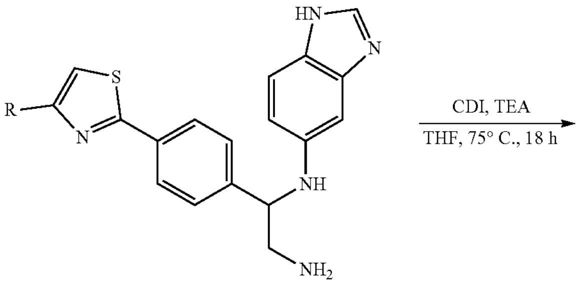

123a-d

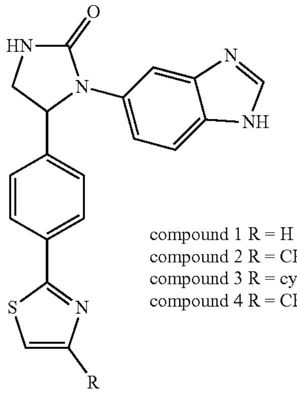

compound 1 R = H
compound 2 R = $CH_3$
compound 3 R = cyclopropyl
compound 4 R = $CF_3$ Synthetic Method 2

4-(2-Cyclopropyl-1,3thiazol-4-yl)benzaldehyde 127, a precursor, was synthesized under two different Suzuki-coupling conditions shown in Scheme 2 below. 2,4-Dibromo-1,3-thiazole 124, a starting material, was selectively coupled at 2-position with cyclopropylboronic acid 125 using $Pd(OAc)_2$ as a catalyst. The resultant product 126 was coupled at 4-position with (4-formylphenyl)boronic acid 118 using $Pd(dppf)Cl_2$ as a catalyst to afford precursor 127 having a 1,3-thiazol-4-yl ring. This precursor was then applied to the procedures shown in Synthetic Method 1 for forming imidazolidinone to obtain the final compound (Compound 5).

Scheme 2

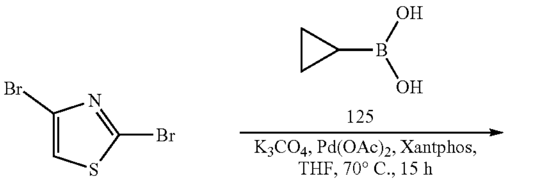

124

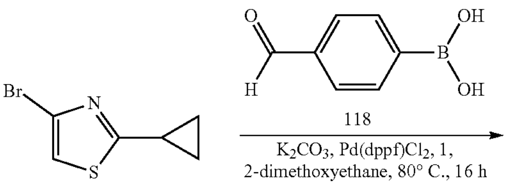

126

-continued

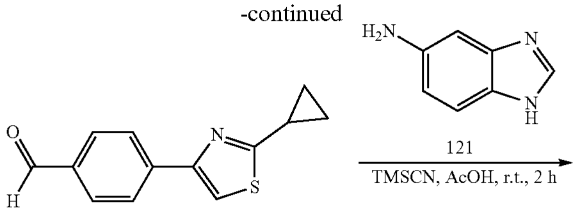

127

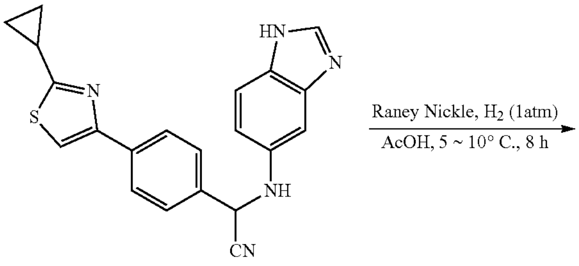

128

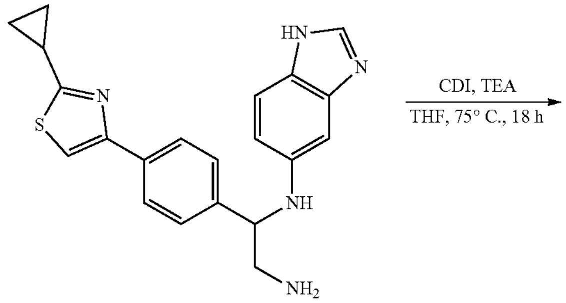

129

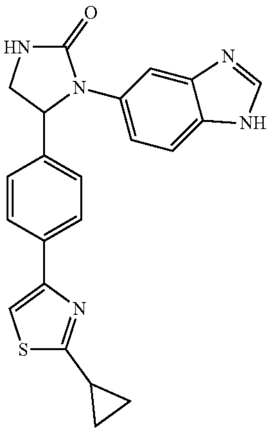

compound 5

Synthetic Method 3

Compounds 6-8, each having a 3-thiazol-5-yl ring, were prepared in eight steps as shown in Scheme 3 below. Commercially available starting material 4-(bromoacetyl)-benzonitrile 130 was transformed into 4-(aminoacetyl)benzonitrile hydrochloride 131 after a substitution reaction using HMTA followed by refluxing in a solution of hydrochloride acid in ethanol. Compound 131 was then acetylated with variable anhydrides 132a-c to obtain amides 133a-c, which were subsequently treated with the Lawesson's reagent in THF or toluene under reflux to afford (1,3-thiazol-5-yl)benzonitrile analogs 134a-c. The benzonitrile analogs 134a-c were reduced by DIBAL-H to form benzaldehyde precursors 135a-c. These precursors were then applied to the procedures shown in Synthetic Method 1 for forming imidazolidinone to obtain Compounds 6-8.

Scheme 3

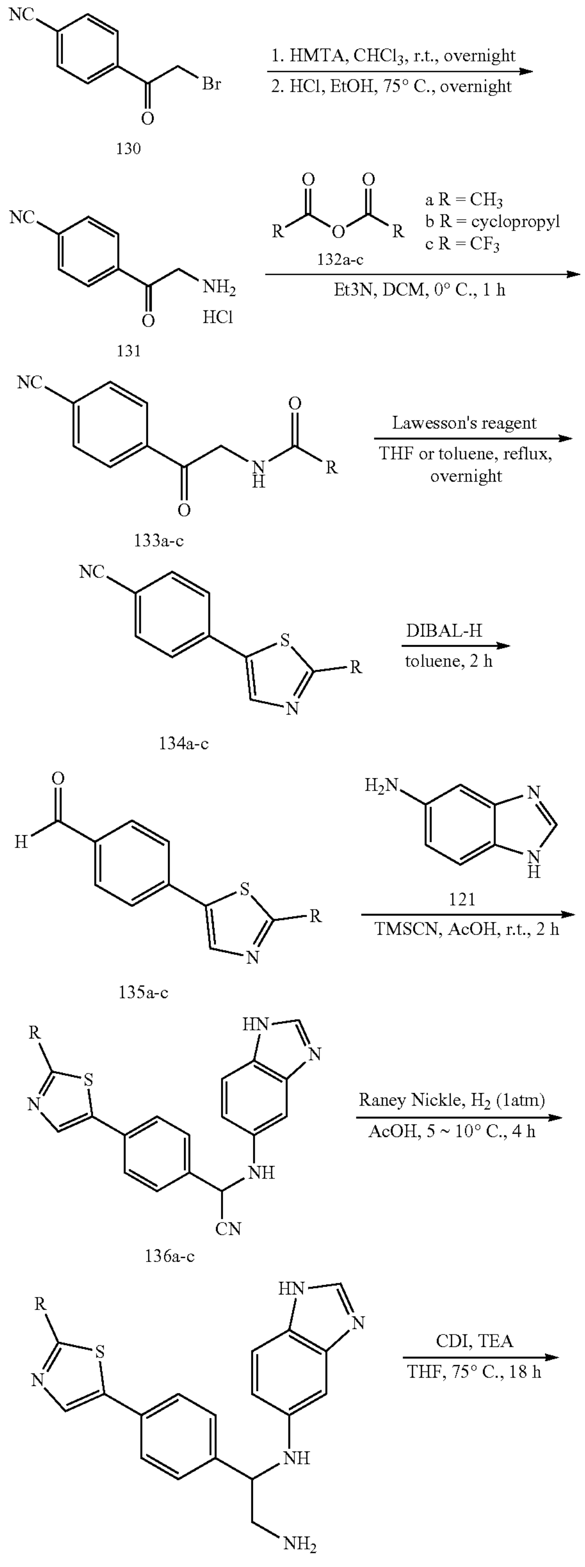

130

131

132a-c 133a-c 134a-c 135a-c

121

136a-c 137a-c

-continued

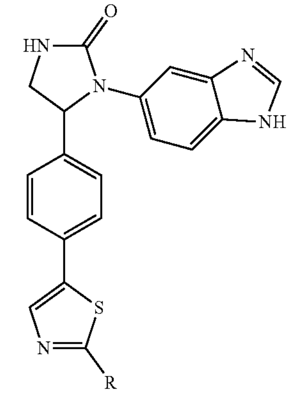

compound 6 R = $CH_3$
compound 7 R = cyclopropyl
compound 8 R = $CF_3$

Synthetic Method 4

Compounds 11 and 29-32, each having a thiophen-2-yl ring, were prepared by the synthetic procedures shown in Scheme 4 below. 4-Bromobenzaldehydes 138a-d were each coupled with 2-substituted thiophene 139a or 139b under a Suzuki-coupling condition to afford benzaldehyde precursors 140a-e. These precursors were then applied to the procedures shown in Synthetic Method 1 for forming imidazolidinone to obtain Compounds 11 and 29-32.

Scheme 4

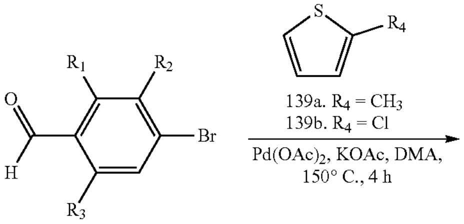

138a-d a. $R_1$ = H, $R_2$ = H, $R_3$ = H
b. $R_1$ = H, $R_2$ = F, $R_3$ = H
c. $R_1$ = F, $R_2$ = H, $R_3$ = H
d. $R_1$ = F, $R_2$ = H, $R_3$ = F

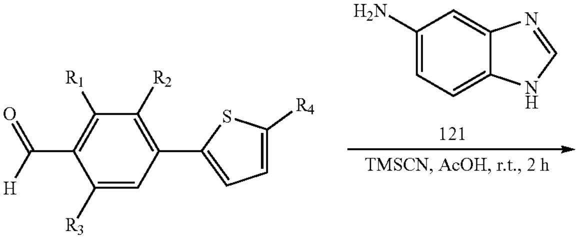

121

140a-e a. $R_1$ = H, $R_2$ = H, $R_3$ = H, $R_4$ = $CH_3$
b. $R_1$ = H, $R_2$ = H, $R_3$ = H, $R_4$ = Cl
c. $R_1$ = H, $R_2$ = F, $R_3$ = H, $R_4$ = Cl
d. $R_1$ = F, $R_2$ = H, $R_3$ = H, $R_4$ = Cl
e. $R_1$ = F, $R_2$ = H, $R_3$ = F, $R_4$ = Cl

-continued

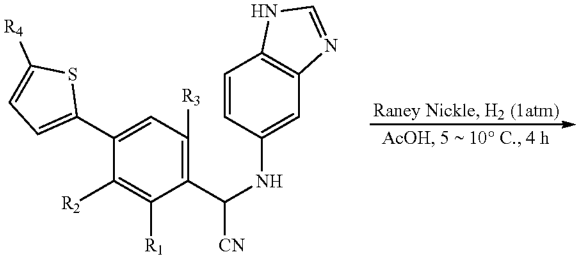

141a-e

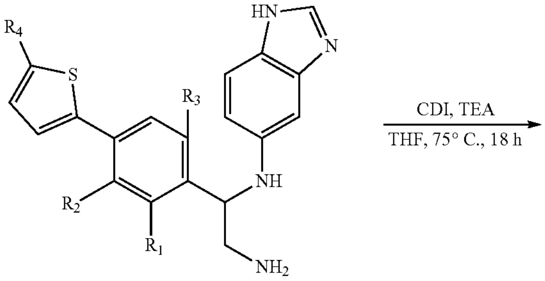

142a-e

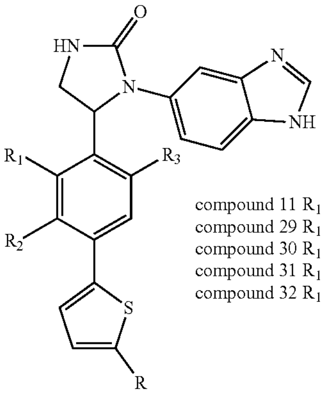

compound 11 $R_1$ = H, $R_2$ = H, $R_3$ = H, $R_4$ = $CH_3$
compound 29 $R_1$ = H, $R_2$ = H, $R_3$ = H, $R_4$ = Cl
compound 30 $R_1$ = H, $R_2$ = F, $R_3$ = H, $R_4$ = Cl
compound 31 $R_1$ = F, $R_2$ = H, $R_3$ = H, $R_4$ = Cl
compound 32 $R_1$ = F, $R_2$ = H, $R_3$ = F, $R_4$ = Cl Synthetic Method 5

Compound 12, having a thiophen-2-yl ring, was prepared by the synthetic procedures shown in Scheme 5. 4-Acetyl benzonitrile 143 was α-methylenated using $FeCl_3.6H_2O$ and $K_2S_2O_8$ in dimethylacetamide (DMA). The resultant α-methylene product 144 reacted with cyclopropanecarbaldehyde under a Stetter condition to form 1,4-dicarbonyl compound 146. This dicarbonyl compound was then treated with the Lawesson's reagent under refluxing in toluene to afford 4-(5-cyclopropylthiophen-2-yl)benzonitrile 147, which was reduced by DABAL-H to form benzaldehyde precursor 148. This precursor was then applied to the procedures shown in Synthetic Method 1 for forming imidazolidinone to obtain Compound 12.

Scheme 5

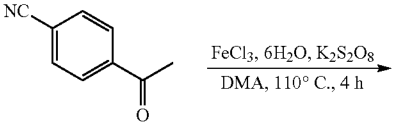

143

-continued

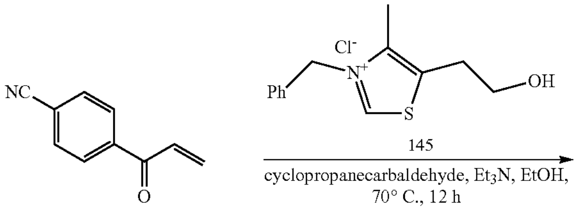

145

144

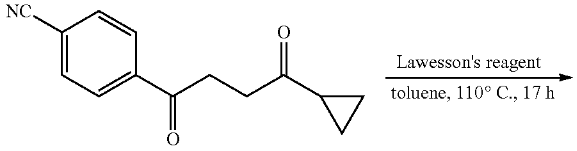

146

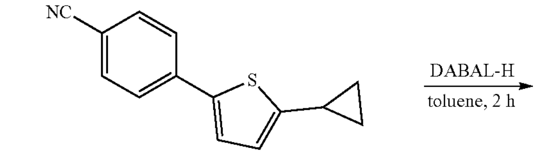

147

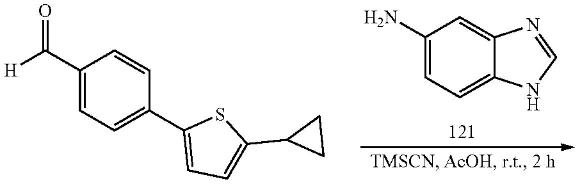

121

148

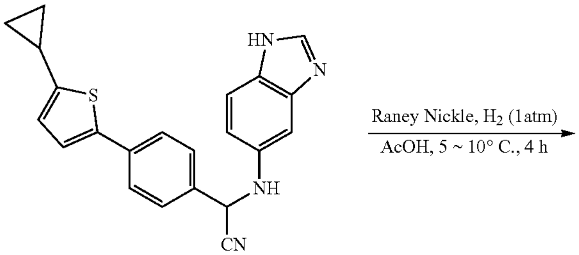

149

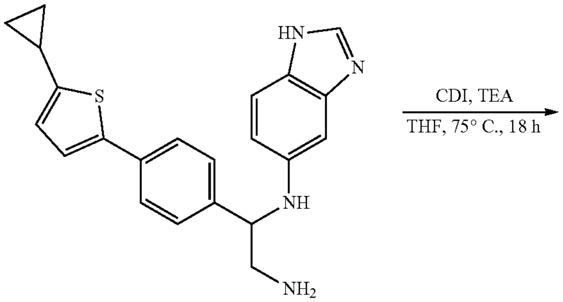

150

-continued

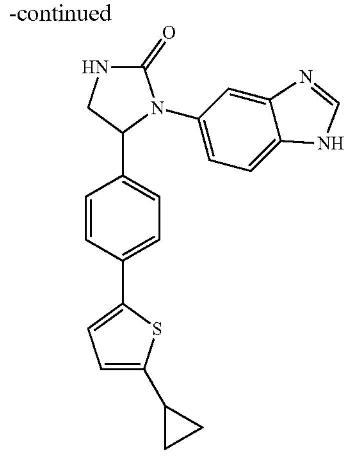

compound 12

Synthetic Method 6

Compounds 13 and 22-24, each having a thiophen-2-yl ring, were prepared by the synthetic procedures shown in Scheme 6. 4-Bromobenzaldehydes 138a-d were each coupled with thiophene under two different Suzuki-coupling conditions to form 4-(thiophen-2-yl)-benzaldehydes 152a-d. The benzaldehydes were iodinated by N-iodosuccinimide (NIS) to produce iodinated products 153a-d, which were trifluoromethylated using methyl difluoro-(fluoro-sulfonyl) acetate 154 and copper iodide to afford precursors 155a-d. These precursors were then applied to the procedures shown in Synthetic Method 1 for forming imidazolidinone to obtain Compounds 13 and 22-24.

Scheme 6

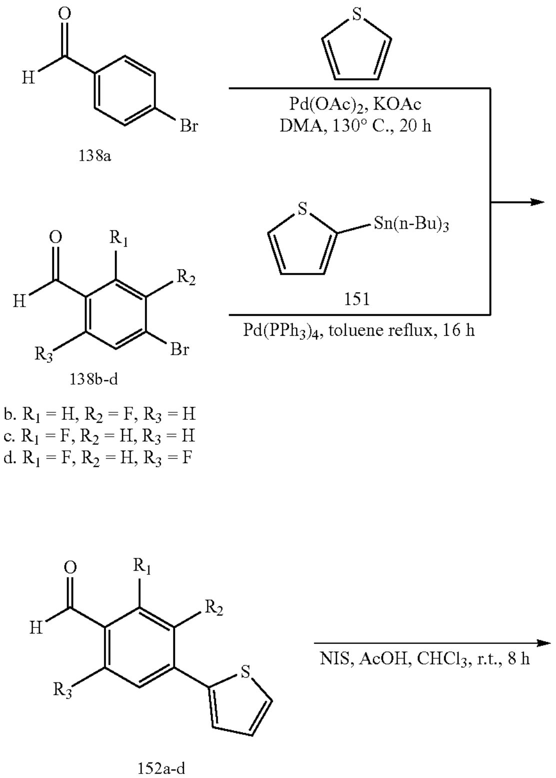

138a

151

138b-d b. $R_1$ = H, $R_2$ = F, $R_3$ = H
c. $R_1$ = F, $R_2$ = H, $R_3$ = H
d. $R_1$ = F, $R_2$ = H, $R_3$ = F 152a-d

-continued

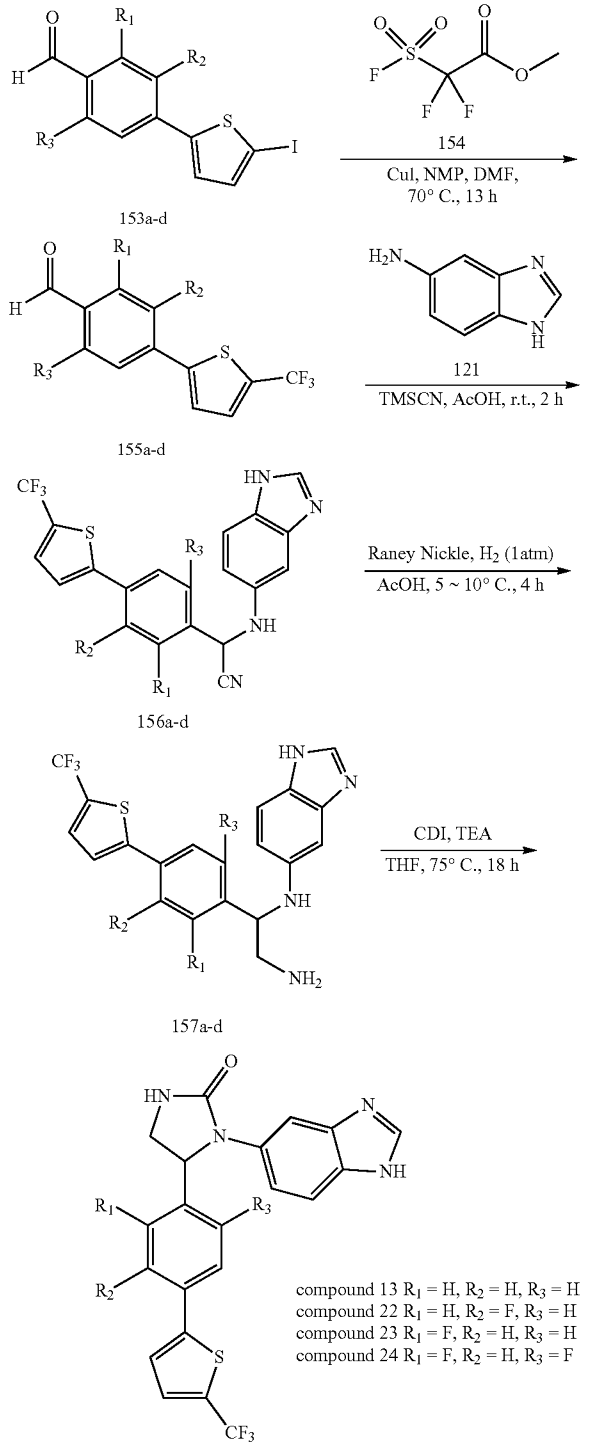

153a-d

154

155a-d

121

156a-d 157a-d compound 13 $R_1$ = H, $R_2$ = H, $R_3$ = H
compound 22 $R_1$ = H, $R_2$ = F, $R_3$ = H
compound 23 $R_1$ = F, $R_2$ = H, $R_3$ = H
compound 24 $R_1$ = F, $R_2$ = H, $R_3$ = F Synthetic Method 7

Compounds 14-16 and 25-28, each having a thiophen-3-yl ring, were prepared by the synthetic procedures shown in Scheme 7. Various (4-formylphenyl)boronic acids were coupled with 3-bromothiophene derivatives 158a-c under a Suzuki-Miyaura coupling condition. The resultant products 159a-g were then applied to the procedures shown in Synthetic Method 1 for forming imidazolidinone to obtain Compounds 14-16 and 25-28.

Scheme 7

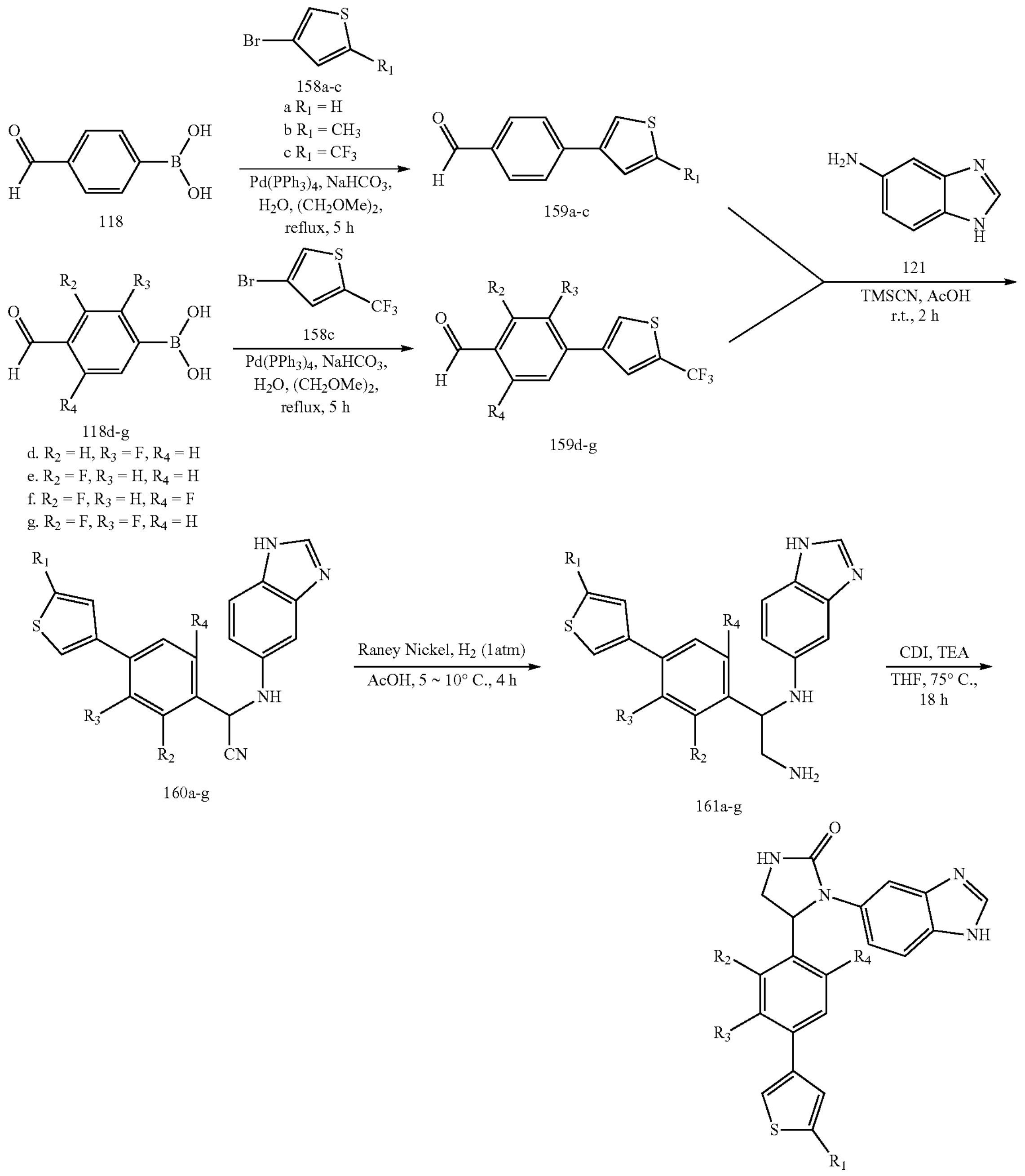

compound 14 $R_1$ = H, $R_2$ = H, $R_3$ = H, $R_4$ = H
compound 15 $R_1$ = $CH_3$, $R_2$ = H, $R_3$ = H, $R_4$ = H
compound 16 $R_1$ = $CF_3$, $R_2$ = H, $R_3$ = H, $R_4$ = H
compound 25 $R_1$ = $CF_3$, $R_2$ = H, $R_3$ = F, $R_4$ = H
compound 26 $R_1$ = $CF_3$, $R_2$ = F, $R_3$ = H, $R_4$ = H
compound 27 $R_1$ = $CF_3$, $R_2$ = F, $R_3$ = H, $R_4$ = F
compound 28 $R_1$ = $CF_3$, $R_2$ = F, $R_3$ = F, $R_4$ = H Synthetic Method 8

Compound 17, having a thiophen-3-yl ring, was prepared by the synthetic procedures shown in Scheme 8 below. Starting material 159a was selectively brominated by bromine or NBS in acetic acid to afford 2-brominated thiophene product 162, which was coupled with cyclopropyl-boronic acid under a Suzuki-coupling condition to form 4-(2-cyclopropyl-thiophen-3-yl)benzaldehyde 163. This benzaldehyde was then applied to the procedures shown in Synthetic Method 1 for forming imidazolidinone to obtain Compound 17.

Scheme 8

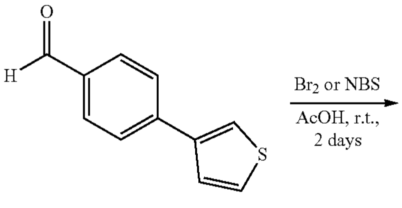

159a

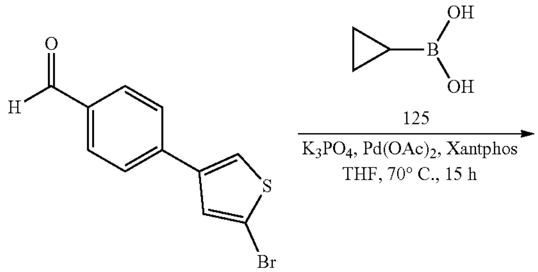

162

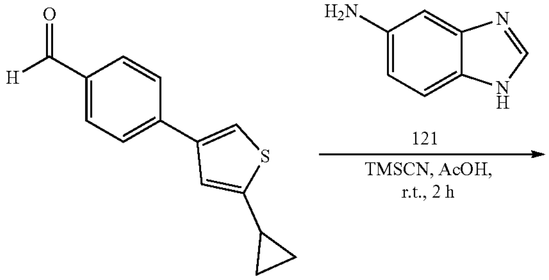

163

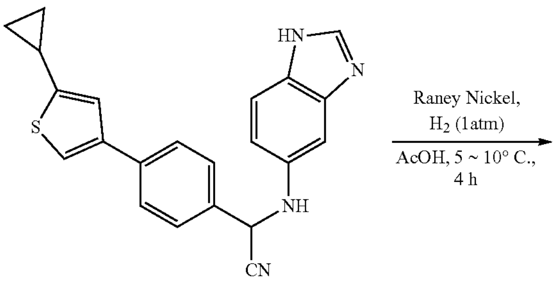

164

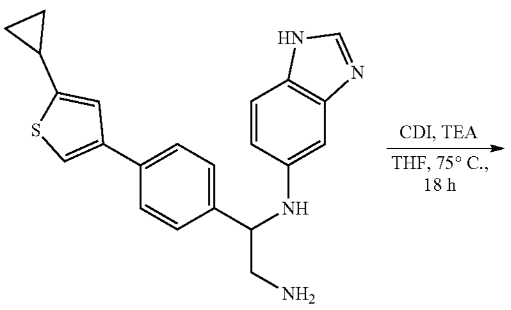

165

-continued

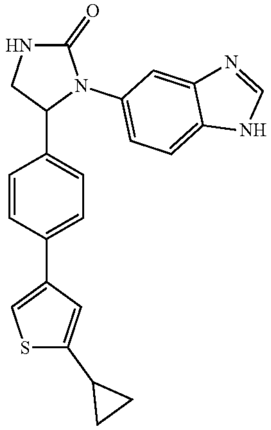

compound 17

Synthetic Method 9

Compound 18, having a 1,2,4-oxadiazol-3-yl ring, was prepared by the synthetic procedures shown in Scheme 9. 4-Formylbenzonitrile 166, a starting material, was protected by monoethyleneglycol (MEG) to form acetal 167, which reacted with hydroxylamine hydrochloride to afford amidoxime 168. The amidoxime was acetylated by cyclopropanecarbonyl chloride and then refluxed in toluene to form 1,2,4-oxadiazole 170, which was deprotected under acidic condition. The resultant product 171 reacted with TMSCN and 1H-benzimidazol-5-amine 121 in acetic acid at room temperature for 2 hours and was then worked up to yield amino acetonitrile 172. The amino acetonitrile was hydrogenated with a Pd/C catalyst in acetic acid at room temperature overnight to afford diamine 173. In the final step, 1,1'-carbonyldiimidazole was added to a solution of diamine 173 in THF and then stirred at 75° C. for 18 hours. Compound 18 was finally obtained after purification by column chromatography.

Scheme 9

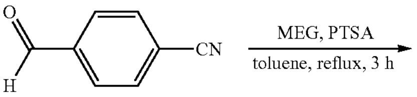

166

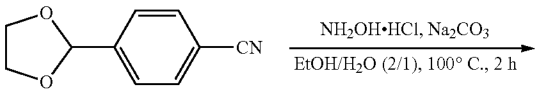

167

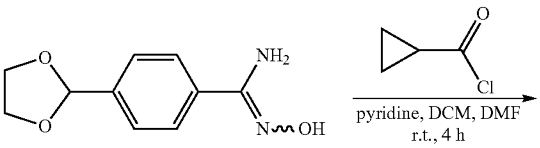

168

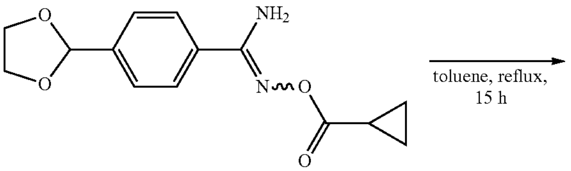

169

-continued

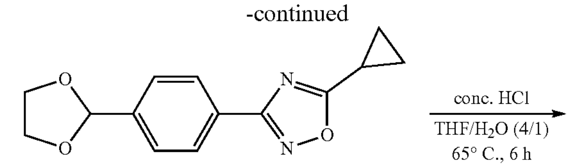

170

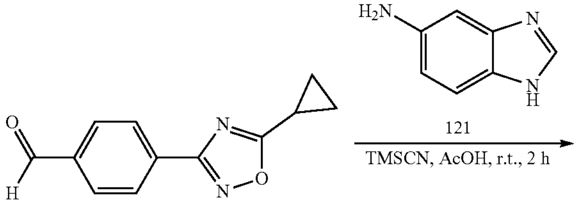

171

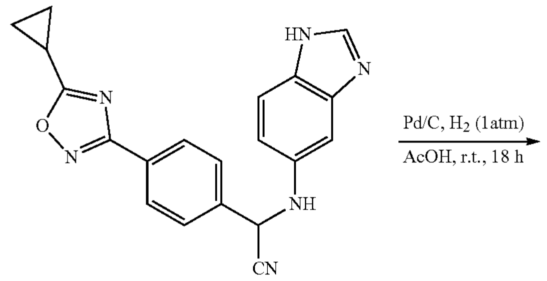

172

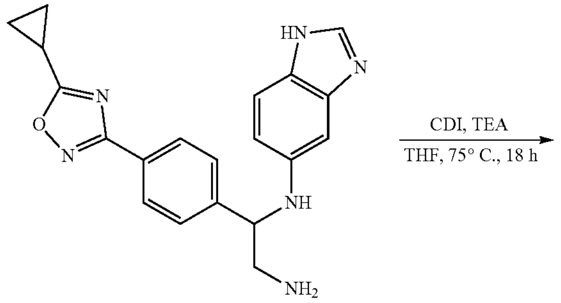

173

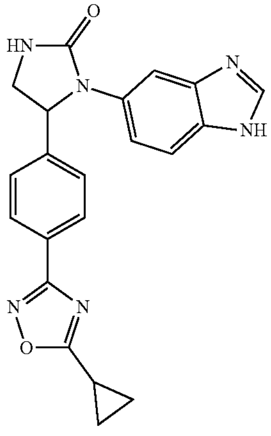

compound 18

Synthetic Method 10

Compound 19, having a 1,2-oxazol-3-yl ring, was prepared by the synthetic procedures shown in Scheme 10. Cyclopropanecarbaldehyde 174, the starting material, reacted with hydroxylamine hydrochloride to afford oxime 175, which was treated first with N-chlorosuccinimide (NCS) and then with 4-ethynylbenzaldehyde 176 in DMF at room temperature to form 1,2-oxazole precursor 177. This precursor was then applied to the procedures shown in Synthetic Method 9 for forming imidazolidinone to obtain Compound 19.

Scheme 10

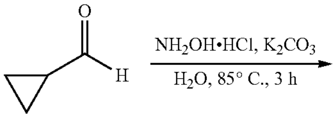

174

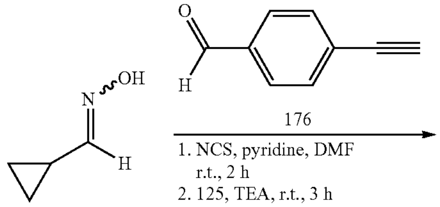

175

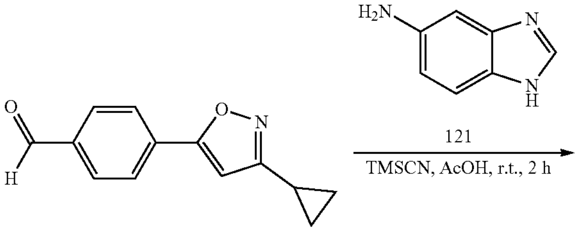

177

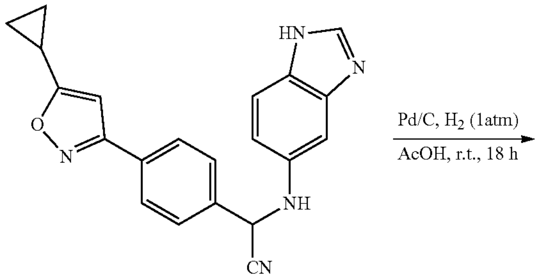

178

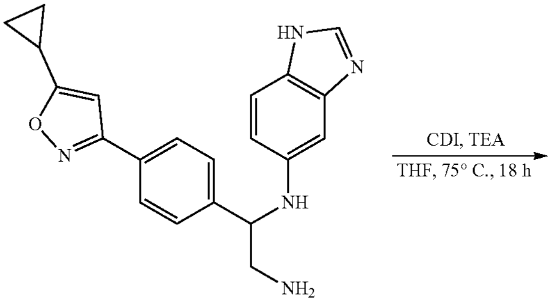

179

-continued

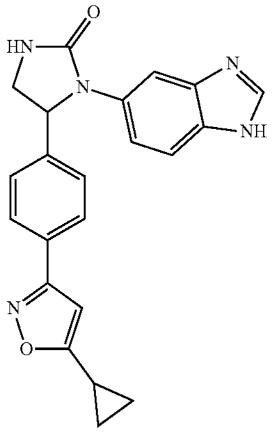

compound 19

Synthetic Method 11

Compounds 20 and 21, each having a 2H-tetrazol-5-yl ring, were prepared by the synthetic procedures shown in Scheme 11. 4-Formylbenzonitrile 166, the starting material, reacted with sodium azide and ammonium chloride in DMF under refluxing to form tetrazole compound 180, which was substituted by variable alkyl halides to afford precursors 181a-b. These precursors were then applied to the procedures shown in Synthetic Method 9 for forming imidazolidinone to obtain Compounds 20 and 21.

Scheme 11

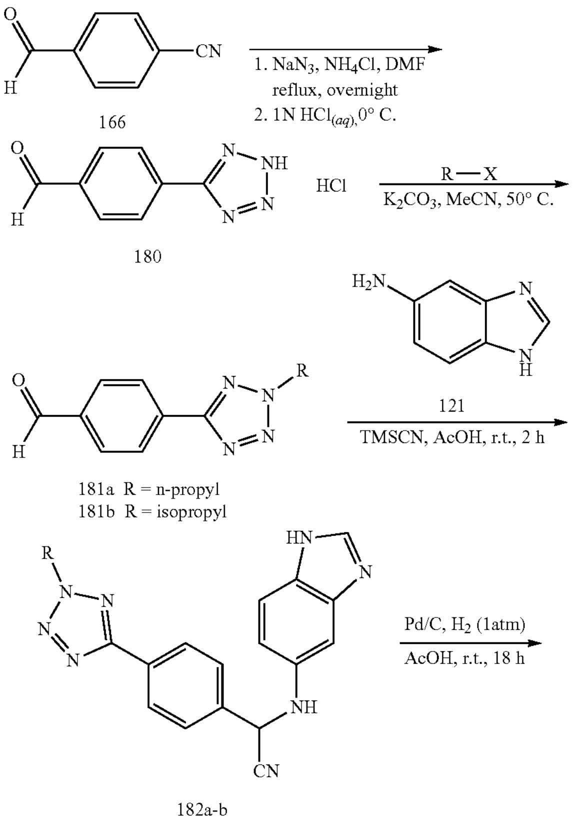

166

180

181a R = n-propyl
181b R = isopropyl 182a-b

-continued

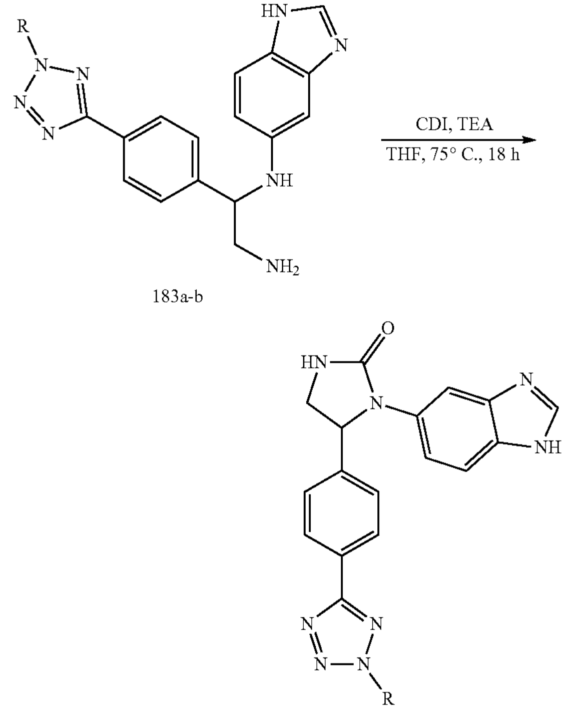

183a-b compound 20 R = n-propyl
compound 21 R = isopropyl

Synthetic Method 12

Compound 37, having a 1,3-thiazol-2-yl ring, was prepared by the synthetic procedures shown in Scheme 12. (4-Acetylphenyl)boronic acid 184 was coupled with 2-bromo-4-(trifluoromethyl)-1,3-thiazole 119d under a Suzuki-coupling condition. The resultant product 185 was oxidized by selenium dioxide to afford glyoxal 186. The glyoxal was mixed with benzimidazolylurea 187 in HCl/AcOH (1/40 v/v) and then refluxed overnight. After removing the solvents under reduced pressure, the residue was treated with excess ammonia solution in methanol for several hours. The crude product was purified by column chromatography to yield Compound 37.

Scheme 12

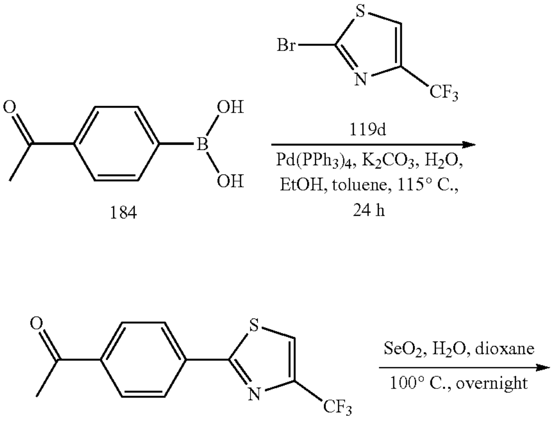

184

185

-continued

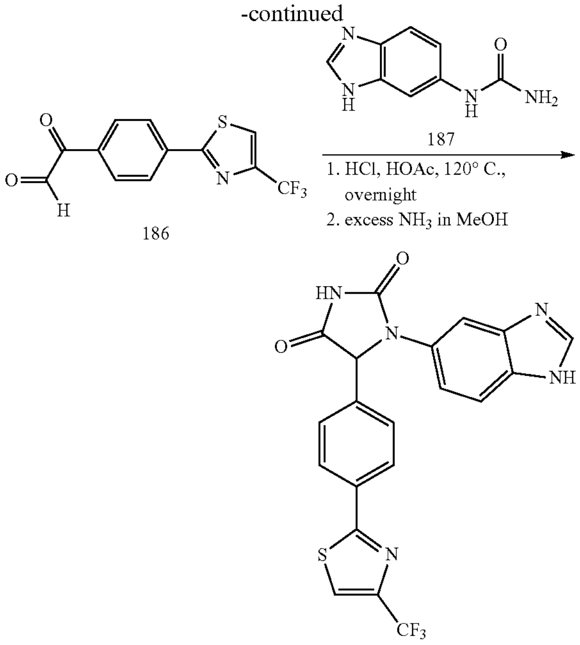

186

187 compound 37

Synthetic Method 13

Compound 38, having a 1,3-thiazol-4-yl ring, was prepared by the synthetic procedures shown in Scheme 13. 4-Bromo-2-cyclopropyl-1,3-thiazole 126, an intermediate prepared following Synthetic Method 2, was coupled with (4-acetylphenyl)boronic acid 184 under a Suzuki-coupling condition. The resultant coupling product 188 was oxidized by selenium dioxide to glyoxal 189. Compound 38 was formed from glyoxal 189 and benzimidazolylurea 187 via a cycloaddition reaction. The procedures were the same those shown in Synthetic Method 12.

Scheme 13

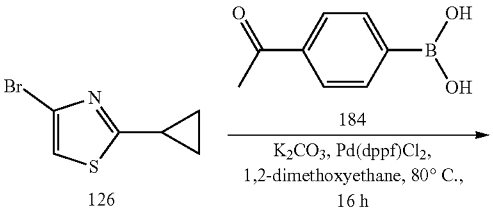

126

184

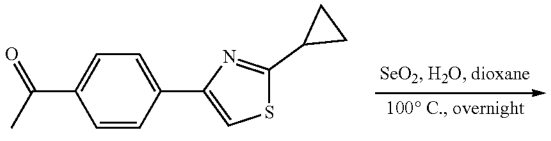

188

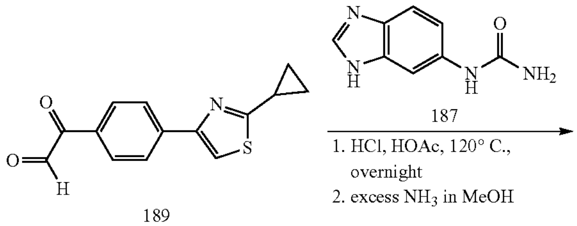

187

189

-continued

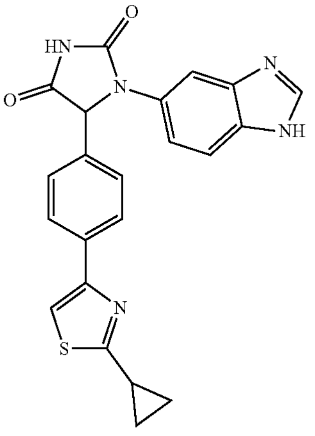

compound 38

Synthetic Method 14

Compounds 39 and 40, each having a 1,3-thiazol-5-yl ring, were prepared by the synthetic procedures shown in Scheme 14. 1,3-Thiazol-5-ylbenzonitriles 134b-c, intermediates prepared following Synthetic Method 3, were acetylated by methylmagnesium bromide. The resultant acetyl products 190b-c were oxidized by selenium dioxide to glyoxals 191b-c. Compounds 39 and 40 were formed from glyoxals 191b-c and benzimidazolylurea 187 via a cycloaddition reaction. The procedures were the same as those shown in Synthetic Method 12.

Scheme 14

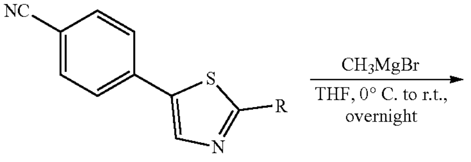

134b R = cyclopropyl
134c R = $CF_3$

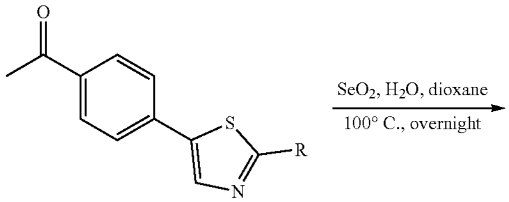

190b R = cyclopropyl
190c R = $CF_3$

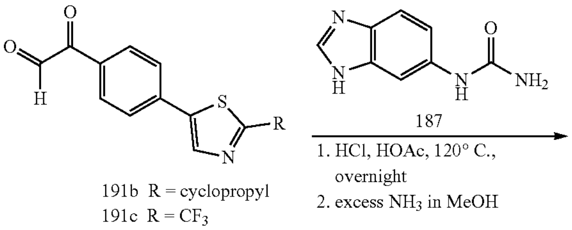

187

191b R = cyclopropyl
191c R = $CF_3$

-continued

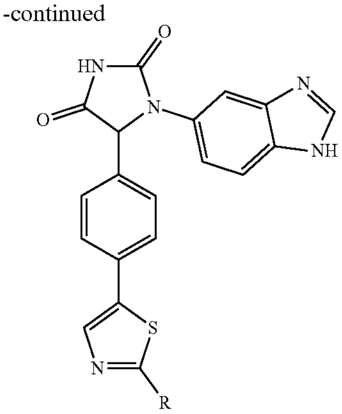

compound 39 R = cyclopropyl
compound 40 R = $CF_3$

Synthetic Method 15

Compounds 41-52, each having a 2H-tetrazol-5-yl ring, were prepared by the synthetic procedures shown in Scheme 15. Starting material 143 reacted with sodium azide and ammonium chloride under refluxing in DMF to form tetrazole 192, which was substituted with variable alkyl halides to give precursors 193a-l. These precursors were then applied to the procedures shown in Synthetic Method 12 for forming hydantoin to yield Compounds 41-52.

Scheme 15

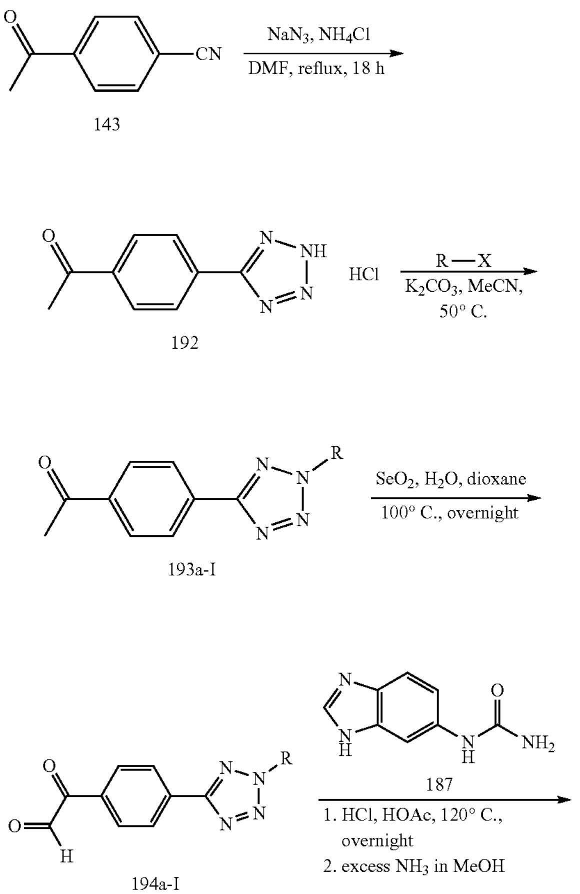

143

192

193a-I

194a-I

-continued

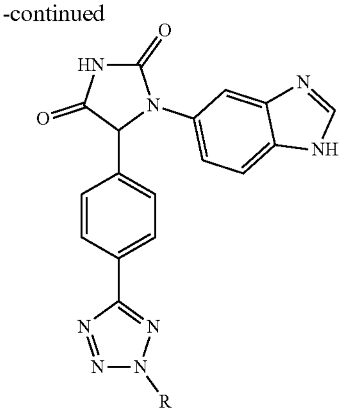

compounds 41-52 compound 41 R = $CH_3$
compound 42 R = n-propyl
compound 43 R = isopropyl
compound 44 R = isbutyl
compound 45 R =

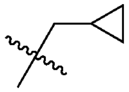

compound 46 R =

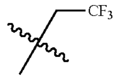

compound 47 R =

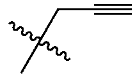

compound 48 R =

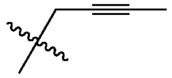

compound 49 R =

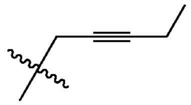

compound 50 R =

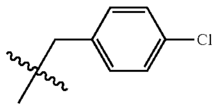

compound 51 R =

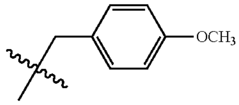

compound 52 R =

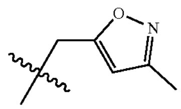

Synthetic Method 16

Compound 57 having a 1,3-thiazol-5-yl ring was prepared by the synthetic procedures shown in the Scheme 16. Starting material 131 was acetylated with adamantane-1-carbonyl chloride 195 to obtain amide 196. Subsequently, the amide 196 was mixed with the Lawesson's reagent under reflux in THF to afford (1,3-thiazol-5-yl)-benzonitrile 197, which was reduced by DIBAL-H to form benzaldehyde 198. The benzaldehyde 198 was then applied to the procedures shown in Synthetic Method 1 for forming imidazolidinone to obtain Compound 57.

Scheme 16

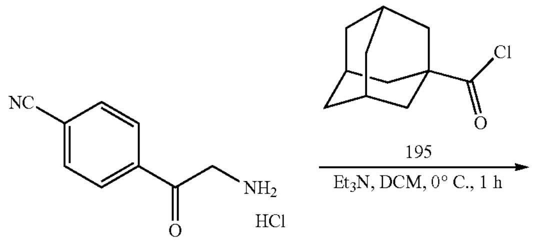

195

131

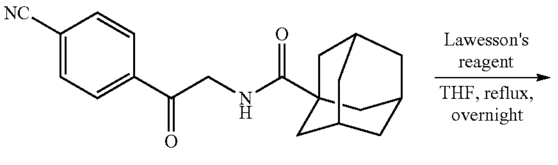

196

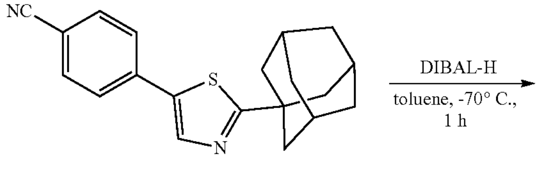

197

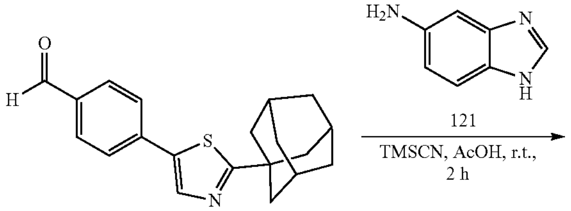

121

198

-continued

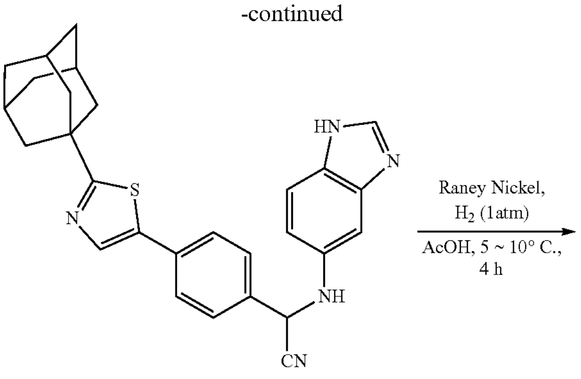

199

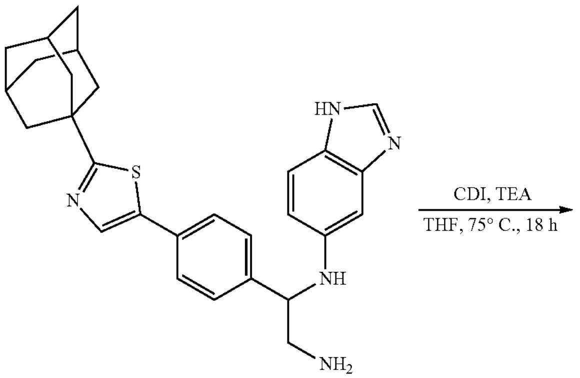

200

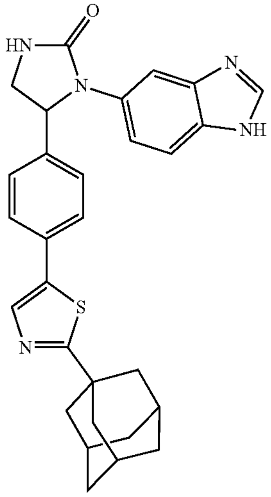

compound 57

Synthetic Method 17

Compounds 58-65 each having a thiophen-3-yl ring were prepared by the synthetic procedures shown in Scheme 17. 2,3-Difluoro-4-formylphenylboronic acid 118g was coupled with 3-bromothiophene derivatives 158a-b and 158d-i under a Suzuki-Miyaura coupling condition. The resulting products 201a-h were then applied to the procedures shown in Synthetic Method 1 for forming imidazolidinone to obtain Compound 58-65.

Scheme 17

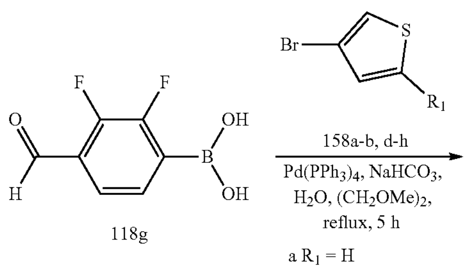

118g a $R_1 = H$
b $R_1 = CH_3$
d $R_1 = F$
e $R_1 = Cl$
f $R_1 = CH_2CH_3$
g $R_1 = CH_2OCH_3$
h $R_1 = CH_2OCH_2CH_3$
i $R_1 = CO_2CH_3$

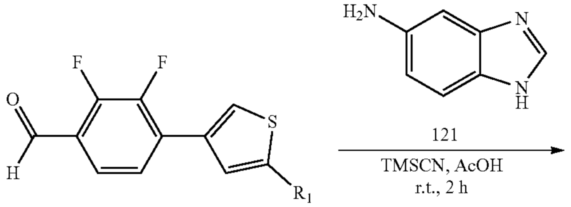

201a-h a $R_1 = F$
b $R_1 = Cl$
c $R_1 = CH_3$
d $R_1 = CH_2CH_3$
e $R_1 = CH_2OCH_3$
f $R_1 = CH_2OCH_2CH_3$
g $R_1 = CO_2CH_3$
h $R_1 = H$

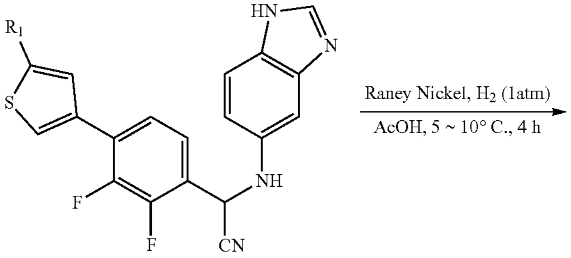

202a-h

-continued

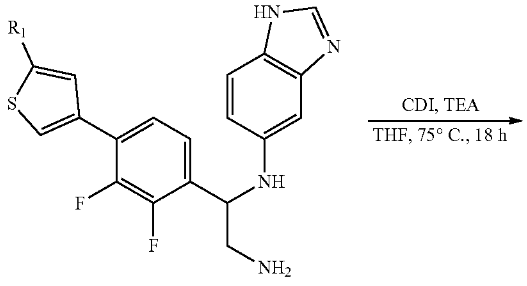

203a-h

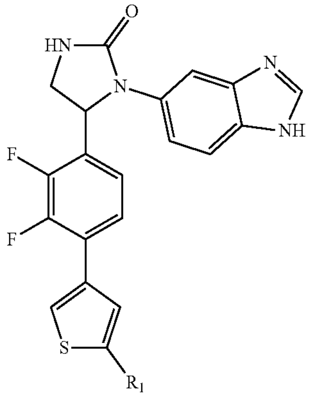

compound 58 $R_1 = F$
compound 59 $R_1 = Cl$
compound 60 $R_1 = CH_3$
compound 61 $R_1 = CH_2CH_3$
compound 62 $R_1 = CH_2OCH_3$
compound 63 $R_1 = CH_2OCH_2CH_3$
compound 64 $R_1 = CO_2CH_3$
compound 65 $R_1 = H$ Synthetic Method 18

Compound 66 was prepared through hydrolysis reaction of compound 64 in a solution of potassium hydroxide in methanol shown in Scheme 18. Compound 67 was prepared through reduction of compound 64 by LAH in dry THF also shown in this scheme.

Scheme 18

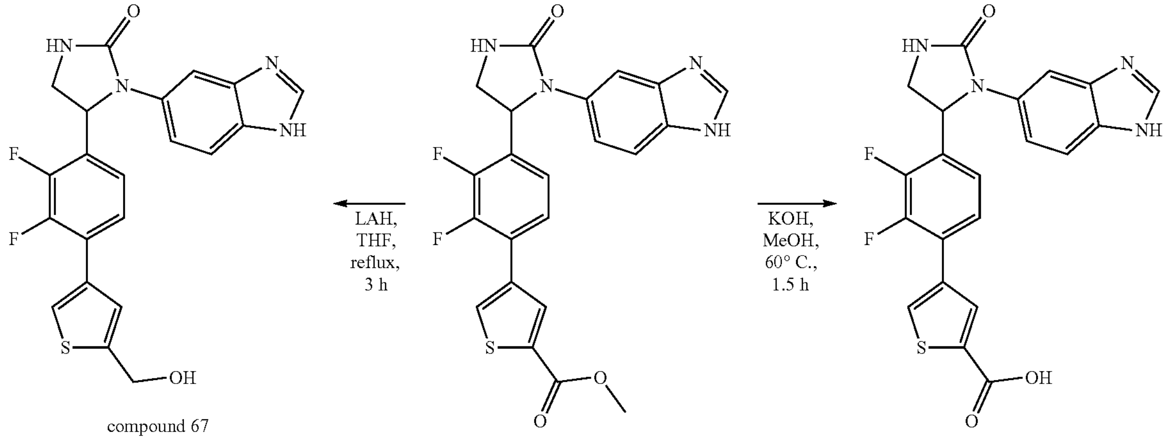

compound 67 compound 64 compound 66

Below are the detailed procedures of preparing Compounds 1-67 following Synthetic Methods 1-18 set forth above and the analytical data of the intermediates and the final products generated in these procedures.

4-(1,3-thiazol-2-yl)benzaldehyde (Compound 120a)

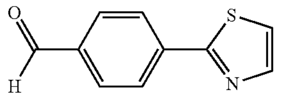 [SMILES: O=Cc1ccc(-c2nccs2)cc1]

The (4-formylphenyl)boronic acid 118 (0.30 g, 2.0 mmol), 2-bromo-1,3-thiazole 119a (0.33 g, 2.0 mmol), $Pd(PPh_3)_4$ (0.12 g, 0.1 mmol), aqueous solution of potassium carbonate (0.4 M, 5 mL), ethanol (5 mL) and toluene (2 mL) were added to a 50 mL flask under nitrogen. The reaction mixture was stirred at 115° C. for 24 hours and then cooled to room temperature. After removing the solvent, the crude residue was purified by column chromatography on silica gel using EA/hexane (1/5) as eluent. The product 120a was obtained as a white solid at a yield of 95%.

4-(4-methyl-1,3-thiazol-2-yl)benzaldehyde (Compound 120b)

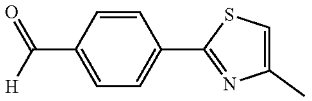

The 4-(4-methyl-1,3-thiazol-2-yl)benzaldehyde 120b was prepared from the Suzuki-coupling of (4-formylphenyl) boronic acid 118 and 2-bromo-4-methyl-1,3-thiazole 119b. The procedures were the same as the synthesis of Compound 120a. The product 120b was obtained as a white solid at a yield of 90%.

4-(4-cyclopropyl-1,3-thiazol-2-yl)benzaldehyde (Compound 120c)

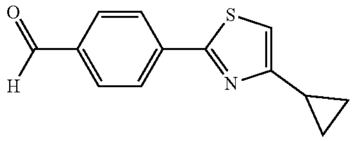 [SMILES: O=Cc1ccc(-c2nc(C3CC3)cs2)cc1]

The 4-(4-cyclopropyl-1,3-thiazol-2-yl)benzaldehyde 120c was prepared from the Suzuki-coupling of (4-formylphenyl)boronic acid 118 and 2-bromo-4-cyclopropyl-1,3-thiazole 119c.

The procedures were the same as the synthesis of Compound 120a. The product 120c was obtained as a white solid at a yield of 92%.

4-[4-(trifluoromethyl)-1,3-thiazol-2-yl]benzaldehyde (Compound 120d)

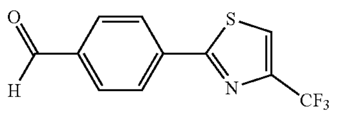 [SMILES: O=Cc1ccc(-c2nc(C(F)(F)F)cs2)cc1]

The 4-[4-(trifluoromethyl)-1,3-thiazol-2-yl]benzaldehyde 120d was prepared from the Suzuki-coupling of (4-formylphenyl)boronic acid 118 and 2-bromo-4-(trifluoromethyl)-1,3-thiazole 119d. The procedures were the same as the synthesis of Compound 120a. The product 120d was obtained as a white solid at a yield of 90%.

(1H-benzimidazol-5-ylamino)[4-(1,3-thiazol-2-yl) phenyl]acetonitrile (Compound 122a)

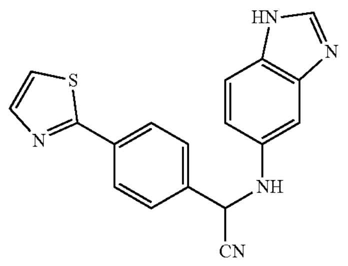 [SMILES: N#CC(Nc1ccc2[nH]cnc2c1)c1ccc(-c2nccs2)cc1]

To the solution of 1H-benzimidazol-5-amine 121 (0.68 g, 5.11 mmol) in acetic acid (20 mL), the Compound 120a (1.06 g, 5.62 mmol) was added and stirred at room temperature for 20 minutes. TMSCN (1 mL) was added dropwise to the reaction mixture and continuously stirred for 2 hours. After reaction completing, the reaction mixture was concentrated under reduced pressure to yield a viscous liquid. The viscous liquid was diluted with ethyl acetate (10 mL) and water. The diluted solution was adjusted to the pH 6-7 with ammonia at an ice-bath. The neutralized solution was extracted with ethyl acetate (20 mL×4), dried over sodium sulfate, filtered and concentrated under reduced pressure to yield a viscous dark-yellow solid. The solid was dissolved in ethyl acetate (15 mL) and brine (15 mL). The mixture was stirred at room temperature for 2 minutes to form the pale-yellow precipitates. The pale-yellow precipitates was filtered and washed with water. The filtrate was dried over sodium sulfate and concentrated under reduced pressure to obtain the pale-yellow solid. Those pale-yellow solids were combined as the desired product 122a at a yield of 96%.

(1H-benzimidazol-5-ylamino)[4-(4-methyl-1,3-thiazol-2-yl)phenyl]acetonitrile (Compound 122b)

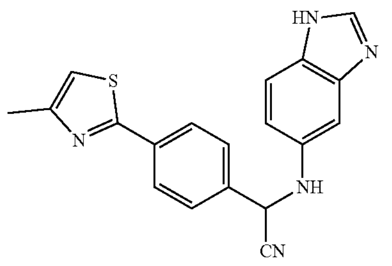 [SMILES: Cc1csc(-c2ccc(C(C#N)Nc3ccc4[nH]cnc4c3)cc2)n1]

The (1H-benzimidazol-5-ylamino)[4-(4-methyl-1,3-thiazol-2-yl)phenyl]acetonitrile 122b was prepared from the addition of 1H-benzimidazol-5-amine 121, TMSCN and Compound 120b. The procedures were the same as the synthesis of Compound 122a. The product 122b was obtained as a pale-yellow solid at a yield of 97%.

(1H-benzimidazol-5-ylamino)[4-(4-cyclopropyl-1,3-thiazol-2-yl)phenyl]acetonitrile (Compound 122c)

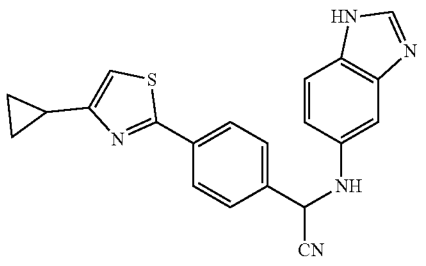 [SMILES: N#CC(Nc1ccc2[nH]cnc2c1)c1ccc(-c2nc(C3CC3)cs2)cc1]

The (1H-benzimidazol-5-ylamino)[4-(4-cyclopropyl-1,3-thiazol-2-yl)phenyl]acetonitrile 122c was prepared from the addition of 1H-benzimidazol-5-amine 121, TMSCN and Compound 120c. The procedures were the same as the synthesis of Compound 122a. The product 122c was obtained as a pale-yellow solid at a yield of 95%.

(1H-benzimidazol-5-ylamino){4-[4-(trifluoromethyl)-1,3-thiazol-2-yl]phenyl}acetonitrile (Compound 122d)

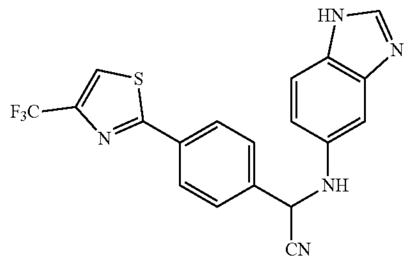 [SMILES: N#CC(Nc1ccc2[nH]cnc2c1)c1ccc(-c2nc(C(F)(F)F)cs2)cc1]

The (1H-benzimidazol-5-ylamino) {4-[4-(trifluoromethyl)-1,3-thiazol-2-yl]phenyl}-acetonitrile 122d was prepared from the addition of 1H-benzimidazol-5-amine 121, TMSCN and Compound 120d. The procedures were the same as the synthesis of Compound 122a. The product 122d was obtained as a pale-yellow solid at a yield of 96%.

$N^1$-(1H-benzimidazol-5-yl)-1-[4-(1,3-thiazol-2-yl) phenyl]ethane-1,2-diamine (Compound 123a)

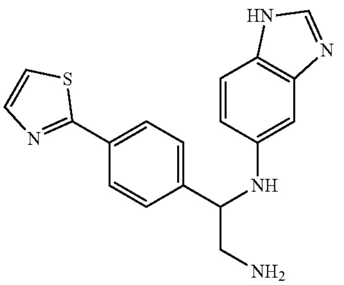 [SMILES: NCC(Nc1ccc2[nH]cnc2c1)c1ccc(-c2nccs2)cc1]

The Compound 122a (5.0 g, 15.08 mmol) was dissolved in acetic acid (200 mL) and then stirred at 10° C. for 5 minutes. The Raney Nickel reagent was added to the stirring solution and refilled hydrogen three times. The reaction mixture was stirred under hydrogen at 10° C. for 8 hours. The catalyst was removed by filtration through celite. The filtrate was concentrated under reduced pressure to obtain the crude product. The crude product was purified by column chromatography on silica gel using methanol/dichloromethane (1/19) as eluent. The product 123a was obtained as a yellow viscous liquid at a yield of 60%.

N[1]-(1H-benzimidazol-5-yl)-1-[4-(4-methyl-1,3-thiazol-2-yl)phenyl]ethane-1,2-diamine (Compound 123b)

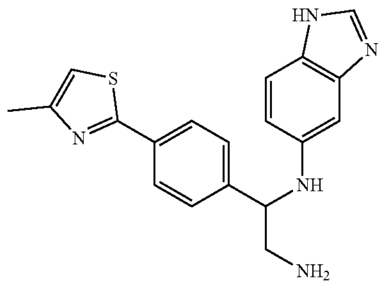 [SMILES: Cc1csc(-c2ccc(C(CN)Nc3ccc4[nH]cnc4c3)cc2)n1]

The N[1]-(1H-benzimidazol-5-yl)-1-[4-(4-methyl-1,3-thiazol-2-yl)phenyl]ethane-1,2-diamine 123b was prepared from the hydrogenation of Compound 122b with the Raney Nickel reagent as catalyst. The procedures were the same as the synthesis of Compound 123a. The product 123b was obtained as a yellow viscous liquid at a yield of 50%.

N[1]-(1H-benzimidazol-5-yl)-1-[4-(4-cyclopropyl-1,3-thiazol-2-yl)phenyl]ethane-1,2-diamine (Compound 123c)

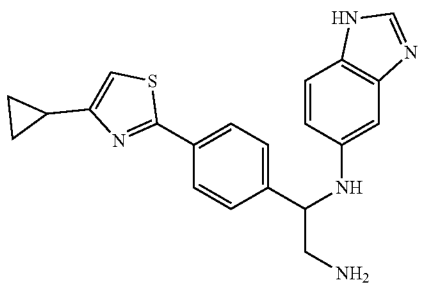 [SMILES: NCC(Nc1ccc2[nH]cnc2c1)c1ccc(-c2nc(C3CC3)cs2)cc1]

The N[1]-(1H-benzimidazol-5-yl)-1-[4-(4-cyclopropyl-1,3-thiazol-2-yl)phenyl]ethane-1,2-diamine 123c was prepared from the hydrogenation of Compound 122c with the Raney Nickel reagent as catalyst. The procedures were the same as the synthesis of Compound 123a. The product 123c was obtained as a yellow viscous liquid at a yield of 54%.

N[1]-(1H-benzimidazol-5-yl)-1-{4-[4-(trifluoromethyl)-1,3-thiazol-2-yl]phenyl}ethane-1,2-diamine (Compound 123d)

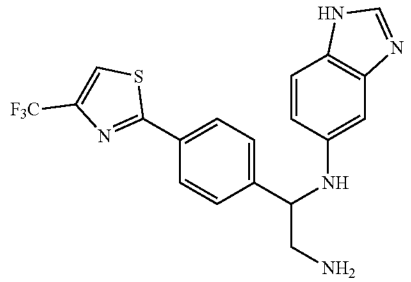 [SMILES: NCC(Nc1ccc2[nH]cnc2c1)c1ccc(-c2nc(C(F)(F)F)cs2)cc1]

The N[1]-(1H-benzimidazol-5-yl)-1-{4-[4-(trifluoromethyl)-1,3-thiazol-2-yl]phenyl}-ethane-1,2-diamine 123d was prepared from the hydrogenation of Compound 122d with the Raney Nickel reagent as catalyst. The procedures were the same as the synthesis of Compound 123a. The product 123d was obtained as a yellow viscous liquid at a yield of 40%.

1-(1H-benzimidazol-5-yl)-5-[4-(1,3-thiazol-2-yl)phenyl]imidazolidin-2-one (Compound 1)

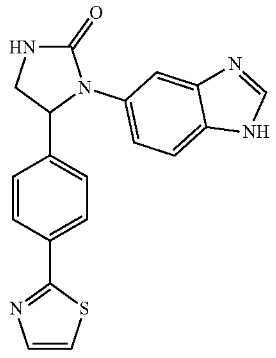 [SMILES: O=C1NCC(c2ccc(-c3nccs3)cc2)N1c1ccc2[nH]cnc2c1]

To the solution of 1,1'-carbonyl diimidazole (2.21 g, 20.5 mmol) and trimethylamine (7.5 mL) in anhydrous THF (100 mL), the solution of Compound 123a (4.56 g, 13.6 mmol) in anhydrous THF (100 mL) was added dropwise by additional funnel at room temperature. The resulting mixture was heated to 75° C. and stirred for 18 hours. After cooling to room temperature, the reaction mixture was concentrated under reduced pressure. The crude residue was purified by column chromatography on silica gel using methanol/dichloromethane (1/19) as eluent. The product (Compound 1) was obtained as a white solid at a yield of 70%. $^1H$ NMR (400 MHz, $CD_3OD$) δ 3.39 (dd, 1H, J=7.0, 9.2 Hz), 4.02 (dd, 1H, J=9.2, 9.2 Hz), 5.55 (dd, 1H, J=7.0, 9.2 Hz), 7.31 (d, 1H, J=8.8 Hz), 7.48 (d, 1H, J=8.8 Hz), 7.52 (d, 2H, J=8.2 Hz), 7.56 (s, 1H), 7.57 (s, 1H), 7.82 (d, 1H, J=3.6 Hz), 7.88 (d, 2H, J=8.2 Hz), 8.06 (s, 1H); LC/MS (ESI) m/z: 362.1 $[M+H]^+$.

1-(1H-benzimidazol-5-yl)-5-[4-(4-methyl-1,3-thiazol-2-yl)phenyl]imidazolidin-2-one (Compound 2)

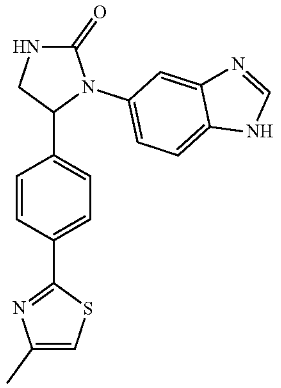 [SMILES: Cc1csc(-c2ccc(C3CNC(=O)N3c3ccc4[nH]cnc4c3)cc2)n1]

The 1-(1H-benzimidazol-5-yl)-5-[4-(4-methyl-1,3-thiazol-2-yl)phenyl]imidazolidin-2-one (Compound 2) was prepared from the cycloaddition of 1,1'-carbonyl diimidazole and Compound 123b. The procedures were the same as the synthesis of Compound 1. The product (Compound 2) was obtained as a white solid at a yield of 66%. $^1$H NMR (400 MHz, DMSO-$d_6$) δ 2.37 (s, 3H), 3.13 (dd, 1H, J=6.6, 8.8 Hz), 3.87 (dd, 1H, J=8.8, 9.2 Hz), 5.58 (dd, 1H, J=6.6, 9.2 Hz), 7.01 (s, 1H), 7.27 (s, 2H), 7.40 (s, 1H), 7.46 (d, 2H, J=8.2 Hz), 7.57 (s, 1H), 7.83 (d, 2H, J=8.2 Hz), 8.07 (s, 1H); LC/MS (ESI) m/z: 376.2 $[M+H]^+$.

1-(1H-benzimidazol-5-yl)-5-[4-(4-cyclopropyl-1,3-thiazol-2-yl)phenyl]imidazolidin-2-one (Compound 3)

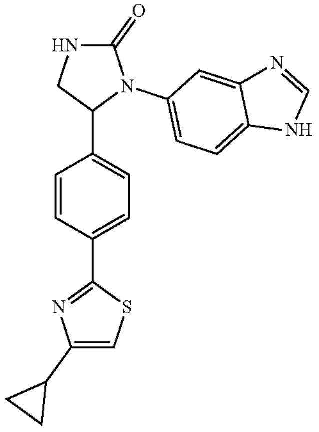 [SMILES: O=C1NCC(c2ccc(-c3nc(C4CC4)cs3)cc2)N1c1ccc2[nH]cnc2c1]

The 1-(1H-benzimidazol-5-yl)-5-[4-(4-cyclopropyl-1,3-thiazol-2-yl)phenyl]imidazolidin-2-one (Compound 3) was prepared from the cycloaddition of 1,1'-carbonyl diimidazole and Compound 123c. The procedures were the same as the synthesis of Compound 1. The product (Compound 3) was obtained as a white solid at a yield of 71%. $^1$H NMR (400 MHz, DMSO-$d_6$) δ 0.80-0.84 (m, 2H), 0.85-0.90 (m, 2H), 2.05-2.09 (m, 1H), 3.12 (dd, 1H, J=6.4, 8.8 Hz), 3.87 (dd, 1H, J=8.8, 9.2 Hz), 5.57 (dd, 1H, J=6.4, 9.2 Hz), 7.02 (s, 1H), 7.26 (s, 2H), 7.39 (d, 1H, J=8.4 Hz), 7.45 (d, 2H, J=7.8 Hz), 7.55 (s, 1H), 7.79 (d, 2H, J=7.8 Hz), 8.07 (s, 1H), 12.27 (s, 1H); LC/MS (ESI) m/z: 402.2 $[M+H]^+$.

1-(1H-benzimidazol-5-yl)-5-{4-[4-(trifluoromethyl)-1,3-thiazol-2-yl]phenyl}imidazolidin-2-one (Compound 4)

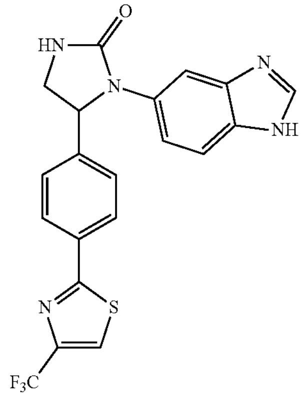 [SMILES: O=C1NCC(c2ccc(-c3nc(C(F)(F)F)cs3)cc2)N1c1ccc2[nH]cnc2c1]

The 1-(1H-benzimidazol-5-yl)-5-{4-[4-(trifluoromethyl)-1,3-thiazol-2-yl]phenyl}-imidazolidin-2-one (Compound 4) was prepared from the cycloaddition of carbonyl diimidazole and Compound 123d. The procedures were the same as the synthesis of Compound 1. The product (Compound 4) was obtained as a white solid at a yield of 67%. $^1$H NMR (300 MHz, DMSO-$d_6$) δ 3.14 (dd, 1H, J=6.3, 8.7 Hz), 3.89 (dd, 1H, J=8.7, 9.0 Hz), 5.62 (dd, 1H, J=6.3, 9.0 Hz), 7.02 (d, 1H, J=8.7 Hz), 7.28 (s, 1H), 7.40 (d, 1H, J=8.7 Hz), 7.52 (d, 2H, J=8.1 Hz), 7.57 (s, 1H), 7.92 (d, 2H, J=8.1 Hz), 8.08 (s, 1H), 8.50 (s, 1H), 12.21 (s, 1H); LC/MS (ESI) m/z: 430.2 $[M+H]^+$.

4-bromo-2-cyclopropyl-1,3-thiazole (Compound 126)

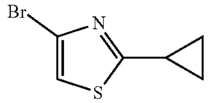

The palladium acetate (0.025 g, 0.11 mmol) and Xantphos (0.066 g, 0.11 mmol) were added in THF (22 mL) that degassed under argon. Then, the reaction mixture was stirred at room temperature for 5 minutes. The 2,4-dibromo-1,3-thiazole 124 (1.09 g, 4.50 mmol), cyclopropylboronic acid 125 (0.58 g, 6.70 mmol) and potassium phosphate (2.86 g) were added to the reaction mixture and flushed with argon. The reaction mixture was stirred at 70° C. for 15 hours. After cooling to room temperature, the reaction mixture was filtered and washed with dichloromethane. The filtrate was concentrated under reduced pressure and purified by column chromatography on silica gel using hexane as eluent. The product 126 was obtained as a colorless oil at a yield of 81%.

4-(2-cyclopropyl-1,3-thiazol-4-yl)benzaldehyde (Compound 127)

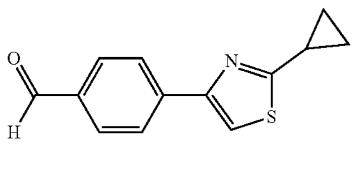 [SMILES: O=Cc1ccc(-c2csc(C3CC3)n2)cc1]

The (4-formylphenyl)boronic acid 118 (0.33 g, 2.2 mmol), 4-bromo-2-cyclopropyl-1,3-thiazole 126 (0.41 g, 2.0 mmol), Pd(dppf)$Cl_2$ (0.08 g, 0.1 mmol), potassium carbonate (0.41 g) and 1,2-dimethoxyethane (20 mL) were added to a 50 mL round-bottom flask under nitrogen. The reaction mixture was stirred at 80° C. for 16 hours and then cooled to room temperature. The reaction mixture was partitioned between ethyl acetate and water. The organic layers were collected, dried over sodium sulfate, filtered and concentrated under reduced pressure. The residue was purified by column chromatography on silica gel using hexane/ether (10/1) as eluent. The product 127 was obtained as a white solid at a yield of 55%. $^1$H NMR (300 MHz, $CDCl_3$) δ 1.10-1.16 (m, 4H), 2.32-2.39 (m, 1H), 7.40 (s, 1H), 7.89 (d, 2H, J=8.4 Hz), 8.03 (d, 2H, J=8.4 Hz), 10.01 (s, 1H); LC/MS (ESI) m/z: 230.1 $[M+H]^+$.

(1H-benzimidazol-5-ylamino)[4-(2-cyclopropyl-1,3-thiazol-4-yl)phenyl]acetonitrile (Compound 128)

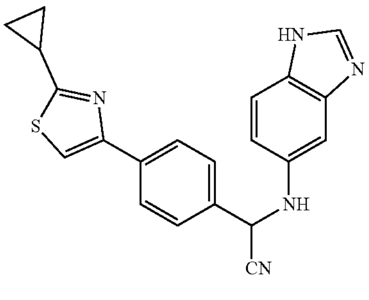 [SMILES: N#CC(Nc1ccc2[nH]cnc2c1)c1ccc(-c2csc(C3CC3)n2)cc1]

The (1H-benzimidazol-5-ylamino)[4-(2-cyclopropyl-1,3-thiazol-4-yl)phenyl]acetonitrile 128 was prepared from the addition of 1H-benzimidazol-5-amine 121, TMSCN and Compound 127. The procedures were the same as the synthesis of Compound 122a. The product 128 was obtained as a pale-yellow solid at a yield of 93%.

N$^1$-(1H-benzimidazol-5-yl)-1-[4-(2-cyclopropyl-1,3-thiazol-4-yl)phenyl]ethane-1,2-diamine (Compound 129)

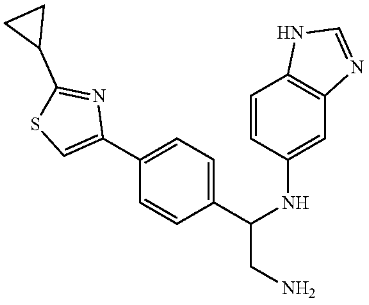 [SMILES: NCC(Nc1ccc2[nH]cnc2c1)c1ccc(-c2csc(C3CC3)n2)cc1]

The N$^1$-(1H-benzimidazol-5-yl)-1-[4-(2-cyclopropyl-1,3-thiazol-4-yl)phenyl]ethane-1,2-diamine 129 was prepared from the hydrogenation of Compound 128 with the Raney Nickel reagent as catalyst. The procedures were the same as the synthesis of Compound 123a. The product 129 was obtained as a yellow viscous liquid at a yield of 52%.

1-(1H-benzimidazol-5-yl)-5-[4-(2-cyclopropyl-1,3-thiazol-4-yl)phenyl]imidazolidin-2-one (Compound 5)

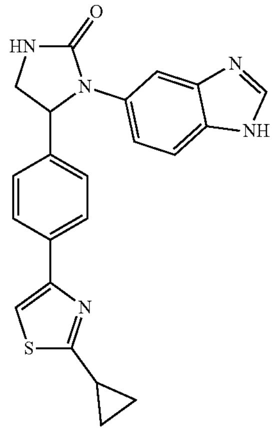 [SMILES: O=C1NCC(c2ccc(-c3csc(C4CC4)n3)cc2)N1c1ccc2[nH]cnc2c1]

The 1-(1H-benzimidazol-5-yl)-5-[4-(2-cyclopropyl-1,3-thiazol-4-yl)phenyl]imidazolidin-2-one (Compound 5) was prepared from the cycloaddition of 1,1'-carbonyl diimidazole and product (129). The procedures were the same as the synthesis of Compound 1. The product (Compound 5) was obtained as a white solid at a yield of 73%. $^1$H NMR (300 MHz, DMSO-$d_6$) δ 0.93-0.98 (m, 2H), 1.08-1.16 (m, 2H), 2.34-2.42 (m, 1H), 3.13 (dd, 1H, J=6.6, 9.0 Hz), 3.85 (dd, 1H, J=8.7, 9.0 Hz), 5.52 (dd, 1H, J=6.6, 8.7 Hz), 6.98 (s, 1H), 7.25 (d, 1H, J=8.1 Hz), 7.37-7.40 (m, 3H), 7.54 (s, 1H), 7.72 (s, 1H), 7.80 (d, 2H, J=8.1 Hz), 8.07 (s, 1H), 12.24 (s, 1H); LC/MS (ESI) m/z: 402.2 $[M+H]^+$.

4-Glycylbenzonitrile Hydrochloride (Compound 131)

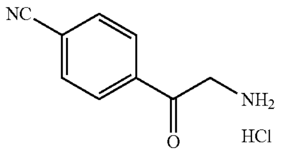 [SMILES: N#Cc1ccc(C(=O)CN)cc1 ; Cl]

The 4-(bromoacetyl)benzonitrile 130 (22.4 g, 100 mmol) and hexamethylenetetramine (HMTA, 15.4 g, 110 mmol) were dissolved in chloroform (900 mL). The reaction mixture was stirred at room temperature overnight. The precipitates were filtered and washed with ethanol and ether. The resulting solids were suspended in the mixture of HCl/ethanol (48 mL/240 mL) and then stirred at 75° C. overnight. The precipitates were filtered when the solution was still warm. The filtrate was concentrated to remove solvents. Some acetone (100 mL) was added and stirred for an hour. The precipitates were filtered and washed with acetone and ether. The product 131 was obtained as an off-white solid in a quantum yield and without further purification. 1H NMR (300 MHz, DMSO-$d_6$) δ 4.62 (s, 2H), 8.06 (d, 2H, J=8.4 Hz), 8.16 (d, 2H, J=8.4 Hz), 8.59 (s, 2H); LC/MS (ESI) m/z: 161.1 $[M+H]^+$.

N-[2-(4-cyanophenyl)-2-oxoethyl]acetamide (Compound 133a)

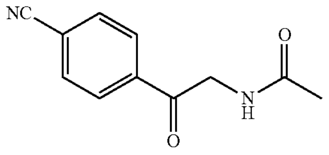

The triethylamine (21 mL) was added to the suspending solution of Compound 131 (10 g, 50.85 mmol) in dichloromethane (330 mL) and stirred at room temperature for 10 minutes. The acetic anhydride (7.79 g, 76.28 mmol) was diluted in dichloromethane (20 mL) and then added to the reaction solution during 30 minutes by additional funnel at an ice-bath. The resulting mixture was continuously stirred at room temperature for an hour. The reaction was quenched by water and extracted with dichloromethane. The organic layers were collected, dried over sodium sulfate, filtered and concentrated under reduced pressure. The crude residue was purified by column chromatography on silica gel using ethyl acetate/hexane (1/2) as eluent. The product 133a was obtained as a yellow solid at a yield of 70%.

N-[2-(4-cyanophenyl)-2-oxoethyl]cyclopropanecarboxamide (Compound 133b)

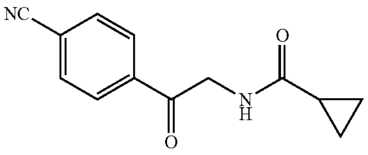 [SMILES: N#Cc1ccc(C(=O)CNC(=O)C2CC2)cc1]

The N-[2-(4-cyanophenyl)-2-oxoethyl]cyclopropanecarboxamide 133b was prepared from the acetylation of Compound 131 with cyclopropanecarboxylic anhydride 132b. The procedures were the same as the synthesis of Compound 133a. The product 133b was obtained as a yellow solid at a yield of 73%. $^1$H NMR (400 MHz, DMSO-$d_6$) δ 0.65-0.68 (m, 4H), 1.70 (m, 1H), 4.64 (d, 2H, J=5.4 Hz), 8.01 (d, 2H, J=8.4 Hz), 8.10 (d, 2H, J=8.4 Hz), 8.51 (t, 1H, d, J=5.4 Hz); LC/MS (ESI) m/z: 229.1 $[M+H]^+$.

N-[2-(4-cyanophenyl)-2-oxoethyl]-2,2,2-trifluoroacetamide (Compound 133c)

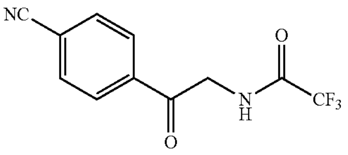 [SMILES: N#Cc1ccc(C(=O)CNC(=O)C(F)(F)F)cc1]

The N-[2-(4-cyanophenyl)-2-oxoethyl]-2,2,2-trifluoroacetamide 133c was prepared from the acetylation of Compound 131 with trifluoroacetic anhydride 132c. The procedures were the same as the synthesis of Compound 133a. The product 133c was obtained as a yellow solid at a yield of 73%.

4-(2-methyl-1,3-thiazol-5-yl)benzonitrile (Compound 134a)

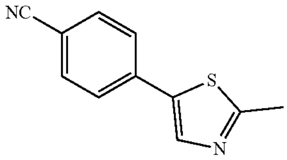

The Compound 133a (0.3 g, 1.48 mmol) and Lawesson's reagent (0.9 g, 2.22 mmol) were dissolved in THF (20 mL). The reaction mixture was refluxed and stirred for 17 hours. After removing the solvent, the crude residue was purified by column chromatography on silica gel using ethyl acetate/hexane (1/10) as eluent. The product 134a was obtained as a yellow solid at a yield of 70%.

4-(2-cyclopropyl-1,3-thiazol-5-yl)benzonitrile (Compound 134b)

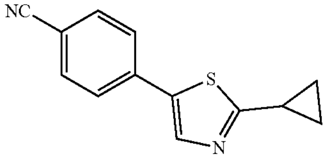 [SMILES: N#Cc1ccc(-c2cnc(C3CC3)s2)cc1]

The 4-(2-cyclopropyl-1,3-thiazol-5-yl)benzonitrile 134b was prepared from the cyclization of Compound 133b with the Lawesson's reagent in THF. The procedures were the same as the synthesis of Compound 134a. The product 134b was obtained as a yellow solid at a yield of 67%. $^1$H NMR (300 MHz, $CDCl_3$) δ 1.10-1.21 (m, 4H), 2.31-2.35 (m, 1H), 7.59 (d, 2H, J=8.4 Hz), 7.66 (d, 2H, J=8.4 Hz), 7.84 (s, 1H); LC/MS (ESI) m/z: 227.1 $[M+H]^+$.

4-[2-(trifluoromethyl)-1,3-thiazol-5-yl]benzonitrile (Compound 134c)

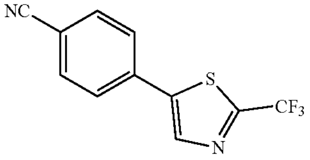 [SMILES: N#Cc1ccc(-c2cnc(C(F)(F)F)s2)cc1]

The 4-[2-(trifluoromethyl)-1,3-thiazol-5-yl]benzonitrile 134c was prepared from the cyclization of Compound 133c with the Lawesson's reagent in toluene. The procedures were the same as the synthesis of Compound 134a. The product 134c was obtained as a yellow solid at a yield of 65%. $^1H$ NMR (400 MHz, $CDCl_3$) δ 7.68 (d, 2H, J=8.8 Hz), 7.74 (d, 2H, J=8.8 Hz), 8.15 (s, 1H); LC/MS (ESI) m/z: 255.1 $[M+H]^+$.

4-(2-methyl-1,3-thiazol-5-yl)benzaldehyde (Compound 135a)

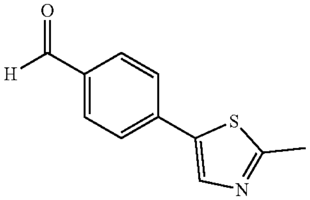

To a solution of Compound 134a (1.57 g, 7.86 mmol) in anhydrous toluene (100 mL) that cooled at −70° C., the solution of DIBAL-H in toluene (1.2M, 13.1 mL) was added dropwise by using additional funnel. The reaction mixture was stirred at −70° C. under argon for an hour and then quenched with 1N $HCl_{(aq)}$ (20 mL). The reaction mixture was stirred continuously at room temperature overnight. The reaction mixture was partition between ethyl acetate and water. The organic layers were collected, washed with brine, dried over sodium sulfate, filtered and concentrated under reduced pressure. The crude residue was purified by column chromatography on silica gel using ethyl acetate/hexane (1/5) as eluent. The product 135a was obtained as a yellow solid at a yield of 63%.

4-(2-cyclopropyl-1,3-thiazol-5-yl)benzaldehyde (Compound 135b)

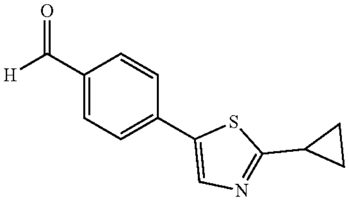 [SMILES: O=Cc1ccc(-c2cnc(C3CC3)s2)cc1]

The 4-(2-cyclopropyl-1,3-thiazol-5-yl)benzaldehyde 135b was prepared from the reduction of Compound 134b with the DIBAL-H reagent. The procedures were the same as the synthesis of Compound 135a. The product 135b was obtained as a yellow solid at a yield of 66%. $^1H$ NMR (300 MHz, $CDCl_3$) δ 1.13-1.20 (m, 4H), 2.31-2.35 (m, 1H), 7.65 (d, 2H, J=6.9 Hz), 7.87-7.89 (m, 3H), 9.99 (s, 1H); LC/MS (ESI) m/z: 230.1 $[M+H]^+$.

4-[2-(trifluoromethyl)-1,3-thiazol-5-yl]benzaldehyde (Compound 135c)

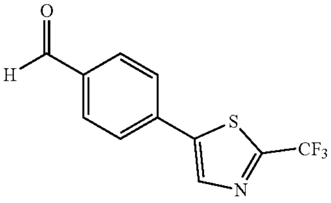 [SMILES: O=Cc1ccc(-c2cnc(C(F)(F)F)s2)cc1]

The 4-[2-(trifluoromethyl)-1,3-thiazol-5-yl]benzaldehyde 135c was prepared from the reduction of Compound 134c with the DIBAL-H reagent. The procedures were the same as the synthesis of Compound 135a. The product 135c was obtained as a yellow solid at a yield of 65%.

(1H-benzimidazol-5-ylamino)[4-(2-methyl-1,3-thiazol-5-yl)phenyl]acetonitrile (Compound 136a)

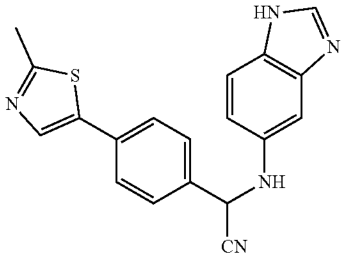 [SMILES: Cc1ncc(-c2ccc(C(C#N)Nc3ccc4[nH]cnc4c3)cc2)s1]

The (1H-benzimidazol-5-ylamino)[4-(2-methyl-1,3-thiazol-5-yl)phenyl]acetonitrile 136a was prepared from the addition of 1H-benzimidazol-5-amine 121, TMSCN and Compound 135a. The procedures were the same as the synthesis of Compound 122a. The product 136a was obtained as a pale-yellow solid at a yield of 90%.

(1H-benzimidazol-5-ylamino)[4-(2-cyclopropyl-1,3-thiazol-5-yl)phenyl]acetonitrile (Compound 136b)

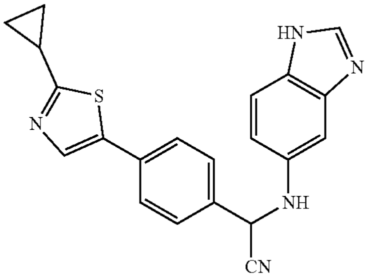 [SMILES: N#CC(Nc1ccc2[nH]cnc2c1)c1ccc(-c2cnc(C3CC3)s2)cc1]

The (1H-benzimidazol-5-ylamino)[4-(2-cyclopropyl-1,3-thiazol-5-yl)phenyl]acetonitrile 136b was prepared from the addition of 1H-benzimidazol-5-amine 121, TMSCN and Compound 135b. The procedures were the same as the synthesis of Compound 122a. The product 136b was obtained as a pale-yellow solid at a yield of 92%.

(1H-benzimidazol-5-ylamino){4-[2-(trifluoromethyl)-1,3-thiazol-5-yl]phenyl}acetonitrile (Compound 136c)

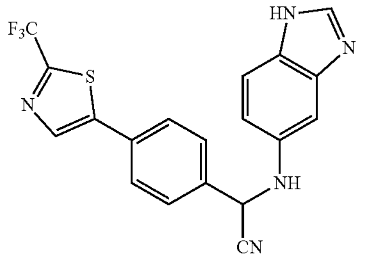 [SMILES: N#CC(Nc1ccc2[nH]cnc2c1)c1ccc(-c2cnc(C(F)(F)F)s2)cc1]

The (1H-benzimidazol-5-ylamino) {4-[2-(trifluoromethyl)-1,3-thiazol-5-yl]phenyl}-acetonitrile 136c was prepared from the addition of 1H-benzimidazol-5-amine 121, TMSCN and Compound 135c. The procedures were the same as the synthesis of Compound 122a. The product 136c was obtained as a pale-yellow solid at a yield of 90%.

$N^1$-(1H-benzimidazol-5-yl)-1-[4-(2-methyl-1,3-thiazol-5-yl)phenyl]ethane-1,2-diamine (Compound 137a)

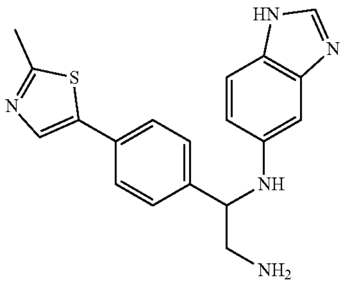 [SMILES: Cc1ncc(-c2ccc(C(CN)Nc3ccc4[nH]cnc4c3)cc2)s1]

The $N^1$-(1H-benzimidazol-5-yl)-1-[4-(2-methyl-1,3-thiazol-5-yl)phenyl]ethane-1,2-diamine 137a was prepared from the hydrogenation of Compound 136a with the Raney Nickel reagent as catalyst. The procedures were the same as the synthesis of Compound 123a. The product 137a was obtained as a yellow viscous liquid at a yield of 50%.

$N^1$-(1H-benzimidazol-5-yl)-1-[4-(2-cyclopropyl-1,3-thiazol-5-yl)phenyl]ethane-1,2-diamine (Compound 137b)

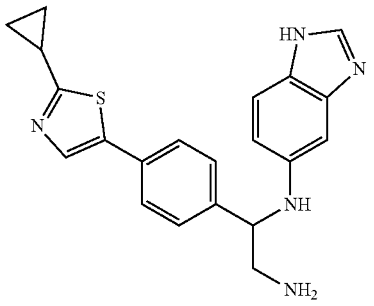 [SMILES: NCC(Nc1ccc2[nH]cnc2c1)c1ccc(-c2cnc(C3CC3)s2)cc1]

The $N^1$-(1H-benzimidazol-5-yl)-1-[4-(2-cyclopropyl-1,3-thiazol-5-yl)phenyl]ethane-1,2-diamine 137b was prepared from the hydrogenation of Compound 136b with the Raney Nickel reagent as catalyst. The procedures were the same as the synthesis of Compound 123a. The product 137b was obtained as a yellow viscous liquid at a yield of 54%.

$N^1$-(1H-benzimidazol-5-yl)-1-{4-[2-(trifluoromethyl)-1,3-thiazol-5-yl]phenyl}ethane-1,2-diamine (Compound 137c)

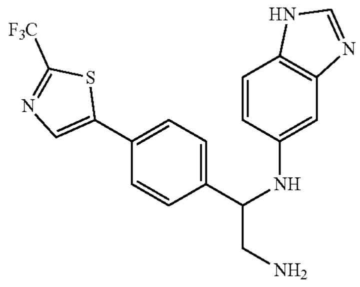 [SMILES: NCC(Nc1ccc2[nH]cnc2c1)c1ccc(-c2cnc(C(F)(F)F)s2)cc1]

The $N^1$-(1H-benzimidazol-5-yl)-1-{4-[2-(trifluoromethyl)-1,3-thiazol-5-yl]phenyl}-ethane-1,2-diamine 137c was prepared from the hydrogenation of Compound 136c with the Raney Nickel reagent as catalyst. The procedures were the same as the synthesis of Compound 123a. The product 137c was obtained as a yellow viscous liquid at a yield of 50%.

1-(1H-benzimidazol-5-yl)-5-[4-(2-methyl-1,3-thiazol-5-yl)phenyl]imidazolidin-2-one (Compound 6)

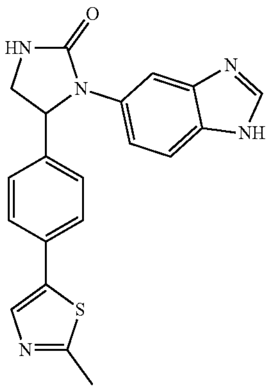 [SMILES: Cc1ncc(-c2ccc(C3CNC(=O)N3c3ccc4[nH]cnc4c3)cc2)s1]

The 1-(1H-benzimidazol-5-yl)-5-[4-(2-methyl-1,3-thiazol-5-yl)phenyl]imidazolidin-2-one (Compound 6) was prepared from the cycloaddition of 1,1'-carbonyl diimidazole and Compound 137a. The procedures were the same as the synthesis of Compound 1. The product (Compound 6) was obtained as a white solid at a yield of 71%. $^1$H NMR (400 MHz, $CD_3OD$) δ 2.64 (s, 3H), 3.30-3.36 (m, 1H), 3.97 (dd, 1H, J=8.6, 9.2 Hz), 5.48 (dd, 1H, J=7.6, 8.6 Hz), 7.29 (d, 1H, J=8.8 Hz), 7.39 (d, 2H, J=8.0 Hz), 7.45-7.46 (m, 3H), 7.55 (s, 1H), 7.76 (s, 1H), 8.06 (s, 1H); LC/MS (ESI) m/z: 376.3 $[M+H]^+$.

1-(1H-benzimidazol-5-yl)-5-[4-(2-cyclopropyl-1,3-thiazol-5-yl)phenyl]imidazolidin-2-one (Compound 7)

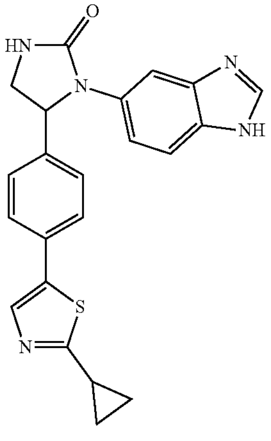

The 1-(1H-benzimidazol-5-yl)-5-[4-(2-cyclopropyl-1,3-thiazol-5-yl)phenyl]imidazolidin-2-one (Compound 7) was prepared from the cycloaddition of 1,1'-carbonyl diimidazole and Compound 137b. The procedures were the same as the synthesis of Compound 1. The product (Compound 7) was obtained as a white solid at a yield of 74%. $^1$H NMR (400 MHz, DMSO-$d_6$) δ 0.92-0.95 (m, 2H), 1.06-1.11 (m, 2H), 2.32-2.39 (m, 1H), 3.10 (dd, 1H, J=6.4, 9.2 Hz), 3.84 (dd, 1H, J=8.4, 9.2 Hz), 5.53 (dd, 1H, J=6.4, 8.4 Hz), 6.99 (s, 1H), 7.26 (s, 1H), 7.37-7.39 (m, 3H), 7.50 (d, 2H, J=8.0 Hz), 7.54 (s, 1H), 7.88 (s, 1H), 8.07 (s, 1H), 12.23 (s, 1H); LC/MS (ESI) m/z: 402.2 $[M+H]^+$.

1-(1H-benzimidazol-5-yl)-5-{4-[2-(trifluoromethyl)-1,3-thiazol-5-yl]phenyl}imidazolidin-2-one (Compound 8)

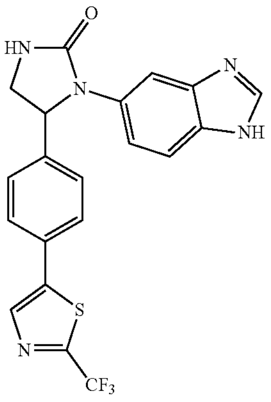 [SMILES: O=C1NCC(c2ccc(-c3cnc(C(F)(F)F)s3)cc2)N1c1ccc2[nH]cnc2c1]

The 1-(1H-benzimidazol-5-yl)-5-{4-[2-(trifluoromethyl)-1,3-thiazol-5-yl]phenyl}-imidazolidin-2-one (Compound 8) was prepared from the cycloaddition of 1,1'-carbonyl diimidazole and Compound 137c. The procedures were the same as the synthesis of Compound 1. The product (Compound 8) was obtained as a white solid at a yield of 70%. $^1$H NMR (400 MHz, $CD_3OD$) δ 3.37 (dd, 1H, J=7.2, 8.8 Hz), 4.01 (dd, 1H, J=8.8, 9.2 Hz), 5.56 (dd, 1H, J=7.2, 9.2 Hz), 7.31 (d, 1H, J=8.0 Hz), 7.47 (d, 1H, J=8.0 Hz), 7.50 (d, 2H, J=8.4 Hz), 7.58 (s, 1H), 7.63 (d, 2H, J=8.4 Hz), 8.07 (s, 1H), 8.18 (s, 1H); LC/MS (ESI) m/z: 430.2 $[M+H]^+$.

(5S)-1-(1H-benzimidazol-5-yl)-5-{4-[2-(trifluoromethyl)-1,3-thiazol-5-yl]phenyl}-imidazolidin-2-one (Compound 9)

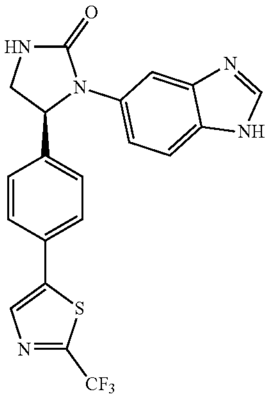 [SMILES: O=C1NC[C@H](c2ccc(-c3cnc(C(F)(F)F)s3)cc2)N1c1ccc2[nH]cnc2c1]

(5R)-1-(1H-benzimidazol-5-yl)-5-{4-[2-(trifluoromethyl)-1,3-thiazol-5-yl]phenyl}-imidazolidin-2-one (Compound 10)

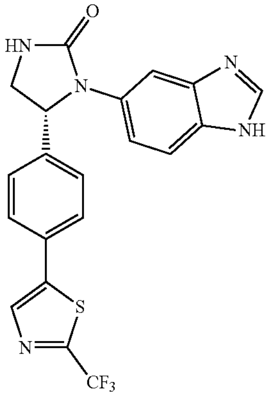 [SMILES: O=C1NC[C@@H](c2ccc(-c3cnc(C(F)(F)F)s3)cc2)N1c1ccc2[nH]cnc2c1]

The enantiomers (Compounds 9 and 10) were separated from Compound 8 by HPLC using CHIRALPAK IC. The isomer fractions were respectively collected and the optical pure isomers (Compounds 9 and 10) were thus obtained by removing the solvent under reduced pressure. $^1H$ NMR (400 MHz, $CD_3OD$) δ 3.37 (dd, 1H, J=7.2, 8.8 Hz), 4.01 (dd, 1H, J=8.8, 9.2 Hz), 5.56 (dd, 1H, J=7.2, 9.2 Hz), 7.31 (d, 1H, J=8.0 Hz), 7.47 (d, 1H, J=8.0 Hz), 7.50 (d, 2H, J=8.4 Hz), 7.58 (s, 1H), 7.63 (d, 2H, J=8.4 Hz), 8.07 (s, 1H), 8.18 (s, 1H); LC/MS (ESI) m/z: 430.2 $[M+H]^+$.

4-(5-methylthiophen-2-yl)benzaldehyde (Compound 140a)

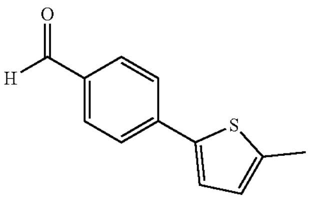

The 4-bromobenzaldehyde 138a (1.85 g, 10.0 mmol), 2-methylthiophene 139a (1.96 g, 20.0 mmol), potassium acetate (1.96 g, 20.0 mmol) and palladium acetate (0.002 g, 0.01 mmol) were dissolved in dimethylacetamide (DMA). The reaction mixture was purged with argon and stirred at 150° C. for 4 hours. The reaction mixture was cooled to room temperature and extracted with dichloromethane. The organic layers were collected, washed with brine, dried over sodium sulfate, filtered and concentrated under reduced pressure. The crude residue was purified by column chromatography on silica gel using pentane/ether (1/4) as eluent. The product 140a was obtained as a white solid at a yield of 92%.

(1H-benzimidazol-5-ylamino)[4-(5-methylthiophen-2-yl)phenyl]acetonitrile (Compound 141a)

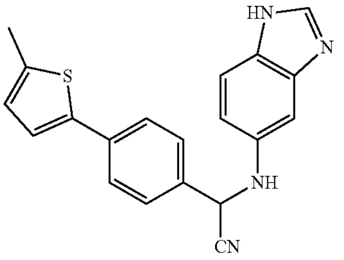 [SMILES: Cc1ccc(-c2ccc(C(C#N)Nc3ccc4[nH]cnc4c3)cc2)s1]

The (1H-benzimidazol-5-ylamino)[4-(5-methylthiophen-2-yl)phenyl]acetonitrile 141a was prepared from the addition of 1H-benzimidazol-5-amine 121, TMSCN and Compound 140a. The procedures were the same as the synthesis of Compound 122a. The product 141a was obtained as a pale-yellow solid at a yield of 90%.

$N^1$-(1H-benzimidazol-5-yl)-1-[4-(5-methylthiophen-2-yl)phenyl]ethane-1,2-diamine (Compound 142a)

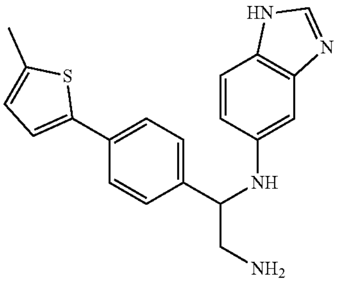 [SMILES: Cc1ccc(-c2ccc(C(CN)Nc3ccc4[nH]cnc4c3)cc2)s1]

The $N^1$-(1H-benzimidazol-5-yl)-1-[4-(5-methylthiophen-2-yl)phenyl]ethane-1,2-diamine 142a was prepared from the hydrogenation of Compound 141a with the Raney Nickel reagent as catalyst. The procedures were the same as the synthesis of Compound 123a. The product 142a was obtained as a yellow viscous liquid at a yield of 55%.

1-(1H-benzimidazol-5-yl)-5-[4-(5-methylthiophen-2-yl)phenyl]imidazolidin-2-one (Compound 11)

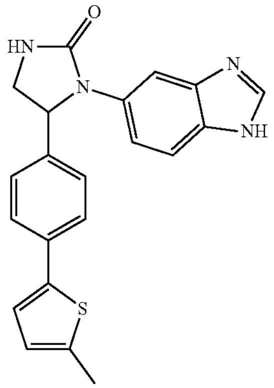 [SMILES: Cc1ccc(-c2ccc(C3CNC(=O)N3c3ccc4[nH]cnc4c3)cc2)s1]

The 1-(1H-benzimidazol-5-yl)-5-[4-(5-methylthiophen-2-yl)phenyl]imidazolidin-2-one (Compound 11) was prepared from the cycloaddition of 1,1'-carbonyl diimidazole and Compound 142a. The procedures were the same as the synthesis of Compound 1. The product (Compound 11) was obtained as a white solid at a yield of 63%. $^1H$ NMR (400 MHz, $CD_3OD$) δ 2.44 (s, 3H), 3.39 (dd, 1H, J=7.6, 8.8 Hz), 3.97 (dd, 1H, J=8.8, 9.2 Hz), 5.40 (dd, 1H, J=7.6, 9.2 Hz), 6.67 (d, 1H, J=3.0 Hz), 7.05 (d, 1H, J=3.0 Hz), 7.26 (d, 1H, J=8.8 Hz), 7.33 (d, 2H, J=8.0 Hz), 7.45-7.47 (m, 3H), 7.52 (s, 1H), 7.99 (s, 1H); LC/MS (ESI) m/z: 375.3 $[M+H]^+$.

4-acryloylbenzonitrile (Compound 144)

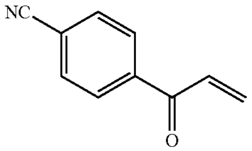

The 4-acetylbenzonitrile 143 (0.73 g, 5.0 mmol), $FeCl_3.6H_2O$ (0.14 g, 0.5 mmol), $K_2S_2O_8$ (2.7 g, 10.0 mmol) and DMA (20 mL) were sequentially added to the round-bottle flask. The reaction mixture was stirred at 110° C. for 4 hours. Upon completion of the reaction (monitored by TLC), the resulting mixture was diluted with ether and washed with brine. The organic layers were dried over sodium sulfate, filtered and concentrated under reduced pressure. The crude residue was purified by column chromatography on silica gel using ethyl acetate/ether (1/4) as eluent. The product 144 was obtained as an off-white solid at a yield of 40%.

4-(4-oxopentanoyl)benzonitrile (Compound 146)

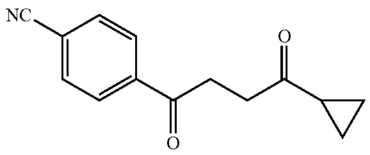 [SMILES: N#Cc1ccc(C(=O)CCC(=O)C2CC2)cc1]

The product 144 (2.0 g, 12.7 mmol), cyclopropanecarbaldehyde (1.2 mL, 15.3 mmol), triethylamine (1.2 mL, 8.6 mmol) and 2-(2-hydroxyethyl)-3-methyl-4-benzylthiazolium chloride 145 (0.65 g, 15.2 mmol) were sequentially added to the round-bottle flask. The reaction mixture was stirred at 70° C. overnight. Upon completion of the reaction (monitored by TLC), the resulting mixture was partitioned between ether and water. The organic layers were washed with water, 2 M HCl and brine. After drying over sodium sulfate, filtering and concentrating in vacuo, the crude residue was purified by column chromatography on silica gel using ethyl acetate/hexane (1/3) as eluent. The product 146 was obtained as a yellow liquid at a yield of 50%.

4-(5-cyclopropylthiophen-2-yl)benzonitrile (Compound 147)

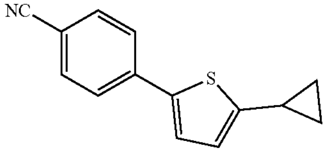 [SMILES: N#Cc1ccc(-c2ccc(C3CC3)s2)cc1]

The 4-(5-cyclopropylthiophen-2-yl)benzonitrile 147 was prepared from the cyclization of product 146 with the Lawesson's reagent in THF. The procedures were the same as the synthesis of Compound 134a. The product 147 was obtained as a yellow solid at a yield of 75%. 4-(5-cyclopropylthiophen-2-yl)benzaldehyde (Compound 148)

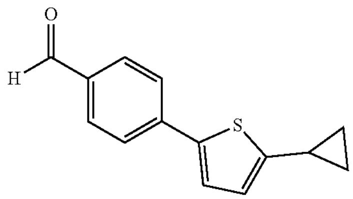 [SMILES: O=Cc1ccc(-c2ccc(C3CC3)s2)cc1]

The 4-(5-cyclopropylthiophen-2-yl)benzaldehyde 148 was prepared from the reduction of Compound 147 with the DIBAL-H reagent. The procedures were the same as the synthesis of Compound 135a. The product 148 was obtained as a yellow solid at a yield of 64%.

(1H-benzimidazol-5-ylamino)[4-(5-cyclopropylthiophen-2-yl)phenyl]acetonitrile (Compound 149)

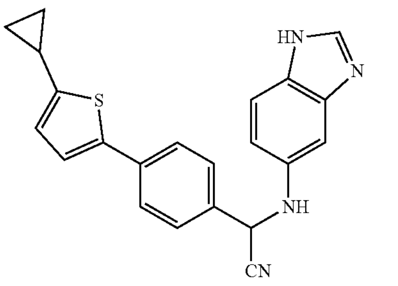 [SMILES: N#CC(Nc1ccc2[nH]cnc2c1)c1ccc(-c2ccc(C3CC3)s2)cc1]

The (1H-benzimidazol-5-ylamino)[4-(5-cyclopropylthiophen-2-yl)phenyl]acetonitrile 149 was prepared from the addition of 1H-benzimidazol-5-amine 121, TMSCN and Compound 148. The procedures were the same as the synthesis of Compound 122a. The product 149 was obtained as a pale-yellow solid at a yield of 91%.

N[1]-(1H-benzimidazol-5-yl)-1-[4-(5-cyclopropylthiophen-2-yl)phenyl]ethane-1,2-diamine (Compound 150)

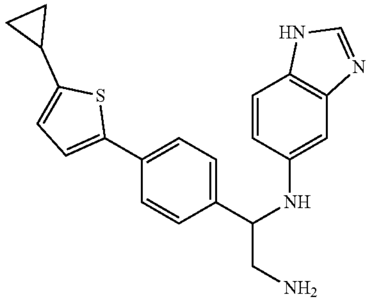 [SMILES: NCC(Nc1ccc2[nH]cnc2c1)c1ccc(-c2ccc(C3CC3)s2)cc1]

The N[1]-(1H-benzimidazol-5-yl)-1-[4-(5-cyclopropylthiophen-2-yl)phenyl]ethane-1,2-diamine 150 was prepared from the hydrogenation of Compound 149 with the Raney Nickel reagent as catalyst. The procedures were the same as the synthesis of Compound 123a. The product 150 was obtained as a yellow viscous liquid at a yield of 53%.

1-(1H-benzimidazol-5-yl)-5-[4-(5-cyclopropylthiophen-2-yl)phenyl]imidazolidin-2-one (Compound 12)

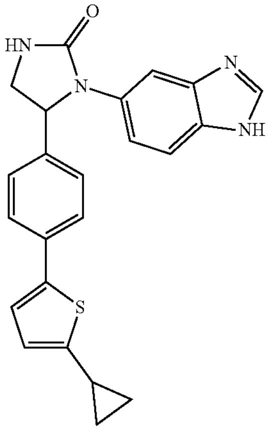 [SMILES: O=C1NCC(c2ccc(-c3ccc(C4CC4)s3)cc2)N1c1ccc2[nH]cnc2c1]

The 1-(1H-benzimidazol-5-yl)-5-[4-(5-cyclopropylthiophen-2-yl)phenyl]imidazolidin-2-one (Compound 12) was prepared from the cycloaddition of 1,1'-carbonyl diimidazole and product 150. The procedures were the same as the synthesis of Compound 1. The product (Compound 12) was obtained as a white solid at a yield of 69%. $^1H$ NMR (400 MHz, $CD_3OD$) δ 0.67-0.71 (m, 2H), 0.96-1.01 (m, 2H), 2.03-2.09 (m, 1H), 3.36 (dd, 1H, J=6.8, 8.8 Hz), 3.97 (dd, 1H, J=8.8, 9.2 Hz), 5.45 (dd, 1H, J=6.8, 9.2 Hz), 6.69 (d, 1H, J=3.6 Hz), 7.08 (d, 1H, J=3.6 Hz), 7.29 (d, 1H, J=8.8 Hz), 7.36 (d, 2H, J=8.4 Hz), 7.46-7.49 (m, 3H), 7.54 (s, 1H), 8.06 (s, 1H); LC/MS (ESI) m/z: 401.3 $[M+H]^+$.

4-(thiophen-2-yl)benzaldehyde (Compound 152a)

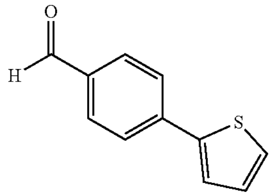 [SMILES: O=Cc1ccc(-c2cccs2)cc1]

The 4-bromobenzaldehyde 138a (1.85 g, 10.0 mmol), thiophene (6.72 g, 80.0 mmol), potassium acetate (1.96 g, 20.0 mmol) and palladium acetate (0.002 g, 0.01 mmol) were dissolved in DMA (50 mL). The reaction mixture was purged with argon and stirred at 130° C. for 20 hours. The reaction mixture was cooled to room temperature and removed the solvent in vacuo. The crude residue was purified by column chromatography on silica gel using pentane/ether (1/4) as eluent. The product 152a was obtained as a light-yellow solid at a yield of 60%.

4-(5-iodothiophen-2-yl)benzaldehyde (Compound 153a)

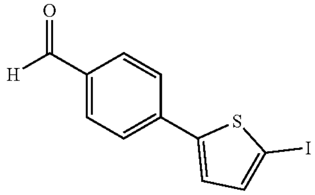 [SMILES: O=Cc1ccc(-c2ccc(I)s2)cc1]

The Compound 152a (0.94 g, 5.0 mmol) and N-iodosuccinimide (2.81 g, 12.5 mmol) were added to the 500 mL flask. The flask was flushed with nitrogen and then added chloroform (200 mL) and acetic acid (16 mL). The reaction mixture was stirred at room temperature for 8 hours. The reaction mixture was washed with saturated sodium thiosulfate solution (75 mL), saturated sodium bicarbonate solution (75 mL), and water (75 mL). The organic layers were collected, dried over sodium sulfate, filtered and concentrated in vacuo. The crude residue was purified by column chromatography on silica gel using dichloromethane/hexane (1/1) as eluent. The product 153a was obtained as a yellow solid at a yield of 75%.

4-[5-(trifluoromethyl)thiophen-2-yl]benzaldehyde (Compound 155a)

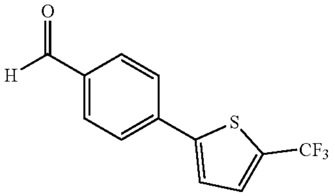 [SMILES: O=Cc1ccc(-c2ccc(C(F)(F)F)s2)cc1]

A mixture of Compound 153a (0.31 g, 1.0 mmol), methyl difluoro(fluorosulfonyl)acetate 154 (0.96 g, 5.0 mmol), copper iodide (0.23 g, 1.2 mmol), N-methylpyrrolidine (NMP, 1.2 mL) and DMF (10 mL) was stirred at 70° C. for 13 hours. The reaction mixture was quenched with saturated aqueous ammonium chloride (15 mL), diluted with water (10 mL), filtered through celite, and extracted with ethyl acetate. The organic layers were collected, dried over sodium sulfate, filtered and concentrated in vacuo. The crude residue was purified by column chromatography on silica gel using ethyl acetate/hexane (1/6) as eluent. The product 155a was obtained as a yellow solid at a yield of 70%.

(1H-benzimidazol-5-ylamino){4-[5-(trifluoromethyl) thiophen-2-yl]phenyl}acetonitrile (Compound 156a)

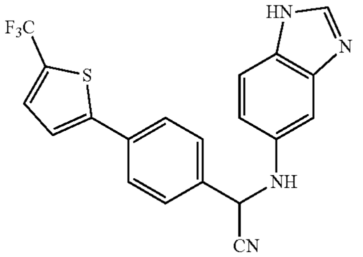 [SMILES: N#CC(Nc1ccc2[nH]cnc2c1)c1ccc(-c2ccc(C(F)(F)F)s2)cc1]

The (1H-benzimidazol-5-ylamino) {4-[5-(trifluoromethyl)thiophen-2-yl]phenyl}-acetonitrile 156a was prepared from the addition of 1H-benzimidazol-5-amine 121, TMSCN and Compound 155a. The procedures were the same as the synthesis of Compound 122a. The product 156a was obtained as a pale-yellow solid at a yield of 88%.

$N^1$-(1H-benzimidazol-5-yl)-1-{4-[5-(trifluoromethyl)thiophen-2-yl]phenyl}ethane-1,2-diamine (Compound 157a)

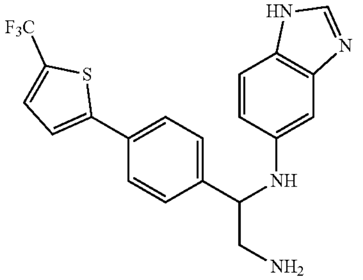

The $N^1$-(1H-benzimidazol-5-yl)-1-{4-[5-(trifluoromethyl)thiophen-2-yl]phenyl}ethane-1,2-diamine 157a was prepared from the hydrogenation of Compound 156a with the Raney Nickel reagent as catalyst. The procedures were the same as the synthesis of Compound 123a. The product 157a was obtained as a yellow viscous liquid at a yield of 49%.

1-(1H-benzimidazol-5-yl)-5-{4-[5-(trifluoromethyl) thiophen-2-yl]phenyl}imidazolidin-2-one (Compound 13)

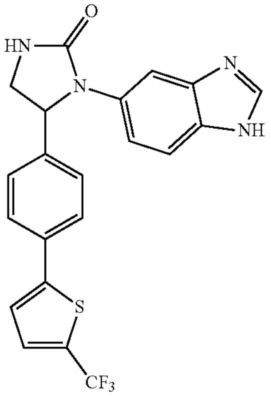

The 1-(1H-benzimidazol-5-yl)-5-{4-[5-(trifluoromethyl) thiophen-2-yl]phenyl}-imidazolidin-2-one (Compound 13) was prepared from the cycloaddition of 1,1'-carbonyl diimidazole and Compound 157a. The procedures were the same as the synthesis of Compound 1. The product (Compound 13) was obtained as a white solid at a yield of 67%. $^1$H NMR (300 MHz, $CD_3OD$) δ 3.36 (dd, 1H, J=6.9, 9.3 Hz), 3.99 (dd, 1H, J=9.3, 9.3 Hz), 5.51 (dd, 1H, J=6.9, 9.3 Hz), 7.29-7.32 (m, 2H), 7.43-7.48 (m, 4H), 7.55-7.60 (m, 3H), 8.06 (s, 1H); LC/MS (ESI) m/z: 429.2 $[M+H]^+$.

4-(thiophen-3-yl)benzaldehyde (Compound 159a)

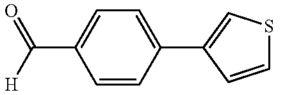 [SMILES: O=Cc1ccc(-c2ccsc2)cc1]

The 3-bromothiophene 158a (1.96 g, 12.0 mmol), (4-formylphenyl)boronic acid 118 (2.70 g, 18.0 mmol), ethylene glycol dimethyl ether (17 mL), water (10 mL) and sodium bicarbonate (3.02 g, 36.0 mmol) were placed in a 50 mL round-bottom flask. After adding $Pd(PPh_3)_4$ (0.69 g, 0.6 mmol) at room temperature, the reaction mixture was refluxed for 5 hours. The resulting mixture was extracted with ethyl acetate and water. The organic layers were collected, washed with brine, dried over sodium sulfate, filtered and concentrated under reduced pressure. The crude residue was purified by column chromatography on silica gel using toluene/hexane (2/1) as eluent. The product 159a was obtained as a pale yellow oil at a yield of 95%.

4-(5-methylthiophen-3-yl)benzaldehyde (Compound 159b)

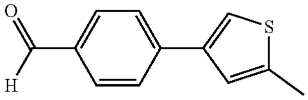

The 4-(5-methylthiophen-3-yl)benzaldehyde 159b was prepared from the Suzuki-Miyaura coupling of (4-formylphenyl)boronic acid 118 and 3-bromo-5-methylthiophene 158b. The procedures were the same as the synthesis of Compound 159a. The product 159b was obtained as a pale-yellow oil at a yield of 92%.

4-[5-(trifluoromethyl)thiophen-3-yl]benzaldehyde (Compound 159c)

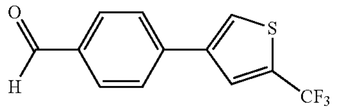

The 4-[5-(trifluoromethyl)thiophen-3-yl]benzaldehyde 159c was prepared from the Suzuki-Miyaura coupling of (4-formylphenyl)boronic acid 118 and 3-bromo-(5-trifluoromethyl)-thiophene 158c. The procedures were the same as the synthesis of Compound 159a. The product 159c was obtained as a pale-yellow oil at a yield of 85%.

(1H-benzimidazol-5-ylamino)[4-(thiophen-3-yl)phenyl]acetonitrile (Compound 160a)

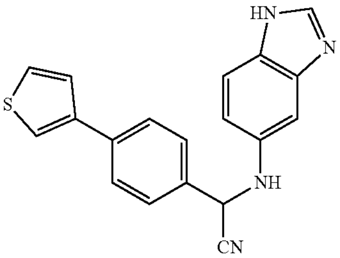 [SMILES: N#CC(Nc1ccc2[nH]cnc2c1)c1ccc(-c2ccsc2)cc1]

The (1H-benzimidazol-5-ylamino)[4-(thiophen-3-yl)phenyl]acetonitrile 160a was prepared from the addition of 1H-benzimidazol-5-amine 121, TMSCN and Compound 159a. The procedures were the same as the synthesis of Compound 122a. The product 160a was obtained as a pale-yellow solid at a yield of 92%.

(1H-benzimidazol-5-ylamino)[4-(5-methylthiophen-3-yl)phenyl]acetonitrile (Compound 160b)

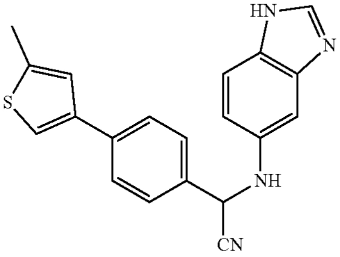 [SMILES: Cc1cc(-c2ccc(C(C#N)Nc3ccc4[nH]cnc4c3)cc2)cs1]

The (1H-benzimidazol-5-ylamino)[4-(5-methylthiophen-3-yl)phenyl]acetonitrile 160b was prepared from the addition of 1H-benzimidazol-5-amine 121, TMSCN and Compound 159b. The procedures were the same as the synthesis of Compound 122a. The product 160b was obtained as a pale-yellow solid at a yield of 90%.

(1H-benzimidazol-5-ylamino){4-[5-(trifluoromethyl)thiophen-3-yl]phenyl}acetonitrile (Compound 160c)

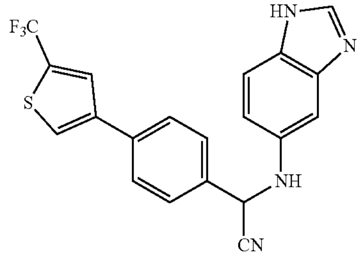 [SMILES: N#CC(Nc1ccc2[nH]cnc2c1)c1ccc(-c2csc(C(F)(F)F)c2)cc1]

The (1H-benzimidazol-5-ylamino) {4-[5-(trifluoromethyl)thiophen-3-yl]phenyl}-acetonitrile 160c was prepared from the addition of 1H-benzimidazol-5-amine 121, TMSCN and Compound 159c. The procedures were the same as the synthesis of Compound 122a. The product 160c was obtained as a pale-yellow solid at a yield of 85%.

$N^1$-(1H-benzimidazol-5-yl)-1-[4-(thiophen-3-yl)phenyl]ethane-1,2-diamine (Compound 161a)

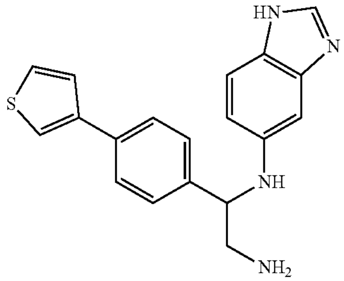 [SMILES: NCC(Nc1ccc2[nH]cnc2c1)c1ccc(-c2ccsc2)cc1]

The $N^1$-(1H-benzimidazol-5-yl)-1-[4-(thiophen-3-yl)phenyl]ethane-1,2-diamine 161a was prepared from the hydrogenation of Compound 160a with the Raney Nickel reagent as catalyst. The procedures were the same as the synthesis of Compound 123a. The product was obtained as a yellow viscous liquid at a yield of 53%.

$N^1$-(1H-benzimidazol-5-yl)-1-[4-(5-methylthiophen-3-yl)phenyl]ethane-1,2-diamine (Compound 161b)

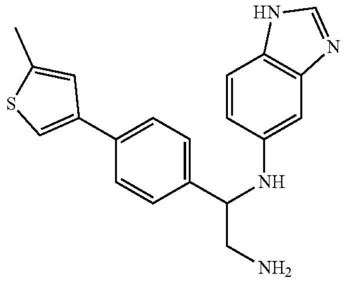 [SMILES: Cc1cc(-c2ccc(C(CN)Nc3ccc4[nH]cnc4c3)cc2)cs1]

The $N^1$-(1H-benzimidazol-5-yl)-1-[4-(5-methylthiophen-3-yl)phenyl]ethane-1,2-diamine 161b was prepared from the hydrogenation of Compound 160b with the Raney Nickel reagent as catalyst. The procedures were the same as the synthesis of Compound 123a. The product 161b was obtained as a yellow viscous liquid at a yield of 50%.

$N^1$-(1H-benzimidazol-5-yl)-1-{4-[5-(trifluoromethyl)thiophen-3-yl]phenyl}ethane-1,2-diamine (Compound 161c)

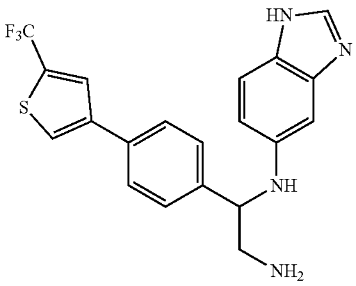 [SMILES: NCC(Nc1ccc2[nH]cnc2c1)c1ccc(-c2csc(C(F)(F)F)c2)cc1]

The $N^1$-(1H-benzimidazol-5-yl)-1-{4-[5-(trifluoromethyl)thiophen-3-yl]phenyl}ethane-1,2-diamine 161c was prepared from the hydrogenation of Compound 160c with the Raney Nickel reagent as catalyst. The procedures were the same as the synthesis of Compound 123a. The product 161c was obtained as a yellow viscous liquid at a yield of 51%.

1-(1H-benzimidazol-5-yl)-5-[4-(thiophen-3-yl)phenyl]imidazolidin-2-one (Compound 14)

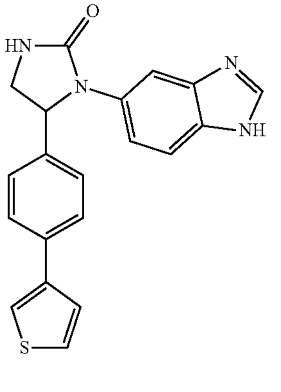 [SMILES: O=C1NCC(c2ccc(-c3ccsc3)cc2)N1c1ccc2[nH]cnc2c1]

The 1-(1H-benzimidazol-5-yl)-5-[4-(thiophen-3-yl)phenyl]imidazolidin-2-one (Compound 14) was prepared from the cycloaddition of 1,1'-carbonyl diimidazole and Compound 161a. The procedures were the same as the synthesis of Compound 1. The product (Compound 14) was obtained as a white solid at a yield of 73%. $^1$H NMR (300 MHz, $CD_3OD$) δ 3.38 (dd, 1H, J=6.9, 9.0 Hz), 3.99 (dd, 1H, J=9.0, 9.3 Hz), 5.48 (dd, 1H, J=6.9, 9.3 Hz), 7.05 (s, 1H), 7.30 (d, 1H, J=8.4 Hz), 7.37-7.48 (m, 4H), 7.54-7.60 (m, 3H), 7.68 (s, 1H), 8.06 (s, 1H); LC/MS (ESI) m/z: 361.3 $[M+H]^+$.

1-(1H-benzimidazol-5-yl)-5-[4-(5-methylthiophen-3-yl)phenyl]imidazolidin-2-one (Compound 15)

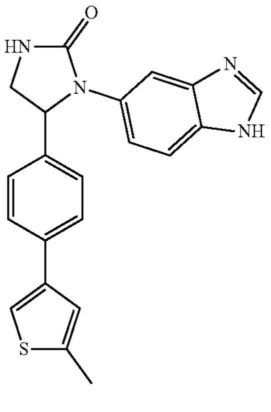 [SMILES: Cc1cc(-c2ccc(C3CNC(=O)N3c3ccc4[nH]cnc4c3)cc2)cs1]

The 1-(1H-benzimidazol-5-yl)-5-[4-(5-methylthiophen-3-yl)phenyl]imidazolidin-2-one (Compound 15) was prepared from the cycloaddition of 1,1'-carbonyl diimidazole and Compound 161b. The procedures were the same as the synthesis of Compound 1. The product (Compound 15) was obtained as a white solid at a yield of 75%. $^1$H NMR (300 MHz, $CD_3OD$) δ 2.40 (s, 3H), 3.30 (dd, 1H, J=7.5, 9.0 Hz), 3.90 (dd, 1H, J=9.0, 9.0 Hz), 5.38 (dd, 1H, J=7.5, 9.0 Hz), 6.95 (s, 1H), 7.17 (s, 1H), 7.26-7.31 (m, 3H), 7.42-7.45 (m, 3H), 7.55 (s, 1H), 8.03 (s, 1H); LC/MS (ESI) m/z: 375.1 $[M+H]^+$.

1-(1H-benzimidazol-5-yl)-5-{4-[5-(trifluoromethyl)thiophen-3-yl]phenyl}imidazolidin-2-one (Compound 16)

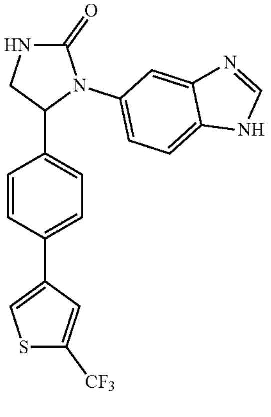 [SMILES: O=C1NCC(c2ccc(-c3csc(C(F)(F)F)c3)cc2)N1c1ccc2[nH]cnc2c1]

The 1-(1H-benzimidazol-5-yl)-5-{4-[5-(trifluoromethyl)thiophen-3-yl]phenyl}-imidazolidin-2-one (Compound 16) was prepared from the cycloaddition of 1,1'-carbonyl diimidazole and Compound 161c. The procedures were the same as the synthesis of Compound 1. The product (Compound 16) was obtained as a white solid at a yield of 67%. $^1$H NMR (300 MHz, $CD_3OD$) δ 3.36 (dd, 1H, J=6.9, 9.0 Hz), 3.99 (dd, 1H, J=9.0, 9.3 Hz), 5.50 (dd, 1H, J=6.9, 9.3 Hz), 7.30 (d, 1H, J=8.1 Hz), 7.41-7.47 (m, 3H), 7.56-7.58 (m, 3H), 7.81 (s, 2H), 8.05 (s, 1H); LC/MS (ESI) m/z: 429.1 $[M+H]^+$.

4-(5-bromothiophen-3-yl)benzaldehyde (Compound 162)

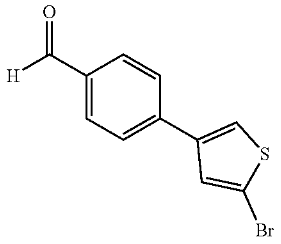 [SMILES: O=Cc1ccc(-c2csc(Br)c2)cc1]

Bromine (5.0 g, 32.0 mmol) in 50 mL of glacial acetic acid was added dropwise to a solution of Compound 159a (6.0 g, 32.0 mmol) in 65 mL of glacial acetic acid. The resulting yellow solution was stirred at room temperature for 2 days. The reaction mixture was diluted with 300 mL of water and extracted with ethyl acetate (100 mL×2). The combined organic layers were washed with saturated aqueous sodium bicarbonate, dried over sodium sulfate, filtered and concentrated under reduced pressure. The crude residue was purified by column chromatography on silica gel using ethyl acetate/hexane (1/9) as eluent. The product 162 was obtained as a yellow solid at a yield of 73%.

4-(5-cyclopropylthiophen-3-yl)benzaldehyde (Compound 163)

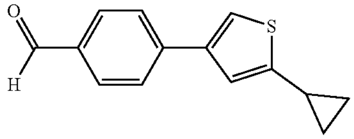 [SMILES: O=Cc1ccc(-c2csc(C3CC3)c2)cc1]

The palladium acetate (0.025 g, 0.11 mmol) and Xantphos (0.066 g, 0.11 mmol) were added in THF (22 mL) that degassed under argon. Then, the reaction mixture was stirred at room temperature for 5 minutes. The 4-(5-bromothiophen-3-yl)benzaldehyde 162 (0.73 g, 3.0 mmol), cyclopropylboronic acid 125 (0.58 g, 6.70 mmol) and potassium phosphate (2.86 g) were added to the reaction mixture and flushed with argon. The reaction mixture was stirred at 70° C. for 15 hours. After cooling to room temperature, the reaction mixture was filtered and washed with dichloromethane. The filtrate was concentrated under reduced pressure and purified by column chromatography on silica gel using hexane as eluent. The product 163 was obtained as a yellow solid at a yield of 84%.

(1H-benzimidazol-5-ylamino)[4-(5-cyclopropylthiophen-3-yl)phenyl]acetonitrile (Compound 164)

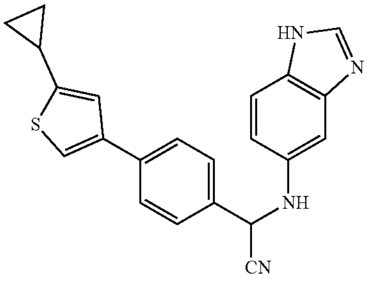 [SMILES: N#CC(Nc1ccc2[nH]cnc2c1)c1ccc(-c2csc(C3CC3)c2)cc1]

The (1H-benzimidazol-5-ylamino)[4-(5-cyclopropylthiophen-3-yl)phenyl]acetonitrile 164 was prepared from the addition of 1H-benzimidazol-5-amine 121, TMSCN and Compound 163. The procedures were the same as the synthesis of Compound 122a. The product 164 was obtained as a pale-yellow solid at a yield of 81%.

$N^1$-(1H-benzimidazol-5-yl)-1-[4-(5-cyclopropylthiophen-3-yl)phenyl]ethane-1,2-diamine (Compound 165)

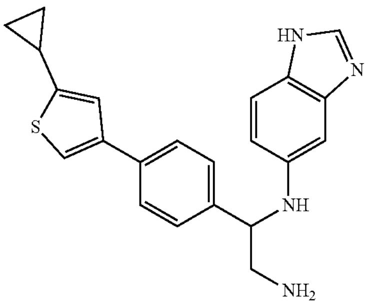 [SMILES: NCC(Nc1ccc2[nH]cnc2c1)c1ccc(-c2csc(C3CC3)c2)cc1]

The $N^1$-(1H-benzimidazol-5-yl)-1-[4-(5-cyclopropylthiophen-3-yl)phenyl]ethane-1,2-diamine 165 was prepared from the hydrogenation of Compound 164 with the Raney Nickel reagent as catalyst. The procedures were the same as the synthesis of Compound 123a. The product 165 was obtained as a yellow viscous liquid at a yield of 49%.

1-(1H-benzimidazol-5-yl)-5-[4-(5-cyclopropylthiophen-3-yl)phenyl]imidazolidin-2-one (Compound 17)

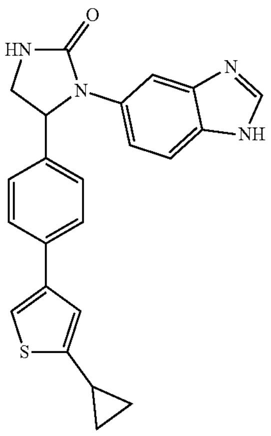 [SMILES: O=C1NCC(c2ccc(-c3csc(C4CC4)c3)cc2)N1c1ccc2[nH]cnc2c1]

The 1-(1H-benzimidazol-5-yl)-5-[4-(5-cyclopropylthiophen-3-yl)phenyl]imidazolidin-2-one (Compound 17) was prepared from the cycloaddition of 1,1'-carbonyl diimidazole and Compound 165. The procedures were the same as the synthesis of Compound 1. The product (Compound 17) was obtained as a white solid at a yield of 65%. $^1$H NMR (300 MHz, $CD_3OD$) δ 0.59-0.63 (m, 2H), 0.91-0.96 (m, 2H), 2.00-2.09 (m, 1H), 3.39 (dd, 1H, J=6.9, 9.0 Hz), 4.00 (dd, 1H, J=9.0, 9.3 Hz), 5.50 (dd, 1H, J=6.9, 9.3 Hz), 6.69 (d, 1H, J=5.4 Hz), 7.05 (d, 1H, J=5.4 Hz), 7.32 (dd, 1H, J=1.8, 8.7 Hz), 7.41-7.45 (m, 3H), 7.46 (d, 2H, J=8.1 Hz), 7.58 (d, 1H, J=1.8 Hz), 8.06 (s, 1H); LC/MS (ESI) m/z: 401.2 $[M+H]^+$.

4-(1,3-dioxolan-2-yl)benzonitrile (Compound 167)

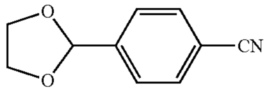

To a round-bottom flask equipped with a Dean-Stark trap was successively added 4-formylbenzonitrile 166 (7.68 g, 58.6 mmol), a catalytic amount of p-TsOH (PTSA) and toluene (150 mL). After stirring 5 minutes at room temperature, the monoethyleneglycol (MEG) (13 mL, 234.3 mmol) was added dropwise. The reaction mixture was refluxed for 3 hours and cooled to room temperature. After removing toluene under reduced pressure, sat. $Na_2CO_{3(aq)}$ was added to quench the reaction and partitioned between DCM and water. The organic phases were collected, washed with brine, dried over sodium sulfate, filtered and concentrated under reduced pressure. The viscous residue was treated with hexane at ice-bath to form the product 167 as a yellow solid in a quantum yield.

4-(1,3-dioxolan-2-yl)-N'-hydroxybenzenecarboximidamide (Compound 168)

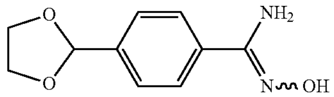 [SMILES: NC(=NO)c1ccc(C2OCCO2)cc1]

To the solution of the Compound 167 (7.6 g, 43.4 mmol) in ethanol/water (2/1, 75 mL), hydroxylamine hydrochloride (10.6 g, 151.8 mmol) and sodium carbonate (9.2 g, 86.8 mmol) were added at room temperature. The reaction mixture was stirred at 100° C. for 2 hours. After concentrating under reduced pressure, the residue was poured into water (50 mL) and stirred for 30 minutes. The precipitates were filtered and washed with cold water to give the product 168 as a white solid at a yield of 83%.

N'-[(cyclopropylcarbonyl)oxy]-4-(1,3-dioxolan-2-yl)benzenecarboximidamide (Compound 169)

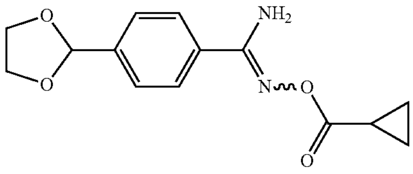 [SMILES: NC(=NOC(=O)C1CC1)c1ccc(C2OCCO2)cc1]

To the suspension of the Compound 168 (1.8 g, 8.65 mmol) in DCM (100 mL), pyridine (1.4 mL, 17.30 mmol) and cyclopropanecarbonyl chloride (0.02 mL, 11.20 mmol) were added dropwise under nitrogen at room temperature. The reaction mixture was stirred at room temperature for 4 hours and then partitioned between DCM and water. The organic phases were collected, washed with brine, dried over sodium sulfate, filtered and concentrated under reduced pressure. The crude residue was purified by column chromatography on silica gel using DCM/methanol (9/1) as eluent to give the product 169 as a white solid at a yield of 60%.

5-cyclopropyl-3-[4-(1,3-dioxolan-2-yl)phenyl]-1,2,4-oxadiazole (Compound 170)

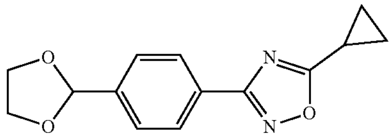 [SMILES: c1cc(C2OCCO2)ccc1-c1noc(C2CC2)n1]

The starting material 169 (1.1 g, 3.98 mmol) was dissolved in toluene (40 mL). The reaction mixture was refluxed for 15 hours and then cooled to room temperature. After removing the solvent under reduced pressure, the crude residue was purified by column chromatography on silica gel using EA/hexane (1/4) as eluent to give the product 170 as a white solid at a yield of 70%.

4-(5-cyclopropyl-1,2,4-oxadiazol-3-yl)benzaldehyde (Compound 171)

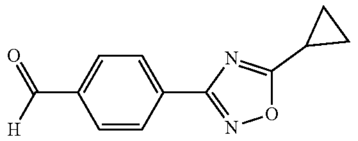 [SMILES: O=Cc1ccc(-c2noc(C3CC3)n2)cc1]

To the solution of the Compound 170 (1.2 g, 4.64 mmol) in THF/$H_2O$ (4/1, 30 mL), the con. HCl was added dropwise. The reaction mixture was stirred at 65° C. for 6 hours and then cooled to room temperature. The reaction mixture was partitioned between DCM and water. The organic phases were collected, washed with brine, dried over sodium sulfate, filtered and concentrated under reduced pressure. The crude residue was purified by column chromatography on silica gel using EA/hexane (1/9) as eluent to give the product 171 as a white solid at a yield of 97%.

(1H-benzimidazol-5-ylamino)[4-(5-cyclopropyl-1,2,4-oxadiazol-3-yl)phenyl]acetonitrile (Compound 172)

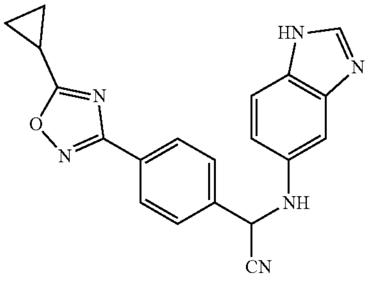 [SMILES: N#CC(Nc1ccc2[nH]cnc2c1)c1ccc(-c2noc(C3CC3)n2)cc1]

The (1H-benzimidazol-5-ylamino)[4-(5-cyclopropyl-1,2,4-oxadiazol-3-yl)phenyl]-acetonitrile 172 was prepared from the addition of 1H-benzimidazol-5-amine 121, TMSCN and Compound 171. The procedures were the same as the synthesis of Compound 122a. The product 172 was obtained as a pale-yellow solid at a yield of 86%.

$N^1$-(1H-benzimidazol-5-yl)-1-[4-(5-cyclopropyl-1,2,4-oxadiazol-3-yl)phenyl]ethane-1,2-diamine (Compound 173)

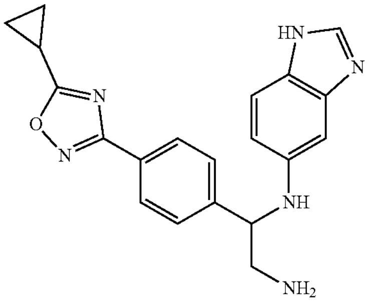

The $N^1$-(1H-benzimidazol-5-yl)-1-[4-(5-cyclopropyl-1,2,4-oxadiazol-3-yl)phenyl]ethane-1,2-diamine 173 was prepared from the hydrogenation of Compound 172 with Pd/C as catalyst. The procedures were the same as the synthesis of Compound 123a. The product 173 was obtained as a yellow viscous liquid at a yield of 55%.

1-(1H-benzimidazol-5-yl)-5-[4-(5-cyclopropyl-1,2,4-oxadiazol-3-yl)phenyl]imidazolidin-2-one (Compound 18)

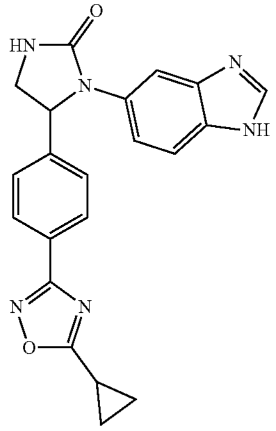 [SMILES: O=C1NCC(c2ccc(-c3noc(C4CC4)n3)cc2)N1c1ccc2[nH]cnc2c1]

The 1-(1H-benzimidazol-5-yl)-5-[4-(5-cyclopropyl-1,2,4-oxadiazol-3-yl)phenyl]-imidazolidin-2-one (Compound 18) was prepared from the cycloaddition of 1,1'-carbonyl diimidazole and Compound 173. The procedures were the same as the synthesis of Compound 1. The product (Compound 18) was obtained as a white solid at a yield of 68%. $^1$H NMR (300 MHz, DMSO-$d_6$) δ 1.12-1.19 (m, 2H), 1.21-1.28 (m, 2H), 2.31-2.38 (m, 1H), 3.13 (dd, 1H, J=6.3, 8.7 Hz), 3.89 (dd, 1H, J=8.7, 9.0 Hz), 5.60 (dd, 1H, J=6.3, 9.0 Hz), 6.98-7.03 (m, 1H), 7.19 (br. s, 1H), 7.35-7.59 (m, 4H), 7.88 (d, 2H, J=7.8 Hz), 8.07 (s, 1H), 12.23 (s, 1H); LC/MS (ESI) m/z: 387.1 $[M+H]^+$.

4-(3-cyclopropyl-1,2-oxazol-5-yl)benzaldehyde (Compound 177)

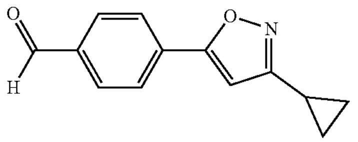

The cyclopropanecarboxaldehyde 174 (1.0 g, 14.26 mmol), hydroxylamine hydrochloride (0.99 g, 14.26 mmol) and potassium carbonate (2.17 g, 15.68 mmol) were dissolved in $H_2O$ (25 mL). The reaction mixture was stirred at 85° C. for 3 hours and then cooled to room temperature. The reaction mixture was partitioned between ether and water. The organic phases were collected, washed with brine, dried over sodium sulfate, filtered and concentrated under reduced pressure. The crude product 175 was used in next step without any further purification. To the solution of Compound 175 and NCS (1.9 g, 14.26 mmol) in DMF (30 mL), the catalytic amount of pyridine was added under argon. The reaction mixture was stirred at room temperature for 2 hours. After cooling to 0° C., 4-ethynylbenzaldehyde 176 (1.9 g, 14.26 mmol) and triethylamine (3 mL) were added. The reaction mixture was continuously stirred at room temperature for 3 hours. The reaction mixture was partitioned between EA and water. The organic phases were collected, washed with brine, dried over sodium sulfate, filtered and concentrated under reduced pressure. The crude residue was purified by column chromatography on silica gel using EA/hexane (1/8) as eluent to give the product 177 as a yellow solid at overall yield of 54%.

(1H-benzimidazol-5-ylamino)[4-(5-cyclopropyl-1,2-oxazol-3-yl)phenyl]acetonitrile (Compound 178)

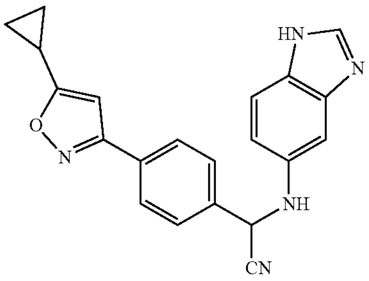 [SMILES: N#CC(Nc1ccc2[nH]cnc2c1)c1ccc(-c2cc(C3CC3)on2)cc1]

The (1H-benzimidazol-5-ylamino)[4-(5-cyclopropyl-1,2-oxazol-3-yl)phenyl]acetonitrile 178 was prepared from the addition of 1H-benzimidazol-5-amine 121, TMSCN and Compound 177. The procedures were the same as the synthesis of Compound 122a. The product 178 was obtained as a pale-yellow solid at a yield of 83%.

$N^1$-(1H-benzimidazol-5-yl)-1-[4-(5-cyclopropyl-1,2-oxazol-3-yl)phenyl]ethane-1,2-diamine (Compound 179)

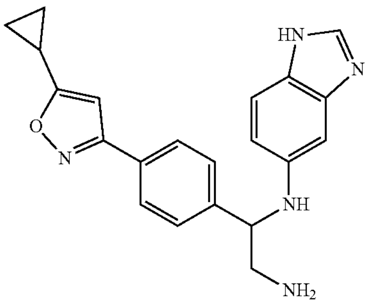 [SMILES: NCC(Nc1ccc2[nH]cnc2c1)c1ccc(-c2cc(C3CC3)on2)cc1]

The $N^1$-(1H-benzimidazol-5-yl)-1-[4-(5-cyclopropyl-1,2-oxazol-3-yl)phenyl]ethane-1,2-diamine 179 was prepared from the hydrogenation of Compound 178 with Pd/C as catalyst. The procedures were the same as the synthesis of Compound 123a. The product 179 was obtained as a yellow viscous liquid at a yield of 49%.

1-(1H-benzimidazol-5-yl)-5-[4-(5-cyclopropyl-1,2-oxazol-3-yl)phenyl]imidazolidin-2-one (Compound 19)

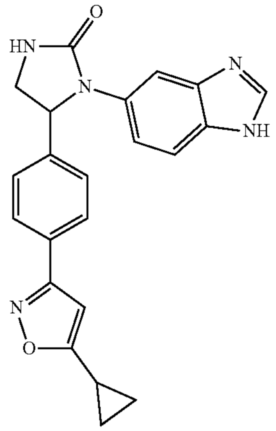 [SMILES: O=C1NCC(c2ccc(-c3cc(C4CC4)on3)cc2)N1c1ccc2[nH]cnc2c1]

The 1-(1H-benzimidazol-5-yl)-5-[4-(5-cyclopropyl-1,2-oxazol-3-yl)phenyl]imidazolidin-2-one (Compound 19) was prepared from the cycloaddition of 1,1'-carbonyl diimidazole and Compound 179. The procedures were the same as the synthesis of Compound 1. The product (Compound 19) was obtained as a white solid at a yield of 58%. $^1$H NMR (400 MHz, DMSO-$d_6$) δ 0.75-0.79 (m, 2H), 0.99-1.04 (m, 2H), 1.98-2.02 (m, 1H), 3.13 (dd, 1H, J=6.3, 9.0 Hz), 3.88 (dd, 1H, J=8.7, 9.0 Hz), 5.59 (dd, 1H, J=6.3, 8.7 Hz), 6.68 (s, 1H), 7.01 (s, 1H), 7.26 (d, 1H, J=8.4 Hz), 7.40 (d, 1H, J=8.4 Hz), 7.49 (d, 2H, J=7.8 Hz), 7.56 (s, 1H), 7.72 (d, 2H, J=7.8 Hz), 7.79 (s, 1H), 8.08 (s, 1H); LC/MS (ESI) m/z: 386.2 $[M+H]^+$.

4-(2H-tetrazol-5-yl)benzaldehyde hydrochloride (Compound 180)

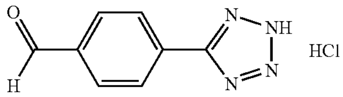

To the solution of 4-formylbenzonitrile 166 (1.31 g, 10.0 mmol) in DMF (10 mL), sodium azide (0.72 g, 11 mmol) and ammonium chloride (0.14 g, 2.5 mmol) were added under nitrogen. The reaction mixture was refluxed overnight and then cooled to room temperature. The reaction mixture was diluted with water and extracted with DCM. The aqueous phase was chilled in ice and acidified by adding 1N $HCl_{(aq)}$. After filtering, the precipitates were washed with water and ether to obtain the product 180 as a yellow solid at a yield of 94%.

4-(2-propyl-2H-tetrazol-5-yl)benzaldehyde (Compound 181a)

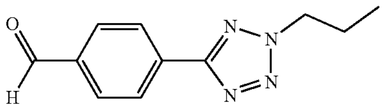 [SMILES: CCCn1nnc(-c2ccc(C=O)cc2)n1]

To the suspension of the Compound 180 (2.1 g, 10.0 mmol) in acetonitrile (20 mL), potassium carbonate (2.76 g, 20 mmol) and 1-bromopropane (2.46 g, 20 mmol) were added under nitrogen. The reaction mixture was stirred at 50° C. overnight and then cooled to room temperature. The reaction mixture was partitioned between EA and water. The organic phases were collected, washed with brine, dried over sodium sulfate, filtered and concentrated under reduced pressure. The crude residue was purified by column chromatography on silica gel using EA/hexane (1/4) as eluent to give the product 181a as a yellow solid at a yield of 76%.

4-[2-(propan-2-yl)-2H-tetrazol-5-yl]benzaldehyde (Compound 181b)

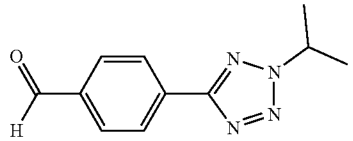 [SMILES: CC(C)n1nnc(-c2ccc(C=O)cc2)n1]

Isopropanol (1.2 g, 20.0 mmol) was added to the solution of the Compound 180 (2.1 g, 10.0 mmol) in trifluoromethanesulfonic acid (20 mL) under nitrogen. The reaction mixture was stirred at room temperature for an hour. The reaction mixture was poured into water and treated with sat. $NaHCO_{3(aq)}$ until pH=8-9. The mixture was partitioned between DCM and water. The organic phases were collected, washed with brine, dried over sodium sulfate, filtered and concentrated under reduced pressure. The crude residue was purified by column chromatography on silica gel using EA/hexane (1/4) as eluent to give the product 181b as a yellow solid at a yield of 54%.

(1H-benzimidazol-5-ylamino)[4-(2-propyl-2H-tetrazol-5-yl)phenyl]acetonitrile (Compound 182a)

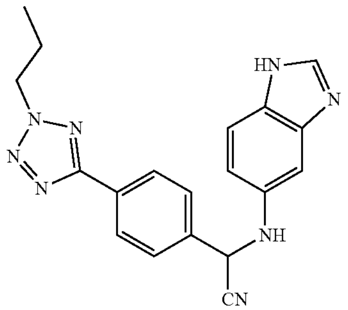 [SMILES: CCCn1nnc(-c2ccc(C(C#N)Nc3ccc4[nH]cnc4c3)cc2)n1]

The (1H-benzimidazol-5-ylamino)[4-(2-propyl-2H-tetrazol-5-yl)phenyl]acetonitrile 182a was prepared from the addition of 1H-benzimidazol-5-amine 121, TMSCN and Compound 181a. The procedures were the same as the synthesis of Compound 122a. The product 182a was obtained as a pale-yellow solid at a yield of 86%.

(1H-benzimidazol-5-ylamino){4-[2-(propan-2-yl)-2H-tetrazol-5-yl]phenyl}acetonitrile (Compound 182b)

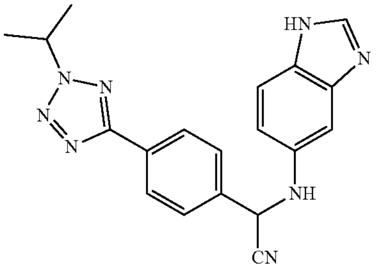 [SMILES: CC(C)n1nnc(-c2ccc(C(C#N)Nc3ccc4[nH]cnc4c3)cc2)n1]

The (1H-benzimidazol-5-ylamino) {4-[2-(propan-2-yl)-2H-tetrazol-5-yl]phenyl}-acetonitrile 182b was prepared from the addition of 1H-benzimidazol-5-amine 121, TMSCN and Compound 181b. The procedures were the same as the synthesis of Compound 122a. The product 182b was obtained as a pale-yellow solid at a yield of 81%.

$N^1$-(1H-benzimidazol-5-yl)-1-[4-(2-propyl-2H-tetrazol-5-yl)phenyl]ethane-1,2-diamine (Compound 183a)

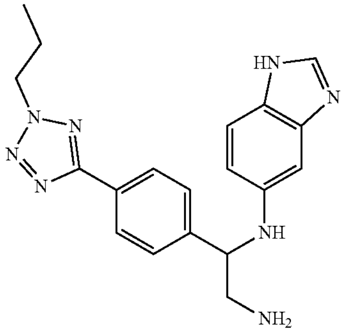 [SMILES: CCCn1nnc(-c2ccc(C(CN)Nc3ccc4[nH]cnc4c3)cc2)n1]

The $N^1$-(1H-benzimidazol-5-yl)-1-[4-(2-propyl-2H-tetrazol-5-yl)phenyl]ethane-1,2-diamine 183a was prepared from the hydrogenation of Compound 182a with Pd/C as catalyst. The procedures were the same as the synthesis of Compound 123a. The product 183a was obtained as a yellow viscous liquid at a yield of 50%.

N[1]-(1H-benzimidazol-5-yl)-1-{4-[2-(propan-2-yl)-2H-tetrazol-5-yl]phenyl}ethane-1,2-diamine (Compound 183b)

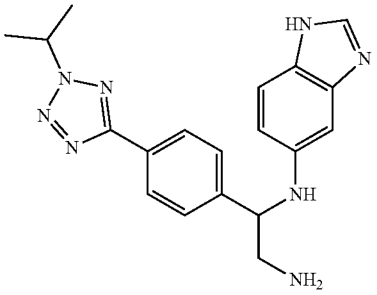 [SMILES: CC(C)n1nnc(-c2ccc(C(CN)Nc3ccc4[nH]cnc4c3)cc2)n1]

The N[1]-(1H-benzimidazol-5-yl)-1-{4-[2-(propan-2-yl)-2H-tetrazol-5-yl]phenyl}ethane-1,2-diamine 183b was prepared from the hydrogenation of Compound 182b with Pd/C as catalyst. The procedures were the same as the synthesis of Compound 123a. The product 183b was obtained as a yellow viscous liquid at a yield of 45%.

1-(1H-benzimidazol-5-yl)-5-[4-(2-propyl-2H-tetrazol-5-yl)phenyl]imidazolidin-2-one (Compound 20)

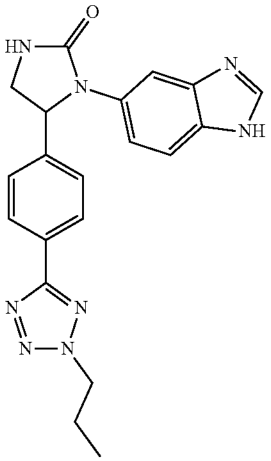 [SMILES: CCCn1nnc(-c2ccc(C3CNC(=O)N3c3ccc4[nH]cnc4c3)cc2)n1]

The 1-(1H-benzimidazol-5-yl)-5-[4-(2-propyl-2H-tetrazol-5-yl)phenyl]imidazolidin-2-one (Compound 20) was prepared from the cycloaddition of 1,1'-carbonyl diimidazole and Compound 183a. The procedures were the same as the synthesis of Compound 1. The product (Compound 20) was obtained as a white solid at a yield of 60%. $^1$H NMR (300 MHz, DMSO-$d_6$) δ 0.83 (t, 3H, J=7.2 Hz), 1.87-1.99 (m, 2H), 3.14 (dd, 1H, J=6.3, 8.7 Hz), 3.89 (dd, 1H, J=8.7, 9.0 Hz), 4.64 (t, 2H, J=7.2 Hz), 5.60 (dd, 1H, J=6.3, 9.0 Hz), 7.01 (s, 1H), 7.26 (d, 1H, J=8.9 Hz), 7.39 (d, 1H, J=8.9 Hz), 7.52-7.57 (m, 3H), 7.98 (d, 2H, J=8.4 Hz), 8.07 (s, 1H), 12.21 (s, 1H); LC/MS (ESI) m/z: 389.2 $[M+H]^+$.

1-(1H-benzimidazol-5-yl)-5-{4-[2-(propan-2-yl)-2H-tetrazol-5-yl]phenyl}imidazolidin-2-one (Compound 21)

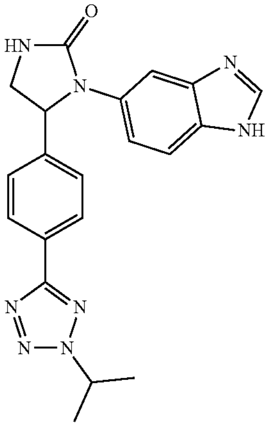 [SMILES: CC(C)n1nnc(-c2ccc(C3CNC(=O)N3c3ccc4[nH]cnc4c3)cc2)n1]

The 1-(1H-benzimidazol-5-yl)-5-{4-[2-(propan-2-yl)-2H-tetrazol-5-yl]phenyl}-imidazolidin-2-one (Compound 21) was prepared from the cycloaddition of 1,1'-carbonyl diimidazole and Compound 183b. The procedures were the same as the synthesis of Compound 1. The product (Compound 21) was obtained as a white solid at a yield of 62%. $^1$H NMR (400 MHz, DMSO-$d_6$) δ 1.56 (d, 6H, J=6.4 Hz), 3.14 (dd, 1H, J=6.4, 8.8 Hz), 3.89 (dd, 1H, J=8.8, 9.2 Hz), 5.09-5.15 (m, 1H), 5.60 (dd, 1H, J=6.4, 9.2 Hz), 7.04 (s, 1H), 7.26 (d, 1H, J=7.6 Hz), 7.39 (d, 1H, J=8.8 Hz), 7.52-7.57 (m, 3H), 7.97 (d, 2H, J=8.4 Hz), 8.07 (s, 1H), 12.25 (s, 1H); LC/MS (ESI) m/z: 389.2 $[M+H]^+$.

3-fluoro-4-(thiophen-2-yl)benzaldehyde (Compound 152b)

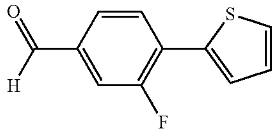

A mixture of tributyl(thiophen-2-yl)stannane 151 (6.62 g, 17.7 mmol), 4-bromo-3-fluorobenzaldehyde 138b (3.0 g, 14.8 mmol) and $Pd(PPh_3)_4$ (0.51 g, 0.43 mmol) in toluene (160 mL) was refluxed for 16 hours. After cooling to room temperature, the solvent was removed under reduced pressure. The residue was diluted with dichloromethane and filtered through celite. The organic phase was washed with water, dried over sodium sulfate, filtered and concentrated. The crude product was purified by column chromatography on silica gel using dichloromethane/hexane (1/9) as eluent. The product 152b was obtained as a pale-yellow solid at a yield of 70%.

2-fluoro-4-(thiophen-2-yl)benzaldehyde (Compound 152c)

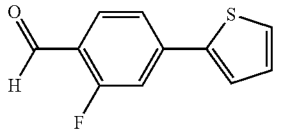 [SMILES: O=Cc1ccc(-c2cccs2)cc1F]

The 2-fluoro-4-(thiophen-2-yl)benzaldehyde 152c was prepared from the Suzuki-coupling of 4-bromo-2-fluorobenzaldehyde 138c and tributyl(thiophen-2-yl)stannane 151 using $Pd(PPh_3)_4$ as a catalyst. The procedures were the same as the synthesis of the Compound 152b. The product 152c was obtained as a pale-yellow solid at a yield of 68%.

2,6-difluoro-4-(thiophen-2-yl)benzaldehyde (Compound 152d)

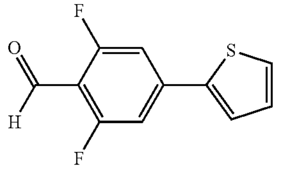 [SMILES: O=Cc1c(F)cc(-c2cccs2)cc1F]

The 2,6-difluoro-4-(thiophen-2-yl)benzaldehyde 152d was prepared from the Suzuki-coupling of 4-bromo-2,6-difluorobenzaldehyde 138d and tributyl(thiophen-2-yl)stannane 151 using $Pd(PPh_3)_4$ as a catalyst. The procedures were the same as the synthesis of the Compound 152b. The product 152d was obtained as a pale-yellow solid at a yield of 56%.

3-fluoro-4-(5-iodothiophen-2-yl)benzaldehyde (Compound 153b)

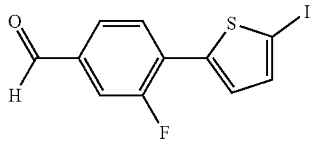 [SMILES: O=Cc1ccc(-c2ccc(I)s2)c(F)c1]

The 3-fluoro-4-(5-iodothiophen-2-yl)benzaldehyde 153b was prepared from the selective iodination of the Compound 152b using N-iodosuccinimide. The procedures were the same as the synthesis of the Compound 153a. The product 153b was obtained as a yellow-green solid at a yield of 77%.

2-fluoro-4-(5-iodothiophen-2-yl)benzaldehyde (Compound 153c)

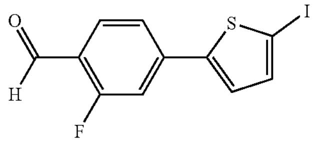 [SMILES: O=Cc1ccc(-c2ccc(I)s2)cc1F]

The 2-fluoro-4-(5-iodothiophen-2-yl)benzaldehyde 153c was prepared from the selective iodination of the Compound 152c using N-iodosuccinimide. The procedures were the same as the synthesis of the Compound 153a. The product 153c was obtained as a yellow-green solid at a yield of 75%.

2,6-difluoro-4-(5-iodothiophen-2-yl)benzaldehyde (Compound 153d)

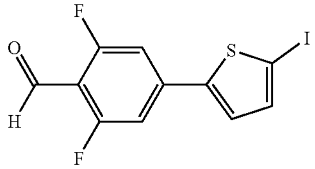 [SMILES: O=Cc1c(F)cc(-c2ccc(I)s2)cc1F]

The 2,6-difluoro-4-(5-iodothiophen-2-yl)benzaldehyde 153d was prepared from the selective iodination of the Compound 152d using N-iodosuccinimide. The procedures were the same as the synthesis of the Compound 153a. The product 153d was obtained as a yellow-green solid at a yield of 71%.

3-fluoro-4-[5-(trifluoromethyl)thiophen-2-yl]benzaldehyde (Compound 155b)

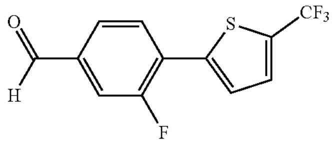 [SMILES: O=Cc1ccc(-c2ccc(C(F)(F)F)s2)c(F)c1]

The 3-fluoro-4-[5-(trifluoromethyl)thiophen-2-yl]benzaldehyde 155b was prepared from the trifluoromethylation of the Compound 153b that treated with methyl difluoro(fluorosulfonyl)acetate 154 and copper iodide. The procedures were the same as the synthesis of the Compound 155a. The product 155b was obtained as a yellow solid at a yield of 70%.

2-fluoro-4-[5-(trifluoromethyl)thiophen-2-yl]benzaldehyde (Compound 155c)

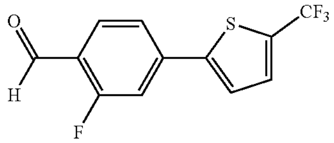 [SMILES: O=Cc1ccc(-c2ccc(C(F)(F)F)s2)cc1F]

The 2-fluoro-4-[5-(trifluoromethyl)thiophen-2-yl]benzaldehyde 155c was prepared from the trifluoromethylation of the Compound 153c that treated with methyl difluoro(fluorosulfonyl)acetate 154 and copper iodide. The procedures were the same as the synthesis of the Compound 155a. The product 155c was obtained as a yellow solid at a yield of 72%.

2,6-difluoro-4-[5-(trifluoromethyl)thiophen-2-yl] benzaldehyde (Compound 155d)

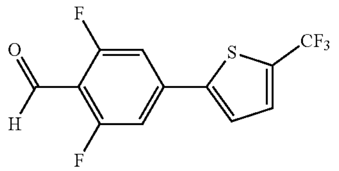 [SMILES: O=Cc1c(F)cc(-c2ccc(C(F)(F)F)s2)cc1F]

The 2,6-difluoro-4-[5-(trifluoromethyl)thiophen-2-yl] benzaldehyde 155d was prepared from the trifluoromethylation of the Compound 153d that treated with methyl difluoro(fluorosulfonyl)acetate 154 and copper iodide. The procedures were the same as the synthesis of the Compound 155a. The product 155d was obtained as a yellow solid at a yield of 67%.

1-(1H-benzimidazol-5-yl)-5-{3-fluoro-4-[5-(trifluoromethyl)thiophen-2-yl]phenyl}-imidazolidin-2-one (Compound 22)

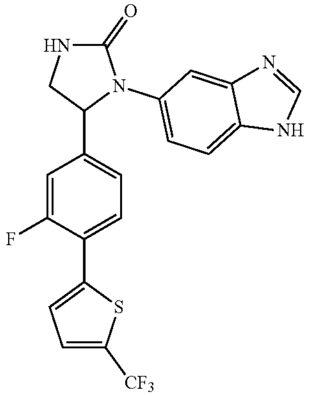

The 1-(1H-benzimidazol-5-yl)-5-{3-fluoro-4-[5-(trifluoromethyl)thiophen-2-yl]phenyl}-imidazolidin-2-one (Compound 22) was prepared from the Compound 155b in three-steps synthesis of imidazolidinone formation. The procedures were the same as the synthesis of Compound 1. The product (Compound 22) was obtained as a white solid at an overall yield of 27%. $^{1}H$ NMR (300 MHz, $CD_3OD$) δ 3.36 (dd, 1H, J=6.9, 9.0 Hz), 4.01 (dd, 1H, J=9.0, 9.6 Hz), 5.54 (dd, 1H, J=6.9, 9.6 Hz), 7.27-7.34 (m, 3H), 7.41 (d, 1H, J=3.9 Hz), 7.48-7.51 (m, 2H), 7.59-7.67 (m, 2H), 8.07 (s, 1H); LC/MS (ESI) m/z: 447.0 $[M+H]^+$.

1-(1H-benzimidazol-5-yl)-5-{2-fluoro-4-[5-(trifluoromethyl)thiophen-2-yl]phenyl}-imidazolidin-2-one (Compound 23)

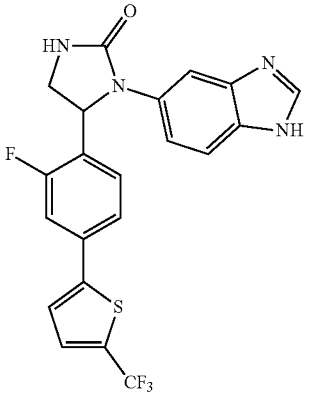

The 1-(1H-benzimidazol-5-yl)-5-{2-fluoro-4-[5-(trifluoromethyl)thiophen-2-yl]phenyl}-imidazolidin-2-one (Compound 23) was prepared from the Compound 155c in three-steps synthesis of imidazolidinone formation. The procedures were the same as the synthesis of Compound 1. The product (Compound 23) was obtained as a white solid at an overall yield of 25%. $^{1}H$ NMR (300 MHz, $CD_3OD$) δ 3.44 (dd, 1H, J=6.0, 9.0 Hz), 4.05 (dd, 1H, J=9.0, 9.3 Hz), 5.83 (dd, 1H, J=6.0, 9.3 Hz), 7.31-7.51 (m, 7H), 7.60 (d, 1H, J=2.1 Hz), 8.08 (s, 1H); LC/MS (ESI) m/z: 447.1 $[M+H]^+$.

1-(1H-benzimidazol-5-yl)-5-{2,6-difluoro-4-[5-(trifluoromethyl)thiophen-2-yl]phenyl}-imidazolidin-2-one (Compound 24)

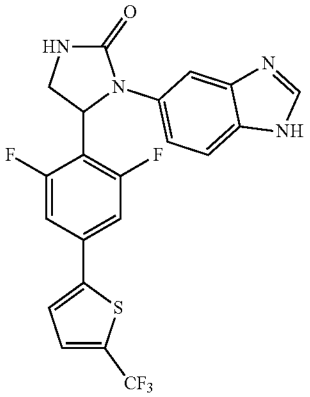

The 1-(1H-benzimidazol-5-yl)-5-{2,6-difluoro-4-[5-(trifluoromethyl)thiophen-2-yl]phenyl}imidazolidin-2-one (Compound 24) was prepared from the Compound 155d in three-steps synthesis of imidazolidinone formation. The procedures were the same as the synthesis of Compound 1. The product (Compound 24) was obtained as a white solid at an overall yield of 21%. $^{1}H$ NMR (300 MHz, $CD_3OD$) δ 3.65 (dd, 1H, J=7.2, 9.3 Hz), 4.05 (dd, 1H, J=9.3, 10.5 Hz), 6.01 (dd, 1H, J=7.2, 10.5 Hz), 7.23-7.28 (m, 3H), 7.39-7.41 (m, 1H), 7.46-7.50 (m, 2H), 7.57 (d, 1H, J=1.8 Hz), 8.08 (s, 1H); LC/MS (ESI) m/z: 465.1 $[M+H]^+$.

3-fluoro-4-[5-(trifluoromethyl)thiophen-3-yl]benzaldehyde (Compound 159d)

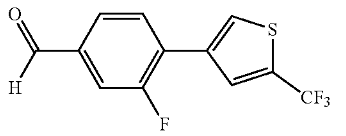 [SMILES: O=Cc1ccc(-c2csc(C(F)(F)F)c2)c(F)c1]

The 3-fluoro-4-[5-(trifluoromethyl)thiophen-3-yl]benzaldehyde 159d was prepared from the Suzuki-Miyaura coupling of (2-fluoro-4-formylphenyl)boronic acid 118d and 3-bromo-(5-trifluoromethyl)thiophene 158c. The procedures were the same as the synthesis of Compound 159a. The product 159d was obtained as a pale-yellow solid at a yield of 60%.

2-fluoro-4-[5-(trifluoromethyl)thiophen-3-yl]benzaldehyde (Compound 159e)

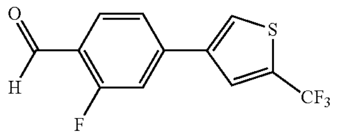 [SMILES: O=Cc1ccc(-c2csc(C(F)(F)F)c2)cc1F]

The 2-fluoro-4-[5-(trifluoromethyl)thiophen-3-yl]benzaldehyde 159e was prepared from the Suzuki-Miyaura coupling of (3-fluoro-4-formylphenyl)boronic acid 118e and 3-bromo-(5-trifluoromethyl)thiophene 158c. The procedures were the same as the synthesis of Compound 159a. The product 159e was obtained as a pale-yellow solid at a yield of 53%.

2,6-difluoro-4-[5-(trifluoromethyl)thiophen-3-yl]benzaldehyde (Compound 159f)

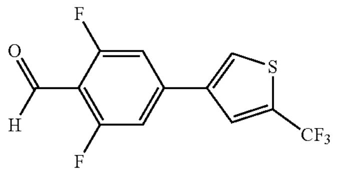 [SMILES: O=Cc1c(F)cc(-c2csc(C(F)(F)F)c2)cc1F]

The 2,6-difluoro-4-[5-(trifluoromethyl)thiophen-3-yl] benzaldehyde 159f was prepared from the Suzuki-Miyaura coupling of (3,5-difluoro-4-formylphenyl)boronic acid 118f and 3-bromo-(5-trifluoromethyl)thiophene 158c. The procedures were the same as the synthesis of Compound 159a. The product 159f was obtained as a pale-yellow solid at a yield of 33%. 2,3-difluoro-4-[5-(trifluoromethyl)thiophen-3-yl]benzaldehyde (Compound 159g)

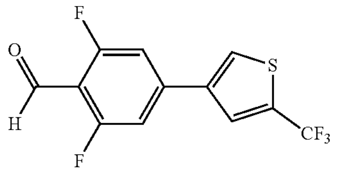 [SMILES: O=Cc1c(F)cc(-c2csc(C(F)(F)F)c2)cc1F]

The 2,3-difluoro-4-[5-(trifluoromethyl)thiophen-3-yl] benzaldehyde 159g was prepared from the Suzuki-Miyaura coupling of (2,3-difluoro-4-formylphenyl)boronic acid 118g and 3-bromo-(5-trifluoromethyl)thiophene 158c. The procedures were the same as the synthesis of Compound 159a. The product 159g was obtained as a pale-yellow solid at a yield of 29%.

1-(1H-benzimidazol-5-yl)-5-{3-fluoro-4-[5-(trifluoromethyl)thiophen-3-yl]phenyl}-imidazolidin-2-one (Compound 25)

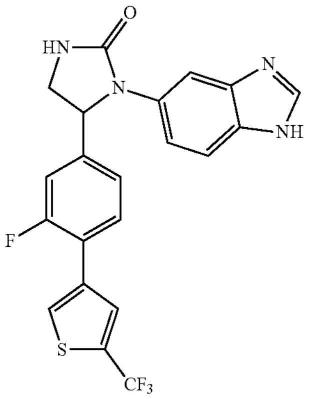 [SMILES: O=C1NCC(c2ccc(-c3csc(C(F)(F)F)c3)c(F)c2)N1c1ccc2[nH]cnc2c1]

The 1-(1H-benzimidazol-5-yl)-5-{3-fluoro-4-[5-(trifluoromethyl)thiophen-3-yl]phenyl}-imidazolidin-2-one (Compound 25) was prepared from the Compound 159d in three-steps synthesis of imidazolidinone formation. The procedures were the same as the synthesis of Compound 1. The product (Compound 25) was obtained as a white solid at an overall yield of 25%. $^1$H NMR (300 MHz, $CD_3OD$) δ 3.37 (dd, 1H, J=6.9, 9.0 Hz), 4.01 (dd, 1H, J=9.0, 9.3 Hz), 5.54 (dd, 1H, J=6.9, 9.3 Hz), 7.24-7.34 (m, 3H), 7.49 (d, 1H, J=8.7 Hz), 7.56-7.61 (m, 2H), 7.80 (d, 1H, J=0.9 Hz), 7.90 (s, 1H), 8.08 (s, 1H); LC/MS (ESI) m/z: 447.0 $[M+H]^+$.

1-(1H-benzimidazol-5-yl)-5-{2-fluoro-4-[5-(trifluoromethyl)thiophen-3-yl]phenyl}-imidazolidin-2-one (Compound 26)

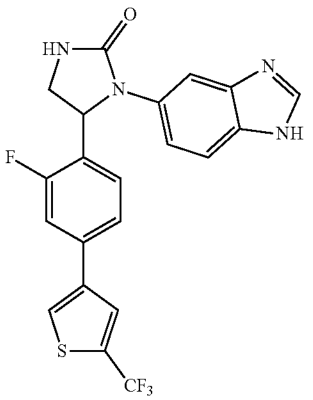 [SMILES: O=C1NCC(c2ccc(-c3csc(C(F)(F)F)c3)cc2F)N1c1ccc2[nH]cnc2c1]

The 1-(1H-benzimidazol-5-yl)-5-{2-fluoro-4-[5-(trifluoromethyl)thiophen-3-yl]phenyl}imidazolidin-2-one (Compound 26) was prepared from the Compound 159e in three-steps synthesis of imidazolidinone formation. The procedures were the same as the synthesis of Compound 1. The product (Compound 26) was obtained as a white solid at an overall yield of 27%. $^{1}$H NMR (300 MHz, $CD_3OD$) δ 3.44 (dd, 1H, J=6.3, 9.0 Hz), 4.05 (dd, 1H, J=9.0, 9.6 Hz), 5.82 (dd, 1H, J=6.3, 9.6 Hz), 7.33 (dd, 1H, J=1.2, 8.7 Hz), 7.42-7.50 (m, 4H), 7.60 (d, 1H, J=2.0 Hz), 7.86 (d, 1H, J=1.2 Hz), 7.93 (d, 1H, J=2.0 Hz), 8.07 (s, 1H); LC/MS (ESI) m/z: 447.0 $[M+H]^+$.

1-(1H-benzimidazol-5-yl)-5-{2,6-difluoro-4-[5-(trifluoromethyl)thiophen-3-yl]phenyl}-imidazolidin-2-one (Compound 27)

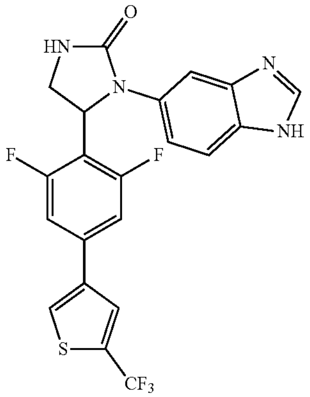 [SMILES: O=C1NCC(c2c(F)cc(-c3csc(C(F)(F)F)c3)cc2F)N1c1ccc2[nH]cnc2c1]

The 1-(1H-benzimidazol-5-yl)-5-{2,6-difluoro-4-[5-(trifluoromethyl)thiophen-3-yl]phenyl}imidazolidin-2-one (Compound 27) was prepared from the Compound 159f in three-steps synthesis of imidazolidinone formation. The procedures were the same as the synthesis of Compound 1. The product (Compound 27) was obtained as a white solid at an overall yield of 21%. $^{1}$H NMR (300 MHz, $CD_3OD$) δ 3.65 (dd, 1H, J=7.2, 9.3 Hz), 4.04 (dd, 1H, J=9.3, 10.2 Hz), 6.00 (dd, 1H, J=7.2, 10.2 Hz), 7.24-7.28 (m, 3H), 7.48 (d, 1H, J=8.7 Hz), 7.56 (d, 1H, J=1.8 Hz), 7.84 (s, 1H), 7.95 (d, 1H, J=1.8 Hz), 8.07 (s, 1H); LC/MS (ESI) m/z: 465.1 $[M+H]^+$.

1-(1H-benzimidazol-5-yl)-5-{2,3-difluoro-4-[5-(trifluoromethyl)thiophen-3-yl]phenyl}-imidazolidin-2-one (Compound 28)

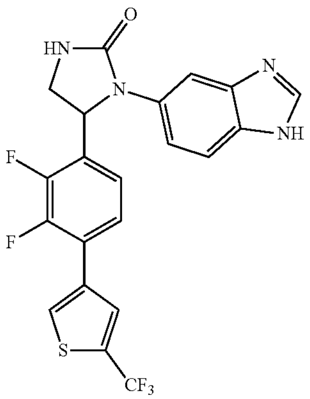 [SMILES: O=C1NCC(c2ccc(-c3csc(C(F)(F)F)c3)c(F)c2F)N1c1ccc2[nH]cnc2c1]

The 1-(1H-benzimidazol-5-yl)-5-{2,3-difluoro-4-[5-(trifluoromethyl)thiophen-3-yl]phenyl}imidazolidin-2-one (Compound 28) was prepared from the Compound 159g in three-steps synthesis of imidazolidinone formation. The procedures were the same as the synthesis of Compound 1. The product (Compound 28) was obtained as a white solid at an overall yield of 20%. $^{1}$H NMR (300 MHz, $CD_3OD$) δ 3.46 (dd, 1H, J=6.3, 9.0 Hz), 4.07 (dd, 1H, J=9.0, 9.6 Hz), 5.87 (dd, 1H, J=6.3, 9.6 Hz), 7.23-7.40 (m, 3H), 7.50 (d, 1H, J=8.4 Hz), 7.61 (d, 1H, J=1.8 Hz), 7.82 (s, 1H), 7.97 (s, 1H), 8.09 (s, 1H); LC/MS (ESI) m/z: 465.1 $[M+H]^+$.

4-(5-chlorothiophen-2-yl)benzaldehyde (Compound 140b)

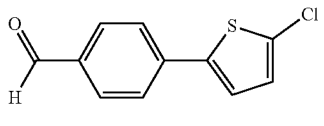 [SMILES: O=Cc1ccc(-c2ccc(Cl)s2)cc1]

The 4-(5-chlorothiophen-2-yl)benzaldehyde 140b was prepared from the Suzuki-coupling of 4-bromobenzaldehyde 138a and 2-chlorothiophene 139b. The procedures were the same as the synthesis of Compound 140a. The product 140b was obtained as a yellow solid at a yield of 74%.

4-(5-chlorothiophen-2-yl)-3-fluorobenzaldehyde (Compound 140c)

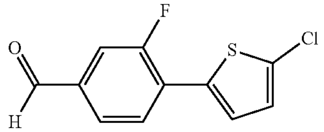 [SMILES: O=Cc1ccc(-c2ccc(Cl)s2)c(F)c1]

The 4-(5-chlorothiophen-2-yl)-3-fluorobenzaldehyde 140c was prepared from the Suzuki-coupling of 4-bromo-3-fluorobenzaldehyde 138b and 2-chlorothiophene 139b. The procedures were the same as the synthesis of Compound 140a. The product 140c was obtained as a yellow solid at a yield of 69%.

4-(5-chlorothiophen-2-yl)-2-fluorobenzaldehyde (Compound 140d)

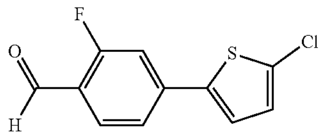 [SMILES: O=Cc1ccc(-c2ccc(Cl)s2)cc1F]

The 4-(5-chlorothiophen-2-yl)-2-fluorobenzaldehyde 140d was prepared from the Suzuki-coupling of 4-bromo-2-fluorobenzaldehyde 138c and 2-chlorothiophene 139b. The procedures were the same as the synthesis of Compound 140a. The product 140d was obtained as a yellow solid at a yield of 67%.

4-(5-chlorothiophen-2-yl)-2,6-difluorobenzaldehyde (Compound 140e)

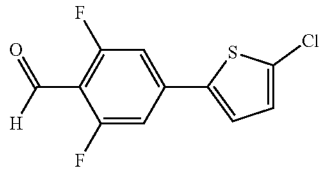 [SMILES: O=Cc1c(F)cc(-c2ccc(Cl)s2)cc1F]

The 4-(5-chlorothiophen-2-yl)-2,6-difluorobenzaldehyde 140e was prepared from the Suzuki-coupling of 4-bromo-2,6-fluorobenzaldehyde 138d and 2-chlorothiophene 139b. The procedures were the same as the synthesis of Compound 140a. The product 140e was obtained as a yellow solid at a yield of 60%.

1-(1H-benzimidazol-5-yl)-5-[4-(5-chlorothiophen-2-yl)phenyl]imidazolidin-2-one (Compound 29)

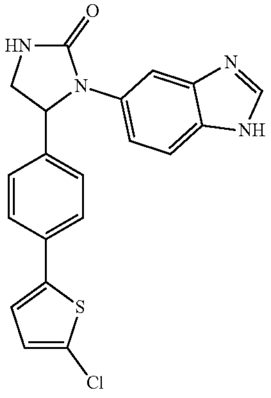 [SMILES: O=C1NCC(c2ccc(-c3ccc(Cl)s3)cc2)N1c1ccc2[nH]cnc2c1]

The 1-(1H-benzimidazol-5-yl)-5-[4-(5-chlorothiophen-2-yl)phenyl]imidazolidin-2-one (Compound 29) was prepared from the Compound 140b in three-steps synthesis of imidazolidinone formation. The procedures were the same as the synthesis of Compound 1. The product (Compound 29) was obtained as a white solid at an overall yield of 28%. $^1$H NMR (300 MHz, $CD_3OD$) δ 3.36 (dd, 1H, J=6.9, 9.0 Hz), 3.99 (dd, 1H, J=9.0, 9.3 Hz), 5.48 (dd, 1H, J=6.9, 9.3 Hz), 6.90 (d, 1H, J=3.9 Hz), 7.12 (d, 1H, J=3.9 Hz), 7.30 (d, 1H, J=9.0 Hz), 7.40 (d, 2H, J=8.4 Hz), 7.45-7.49 (m, 3H), 7.54 (d, 1H, J=2.1 Hz), 8.06 (s, 1H); LC/MS (ESI) m/z: 395.0 $[M+H]^+$.

1-(1H-benzimidazol-5-yl)-5-[4-(5-chlorothiophen-2-yl)-3-fluorophenyl]imidazolidin-2-one (Compound 30)

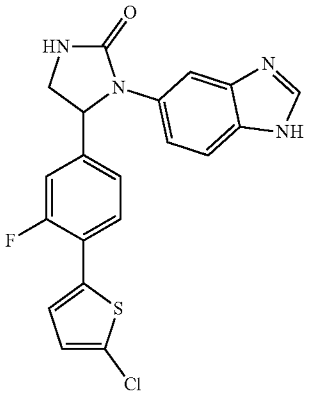 [SMILES: O=C1NCC(c2ccc(-c3ccc(Cl)s3)c(F)c2)N1c1ccc2[nH]cnc2c1]

The 1-(1H-benzimidazol-5-yl)-5-[4-(5-chlorothiophen-2-yl)-3-fluorophenyl]-imidazolidin-2-one (Compound 30) was prepared from the Compound 140c in three-steps synthesis of imidazolidinone formation. The procedures were the same as the synthesis of Compound 1. The product (Compound 30) was obtained as a white solid at an overall yield of 24%. $^1$H NMR (400 MHz, $CD_3OD$) δ 3.36 (dd, 1H, J=6.8, 9.2 Hz), 4.00 (dd, 1H, J=9.2, 9.2 Hz), 5.52 (dd, 1H, J=6.8, 9.2 Hz), 6.95 (d, 1H, J=4.0 Hz), 7.23-7.26 (m, 3H), 7.31 (d, 1H, J=8.0 Hz), 7.49 (d, 1H, J=8.4 Hz), 7.56-7.59 (m, 2H), 8.08 (s, 1H); LC/MS (ESI) m/z: 413.0 $[M+H]^+$.

1-(1H-benzimidazol-5-yl)-5-[4-(5-chlorothiophen-2-yl)-2-fluorophenyl]imidazolidin-2-one (Compound 31)

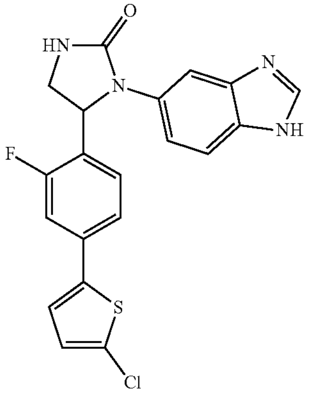 [SMILES: O=C1NCC(c2ccc(-c3ccc(Cl)s3)cc2F)N1c1ccc2[nH]cnc2c1]

The 1-(1H-benzimidazol-5-yl)-5-[4-(5-chlorothiophen-2-yl)-2-fluorophenyl]-imidazolidin-2-one (Compound 31) was prepared from the Compound 140d in three-steps synthesis of imidazolidinone formation. The procedures were the same as the synthesis of Compound 1. The product (Compound 31) was obtained as a white solid at an overall yield of 25%. $^1$H NMR (300 MHz, $CD_3OD$) δ 3.42 (dd, 1H, J=6.6, 9.0 Hz), 4.03 (dd, 1H, J=9.0, 9.6 Hz), 5.78 (dd, 1H, J=6.6, 9.6 Hz), 6.91 (d, 1H, J=4.2 Hz), 7.17 (d, 1H, J=4.2 Hz), 7.24-7.42 (m, 4H), 7.48 (d, 1H, J=8.4 Hz), 7.58 (d, 1H, J=1.8 Hz), 8.07 (s, 1H); LC/MS (ESI) m/z: 413.0 $[M+H]^+$.

1-(1H-benzimidazol-5-yl)-5-[4-(5-chlorothiophen-2-yl)-2,6-difluorophenyl]imidazolidin-2-one (Compound 32)

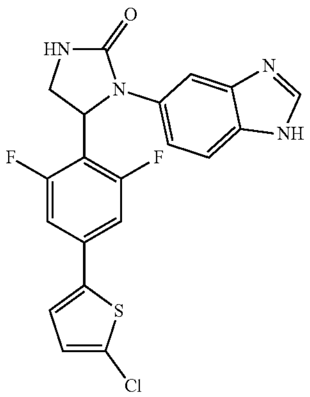 [SMILES: O=C1NCC(c2c(F)cc(-c3ccc(Cl)s3)cc2F)N1c1ccc2[nH]cnc2c1]

The 1-(1H-benzimidazol-5-yl)-5-[4-(5-chlorothiophen-2-yl)-2,6-difluorophenyl]-imidazolidin-2-one (Compound 32) was prepared from the Compound 140e in three-steps synthesis of imidazolidinone formation. The procedures were the same as the synthesis of Compound 1. The product (Compound 32) was obtained as a white solid at an overall yield of 20%.

(5R)-1-(1H-benzimidazol-5-yl)-5-{4-[5-(trifluoromethyl)thiophen-2-yl]phenyl}imidazolidin-2-one (Compound 33)

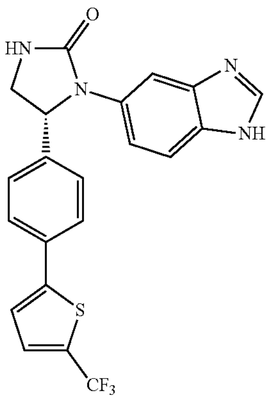

(5S)-1-(1H-benzimidazol-5-yl)-5-{4-[5-(trifluoromethyl)thiophen-2-yl]phenyl}imidazolidin-2-one (Compound 34)

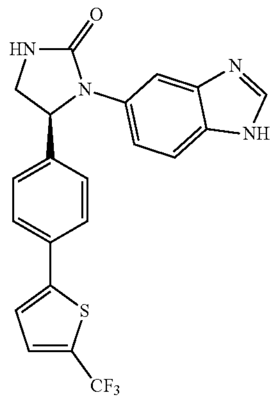

The enantiomers (Compounds 33 and 34) were separated from Compound 13 by HPLC using CHIRALPAK AD-H. The isomer fractions were respectively collected and the optical pure isomers (Compounds 33 and 34) were thus obtained by removing the solvent under reduced pressure. $^1H$ NMR (300 MHz, $CD_3OD$) δ 3.36 (dd, 1H, J=6.9, 9.3 Hz), 3.99 (dd, 1H, J=9.3, 9.3 Hz), 5.51 (dd, 1H, J=6.9, 9.3 Hz), 7.29-7.32 (m, 2H), 7.43-7.48 (m, 4H), 7.55-7.60 (m, 3H), 8.06 (s, 1H); LC/MS (ESI) m/z: 429.2 $[M+H]^+$.

(5R)-1-(1H-benzimidazol-5-yl)-5-{4-[5-(trifluoromethyl)thiophen-3-yl]phenyl}imidazolidin-2-one (Compound 35)

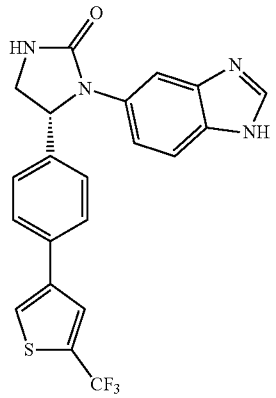 [SMILES: O=C1NC[C@@H](c2ccc(-c3csc(C(F)(F)F)c3)cc2)N1c1ccc2[nH]cnc2c1]

(5S)-1-(1H-benzimidazol-5-yl)-5-{4-[5-(trifluoromethyl)thiophen-3-yl]phenyl}imidazolidin-2-one (Compound 36)

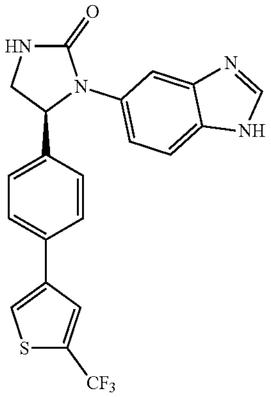 [SMILES: O=C1NC[C@H](c2ccc(-c3csc(C(F)(F)F)c3)cc2)N1c1ccc2[nH]cnc2c1]

The enantiomers (Compounds 35 and 36) were separated from Compound 16 by HPLC using CHIRALPAK AD-H. The isomer fractions were respectively collected and the optical pure isomers (Compounds 35 and 36) were thus obtained by removing the solvent under reduced pressure. $^1$H NMR (300 MHz, $CD_3OD$) δ 3.36 (dd, 1H, J=6.9, 9.0 Hz), 3.99 (dd, 1H, J=9.0, 9.3 Hz), 5.50 (dd, 1H, J=6.9, 9.3 Hz), 7.30 (d, 1H, J=8.1 Hz), 7.41-7.47 (m, 3H), 7.56-7.58 (m, 3H), 7.81 (s, 2H), 8.05 (s, 1H); LC/MS (ESI) m/z: 429.1 $[M+H]^+$.

1-{4-[4-(trifluoromethyl)-1,3-thiazol-2-yl]phenyl}ethanone (Compound 185)

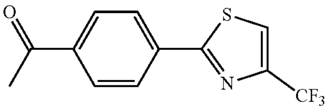 [SMILES: CC(=O)c1ccc(-c2nc(C(F)(F)F)cs2)cc1]

The 1-{4-[4-(trifluoromethyl)-1,3-thiazol-2-yl]phenyl}ethanone 185 was prepared from the Suzuki-coupling of (4-acetylphenyl)boronic acid 184 and Compound 119d. The procedures were the same as the synthesis of Compound 120a. The product 185 was obtained as a white solid at a yield of 83%. $^1$H NMR (400 MHz, $CDCl_3$) δ 2.65 (s, 3H), 7.82 (s, 1H), 8.05 (d, 2H, J=8.6 Hz), 8.09 (d, 2H, J=8.6 Hz); LC/MS (ESI) m/z: 271.7 $[M+H]^+$.

oxo{4-[4-(trifluoromethyl)-1,3-thiazol-2-yl]phenyl}acetaldehyde (Compound 186)

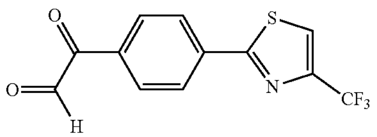 [SMILES: O=CC(=O)c1ccc(-c2nc(C(F)(F)F)cs2)cc1]

The Compound 185 (10.0 g, 36.86 mmol) and selenium dioxide (6.95 g, 62.67 mmol) were dissolved in $H_2O$/1,4-dioxane (8 mL/160 mL). The reaction mixture was stirred at 100° C. overnight. The black solid was filtered through celite and washed with ethyl acetate. The filtrate was concentrated under the reduced pressure. The residue was purified by column chromatography on silica gel using ethyl acetate/hexane (1/1) as eluent. The product 186 was obtained as a yellow solid at a yield of 100%.

1-(1H-benzimidazol-5-yl)-5-{4-[4-(trifluoromethyl)-1,3-thiazol-2-yl]phenyl}imidazolidine-2,4-dione (Compound 37)

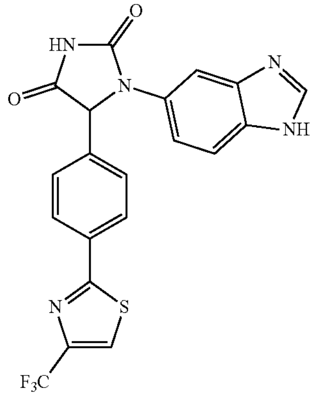 [SMILES: O=C1NC(=O)N(c2ccc3[nH]cnc3c2)C1c1ccc(-c2nc(C(F)(F)F)cs2)cc1]

The Compound 186 (9.0 g, 31.55 mmol) and 1-(1H-benzimidazol-6-yl)urea 187 (5.56 g, 31.55 mmol) were dissolved in HCl/AcOH (3 mL/120 mL). The reaction mixture was stirred at 120° C. overnight. After removing the solvents, the residue was treated with the excess ammonia in methanol at an ice-bath and stirred at room temperature for an hour. The precipitates were filtered and washed with ethyl acetate and water to get the pure product. The filtrate was concentrated and recrystallized in ethyl acetate. The white solids were collected as the product (Compound 37) at a yield of 45%. $^1$H NMR (300 MHz, DMSO-$d_6$) δ 6.13 (s, 1H), 7.27 (s, 1H), 7.43 (s, 1H), 7.55 (d, 2H, J=8.4 Hz), 7.71 (s, 1H), 7.94 (d, 2H, J=8.4 Hz), 8.16 (s, 1H), 8.52 (s, 1H), 11.43 (s, 1H), 12.41 (s, 1H); LC/MS (ESI) m/z: 444.2 $[M+H]^+$.

1-[4-(2-cyclopropyl-1,3-thiazol-4-yl)phenyl]ethanone (Compound 188)

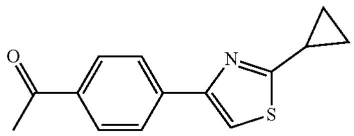 [SMILES: CC(=O)c1ccc(-c2csc(C3CC3)n2)cc1]

The 1-[4-(2-cyclopropyl-1,3-thiazol-4-yl)phenyl]ethanone 188 was prepared from the Suzuki-coupling of (4-acetylphenyl)boronic acid 184 and Compound 126 with Pd(dppf)$Cl_2$ as catalyst. The procedures were the same as the synthesis of Compound 127. The product 188 was obtained as a white solid at a yield of 57%. $^1$H NMR (400 MHz, $CDCl_3$) δ 1.09-1.16 (m, 4H), 2.32-2.37 (m, 1H), 2.60 (s, 3H), 7.35 (s, 1H), 7.94 (d, 2H, J=8.8 Hz), 7.97 (d, 2H, J=8.8 Hz); LC/MS (ESI) m/z: 244.1 $[M+H]^+$.

[4-(2-cyclopropyl-1,3-thiazol-4-yl)phenyl](oxo)acetaldehyde (Compound 189)

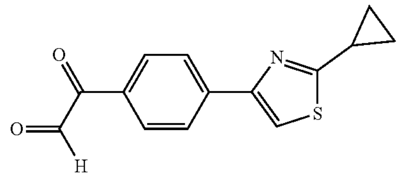 [SMILES: O=CC(=O)c1ccc(-c2csc(C3CC3)n2)cc1]

The [4-(2-cyclopropyl-1,3-thiazol-4-yl)phenyl](oxo)acetaldehyde 189 was prepared from the oxidation of Compound 188 by selenium dioxide. The procedures were the same as the synthesis of Compound 186. The product 189 was obtained as a yellow solid at a yield of 100%.

1-(1H-benzimidazol-5-yl)-5-[4-(2-cyclopropyl-1,3-thiazol-4-yl)phenyl]imidazolidine-2,4-dione (Compound 38)

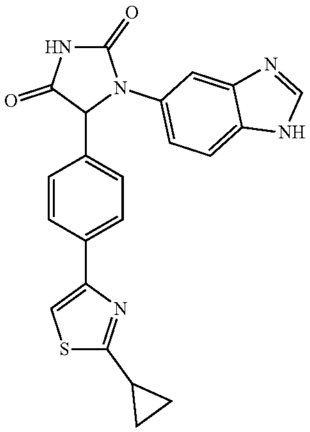 [SMILES: O=C1NC(=O)N(c2ccc3[nH]cnc3c2)C1c1ccc(-c2csc(C3CC3)n2)cc1]

The 1-(1H-benzimidazol-5-yl)-5-[4-(2-cyclopropyl-1,3-thiazol-4-yl)phenyl]-imidazolidine-2,4-dione (Compound 38) was prepared from the cycloaddition of 1-(1H-benzimidazol-6-yl)urea 187 and Compound 189. The procedures were the same as the synthesis of Compound 37. The product (Compound 38) was obtained as a white solid at a yield of 49%. $^1$H NMR (400 MHz, DMSO-$d_6$) δ 1.00-1.03 (m, 2H), 1.08-1.11 (m, 2H), 2.36-2.42 (m, 1H), 6.03 (s, 1H), 7.28 (s, 1H), 7.41 (d, 2H, J=8.0 Hz), 7.48 (s, 1H), 7.69 (s, 1H), 7.77 (s, 1H), 7.83 (d, 2H, J=8.0 Hz), 8.15 (s, 1H), 11.38 (s, 1H), 12.41 (s, 1H); LC/MS (ESI) m/z: 416.2 $[M+H]^+$.

1-[4-(2-cyclopropyl-1,3-thiazol-5-yl)phenyl]ethanone (Compound 190b)

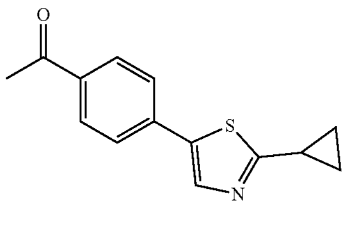 [SMILES: CC(=O)c1ccc(-c2cnc(C3CC3)s2)cc1]

To the solution of Compound 134b (0.23 g, 1.0 mmol) in anhydrous THF (4 mL), the methylmagnesium bromide in THF (1M, 2 mL) was added dropwise at 0° C. Then, the reaction mixture was stirred at room temperature overnight. The saturated aqueous solution of ammonium chloride was added to quench the reaction. The aqueous layer was extracted with ethyl acetate. The organic layers were collected, washed with brine, dried over sodium sulfate, filtered and concentrated under reduced pressure. The residue was purified by column chromatography on silica gel using ethyl acetate/hexane (1/4) as eluent. The product 190b was obtained as a yellow solid at a yield of 48%. $^1$H NMR (300 MHz, $CDCl_3$) δ 1.13-1.19 (m, 4H), 2.30-2.35 (m, 1H), 2.61 (s, 3H), 7.58 (d, 2H, J=8.0 Hz), 7.85 (s, 1H), 7.96 (d, 2H, J=8.0 Hz); LC/MS (ESI) m/z: 244.1 $[M+H]^+$.

1-{4-[2-(trifluoromethyl)-1,3-thiazol-5-yl]phenyl}ethanone (Compound 190c)

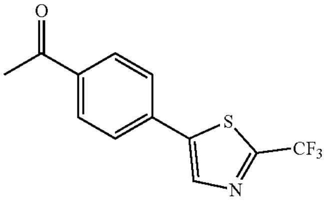 [SMILES: CC(=O)c1ccc(-c2cnc(C(F)(F)F)s2)cc1]

The 1-{4-[2-(trifluoromethyl)-1,3-thiazol-5-yl]phenyl}ethanone 190c was prepared from the methylation of Compound 134c. The procedures were the same as the synthesis of Compound 190b. The product 190c was obtained as a yellow solid at a yield of 49%. $^1$H NMR (400 MHz, $CDCl_3$) δ 2.64 (s, 3H), 7.69 (d, 2H, J=8.0 Hz), 8.04 (d, 2H, J=8.0 Hz), 8.17 (s, 1H); LC/MS (ESI) m/z: 271.7 $[M+H]^+$.

[4-(2-cyclopropyl-1,3-thiazol-5-yl)phenyl](oxo)acetaldehyde (Compound 191b)

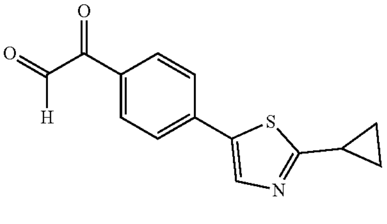 [SMILES: O=CC(=O)c1ccc(-c2cnc(C3CC3)s2)cc1]

The [4-(2-cyclopropyl-1,3-thiazol-5-yl)phenyl](oxo)acetaldehyde 191b was prepared from the oxidation of Compound 190b by selenium dioxide. The procedures were the same as the synthesis of Compound 186. The product 191b was obtained as a yellow solid at a yield of 100%.

oxo{4-[2-(trifluoromethyl)-1,3-thiazol-5-yl]phenyl}acetaldehyde (Compound 191c)

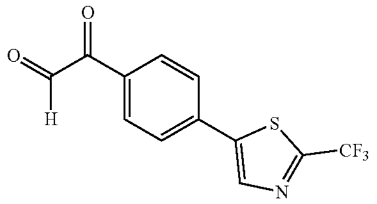 [SMILES: O=CC(=O)c1ccc(-c2cnc(C(F)(F)F)s2)cc1]

The oxo{4-[2-(trifluoromethyl)-1,3-thiazol-5-yl]phenyl}acetaldehyde 191c was prepared from the oxidation of Compound 190c by selenium dioxide. The procedures were the same as the synthesis of Compound 186. The product 191c was obtained as a yellow solid at a yield of 100%.

1-(1H-benzimidazol-5-yl)-5-[4-(2-cyclopropyl-1,3-thiazol-5-yl)phenyl]imidazolidine-2,4-dione (Compound 39)

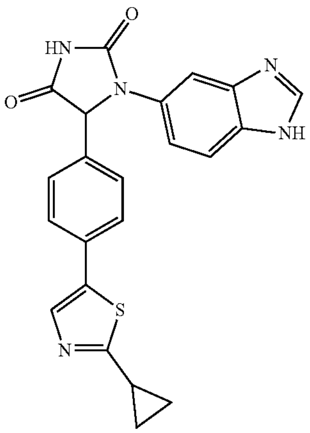 [SMILES: O=C1NC(=O)N(c2ccc3[nH]cnc3c2)C1c1ccc(-c2cnc(C3CC3)s2)cc1]

The 1-(1H-benzimidazol-5-yl)-5-[4-(2-cyclopropyl-1,3-thiazol-5-yl)phenyl]-imidazolidine-2,4-dione (Compound 39) was prepared from the cycloaddition of 1-(1H-benzimidazol-6-yl)urea 187 and Compound 191b. The procedures were the same as the synthesis of Compound 37. The product (Compound 39) was obtained as a white solid at a yield of 57%. $^1$H NMR (400 MHz, DMSO-$d_6$) δ 0.93-0.99 (m, 2H), 1.01-1.11 (m, 2H), 2.33-2.39 (m, 1H), 6.05 (s, 1H), 7.33 (d, 1H, J=8.6 Hz), 7.41 (d, 2H, J=8.0 Hz), 7.48 (d, 1H, J=8.6 Hz), 7.53 (d, 2H, J=8.0 Hz), 7.70 (d, 1H, J=1.2 Hz), 7.91 (s, 1H), 8.18 (s, 1H), 11.39 (s, 1H), 12.47 (s, 1H); LC/MS (ESI) m/z: 416.2 [M+H]$^+$.

1-(1H-benzimidazol-5-yl)-5-{4-[2-(trifluoromethyl)-1,3-thiazol-5-yl]phenyl}imidazolidine-2,4-dione (Compound 40)

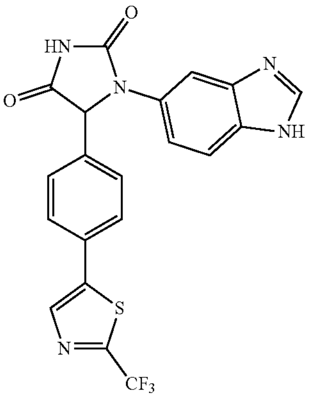 [SMILES: O=C1NC(=O)N(c2ccc3[nH]cnc3c2)C1c1ccc(-c2cnc(C(F)(F)F)s2)cc1]

The 1-(1H-benzimidazol-5-yl)-5-{4-[2-(trifluoromethyl)-1,3-thiazol-5-yl]phenyl}-imidazolidine-2,4-dione (Compound 40) was prepared from the cycloaddition of 1-(1H-benzimidazol-6-yl)urea 187 and Compound 191c. The procedures were the same as the synthesis of Compound 37. The product (Compound 40) was obtained as a white solid at a yield of 30%. $^1$H NMR (400 MHz, DMSO-$d_6$) δ 6.12 (s, 1H), 7.35 (s, 1H), 7.47-7.52 (m, 3H), 7.71-7.75 (m, 3H), 8.16 (s, 1H), 8.48 (s, 1H), 11.44 (s, 1H), 12.43 (s, 1H); LC/MS (ESI) m/z: 444.2 [M+H]$^+$.

1-[4-(2H-tetrazol-5-yl)phenyl]ethanone (Compound 192)

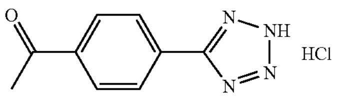

To the solution of 4-acetylbenzonitrile 143 (4.35 g, 30.0 mmol) in DMF (30 mL), sodium azide (2.15 g, 33 mmol) and ammonium chloride (0.40 g, 7.5 mmol) were added under nitrogen. The reaction mixture was refluxed overnight and then cooled to room temperature. The reaction mixture was diluted with water and extracted with DCM. The aqueous phase was chilled in ice and acidified by adding 1N $HCl_{(aq)}$. After filtering, the precipitates were washed with water and ether to obtain the product 192 as a yellow solid at a yield of 94%.

1-(1H-benzimidazol-5-yl)-5-[4-(2-methyl-2H-tetrazol-5-yl)phenyl]imidazolidine-2,4-dione (Compound 41)

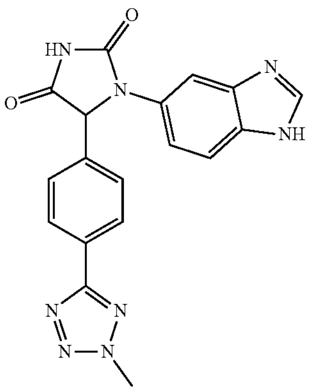 [SMILES: Cn1nnc(-c2ccc(C3C(=O)NC(=O)N3c3ccc4[nH]cnc4c3)cc2)n1]

The 1-(1H-benzimidazol-5-yl)-5-[4-(2-methyl-2H-tetrazol-5-yl)phenyl]imidazolidine-2,4-dione (Compound 41) was prepared from the cycloaddition of 1-(1H-benzimidazol-6-yl)urea 187 and Compound 194a. The procedures were the same as the synthesis of Compound 37. The product (Compound 41) was obtained as a white solid at a yield of 17%. $^1$H NMR (400 MHz, DMSO-$d_6$) δ 4.38 (s, 3H), 6.12 (s, 1H), 7.28 (br s, 1H), 7.47 (br s, 1H), 7.57 (d, 2H, J=8.4 Hz), 7.72 (s, 1H), 8.00 (d, 2H, J=8.4 Hz), 8.16 (s, 1H), 11.46 (br s, 1H), 12.44 (br s, 1H); LC/MS (ESI) m/z: 375.1 $[M+H]^+$.

1-(1H-benzimidazol-5-yl)-5-[4-(2-propyl-2H-tetrazol-5-yl)phenyl]imidazolidine-2,4-dione (Compound 42)

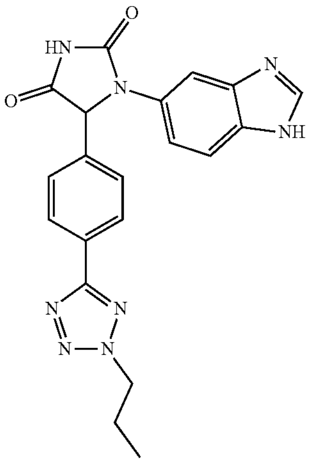 [SMILES: CCCn1nnc(-c2ccc(C3C(=O)NC(=O)N3c3ccc4[nH]cnc4c3)cc2)n1]

The 1-(1H-benzimidazol-5-yl)-5-[4-(2-propyl-2H-tetrazol-5-yl)phenyl]imidazolidine-2,4-dione (Compound 42) was prepared from the cycloaddition of 1-(1H-benzimidazol-6-yl)urea 187 and Compound 194b. The procedures were the same as the synthesis of Compound 37. The product (Compound 42) was obtained as a white solid at a yield of 33%. $^1$H NMR (300 MHz, DMSO-$d_6$) δ 0.84 (t, 3H, J=7.5 Hz), 1.87-1.99 (m, 2H), 4.65 (t, 2H, J=6.8 Hz), 6.12 (s, 1H), 7.34 (br s, 1H), 7.47 (br s, 1H), 7.57 (d, 2H, J=8.4 Hz), 7.71 (s, 1H), 8.00 (d, 2H, J=8.4 Hz), 8.15 (s, 1H), 11.43 (s, 1H), 12.41 (s, 1H); LC/MS (ESI) m/z: 403.2 $[M+H]^+$.

1-(1H-benzimidazol-5-yl)-5-{4-[2-(propan-2-yl)-2H-tetrazol-5-yl]phenyl}imidazolidine-2,4-dione (Compound 43)

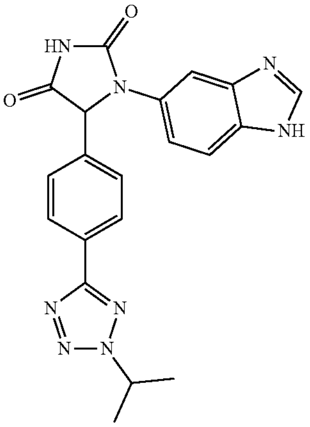 [SMILES: CC(C)n1nnc(-c2ccc(C3C(=O)NC(=O)N3c3ccc4[nH]cnc4c3)cc2)n1]

The 1-(1H-benzimidazol-5-yl)-5-{4-[2-(propan-2-yl)-2H-tetrazol-5-yl]phenyl}-imidazolidine-2,4-dione (Compound 43) was prepared from the cycloaddition of 1-(1H-benzimidazol-6-yl)urea 187 and Compound 194c. The procedures were the same as the synthesis of Compound 37. The product (Compound 43) was obtained as a white solid at a yield of 28%. $^1$H NMR (400 MHz, DMSO-$d_6$) δ 1.57 (d, 6H, J=6.4 Hz), 5.09-5.16 (m, 1H), 6.11 (s, 1H), 7.27 (br s, 1H), 7.42 (br s, 1H), 7.57 (d, 2H, J=8.4 Hz), 7.71 (s, 1H), 8.00 (d, 2H, J=8.4 Hz), 8.15 (s, 1H), 11.43 (s, 1H), 12.41 (s, 1H); LC/MS (ESI) m/z: 403.2 $[M+H]^+$.

1-(1H-benzimidazol-5-yl)-5-{4-[2-(2-methylpropyl)-2H-tetrazol-5-yl]phenyl}imidazolidine-2,4-dione (Compound 44)

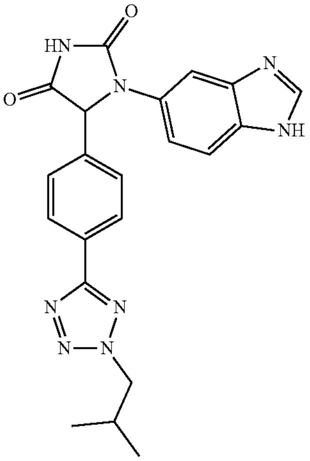 [SMILES: CC(C)Cn1nnc(-c2ccc(C3C(=O)NC(=O)N3c3ccc4[nH]cnc4c3)cc2)n1]

The 1-(1H-benzimidazol-5-yl)-5-{4-[2-(2-methylpropyl)-2H-tetrazol-5-yl]phenyl}-imidazolidine-2,4-dione (Compound 44) was prepared from the cycloaddition of 1-(1H- benzimidazol-6-yl)urea 187 and Compound 194d. The procedures were the same as the synthesis of Compound 37. The product (Compound 44) was obtained as a white solid at a yield of 34%. $^1$H NMR (400 MHz, DMSO-$d_6$) δ 0.86 (d, 6H, J=6.4 Hz), 2.22-2.29 (m, 1H), 4.53 (d, 2H, J=6.8 Hz), 6.12 (s, 1H), 7.28 (br s, 1H), 7.47 (br s, 1H), 7.57 (d, 2H, J=8.0 Hz), 7.72 (s, 1H), 8.01 (d, 2H, J=8.0 Hz), 8.16 (s, 1H), 11.45 (s, 1H), 12.42 (s, 1H); LC/MS (ESI) m/z: 417.2 [M+H]$^+$.

1-(1H-benzimidazol-5-yl)-5-{4-[2-(cyclopropylmethyl)-2H-tetrazol-5-yl]phenyl}-imidazolidine-2,4-dione (Compound 45)

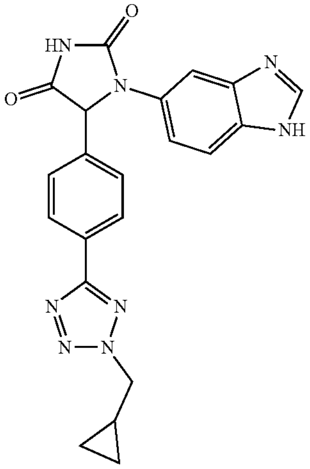 [SMILES: O=C1NC(=O)N(c2ccc3[nH]cnc3c2)C1c1ccc(-c2nnn(CC3CC3)n2)cc1]

The 1-(1H-benzimidazol-5-yl)-5-{4-[2-(cyclopropylmethyl)-2H-tetrazol-5-yl]phenyl}-imidazolidine-2,4-dione (Compound 45) was prepared from the cycloaddition of 1-(1H-benzimidazol-6-yl)urea 187 and Compound 194e. The procedures were the same as the synthesis of Compound 37. The product (Compound 45) was obtained as a white solid at a yield of 31%. $^1$H NMR (300 MHz, DMSO-$d_6$) δ 0.42-0.45 (m, 2H), 0.54-0.58 (m, 2H), 1.33-1.41 (m, 1H), 4.57 (d, 2H, J=7.2 Hz), 6.12 (s, 1H), 7.29 (br s, 1H), 7.46 (br s, 1H), 7.58 (d, 2H, J=8.4 Hz), 7.72 (s, 1H), 8.01 (d, 2H, J=8.4 Hz), 8.15 (s, 1H), 11.43 (s, 1H), 12.41 (s, 1H); LC/MS (ESI) m/z: 415.1 [M+H]$^+$.

1-(1H-benzimidazol-5-yl)-5-{4-[2-(2,2,2-trifluoroethyl)-2H-tetrazol-5-yl]phenyl}-imidazolidine-2,4-dione (Compound 46)

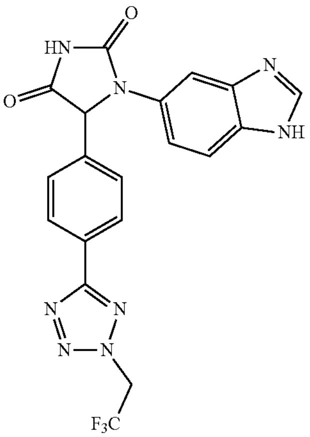 [SMILES: O=C1NC(=O)N(c2ccc3[nH]cnc3c2)C1c1ccc(-c2nnn(CC(F)(F)F)n2)cc1]

The 1-(1H-benzimidazol-5-yl)-5-{4-[2-(2,2,2-trifluoroethyl)-2H-tetrazol-5-yl]phenyl}-imidazolidine-2,4-dione (Compound 46) was prepared from the cycloaddition of 1-(1H-benzimidazol-6-yl)urea 187 and Compound 194f. The procedures were the same as the synthesis of Compound 37. The product (Compound 46) was obtained as a white solid at a yield of 36%. $^1$H NMR (300 MHz, DMSO-$d_6$) δ 6.01 (q, 2H, J=8.7 Hz), 6.15 (s, 1H), 7.36 (br s, 1H), 7.48 (br s, 1H), 7.61 (d, 2H, J=8.4 Hz), 7.73 (s, 1H), 8.04 (d, 2H, J=8.4 Hz), 8.17 (s, 1H), 11.49 (br s, 1H), 12.41 (br s, 1H); LC/MS (ESI) m/z: 443.2 [M+H]$^+$.

1-(1H-benzimidazol-5-yl)-5-{4-[2-(prop-2-yn-1-yl)-2H-tetrazol-5-yl]phenyl}imidazolidine-2,4-dione (Compound 47)

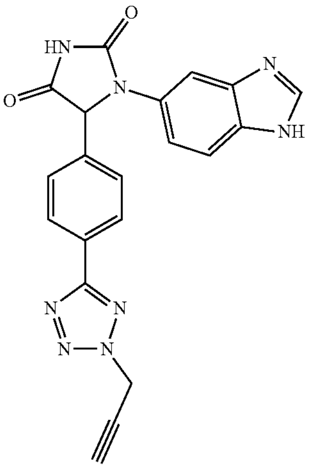 [SMILES: C#CCn1nnc(-c2ccc(C3C(=O)NC(=O)N3c3ccc4[nH]cnc4c3)cc2)n1]

The 1-(1H-benzimidazol-5-yl)-5-{4-[2-(prop-2-yn-1-yl)-2H-tetrazol-5-yl]phenyl}-imidazolidine-2,4-dione (Compound 47) was prepared from the cycloaddition of 1-(1H-benzimidazol-6-yl)urea 187 and Compound 194g. The procedures were the same as the synthesis of Compound 37. The product (Compound 47) was obtained as a white solid at a yield of 36%. $^1$H NMR (300 MHz, DMSO-$d_6$) δ 5.75 (d, 1H, J=1.5 Hz), 6.07 (d, 1H, J=6.6 Hz), 6.14 (s, 1H), 7.29 (br s, 1H), 7.47 (br s, 1H), 7.59 (d, 2H, J=8.0 Hz), 7.72 (s, 1H), 8.02 (d, 2H, J=8.0 Hz), 8.16 (s, 1H), 8.24 (dd, 1H, J=1.5, 6.6 Hz), 11.47 (br s, 1H), 12.44 (s, 1H); LC/MS (ESI) m/z: 399.1 $[M+H]^+$.

1-(1H-benzimidazol-5-yl)-5-{4-[2-(but-2-yn-1-yl)-2H-tetrazol-5-yl]phenyl}imidazolidine-2,4-dione (Compound 48)

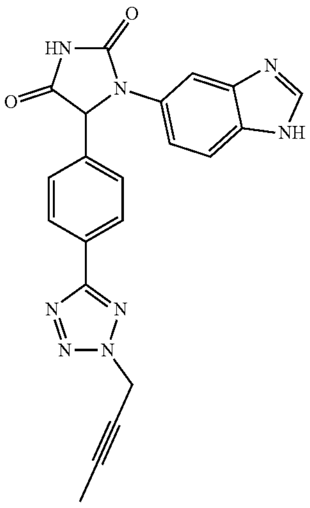 [SMILES: CC#CCn1nnc(-c2ccc(C3C(=O)NC(=O)N3c3ccc4[nH]cnc4c3)cc2)n1]

The 1-(1H-benzimidazol-5-yl)-5-{4-[2-(but-2-yn-1-yl)-2H-tetrazol-5-yl]phenyl}-imidazolidine-2,4-dione (Compound 48) was prepared from the cycloaddition of 1-(1H-benzimidazol-6-yl)urea 187 and Compound 194h. The procedures were the same as the synthesis of Compound 37. The product (Compound 48) was obtained as a white solid at a yield of 34%. $^1$H NMR (300 MHz, DMSO-$d_6$) δ 1.83 (s, 3H), 5.65 (d, 2H, J=1.8 Hz), 6.13 (s, 1H), 7.34 (d, 1H, J=6.6 Hz), 7.48 (d, 1H, J=8.7 Hz), 7.58 (d, 2H, J=7.8 Hz), 7.72 (s, 1H), 8.02 (d, 2H, J=7.8 Hz), 8.16 (s, 1H), 11.44 (s, 1H), 12.41 (s, 1H); LC/MS (ESI) m/z: 413.1 $[M+H]^+$.

1-(1H-benzimidazol-5-yl)-5-{4-[2-(pent-2-yn-1-yl)-2H-tetrazol-5-yl]phenyl}imidazolidine-2,4-dione (Compound 49)

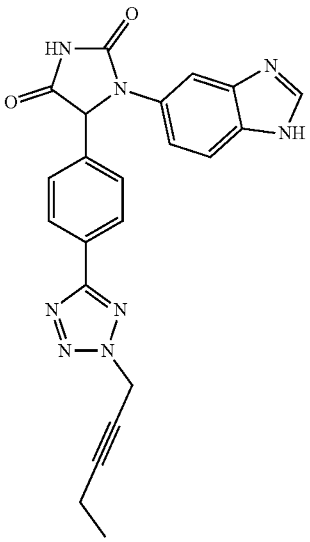 [SMILES: CCC#CCn1nnc(-c2ccc(C3C(=O)NC(=O)N3c3ccc4[nH]cnc4c3)cc2)n1]

The 1-(1H-benzimidazol-5-yl)-5-{4-[2-(pent-2-yn-1-yl)-2H-tetrazol-5-yl]phenyl}-imidazolidine-2,4-dione (Compound 49) was prepared from the cycloaddition of 1-(1H-benzimidazol-6-yl)urea 187 and Compound 194i. The procedures were the same as the synthesis of Compound 37. The product (Compound 49) was obtained as a white solid at a yield of 32%. $^1$H NMR (300 MHz, DMSO-$d_6$) δ 1.03 (t, 3H, J=7.5 Hz), 2.17-2.26 (m, 2H), 5.65 (t, 2H, J=2.1 Hz), 6.11 (s, 1H), 7.29 (br s, 1H), 7.46 (br s, 1H), 7.58 (d, 2H, J=8.4 Hz), 7.71 (s, 1H), 8.01 (d, 2H, J=8.4 Hz), 8.15 (s, 1H), 11.43 (br s, 1H), 12.42 (br s, 1H); LC/MS (ESI) m/z: 427.1 $[M+H]^+$.

1-(1H-benzimidazol-5-yl)-5-{4-[2-(4-chlorobenzyl)-2H-tetrazol-5-yl]phenyl}imidazolidine-2,4-dione (Compound 50)

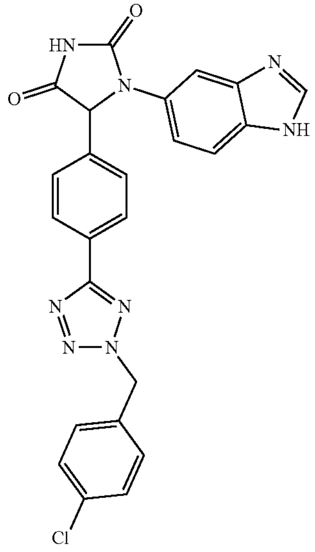 [SMILES: O=C1NC(=O)N(c2ccc3[nH]cnc3c2)C1c1ccc(-c2nnn(Cc3ccc(Cl)cc3)n2)cc1]

The 1-(1H-benzimidazol-5-yl)-5-{4-[2-(4-chlorobenzyl)-2H-tetrazol-5-yl]phenyl}-imidazolidine-2,4-dione (Compound 50) was prepared from the cycloaddition of 1-(1H-benzimidazol-6-yl)urea 187 and Compound 194j. The procedures were the same as the synthesis of Compound 37. The product (Compound 50) was obtained as a white solid at a yield of 43%. $^1$H NMR (300 MHz, DMSO-$d_6$) δ 5.98 (s, 2H), 6.11 (s, 1H), 7.25 (d, 1H, J=8.1 Hz), 7.36-7.50 (m, 5H), 7.56 (d, 2H, J=8.4 Hz), 7.70 (s, 1H), 7.99 (d, 2H, J=8.4 Hz), 8.15 (s, 1H), 11.44 (s, 1H), 12.41 (s, 1H); LC/MS (ESI) m/z: 485.1 $[M+H]^+$.

1-(1H-benzimidazol-5-yl)-5-{4-[2-(4-methoxybenzyl)-2H-tetrazol-5-yl]phenyl}-imidazolidine-2,4-dione (Compound 51)

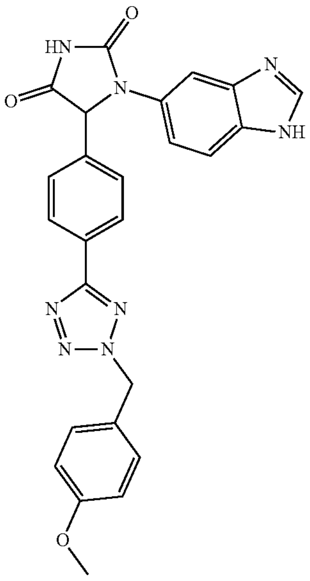 [SMILES: COc1ccc(Cn2nnc(-c3ccc(C4C(=O)NC(=O)N4c4ccc5[nH]cnc5c4)cc3)n2)cc1]

The 1-(1H-benzimidazol-5-yl)-5-{4-[2-(4-methoxybenzyl)-2H-tetrazol-5-yl]phenyl}-imidazolidine-2,4-dione (Compound 51) was prepared from the cycloaddition of 1-(1H-benzimidazol-6-yl)urea 187 and Compound 194k. The procedures were the same as the synthesis of Compound 37. The product (Compound 51) was obtained as a white solid at a yield of 22%. $^1$H NMR (300 MHz, DMSO-$d_6$) δ 3.71 (s, 3H), 5.86 (s, 2H), 6.15 (s, 1H), 6.91 (d, 2H, J=8.4 Hz), 7.33 (d, 2H, J=8.4 Hz), 7.42 (br s, 2H), 7.55 (d, 2H, J=8.1 Hz), 7.70 (s, 1H), 7.98 (d, 2H, J=8.1 Hz), 8.15 (s, 1H), 11.43 (s, 1H), 12.41 (s, 1H); LC/MS (ESI) m/z: 481.2 $[M+H]^+$.

1-(1H-benzimidazol-5-yl)-5-(4-{2-[(3-methyl-1,2-oxazol-5-yl)methyl]-2H-tetrazol-5-yl}phenyl)imidazolidine-2,4-dione (Compound 52)

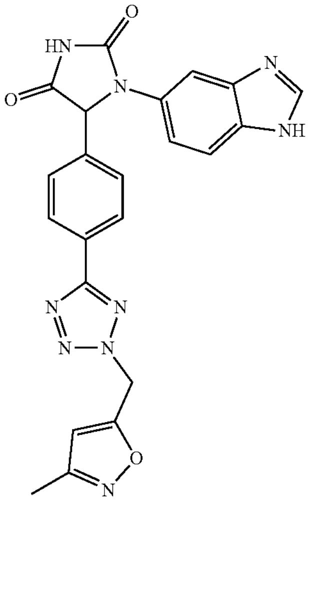 [SMILES: Cc1cc(Cn2nnc(-c3ccc(C4C(=O)NC(=O)N4c4ccc5[nH]cnc5c4)cc3)n2)on1]

The 1-(1H-benzimidazol-5-yl)-5-(4-{2-[(3-methyl-1,2-oxazol-5-yl)methyl]-2H-tetrazol-5-yl}phenyl)imidazolidine-2,4-dione (Compound 52) was prepared from the cycloaddition of 1-(1H-benzimidazol-6-yl)urea 187 and Compound 194l. The procedures were the same as the synthesis of Compound 37. The product (Compound 52) was obtained as a white solid at a yield of 52%. $^1$H NMR (400 MHz, DMSO-$d_6$) δ 2.20 (s, 3H), 6.12 (s, 1H), 6.24 (s, 2H), 6.51 (s, 1H), 7.27 (br s, 1H), 7.46 (br s, 1H), 7.58 (d, 2H, J=8.0 Hz), 7.71 (s, 1H), 8.00 (d, 2H, J=8.0 Hz), 8.16 (s, 1H), 11.30 (br s, 1H), 12.42 (br s, 1H); LC/MS (ESI) m/z: 456.1 $[M+H]^+$.

N-[2-(4-cyanophenyl)-2-oxoethyl]tricyclo[3.3.1.1$^{3,7}$]decane-1-carboxamide (Compound 196)

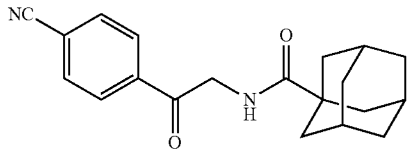 [SMILES: N#Cc1ccc(C(=O)CNC(=O)C23CC4CC(CC(C4)C2)C3)cc1]

The N-[2-(4-cyanophenyl)-2-oxoethyl]tricyclo[3.3.1.1$^{3,7}$]decane-1-carboxamide 196 was prepared through the acetylation of compound 131 with adamantane-1-carbonyl chloride 195. The experimental procedures were the same as the synthesis of compound 133a. The product 196 was obtained as a yellow solid at a yield of 53%. $^1$H NMR (400 MHz, $CDCl_3$) δ 1.71-1.78 (m, 6H), 1.92 (s, 6H), 2.07 (s, 3H), 4.74 (d, 2H, J=4.0 Hz), 6.65 (s, 1H), 7.81 (d, 2H, J=8.6 Hz), 8.07 (d, 2H, J=8.6 Hz); LC/MS (ESI) m/z: 323.3 $[M+H]^+$.

4-[2-(tricyclo[3.3.1.1$^{3,7}$]dec-1-yl)-1,3-thiazol-5-yl]benzonitrile (Compound 197)

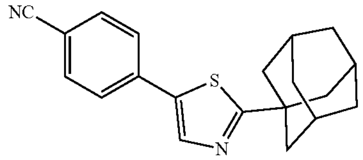 [SMILES: N#Cc1ccc(-c2cnc(C34CC5CC(CC(C5)C3)C4)s2)cc1]

The 4-[2-(tricyclo[3.3.1.1$^{3,7}$]dec-1-yl)-1,3-thiazol-5-yl]benzonitrile 197 was prepared from the cyclization of compound 196 with the Lawesson's reagent in THF. The experimental procedures were the same as the synthesis of compound 134a. The product 197 was obtained as a white solid at a yield of 49%. $^1$H NMR (400 MHz, $CDCl_3$) δ 1.80 (s, 6H), 2.08 (s, 6H), 2.13 (s, 3H), 7.61-7.67 (m, 4H), 7.94 (s, 1H); LC/MS (ESI) m/z: 321.3 $[M+H]^+$.

4-[2-(tricyclo[3.3.1.1$^{3,7}$]dec-1-yl)-1,3-thiazol-5-yl] benzaldehyde (Compound 198)

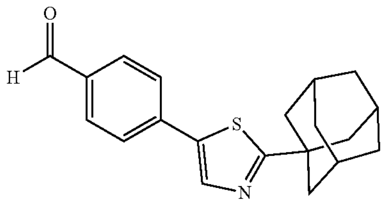 [SMILES: O=Cc1ccc(-c2cnc(C34CC5CC(CC(C5)C3)C4)s2)cc1]

The 4-[2-(tricyclo[3.3.1.1$^{3,7}$]dec-1-yl)-1,3-thiazol-5-yl] benzaldehyde 198 was prepared from the reduction of compound 197 with the DIBAL-H reagent. The experimental procedures were the same as the synthesis of compound 135a. The product 198 was obtained as a yellow solid at a yield of 83%. $^1$H NMR (300 MHz, $CDCl_3$) δ 1.81 (s, 6H), 2.10 (s, 6H), 2.14 (s, 3H), 7.70 (d, 2H, J=8.4 Hz), 7.89 (d, 2H, J=8.4 Hz), 7.98 (s, 1H), 10.00 (s, 1H); LC/MS (ESI) m/z: 324.3 $[M+H]^+$.

(1H-benzimidazol-5-ylamino){4-[2-(tricyclo[3.3.1.1$^{3,7}$]dec-1-yl)-1,3-thiazol-5-yl] phenyl}acetonitrile (Compound 199)

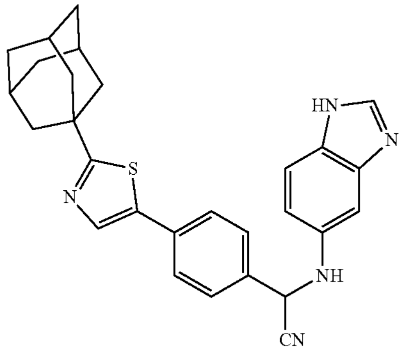 [SMILES: N#CC(Nc1ccc2[nH]cnc2c1)c1ccc(-c2cnc(C34CC5CC(CC(C5)C3)C4)s2)cc1]

The (1H-benzimidazol-5-ylamino) {4-[2-(tricyclo[3.3.1.1$^{3,7}$]dec-1-yl)-1,3-thiazol-5-yl]phenyl}acetonitrile 199 was prepared from the addition of 1H-benzimidazol-5-amine 121, TMSCN and compound 198. The experimental procedures were the same as the synthesis of compound 122a. The product 199 was obtained as a pale-yellow solid at a yield of 91%.

N$^1$-(1H-benzimidazol-5-yl)-1-{4-[2-(tricyclo[3.3.1.1$^{3,7}$]dec-1-yl)-1,3-thiazol-5-yl]phenyl}ethane-1,2-diamine (Compound 200)

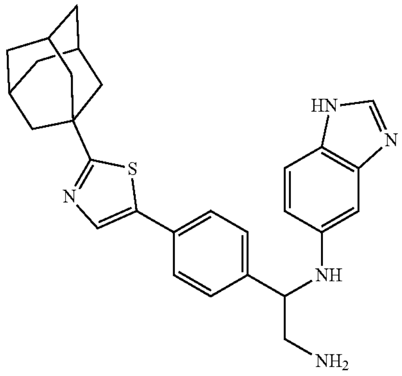 [SMILES: NCC(Nc1ccc2[nH]cnc2c1)c1ccc(-c2cnc(C34CC5CC(CC(C5)C3)C4)s2)cc1]

The N$^1$-(1H-benzimidazol-5-yl)-1-{4-[2-(tricyclo[3.3.1.1$^{3,7}$]dec-1-yl)-1,3-thiazol-5-yl]phenyl}ethane-1,2-diamine 200 was prepared from the hydrogenation of compound 199 with the Raney Nickel reagent as catalyst. The experimental procedures were the same as the synthesis of compound 123a. The product 200 was obtained as a yellow viscous liquid at a yield of 60%.

1-(1H-benzimidazol-5-yl)-5-{4-[2-(tricyclo[3.3.1.1$^{3,7}$]dec-1-yl)-1,3-thiazol-5-yl]phenyl}imidazolidin-2-one (Compound 57)

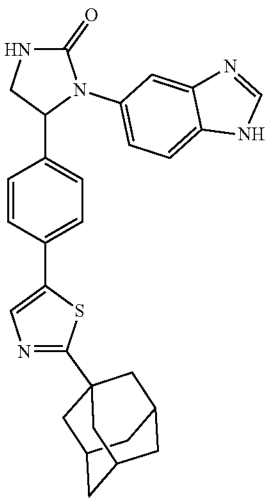 [SMILES: O=C1NCC(c2ccc(-c3cnc(C45CC6CC(CC(C6)C4)C5)s3)cc2)N1c1ccc2[nH]cnc2c1]

The 1-(1H-benzimidazol-5-yl)-5-{4-[2-(tricyclo[3.3.1.1$^{3,7}$]dec-1-yl)-1,3-thiazol-5-yl]phenyl}imidazolidin-2-one (Compound 57) was prepared from the cycloaddition of 1,1'-carbonyl diimidazole and compound 200. The experimental procedures were the same as the synthesis of Compound 1. The product (Compound 57) was obtained as a yellow solid at a yield of 78%. $^1$H NMR (400 MHz, $CD_3OD$) δ 1.75 (s, 6H), 2.03 (s, 6H), 2.05 (s, 3H), 3.32-3.36 (m, 1H), 3.97 (dd, 1H, J=9.2, 9.2 Hz), 5.49 (dd, 1H, J=6.8, 9.2 Hz), 7.30 (d, 1H, J=8.8 Hz), 7.40 (d, 2H, J=8.4 Hz), 7.45-7.49 (m, 3H), 7.56 (s, 1H), 7.79 (s, 1H), 8.06 (s, 1H); LC/MS (ESI) m/z: 496.4 $[M+H]^+$.

2,3-difluoro-4-(5-fluorothiophen-3-yl)benzaldehyde (Compound 201a)

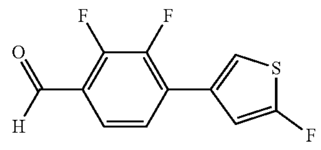 [SMILES: O=Cc1ccc(-c2csc(F)c2)c(F)c1F]

The 2,3-difluoro-4-(5-fluorothiophen-3-yl)benzaldehyde 201a was prepared from the Suzuki-Miyaura coupling of 2,3-difluoro-4-formylphenylboronic acid 118g and 4-bromo-2-fluorothiophene 158d. The experimental procedures were the same as the synthesis of compound 159a. The product 201a was obtained as a pale-yellow oil at a yield of 42%.

4-(5-chlorothiophen-3-yl)-2,3-difluorobenzaldehyde (Compound 201b)

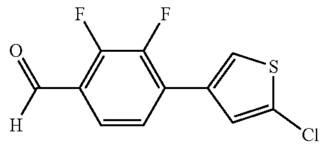 [SMILES: O=Cc1ccc(-c2csc(Cl)c2)c(F)c1F]

The 4-(5-chlorothiophen-3-yl)-2,3-difluorobenzaldehyde 201b was prepared from the Suzuki-Miyaura coupling of 2,3-difluoro-4-formylphenylboronic acid 118g and 4-bromo-2-chlorothiophene 158e. The experimental procedures were the same as the synthesis of compound 159a. The product 201b was obtained as a pale-yellow oil at a yield of 45%.

2,3-difluoro-4-(5-methylthiophen-3-yl)benzaldehyde (Compound 201c)

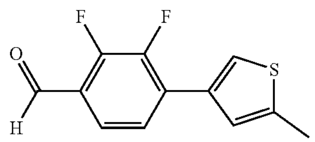 [SMILES: Cc1cc(-c2ccc(C=O)c(F)c2F)cs1]

The 2,3-difluoro-4-(5-methylthiophen-3-yl)benzaldehyde 201c was prepared from the Suzuki-Miyaura coupling of 2,3-difluoro-4-formylphenylboronic acid 118g and 4-bromo-2-methylthiophene 158b. The experimental procedures were the same as the synthesis of compound 159a. The product 201c was obtained as a pale-yellow oil at a yield of 53%.

4-(5-ethylthiophen-3-yl)-2,3-difluorobenzaldehyde (Compound 201d)

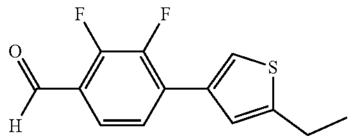 [SMILES: CCc1cc(-c2ccc(C=O)c(F)c2F)cs1]

The 4-(5-ethylthiophen-3-yl)-2,3-difluorobenzaldehyde 201d was prepared from the Suzuki-Miyaura coupling of 2,3-difluoro-4-formylphenylboronic acid 118g and 4-bromo-2-ethylthiophene 158f. The experimental procedures were the same as the synthesis of compound 159a. The product 201d was obtained as a pale-yellow oil at a yield of 56%.

2,3-difluoro-4-[5-(methoxymethyl)thiophen-3-yl]benzaldehyde (Compound 201e)

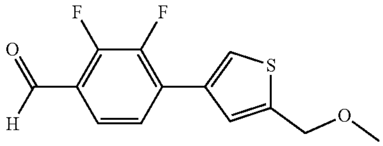 [SMILES: COCc1cc(-c2ccc(C=O)c(F)c2F)cs1]

The 2,3-difluoro-4-[5-(methoxymethyl)thiophen-3-yl]benzaldehyde 201e was prepared from the Suzuki-Miyaura coupling of 2,3-difluoro-4-formylphenylboronic acid 118g and 4-bromo-2-(methoxymethyl)thiophene 158g. The experimental procedures were the same as the synthesis of compound 159a. The product 201e was obtained as a pale-yellow oil at a yield of 49%.

4-[5-(ethoxymethyl)thiophen-3-yl]-2,3-difluorobenzaldehyde (Compound 201f)

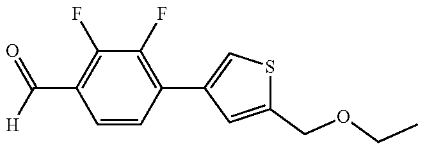 [SMILES: CCOCc1cc(-c2ccc(C=O)c(F)c2F)cs1]

The 4-[5-(ethoxymethyl)thiophen-3-yl]-2,3-difluorobenzaldehyde 201f was prepared from the Suzuki-Miyaura coupling of 2,3-difluoro-4-formylphenylboronic acid 118g and 4-bromo-2-(ethoxymethyl)thiophene 158h. The experimental procedures were the same as the synthesis of compound 159a. The product 201f was obtained as a pale-yellow oil at a yield of 48%.

methyl 4-(2,3-difluoro-4-formylphenyl)thiophene-2-carboxylate (Compound 201g)

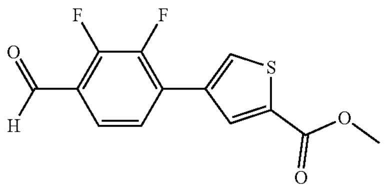 [SMILES: COC(=O)c1cc(-c2ccc(C=O)c(F)c2F)cs1]

The methyl 4-(2,3-difluoro-4-formylphenyl)thiophene-2-carboxylate 201g was prepared from the Suzuki-Miyaura coupling of 2,3-difluoro-4-formylphenylboronic acid 118g and methyl 4-bromothiophene-2-carboxylate 158i. The experimental procedures were the same as the synthesis of compound 159a. The product 201g was obtained as a pale-yellow oil at a yield of 42%.

2,3-difluoro-4-(thiophen-3-yl)benzaldehyde (Compound 201h)

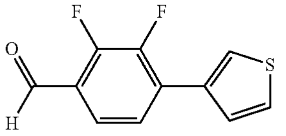 [SMILES: O=Cc1ccc(-c2ccsc2)c(F)c1F]

The 2,3-difluoro-4-(thiophen-3-yl)benzaldehyde 201h was prepared from the Suzuki-Miyaura coupling of 2,3-difluoro-4-formylphenylboronic acid 118g and 3-bromothiophene 158a. The experimental procedures were the same as the synthesis of compound 159a. The product 201h was obtained as a pale-yellow oil at a yield of 54%.

(1H-benzimidazol-5-ylamino)[2,3-difluoro-4-(5-fluorothiophen-3-yl)phenyl]acetonitrile (Compound 202a)

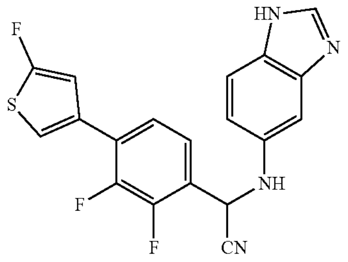 [SMILES: N#CC(Nc1ccc2[nH]cnc2c1)c1ccc(-c2csc(F)c2)c(F)c1F]

The (1H-benzimidazol-5-ylamino)[2,3-difluoro-4-(5-fluorothiophen-3-yl)phenyl]-acetonitrile 202a was prepared from the addition of 1H-benzimidazol-5-amine 121, TMSCN and compound 201a. The experimental procedures were the same as the synthesis of compound 122a. The product 202a was obtained as a pale-yellow solid at a yield of 85%.

(1H-benzimidazol-5-ylamino)[4-(5-chlorothiophen-3-yl)-2,3-difluorophenyl]acetonitrile (Compound 202b)

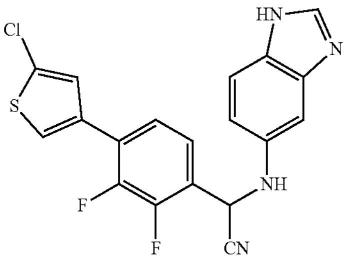 [SMILES: N#CC(Nc1ccc2[nH]cnc2c1)c1ccc(-c2csc(Cl)c2)c(F)c1F]

The (1H-benzimidazol-5-ylamino)[4-(5-chlorothiophen-3-yl)-2,3-difluorophenyl]acetonitrile 202b was prepared from the addition of 1H-benzimidazol-5-amine 121, TMSCN and compound 201b. The experimental procedures were the same as the synthesis of compound 122a. The product 202b was obtained as a pale-yellow solid at a yield of 79%.

(1H-benzimidazol-5-ylamino)[2,3-difluoro-4-(5-methylthiophen-3-yl)phenyl]acetonitrile (Compound 202c)

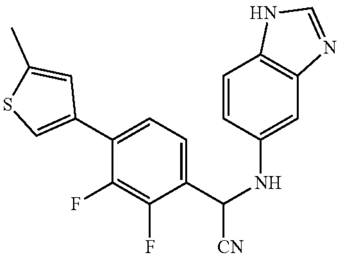 [SMILES: Cc1cc(-c2ccc(C(C#N)Nc3ccc4[nH]cnc4c3)c(F)c2F)cs1]

The (1H-benzimidazol-5-ylamino)[2,3-difluoro-4-(5-methylthiophen-3-yl)phenyl]acetonitrile 202c was prepared from the addition of 1H-benzimidazol-5-amine 121, TMSCN and compound 201c. The experimental procedures were the same as the synthesis of compound 122a. The product 202c was obtained as a pale-yellow solid at a yield of 88%.

(1H-benzimidazol-5-ylamino)[4-(5-ethylthiophen-3-yl)-2,3-difluorophenyl]acetonitrile (Compound 202d)

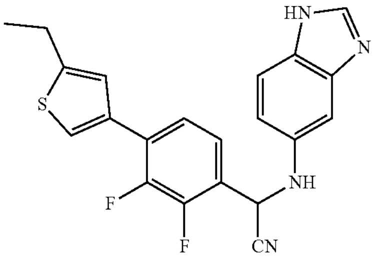 [SMILES: CCc1cc(-c2ccc(C(C#N)Nc3ccc4[nH]cnc4c3)c(F)c2F)cs1]

The (1H-benzimidazol-5-ylamino)[4-(5-ethylthiophen-3-yl)-2,3-difluorophenyl]-acetonitrile 202d was prepared from the addition of 1H-benzimidazol-5-amine 121, TMSCN and compound 201d. The experimental procedures were the same as the synthesis of compound 122a. The product 202d was obtained as a pale-yellow solid at a yield of 81%.

(1H-benzimidazol-5-ylamino){2,3-difluoro-4-[5-(methoxymethyl)thiophen-3-yl]phenyl}acetonitrile (Compound 202e)

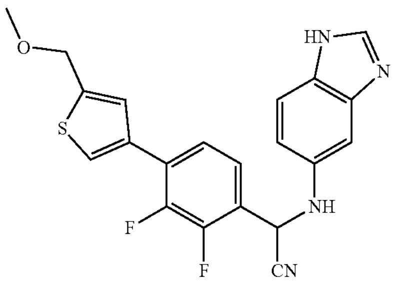 [SMILES: COCc1cc(-c2ccc(C(C#N)Nc3ccc4[nH]cnc4c3)c(F)c2F)cs1]

The (1H-benzimidazol-5-ylamino) {2,3-difluoro-4-[5-(methoxymethyl)thiophen-3-yl]phenyl}acetonitrile 202e was prepared from the addition of 1H-benzimidazol-5-amine 121, TMSCN and compound 201e. The experimental procedures were the same as the synthesis of compound 122a. The product 202e was obtained as a pale-yellow solid at a yield of 84%.

(1H-benzimidazol-5-ylamino){4-[5-(ethoxymethyl) thiophen-3-yl]-2,3-difluorophenyl}acetonitrile (Compound 202f)

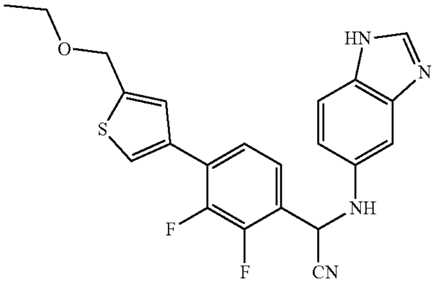 [SMILES: CCOCc1cc(-c2ccc(C(C#N)Nc3ccc4[nH]cnc4c3)c(F)c2F)cs1]

The (1H-benzimidazol-5-ylamino) {4-[5-(ethoxymethyl) thiophen-3-yl]-2,3-difluorophenyl}acetonitrile 202f was prepared from the addition of 1H-benzimidazol-5-amine 121, TMSCN and compound 201f. The experimental procedures were the same as the synthesis of compound 122a. The product 202f was obtained as a pale-yellow solid at a yield of 90%.

Methyl 4-{4-[(1H-benzimidazol-5-ylamino)(cyano) methyl]-2,3-difluorophenyl}thiophene-2-carboxylate (Compound 202g)

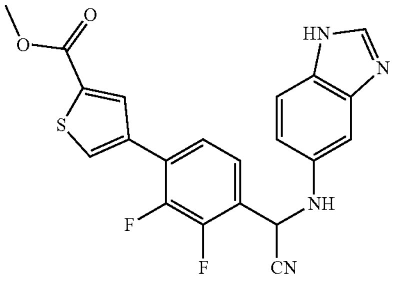 [SMILES: COC(=O)c1cc(-c2ccc(C(C#N)Nc3ccc4[nH]cnc4c3)c(F)c2F)cs1]

The methyl 4-{4-[(1H-benzimidazol-5-ylamino)(cyano) methyl]-2,3-difluorophenyl}thiophene-2-carboxylate 202g was prepared from the addition of 1H-benzimidazol-5-amine 121, TMSCN and compound 201g. The experimental procedures were the same as the synthesis of compound 122a. The product 202g was obtained as a pale-yellow solid at a yield of 81%.

(1H-benzimidazol-5-ylamino)[2,3-difluoro-4-(thiophen-3-yl)phenyl]acetonitrile (Compound 202h)

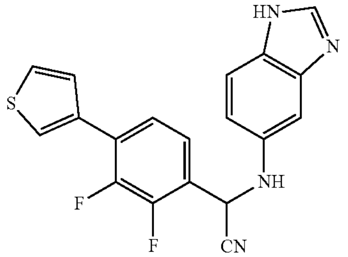 [SMILES: N#CC(Nc1ccc2[nH]cnc2c1)c1ccc(-c2ccsc2)c(F)c1F]

The (1H-benzimidazol-5-ylamino)[2,3-difluoro-4-(thiophen-3-yl)phenyl]acetonitrile 202h was prepared from the addition of 1H-benzimidazol-5-amine 121, TMSCN and compound 201h. The experimental procedures were the same as the synthesis of compound 122a. The product 202h was obtained as a pale-yellow solid at a yield of 92%.

$N^1$-(1H-benzimidazol-5-yl)-1-[2,3-difluoro-4-(5-fluorothiophen-3-yl)phenyl]ethane-1,2-diamine (Compound 203a)

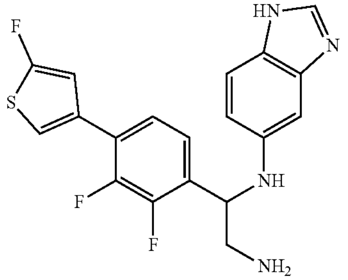 [SMILES: NCC(Nc1ccc2[nH]cnc2c1)c1ccc(-c2csc(F)c2)c(F)c1F]

The N[1]-(1H-benzimidazol-5-yl)-1-[2,3-difluoro-4-(5-fluorothiophen-3-yl)phenyl]ethane-1,2-diamine 203a was prepared from the hydrogenation of compound 202a with the Raney Nickel reagent as catalyst. The experimental procedures were the same as the synthesis of compound 123a. The product 203a was obtained as a yellow viscous liquid at a yield of 43%.

N[1]-(1H-benzimidazol-5-yl)-1-[4-(5-chlorothiophen-3-yl)-2,3-difluorophenyl]ethane-1,2-diamine (Compound 203b)

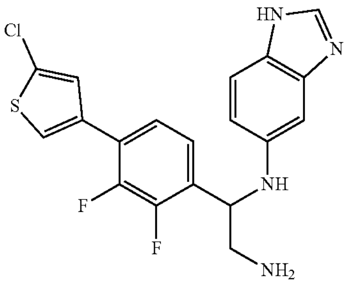 [SMILES: NCC(Nc1ccc2[nH]cnc2c1)c1ccc(-c2csc(Cl)c2)c(F)c1F]

The N[1]-(1H-benzimidazol-5-yl)-1-[4-(5-chlorothiophen-3-yl)-2,3-difluorophenyl]ethane-1,2-diamine 203b was prepared from the hydrogenation of compound 202b with the Raney Nickel reagent as catalyst. The experimental procedures were the same as the synthesis of compound 123a. The product 203b was obtained as a yellow viscous liquid at a yield of 40%.

N[1]-(1H-benzimidazol-5-yl)-1-[2,3-difluoro-4-(5-methylthiophen-3-yl)phenyl]ethane-1,2-diamine (Compound 203c)

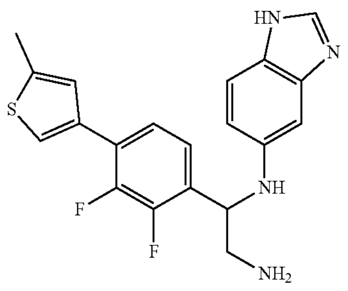 [SMILES: Cc1cc(-c2ccc(C(CN)Nc3ccc4[nH]cnc4c3)c(F)c2F)cs1]

The N[1]-(1H-benzimidazol-5-yl)-1-[2,3-difluoro-4-(5-methylthiophen-3-yl)phenyl]ethane-1,2-diamine 203c was prepared from the hydrogenation of compound 202c with the Raney Nickel reagent as catalyst. The experimental procedures were the same as the synthesis of compound 123a. The product 203c was obtained as a yellow viscous liquid at a yield of 53%.

N[1]-(1H-benzimidazol-5-yl)-1-[4-(5-ethylthiophen-3-yl)-2,3-difluorophenyl]ethane-1,2-diamine (Compound 203d)

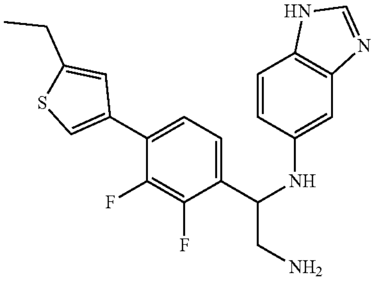 [SMILES: CCc1cc(-c2ccc(C(CN)Nc3ccc4[nH]cnc4c3)c(F)c2F)cs1]

The N[1]-(1H-benzimidazol-5-yl)-1-[4-(5-ethylthiophen-3-yl)-2,3-difluorophenyl]ethane-1,2-diamine 203d was prepared from the hydrogenation of compound 202d with the Raney Nickel reagent as catalyst. The experimental procedures were the same as the synthesis of compound 123a. The product 203d was obtained as a yellow viscous liquid at a yield of 51%.

N[1]-(1H-benzimidazol-5-yl)-1-{2,3-difluoro-4-[5-(methoxymethyl)thiophen-3-yl]phenyl}ethane-1,2-diamine (Compound 203e)

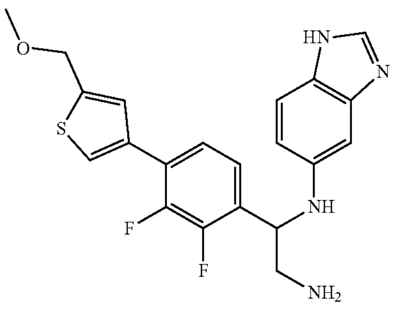 [SMILES: COCc1cc(-c2ccc(C(CN)Nc3ccc4[nH]cnc4c3)c(F)c2F)cs1]

The N[1]-(1H-benzimidazol-5-yl)-1-{2,3-difluoro-4-[5-(methoxymethyl)thiophen-3-yl]phenyl}ethane-1,2-diamine 203e was prepared from the hydrogenation of compound 202e with the Raney Nickel reagent as catalyst. The experimental procedures were the same as the synthesis of compound 123a. The product 203e was obtained as a yellow viscous liquid at a yield of 46%.

N[1]-(1H-benzimidazol-5-yl)-1-{4-[5-(ethoxymethyl)thiophen-3-yl]-2,3-difluorophenyl}ethane-1,2-diamine (Compound 203f)

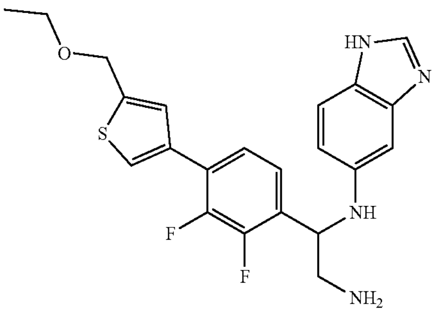 [SMILES: CCOCc1cc(-c2ccc(C(CN)Nc3ccc4[nH]cnc4c3)c(F)c2F)cs1]

The N[1]-(1H-benzimidazol-5-yl)-1-{4-[5-(ethoxymethyl)thiophen-3-yl]-2,3-difluorophenyl}ethane-1,2-diamine 203f was prepared from the hydrogenation of compound 202f with the Raney Nickel reagent as catalyst. The experimental procedures were the same as the synthesis of compound 123a. The product 203f was obtained as a yellow viscous liquid at a yield of 49%.

methyl 4-{4-[2-amino-1-(1H-benzimidazol-5-ylamino)ethyl]-2,3-difluorophenyl}thiophene-2-carboxylate (Compound 203g)

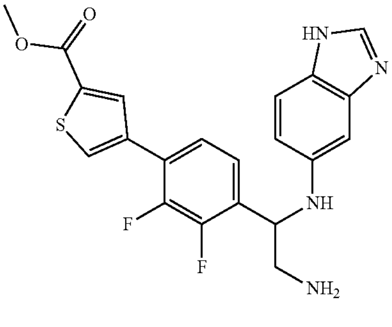 [SMILES: COC(=O)c1cc(-c2ccc(C(CN)Nc3ccc4[nH]cnc4c3)c(F)c2F)cs1]

The methyl 4-{4-[2-amino-1-(1H-benzimidazol-5-ylamino)ethyl]-2,3-difluorophenyl}thiophene-2-carboxylate 203g was prepared from the hydrogenation of compound 202g with the Raney Nickel reagent as catalyst. The experimental procedures were the same as the synthesis of compound 123a. The product 203g was obtained as a yellow viscous liquid at a yield of 47%.

N[1]-(1H-benzimidazol-5-yl)-1-[2,3-difluoro-4-(thiophen-3-yl)phenyl]ethane-1,2-diamine (Compound 203h)

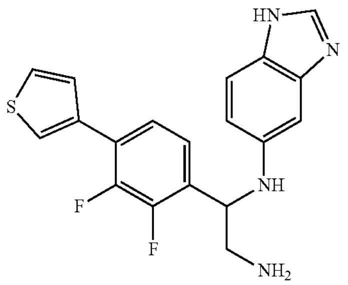 [SMILES: NCC(Nc1ccc2[nH]cnc2c1)c1ccc(-c2ccsc2)c(F)c1F]

The N[1]-(1H-benzimidazol-5-yl)-1-[2,3-difluoro-4-(thiophen-3-yl)phenyl]ethane-1,2-diamine 203h was prepared from the hydrogenation of compound 202h with the Raney Nickel reagent as catalyst. The experimental procedures were the same as the synthesis of compound 123a. The product 203h was obtained as a yellow viscous liquid at a yield of 58%.

1-(1H-benzimidazol-5-yl)-5-[2,3-difluoro-4-(5-fluorothiophen-3-yl)phenyl]imidazolidin-2-one (Compound 58)

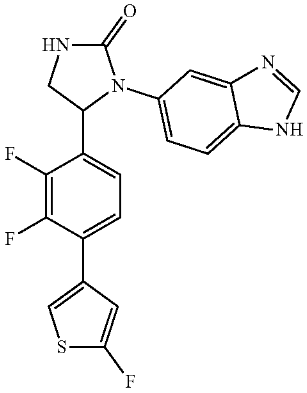 [SMILES: O=C1NCC(c2ccc(-c3csc(F)c3)c(F)c2F)N1c1ccc2[nH]cnc2c1]

The 1-(1H-benzimidazol-5-yl)-5-[2,3-difluoro-4-(5-fluorothiophen-3-yl)phenyl]imidazolidin-2-one (Compound 58) was prepared from the cycloaddition of 1,1'-carbonyl diimidazole and compound 203a. The experimental procedures were the same as the synthesis of Compound 1. The product (Compound 58) was obtained as a white solid at a yield of 71%.

1-(1H-benzimidazol-5-yl)-5-[4-(5-chlorothiophen-3-yl)-2,3-difluorophenyl]imidazolidin-2-one (Compound 59)

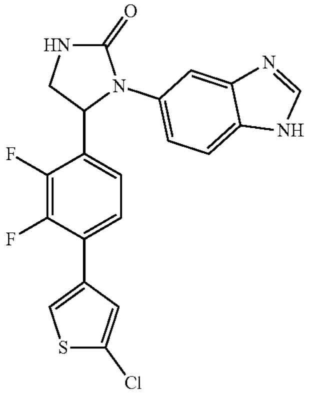 [SMILES: O=C1NCC(c2ccc(-c3csc(Cl)c3)c(F)c2F)N1c1ccc2[nH]cnc2c1]

The 1-(1H-benzimidazol-5-yl)-5-[4-(5-chlorothiophen-3-yl)-2,3-difluorophenyl]imidazolidin-2-one (Compound 59) was prepared from the cycloaddition of 1,1'-carbonyl diimidazole and compound 203b. The experimental procedures were the same as the synthesis of Compound 1. The product (Compound 59) was obtained as a white solid at a yield of 74%. $^1$H NMR (300 MHz, $CD_3OD$) δ 3.44 (dd, 1H, J=6.3, 9.3 Hz), 4.05 (dd, 1H, J=9.3, 9.6 Hz), 5.83 (dd, 1H, J=6.3, 9.6 Hz), 7.17-7.34 (m, 4H), 7.48-7.51 (m, 2H), 7.60 (d, 1H, J=1.8 Hz), 8.07 (d, 1H, J=3.9 Hz); LC/MS (ESI) m/z: 431.0 $[M+H]^+$.

1-(1H-benzimidazol-5-yl)-5-[2,3-difluoro-4-(5-methylthiophen-3-yl)phenyl]imidazolidin-2-one (Compound 60)

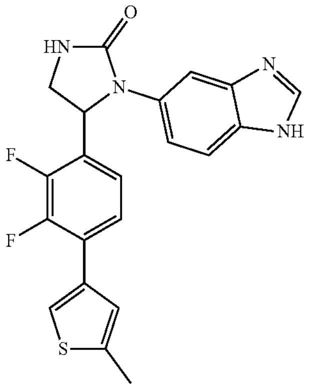 [SMILES: Cc1cc(-c2ccc(C3CNC(=O)N3c3ccc4[nH]cnc4c3)c(F)c2F)cs1]

The 1-(1H-benzimidazol-5-yl)-5-[2,3-difluoro-4-(5-methylthiophen-3-yl)phenyl]imidazolidin-2-one (Compound 60) was prepared from the cycloaddition of 1,1'-carbonyl diimidazole and compound 203c. The experimental procedures were the same as the synthesis of Compound 1. The product (Compound 60) was obtained as a white solid at a yield of 70%. $^1$H NMR (300 MHz, $CD_3OD$) δ 2.45 (s, 3H), 3.43 (dd, 1H, J=6.3, 9.0 Hz), 4.04 (dd, 1H, J=9.0, 9.3 Hz), 5.81 (dd, 1H, J=6.3, 9.3 Hz), 7.02 (s, 1H), 7.18-7.38 (m, 4H), 7.49 (d, 1H, J=8.4 Hz), 7.59 (s, 1H), 8.07 (s, 1H); LC/MS (ESI) m/z: 411.3 $[M+H]^+$.

1-(1H-benzimidazol-5-yl)-5-[4-(5-ethylthiophen-3-yl)-2,3-difluorophenyl]imidazolidin-2-one (Compound 61)

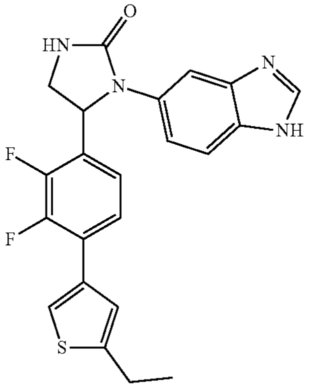 [SMILES: CCc1cc(-c2ccc(C3CNC(=O)N3c3ccc4[nH]cnc4c3)c(F)c2F)cs1]

The 1-(1H-benzimidazol-5-yl)-5-[4-(5-ethylthiophen-3-yl)-2,3-difluorophenyl]-imidazolidin-2-one (Compound 61) was prepared from the cycloaddition of 1,1'-carbonyl diimidazole and compound 203d. The experimental procedures were the same as the synthesis of Compound 1. The product (Compound 61) was obtained as a white solid at a yield of 70%. $^1$H NMR (400 MHz, $CD_3OD$) δ 1.28 (t, 3H, J=7.6 Hz), 2.83 (q, 2H, J=7.6 Hz), 3.44 (dd, 1H, J=6.4, 9.2 Hz), 4.05 (dd, 1H, J=9.2, 9.6 Hz), 5.82 (dd, 1H, J=6.4, 9.6 Hz), 7.05 (s, 1H), 7.15-7.19 (m, 1H), 7.26-7.34 (m, 2H), 7.41 (s, 1H), 7.50 (d, 1H, J=8.8 Hz), 7.60 (s, 1H), 8.08 (s, 1H); LC/MS (ESI) m/z: 425.1 $[M+H]^+$.

1-(1H-benzimidazol-5-yl)-5-{2,3-difluoro-4-[5-(methoxymethyl)thiophen-3-yl]phenyl}imidazolidin-2-one (Compound 62)

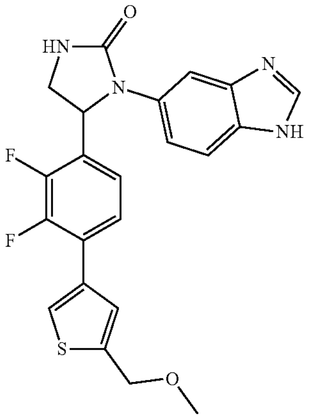 [SMILES: COCc1cc(-c2ccc(C3CNC(=O)N3c3ccc4[nH]cnc4c3)c(F)c2F)cs1]

The 1-(1H-benzimidazol-5-yl)-5-{2,3-difluoro-4-[5-(methoxymethyl)thiophen-3-yl]phenyl}imidazolidin-2-one (Compound 62) was prepared from the cycloaddition of 1,1'-carbonyl diimidazole and compound 203e. The experimental procedures were the same as the synthesis of Compound 1. The product (Compound 62) was obtained as a white solid at a yield of 76%. $^1$H NMR (400 MHz, $CD_3OD$) δ 3.34 (s, 3H), 3.45 (dd, 1H, J=6.8, 9.2 Hz), 4.05 (dd, 1H, J=9.2, 9.2 Hz), 4.59 (s, 2H), 5.82 (dd, 1H, J=6.4, 9.2 Hz), 7.17-7.21 (m, 1H), 7.28-7.34 (m, 3H), 7.50 (d, 1H, J=8.4 Hz), 7.60 (s, 1H), 7.62 (s, 1H), 8.08 (s, 1H); LC/MS (ESI) m/z: 441.3 $[M+H]^+$.

1-(1H-benzimidazol-5-yl)-5-{4-[5-(ethoxymethyl) thiophen-3-yl]-2,3-difluorophenyl}imidazolidin-2-one (Compound 63)

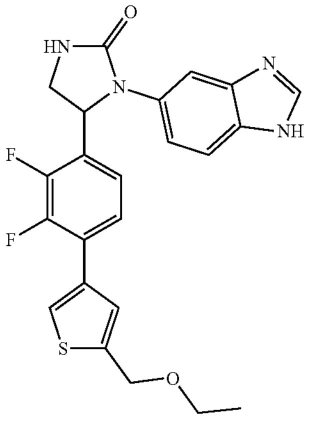 [SMILES: CCOCc1cc(-c2ccc(C3CNC(=O)N3c3ccc4[nH]cnc4c3)c(F)c2F)cs1]

The 1-(1H-benzimidazol-5-yl)-5-{4-[5-(ethoxymethyl) thiophen-3-yl]-2,3-difluorophenyl}imidazolidin-2-one (Compound 63) was prepared from the cycloaddition of 1,1'-carbonyl diimidazole and compound 203f. The experimental procedures were the same as the synthesis of Compound 1. The product (Compound 63) was obtained as a white solid at a yield of 72%. $^1$H NMR (400 MHz, $CD_3OD$) δ 1.19 (t, 3H, J=7.2 Hz), 3.45 (dd, 1H, J=6.4, 9.2 Hz), 3.54 (q, 2H, J=7.2 Hz), 4.05 (dd, 1H, J=9.2, 9.6 Hz), 4.63 (s, 2H), 5.83 (dd, 1H, J=6.4, 9.6 Hz), 7.17-7.20 (m, 1H), 7.26-7.34 (m, 3H), 7.50 (d, 1H, J=8.4 Hz), 7.61 (m, 2H), 8.08 (s, 1H); LC/MS (ESI) m/z: 455.3 $[M+H]^+$.

methyl 4-{4-[3-(1H-benzimidazol-5-yl)-2-oxoimidazolidin-4-yl]-2,3-difluorophenyl}thiophene-2-carboxylate (Compound 64)

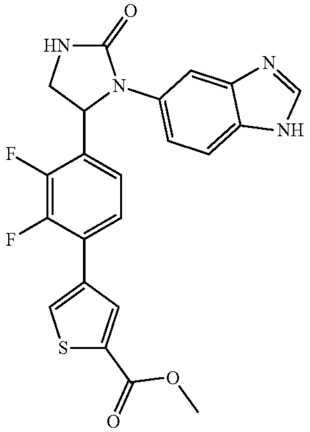 [SMILES: COC(=O)c1cc(-c2ccc(C3CNC(=O)N3c3ccc4[nH]cnc4c3)c(F)c2F)cs1]

The methyl 4-{4-[3-(1H-benzimidazol-5-yl)-2-oxoimidazolidin-4-yl]-2,3-difluorophenyl}thiophene-2-carboxylate (Compound 64) was prepared from the cycloaddition of 1,1'-carbonyl diimidazole and compound 203g. The experimental procedures were the same as the synthesis of Compound 1. The product (Compound 64) was obtained as a white solid at a yield of 75%. $^1$H NMR (300 MHz, DMSO-$d_6$) δ 3.16-3.29 (m, 1H), 3.81 (s, 3H), 3.94 (dd, 1H, J=9.0, 9.3 Hz), 5.84 (dd, 1H, J=5.4, 9.3 Hz), 7.11 (s, 1H), 7.17 (dd, 1H, J=6.9, 7.5 Hz), 7.30 (br s, 1H), 7.43-7.54 (m, 2H), 7.61 (s, 1H), 8.06-8.10 (m, 1H), 8.22 (s, 1H), 8.23 (s, 1H), 12.29 (br s, 1H); LC/MS (ESI) m/z: 455.1 $[M+H]^+$.

1-(1H-benzimidazol-5-yl)-5-[2,3-difluoro-4-(thiophen-3-yl)phenyl]imidazolidin-2-one (Compound 65)

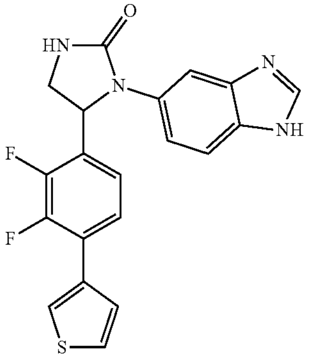 [SMILES: O=C1NCC(c2ccc(-c3ccsc3)c(F)c2F)N1c1ccc2[nH]cnc2c1]

The 1-(1H-benzimidazol-5-yl)-5-[2,3-difluoro-4-(thiophen-3-yl)phenyl]imidazolidin-2-one (Compound 65) was prepared from the cycloaddition of 1,1'-carbonyl diimidazole and compound 203h. The experimental procedures were the same as the synthesis of Compound 1. The product (Compound 65) was obtained as a white solid at a yield of 79%. $^1$H NMR (400 MHz, $CD_3OD$) δ 3.45 (dd, 1H, J=6.8, 9.2 Hz), 4.06 (dd, 1H, J=9.2, 9.6 Hz), 5.83 (dd, 1H, J=6.8, 9.6 Hz), 7.20 (m, 1H), 7.31-7.36 (m, 3H), 7.44-7.52 (m, 2H), 7.61 (s, 1H), 7.66 (s, 1H), 8.08 (s, 1H); LC/MS (ESI) m/z: 397.1 $[M+H]^+$.

4-{4-[3-(1H-benzimidazol-5-yl)-2-oxoimidazolidin-4-yl]-2,3-difluorophenyl}thiophene-2-carboxylic acid (Compound 66)

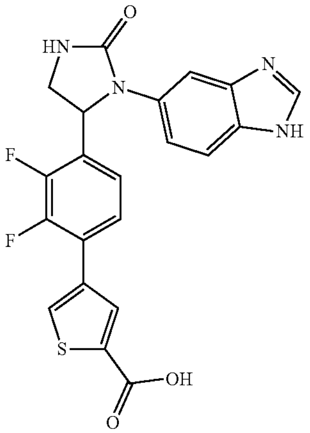 [SMILES: O=C(O)c1cc(-c2ccc(C3CNC(=O)N3c3ccc4[nH]cnc4c3)c(F)c2F)cs1]

To the solution of the compound 64 (0.45 g, 1.0 mmol) in methanol (10 mL), potassium hydroxide (0.07 g, 1.2 mmol) was added. The reaction mixture was stirred at 60° C. for 1.5 hours and then cooled to room temperature. The reaction mixture was neutralized by 1N $HCl_{(aq)}$ to pH 7. After removing the solvent, the crude residue was purified by reverse phase column chromatography on C-18 silica gel using methanol/$H_2O$ (1/1) as eluent to give the product 66 as a white solid at a yield of 81%. $^1H$ NMR (400 MHz, DMSO-$d_6$) δ 3.26 (dd, 1H, J=5.6, 9.2 Hz), 3.92 (dd, 1H, J=9.2, 9.2 Hz), 4.18 (br s, 1H), 5.80 (dd, 1H, J=5.6, 9.2 Hz), 7.12-7.15 (m, 2H), 7.29 (br s, 1H), 7.40-7.46 (m, 2H), 7.52 (s, 1H), 7.61 (s, 1H), 7.67 (s, 1H), 8.09 (s, 1H); LC/MS (ESI) m/z: 441.0 $[M+H]^+$.

1-(1H-benzimidazol-5-yl)-5-{2,3-difluoro-4-[5-(hydroxymethyl)thiophen-3-yl]phenyl}imidazolidin-2-one (Compound 67)

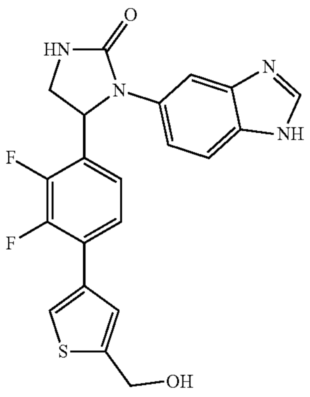 [SMILES: O=C1NCC(c2ccc(-c3csc(CO)c3)c(F)c2F)N1c1ccc2[nH]cnc2c1]

A solution of compound 64 (0.45 g, 1.0 mmol) in dry THF (5 mL) was added dropwise to a refluxing, magnetically stirring slurry of LAH (1.5 mmol) in dry THF (7.5 mL). The reaction mixture was held at reflux for 3 hours, terminated by dropwise addition of 1 mL saturated $MgSO_4$ solution and filtered by Celite. The filtrate was partitioned between ethyl acetate and water. The organic phases were dried over $MgSO_4$ and evaporated on a rotary evaporator. The residue was purified by column chromatography on silica gel using methanol/DCM (1/10) as eluent to give the product 67 as a white solid at a yield of 92%.

Separation of Enantiomers of Compound 8

The chiral separation of Compound 8 was completed by HPLC using CHIRALPAK IC. The isomer fractions were respectively collected and the optical pure isomers (Compounds 9 and 10) were thus obtained by removing the solvent under reduced pressure. Results of this separation are shown below:

Column: CHIRALPAK IC (IC00CE-OL002),
Column size: 0.46 cm I.D.×25 cm L,
Injection: 0.5 ul,
Mobile phase: 100% methanol,
Flow rate: 1.0 ml/min,
Detection: UV 214 nm,
Temperature: 35° C.,
HPLC equipment: Shimadzu LC-20AD (CP-HPLC-06),
Retention E1 (Compound 9): 5.494 min,
Retention E2 (Compound 10): 6.379 min.

Separation of Enantiomers of Compound 13

The chiral separation of Compound 13 was completed by HPLC using CHIRALPAK AD-H. The isomer fractions were respectively collected and the optical pure isomers (Compounds 33 and 34) were thus obtained by removing the solvent under reduced pressure. Results of this separation are shown below:

Column: CHIRALPAK AD-H (ADH0CD-UE022),
Column size: 0.46 cm I.D.×15 cm L,
Injection: 1.0 ul,
Mobile phase: Hexane/EtOH=60/40 (v/v),
Flow rate: 1.0 ml/min,
Detection: UV 214 nm,
Temperature: 35° C.,
HPLC equipment: Shimadzu LC-20AT (CP-HPLC-09),
Retention E1 (Compound 33): 4.270 min,
Retention E2 (Compound 34): 5.679 min.

Separation of Enantiomers of Compound 16

The chiral separation of Compound 16 was completed by HPLC using CHIRALPAK AD-H. The isomer fractions were respectively collected and the optical pure isomers (Compounds 35 and 36) were thus obtained by removing the solvent under reduced pressure. Results of this separation are shown below:

Column: CHIRALPAK AD-H (ADH0CD-UE022),
Column size: 0.46 cm I.D.×15 cm L,
Injection: 2.0 ul,
Mobile phase: Hexane/EtOH=70/30 (v/v),
Flow rate: 1.0 ml/min,
Detection: UV 214 nm,
Temperature: 35° C.,
HPLC equipment: Shimadzu LC-20AD (CP-HPLC-08),
Retention E1 (Compound 35): 7.273 min,
Retention E2 (Compound 36): 9.232 min.

Separation of Enantiomers of Compound 25

The chiral separation of Compound 25 was completed by HPLC using CHIRALPAK AD-H. The isomer fractions were respectively collected and the optical pure isomers (Compounds 53 and 54) were thus obtained by removing the solvent under reduced pressure. Results of this separation are shown below:

Column: CHIRALPAK AD-H (ADH0CD-UE022),
Column size: 0.46 cm I.D.×15 cm L,
Injection: 2.0 ul,
Mobile phase: Hexane/EtOH=70/30 (v/v),
Flow rate: 1.0 ml/min,
Detection: UV 214 nm,
Temperature: 35° C.,
HPLC equipment: Shimadzu LC-20AD (CP-HPLC-08),
Retention E1 (Compound 53): 2.166 min,
Retention E2 (Compound 54): 2.767 min.

Separation of Enantiomers of Compound 28

The chiral separation of Compound 28 was completed by HPLC using CHIRALPAK AD-H. The isomer fractions were respectively collected and the optical pure isomers (Compounds 55 and 56) were thus obtained by removing the solvent under reduced pressure. Results of this separation are shown below:

Column: CHIRALPAK AD-H (ADH0CD-UE022),
Column size: 0.46 cm I.D.×15 cm L,
Injection: 2.0 ul,
Mobile phase: Hexane/EtOH=70/30 (v/v),
Flow rate: 1.0 ml/min,
Detection: UV 214 nm,
Temperature: 35° C.,
HPLC equipment: Shimadzu LC-20AD (CP-HPLC-08),
Retention E1 (Compound 55): 3.827 min,
Retention E2 (Compound 56): 7.914 min.

Example 2: In Vitro Activity Screening of Compounds

QC Activity Assay

An enzymatic activity assay of QC was conducted at 25° C. using a fluorescent substrate, i.e., L-glutaminyl 2-naphthylamide (Gln-βNA). See Huang et al., *Biochem. J.* 2008, 411, 181-190. A 100 μl reaction mixture was prepared. It contained 300 μM of fluorogenic substrate, ~0.2 units of auxiliary enzyme human pyroglutamyl aminopeptidase I (PAP I) (in which one unit is defined as the amount of human PAP I needed to hydrolyzes 1 μmol of pGlu-βNA per minute under the same assay condition), and an appropriately diluted aliquot of recombinant QC in 50 mM of Tris-HCl at pH 8.0. Excitation and emission wavelengths were set at 320 and 410 nm, respectively. The reaction was initiated by the addition of QC. The enzymatic activity of QC was determined from the amount of released βNA and was calculated using a standard curve for βNA under the same assay conditions. Measurements were made using a Synergy H4 microplate reader (BioTek, Winooski, Vt., USA).

Enzyme Kinetic Assay

Kinetic constants were determined at pH 8.0 and 25° C. using Gln-βNA as the substrate. Also see Huang et al., *Biochem. J.* 2008, 411, 181-190. The reaction was initiated by adding QC to the 100 μl reaction mixture described above. The initial rate was measured with less than 10% substrate depletion for the first 2-12 minutes. Since a weak substrate inhibition was observed, kinetic parameters $K_m$, V, and $K_i$ were evaluated by fitting an equation, i.e., $v_0=V_{max}[S]/(K_m+[S]+[S]2/K_i)$, to initial velocity data by nonlinear regression using a KaleidaGraph software (Synergy Software, Reading, Pa., USA), where $v_0$ is an initial velocity, $V_{max}$ is an limiting rate, [S] is a substrate concentration, $K_m$ is a Michaelis constant, and $K_i$ is an inhibition constant.

QC Inhibition Assay

An inhibition activity assay of QC inhibitors was conducted. See Huang et al., *J. Biol. Chem.* 2011, 286, 12439-12449. A reaction mixture containing 300 μM of Gln-βNA and ~0.2 units of human PAP I was prepared. QC was first incubated with an inhibitor at 25° C. for 30 minutes and the enzyme-inhibitor mixture was then added to the reaction mixture to initiate the cyclization reaction. An $IC_{50}$ value was obtained by fitting an initial reaction rate versus an inhibitor concentration using KaleidaGraph. A $K_i$ value of the inhibitor was calculated according to an equation $IC_{50}=K_i(1+[S]/K_m)$. See Segel, Enzyme Kinetics: Behavior and Analysis of Rapid Equilibrium and Steady-State Enzyme Systems, pp. 100-118. New York: John Wiley & Sons, 1993. In this equation, [S] is a substrate (i.e., Gln-βNA) concentration and $K_m$ is a Michaelis-Menten constant. The lower the $K_i$ value, the higher the inhibitor's QC inhibition rate.

The $K_i$ values of Compounds 1-29, 33-57, and 59-65, obtained from the inhibition assay set forth above, are shown in Table 2 below.

TABLE 2

| Compound | $K_i$ (μM) |
|---|---|
| 1 | 0.053 |
| 2 | 0.100 |
| 3 | 0.348 |
| 7 | 0.021 |
| 8 | 0.049 |
| 9 | 0.016 |
| 10 | 0.964 |
| 11 | 0.100 |
| 12 | 0.132 |
| 13 | 0.124 |
| 14 | 0.106 |
| 15 | 0.076 |
| 16 | 0.112 |
| 17 | 0.151 |
| 18 | 0.134 |
| 19 | 0.058 |
| 20 | 0.057 |
| 21 | 0.036 |
| 22 | 0.156 |
| 23 | 0.124 |
| 24 | 0.101 |
| 25 | 0.071 |
| 26 | 0.114 |
| 27 | 0.066 |
| 28 | 0.039 |
| 29 | 0.072 |
| 33 | 0.736 |
| 34 | 0.069 |
| 35 | 2.053 |
| 36 | 0.032 |
| 37 | 0.018 |
| 38 | 0.004 |
| 39 | 0.004 |
| 40 | 0.009 |
| 41 | 0.012 |
| 42 | 0.005 |
| 43 | 0.008 |
| 44 | 0.010 |
| 45 | 0.004 |
| 46 | 0.008 |
| 47 | 0.006 |
| 48 | 0.010 |
| 49 | 0.010 |
| 50 | 0.013 |
| 51 | 0.024 |
| 52 | 0.397 |
| 53 | 3.417 |
| 54 | 0.023 |
| 55 | 1.592 |
| 56 | 0.007 |
| 57 | 0.087 |
| 59 | 0.019 |
| 60 | 0.007 |
| 61 | 0.016 |
| 62 | 0.006 |
| 63 | 0.011 |
| 64 | 0.013 |
| 65 | 0.020 |

As shown in this table, Compounds 1-29, 33-57, and 59-65 all have $K_i$ values within the nano molar range. Note that a low $K_i$ value indicates a high QC inhibition rate. Clearly, these compounds possess superior inhibition potency against QC.

Inhibition of QC has been reported to diminish aggregation of Aβ and HTT in cultured macrophage cells and in *Drosophila* and mouse models. Thus, Compounds 1-29, 33-57, and 59-65, as potent QC inhibitors, are drug candidates for treating AD or HD.

Example 3: In Vivo Activity of Compounds

Compound 37 showed strong potency ($K_i$=0.018 μM) in inhibiting QC and a desired pharmacokinetic property (F %=11) in mice (F % being the fraction of an oral administered drug that reaches systemic circulation). The compound was therefore selected for further animal studies in a transgenic mouse model using APP/PS1 mice (Jackson Lab, ME). See Schilling et al., *Nat. Med.* 2008, 14, 1106-1111 and Li et al., *J. Med. Chem.* 2017, 60, 6664-6677. APP/PS1 mice are double transgenic mice expressing a chimeric mouse/human amyloid precursor protein (Mo/HuAPP695swe) and a mutant human presenilin 1 (PS1-dE9), both directed to CNS neurons. These two mutations are associated with early-onset Alzheimer's disease. In the animal studies, 4-month-old APP/PS1 mice were housed at a 12 hour day/12 hour night cycle with free access to water and food. Compound 37 was orally administered to the APP/PS1 mice for 3.5 months to determine its in vivo activity. The cognitive function and brain pathology of each mouse were analyzed after the administration. The resultant analytical data exhibited depletion of Aβ deposits in brain tissues of the APP/PS1 mice.

The same in vivo assay was performed on Compound 28, which showed that this compound had high inhibitory activity ($K_i$=0.039 μM) and a superior pharmacokinetic property with desired oral bioavailability (F %=25) in APP/PS1 mice.

The above two assays demonstrate both the potency and the efficacy of Compounds 28 and 37 as QC inhibitors for treating AD.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed herein is only an example of a series of equivalent or similar features.

From the above description, one skilled in the art can easily ascertain the essential characteristics of the present invention and, without departing from the spirit and scope thereof, can make various changes and modifications of the invention to adapt it to various usages and conditions. Thus, other embodiments are also within the scope of the following claims.

What is claimed is:

1. A compound of formula (I):

(I)

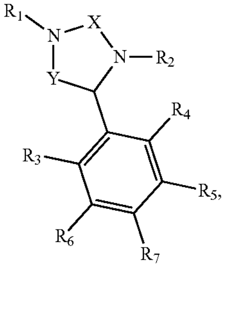

wherein $R_1$ is H or $C_{1-6}$ alkyl;

$R_2$ is a moiety containing a phenyl ring fused to a 5-membered heteroaryl ring, $R_2$ being linked to N through the phenyl ring;

$R_3$, $R_4$, $R_5$, $R_6$, and $R_7$, independently, are H, halo, nitro, cyano, amino, OH, $CF_3$, $C_{1-6}$ alkoxyl, $C_{1-6}$ alkyl, $C_{2-6}$ alkenyl, $C_{2-6}$ alkynyl, $C_{3-10}$ cycloalkyl, heterocycloalkyl, aryl, or heteroaryl that is optionally substituted by one or more substituents selected from halo, nitro, cyano, amino, OH, $CF_3$, —COOH, —$COOC_{1-6}$ alkyl, $C_{1-6}$ alkoxyl, $C_{1-6}$ alkyl, $C_{2-6}$ alkenyl, $C_{2-6}$ alkynyl, $C_{3-10}$ cycloalkyl, heterocycloalkyl, aryl, and heteroaryl, in which at least one of $R_3$, $R_4$, $R_5$, $R_6$, and $R_7$ is heteroaryl; and each of $C_{1-6}$ alkoxyl, $C_{1-6}$ alkyl, $C_{2-6}$ alkenyl, $C_{2-6}$ alkynyl, $C_{3-10}$ cycloalkyl, heterocycloalkyl, aryl, and heteroaryl, second or third occurrence, is optionally substituted with halo, nitro, cyano, amino, OH, $CF_3$, $C_{1-6}$ alkoxyl, $C_{1-6}$ alkyl, $C_{2-6}$ alkenyl, $C_{2-6}$ alkynyl, $C_{3-10}$ cycloalkyl, heterocycloalkyl, aryl, or heteroaryl;

X is $CH_2$ or C═O; and

Y is $CH_2$ or C═O.

2. The compound of claim 1, wherein Y is $CH_2$.

3. The compound of claim 2, wherein $R_1$ is H, X is C═O, and $R_2$ is

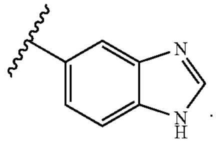 [SMILES: *c1ccc2[nH]cnc2c1]

4. The compound of claim 3, wherein $R_3$, $R_4$, $R_5$, and $R_6$, independently, are H, $CH_3$, Cl, or F.

5. The compound of claim 4, wherein $R_7$ is heteroaryl selected from the group consisting of

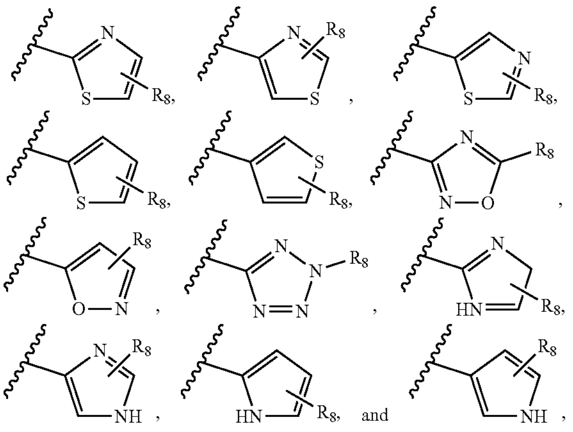

in which $R_8$ is H, halo, nitro, cyano, amino, OH, $CF_3$, —COOH, —$COOC_{1-6}$ alkyl, $C_{1-6}$ alkoxyl, $C_{1-6}$ alkyl, $C_{2-6}$ alkenyl, $C_{2-6}$ alkynyl, $C_{3-10}$ cycloalkyl, heterocycloalkyl, aryl, or heteroaryl, each of $C_{1-6}$ alkoxyl, $C_{1-6}$ alkyl, $C_{2-6}$ alkenyl, $C_{2-6}$ alkynyl, $C_{3-10}$ cycloalkyl, heterocycloalkyl, aryl, and heteroaryl being optionally substituted with halo, nitro, cyano, amino, OH, $CF_3$, $C_{1-6}$ alkoxyl, $C_{1-6}$ alkyl, $C_{2-6}$ alkenyl, $C_{2-6}$ alkynyl, $C_{3-10}$ cycloalkyl, heterocycloalkyl, aryl, or heteroaryl.

6. The compound of claim 5, wherein $R_8$ is H, F, Cl, $CH_3$, $CF_3$, ethyl, n-propyl,

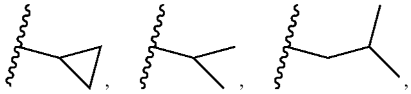

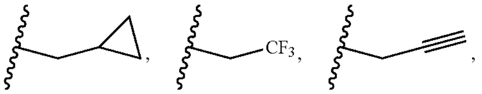
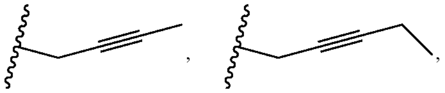
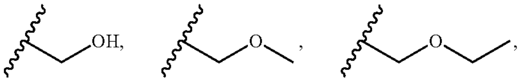
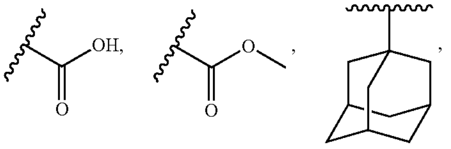
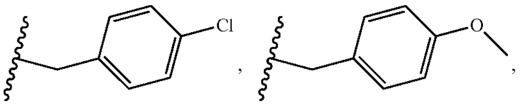
or
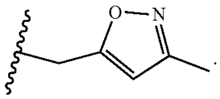
7. The compound of claim 6, wherein $R_7$ is selected from the group consisting of
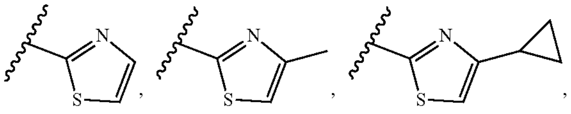
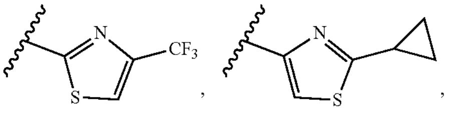
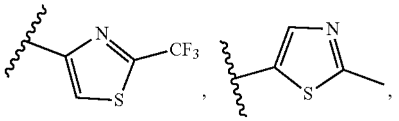
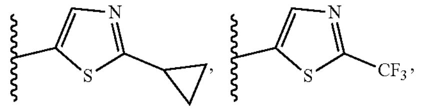
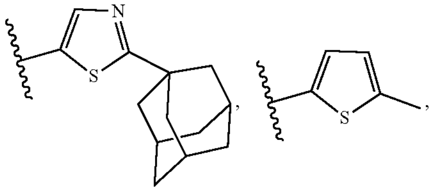
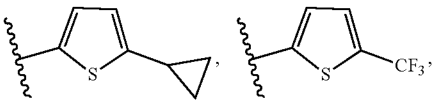
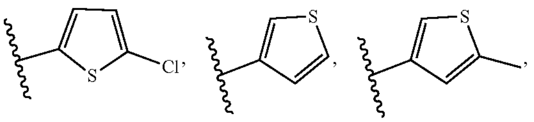
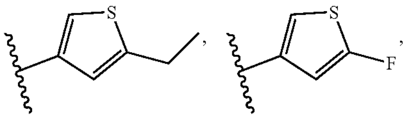
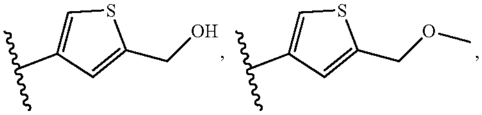
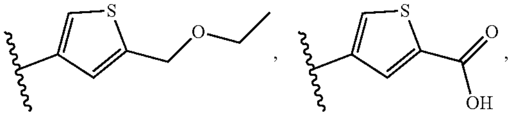
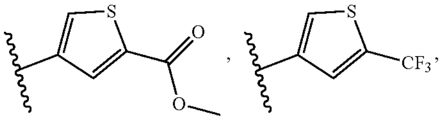
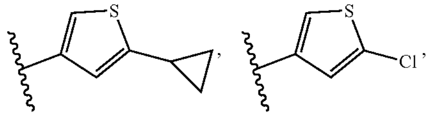
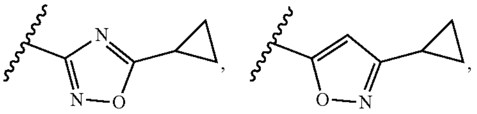
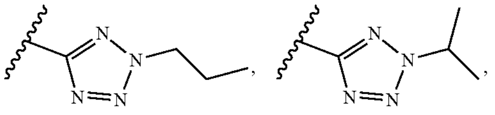
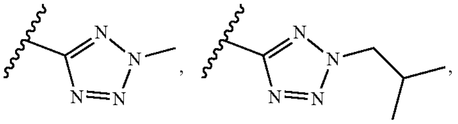
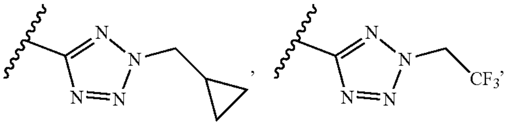
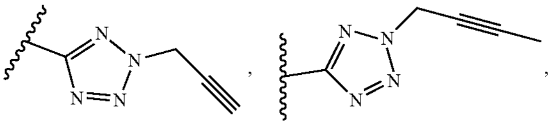
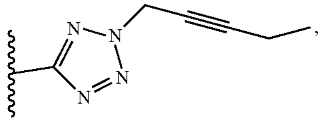
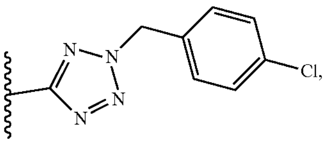
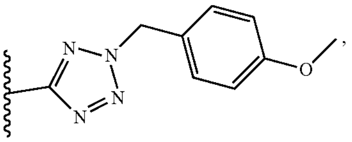
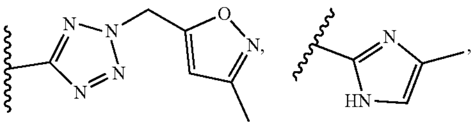

-continued

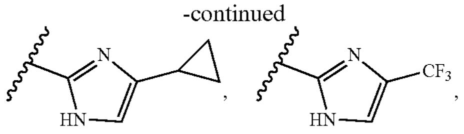

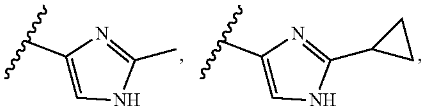

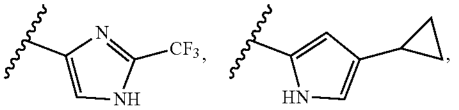

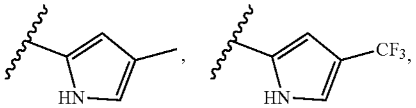

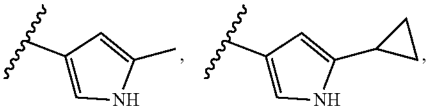

and

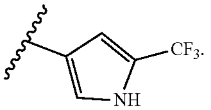

8. The compound of claim 1, wherein Y is C=O.

9. The compound of claim 8, wherein $R_1$ is H, X is C=O, and $R_2$ is

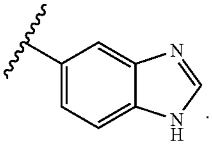 [SMILES: *c1ccc2[nH]cnc2c1]

10. The compound of claim 9, wherein $R_3$, $R_4$, $R_5$, and $R_6$, independently, are H, $CH_3$, Cl, or F.

11. The compound of claim 10, wherein $R_7$ is heteroaryl selected from the group consisting of

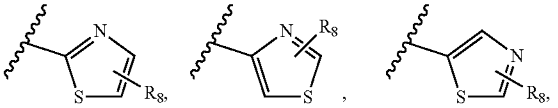

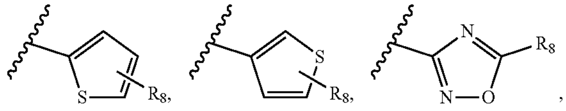

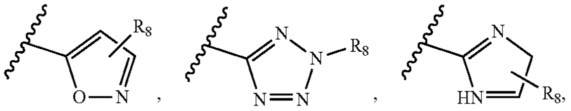

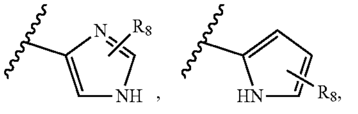

and

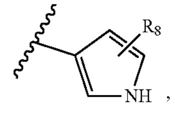

in which $R_8$ is H, halo, nitro, cyano, amino, OH, $CF_3$, —COOH, —$COOC_{1-6}$ alkyl, $C_{1-6}$ alkoxyl, $C_{1-6}$ alkyl, $C_{2-6}$ alkenyl, $C_{2-6}$ alkynyl, $C_{3-10}$ cycloalkyl, heterocycloalkyl, aryl, or heteroaryl, each of $C_{1-6}$ alkoxyl, $C_{1-6}$ alkyl, $C_{2-6}$ alkenyl, $C_{2-6}$ alkynyl, $C_{3-10}$ cycloalkyl, heterocycloalkyl, aryl, and heteroaryl being optionally substituted with halo, nitro, cyano, amino, OH, $CF_3$, $C_{1-6}$ alkoxyl, $C_{1-6}$ alkyl, $C_{2-6}$ alkenyl, $C_{2-6}$ alkynyl, $C_{3-10}$ cycloalkyl, heterocycloalkyl, aryl, or heteroaryl.

12. The compound of claim 11, wherein $R_8$ is H, F, Cl, $CH_3$, $CF_3$, ethyl, n-propyl,

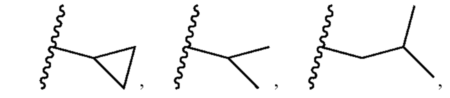

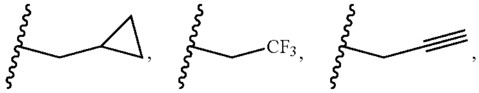

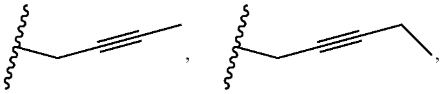

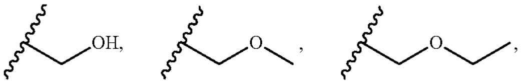

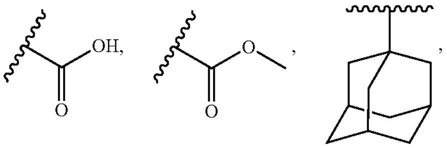

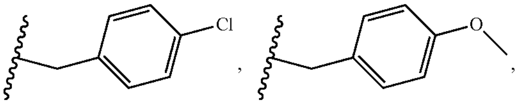

or

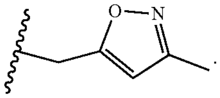

13. The compound of claim 12, wherein $R_7$ is selected from the group consisting of

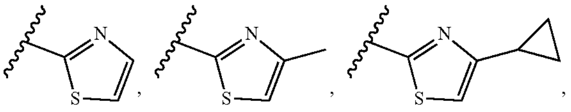

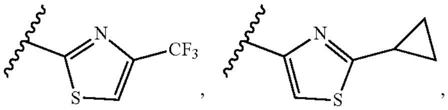

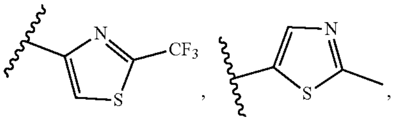

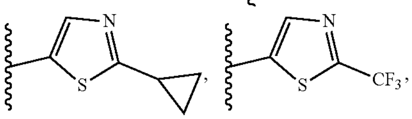

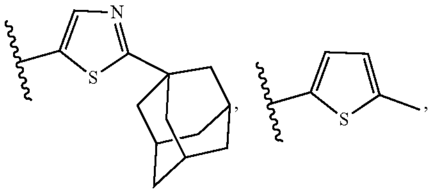

-continued
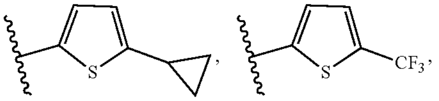
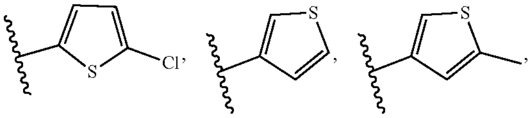
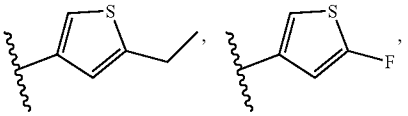
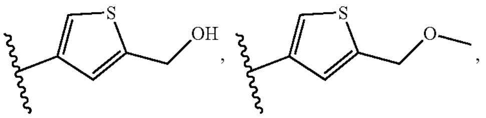
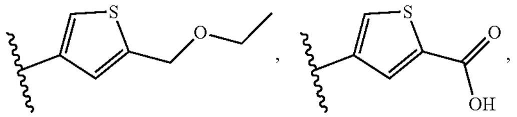
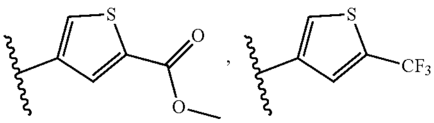
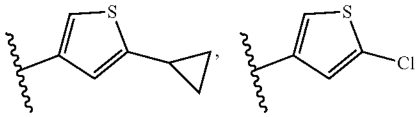
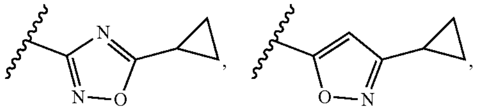
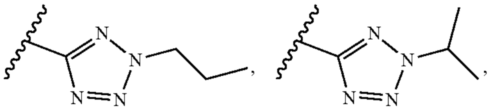
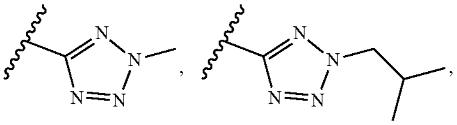
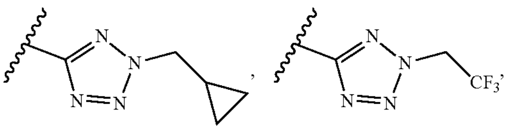
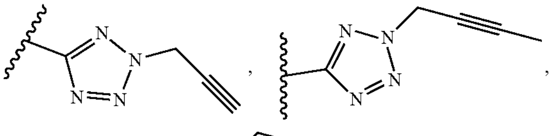
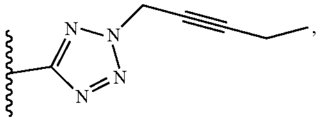
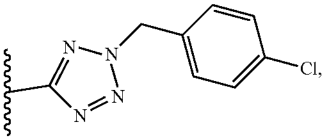
-continued
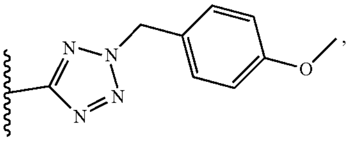
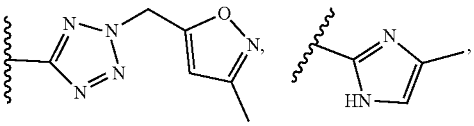
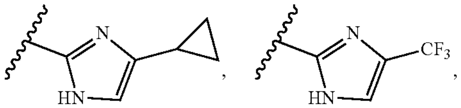
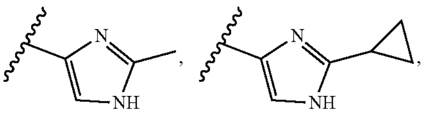
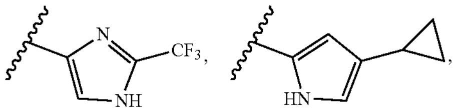
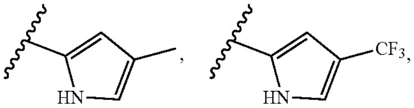
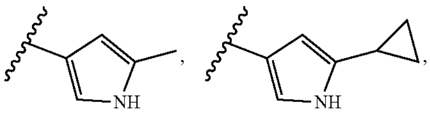
and
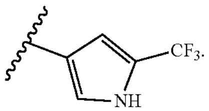
14. The compound of claim 1, wherein $R_1$ is H and X is C═O.
15. The compound of claim 1, wherein $R_2$ is
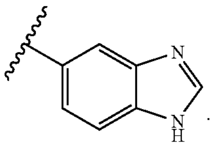 [SMILES: *c1ccc2[nH]cnc2c1]
16. The compound of claim 1, wherein $R_3$, $R_4$, $R_5$, and $R_6$, independently, are H, $CH_3$, Cl, or F.
17. The compound of claim 1, wherein $R_7$ is heteroaryl selected from the group consisting of
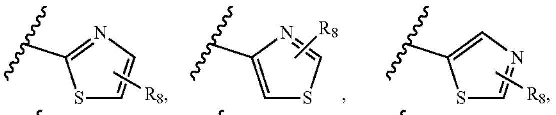
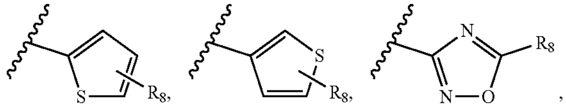

-continued

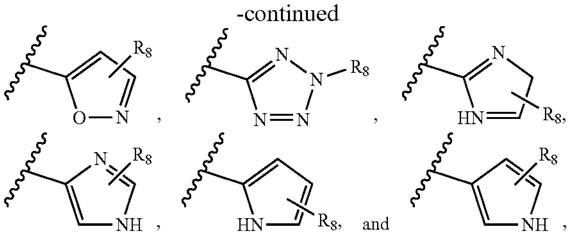

in which $R_8$ is H, halo, nitro, cyano, amino, OH, $CF_3$, —COOH, —$COOC_{1-6}$ alkyl, $C_{1-6}$ alkoxyl, $C_{1-6}$ alkyl, $C_{2-6}$ alkenyl, $C_{2-6}$ alkynyl, $C_{3-10}$ cycloalkyl, heterocycloalkyl, aryl, or heteroaryl, each of $C_{1-6}$ alkoxyl, $C_{1-6}$ alkyl, $C_{2-6}$ alkenyl, $C_{2-6}$ alkynyl, $C_{3-10}$ cycloalkyl, heterocycloalkyl, aryl, and heteroaryl being optionally substituted with halo, nitro, cyano, amino, OH, $CF_3$, $C_{1-6}$ alkoxyl, $C_{1-6}$ alkyl, $C_{2-6}$ alkenyl, $C_{2-6}$ alkynyl, $C_{3-10}$ cycloalkyl, heterocycloalkyl, aryl, or heteroaryl.

18. The compound of claim 17, wherein $R_8$ is H, F, Cl, $CH_3$, $CF_3$, ethyl, n-propyl,

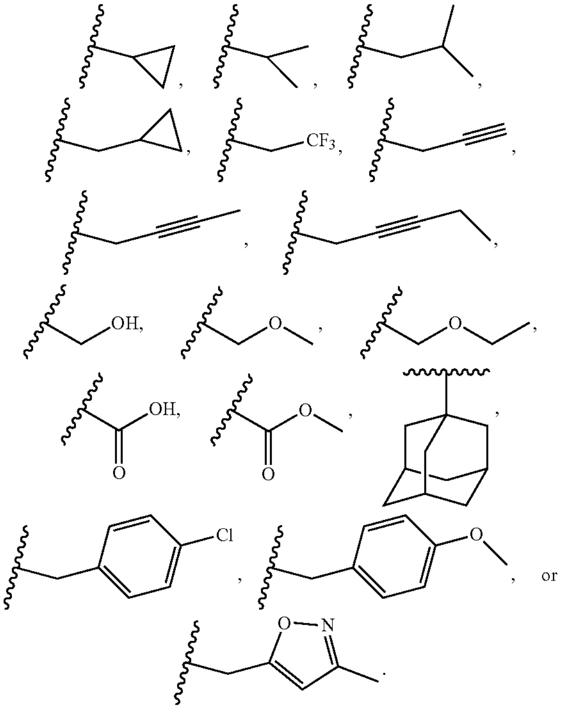

19. The compound of claim 18, wherein $R_7$ is selected from the group consisting of

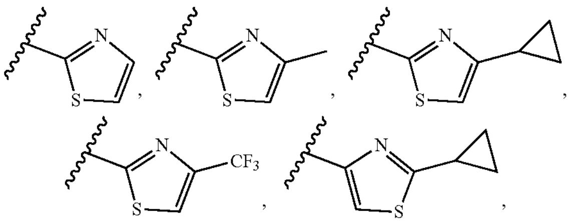

-continued

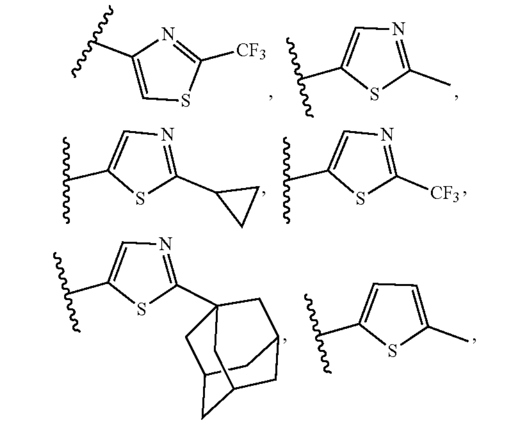

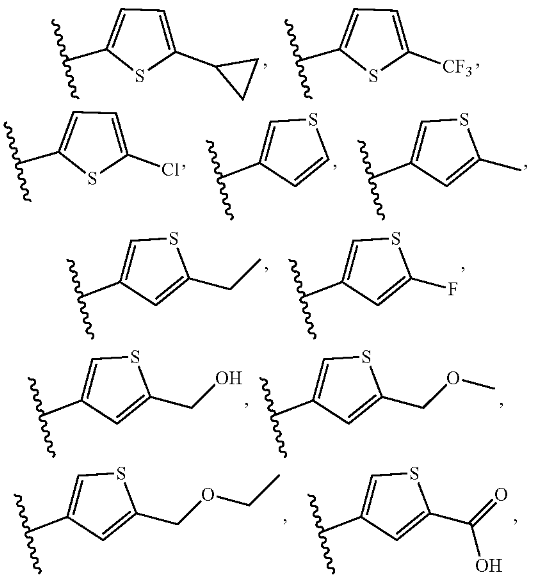

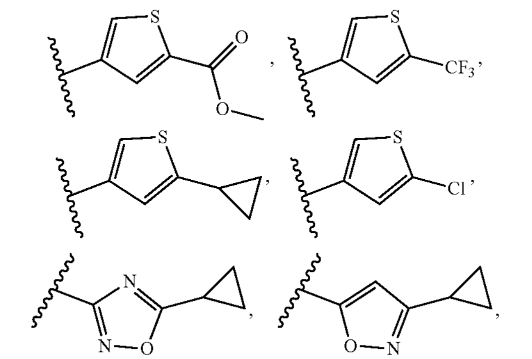

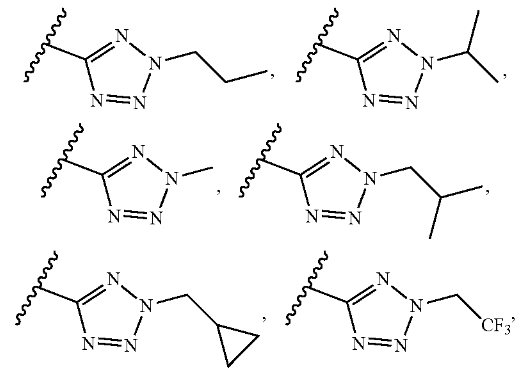

-continued
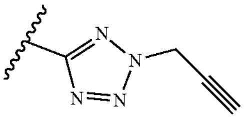 , 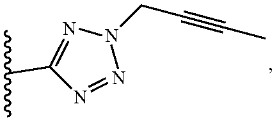 ,
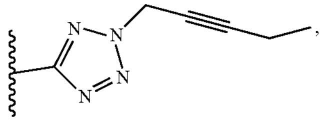 ,
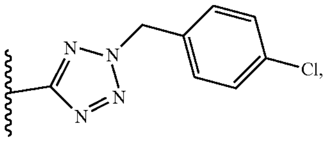 ,
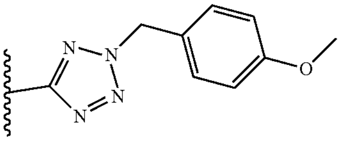 ,
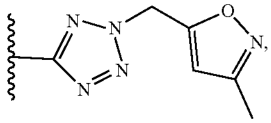 , 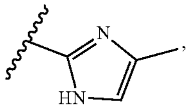 ,
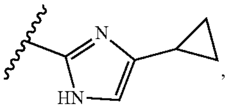 , 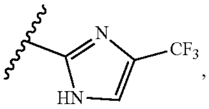 ,
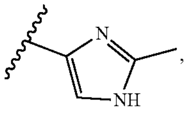 , 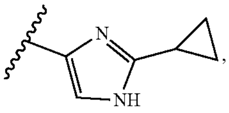 ,
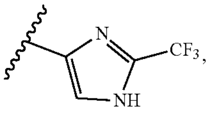 , 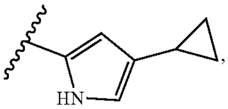 ,
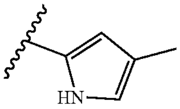 , 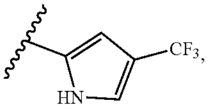 ,
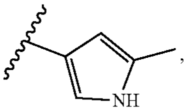 , 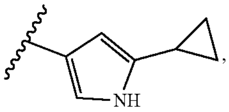 , and
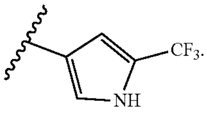 .
20. The compound of claim 1, wherein the compound is one of the following compounds:
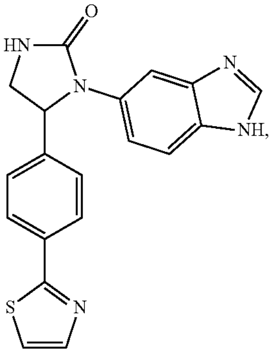 1
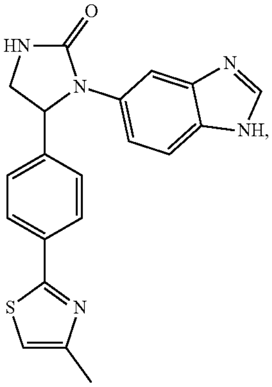 2
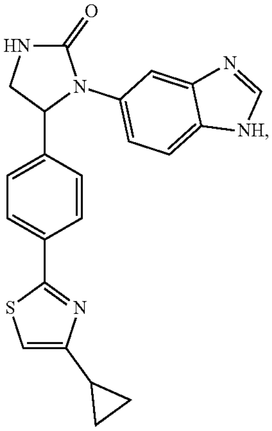 3
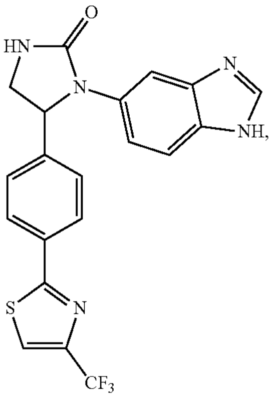 4

5
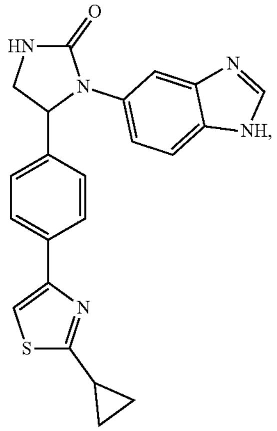
6
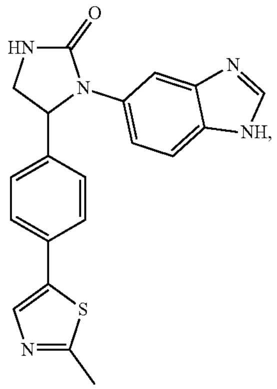
7
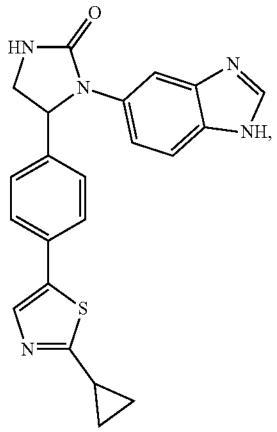
8
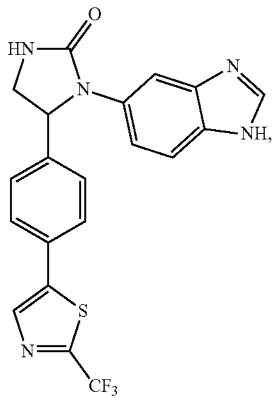
9
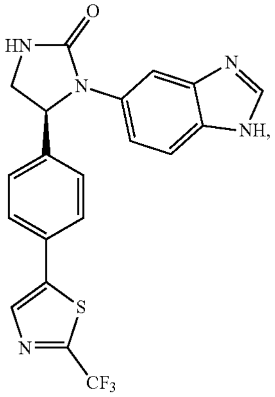
10
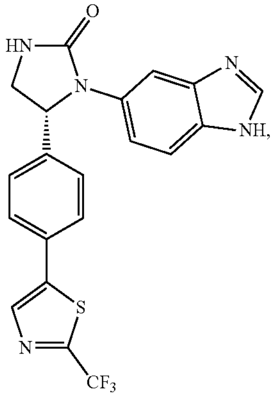
11
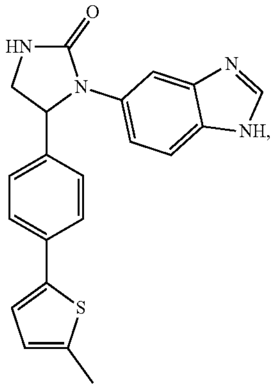
12
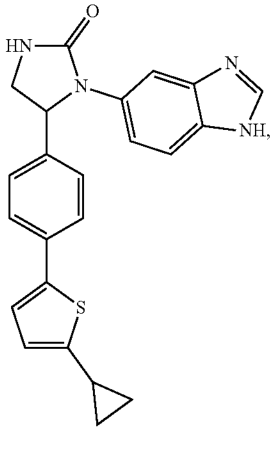

13
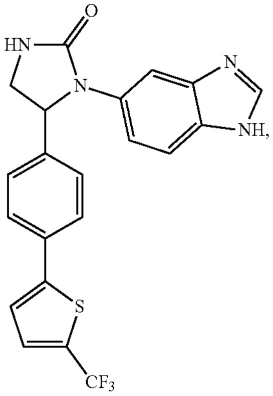
14
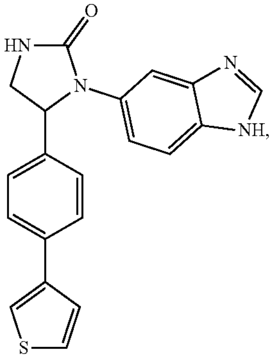
15
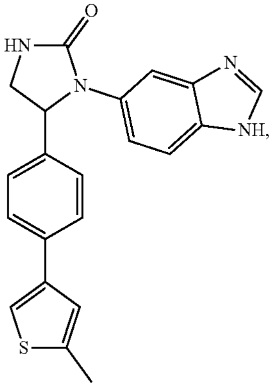
16
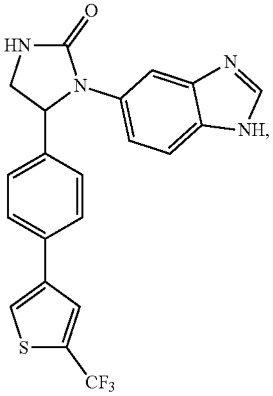
17
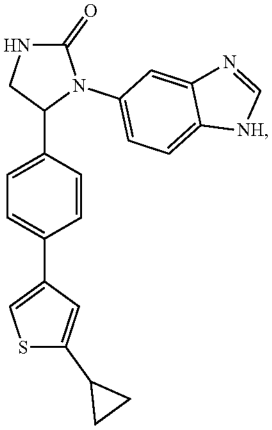
18
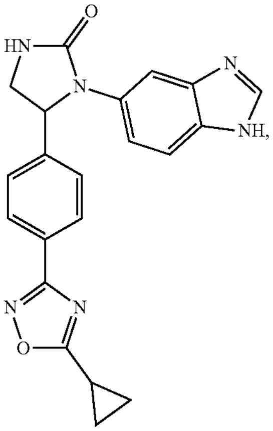
19
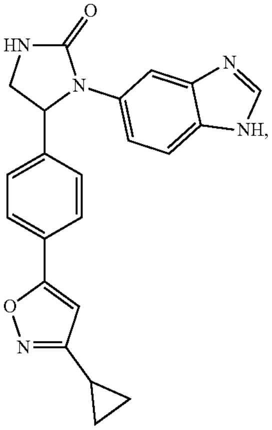

-continued
20
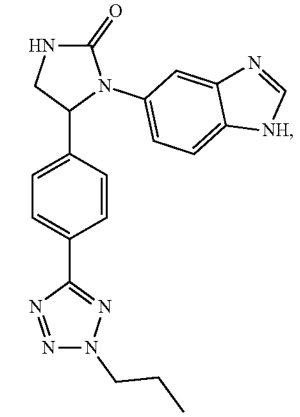
21
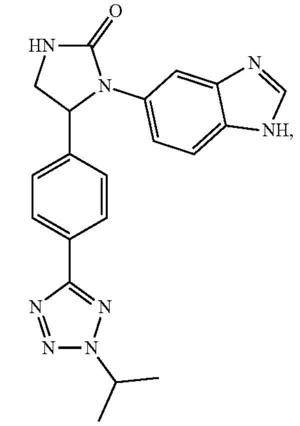
22
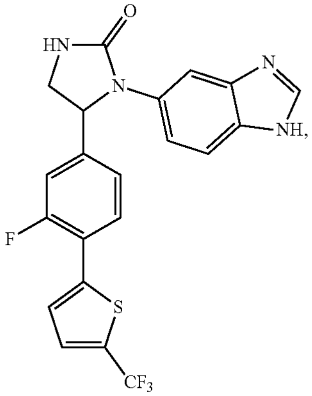
23
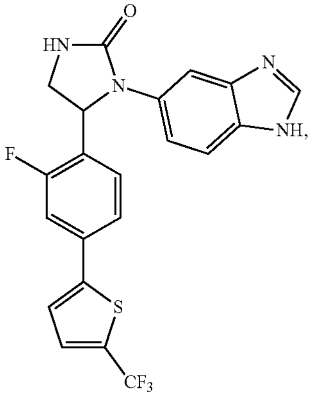
-continued
24
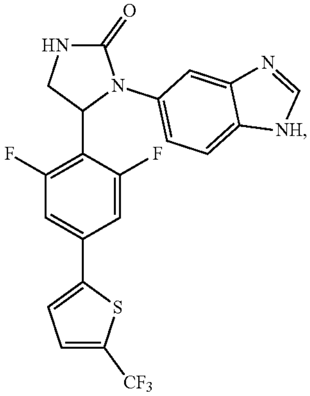
25
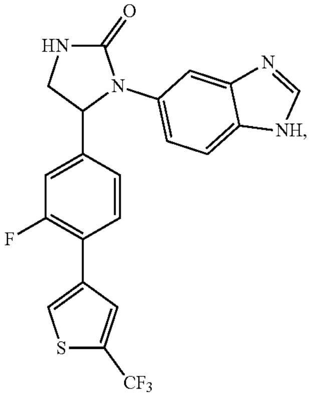
26
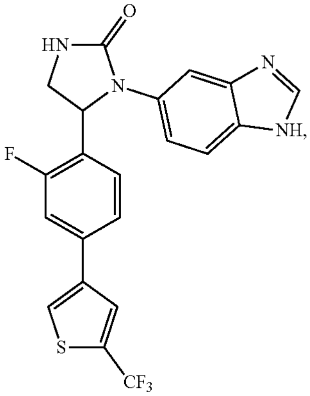
27
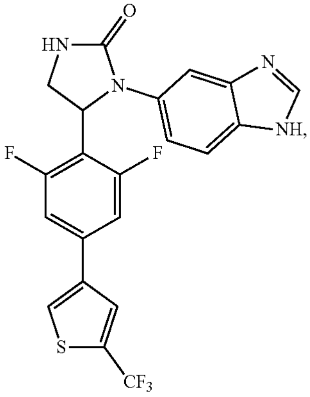

-continued
28
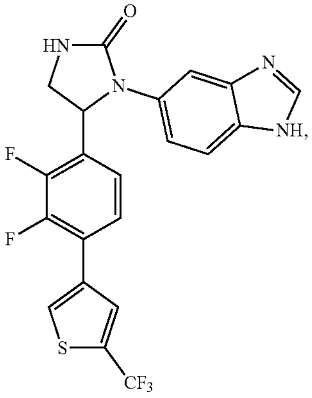
29
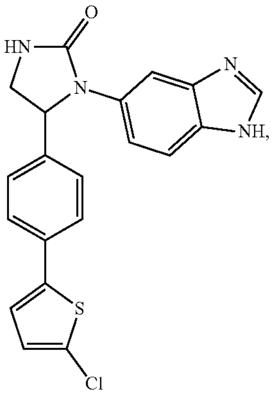
30
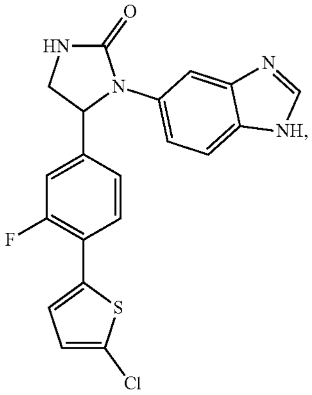
31
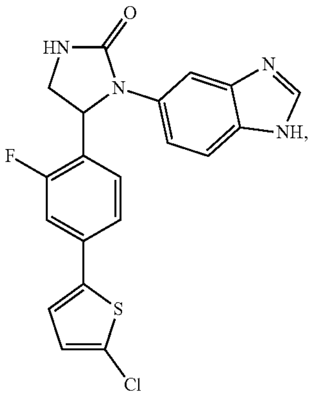
-continued
32
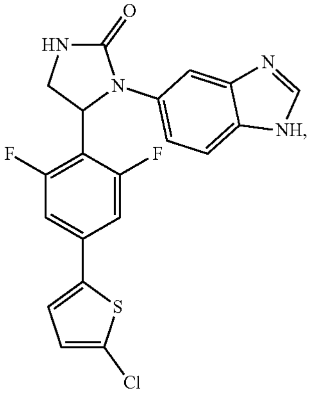
33
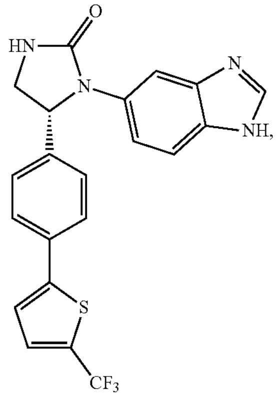
34
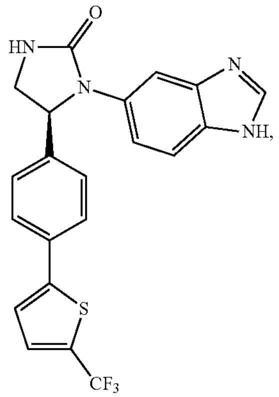
35
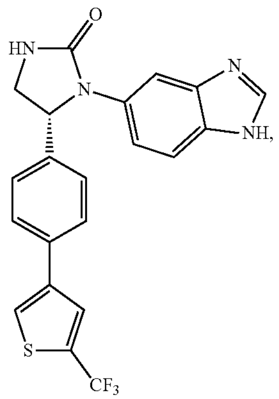

-continued
36
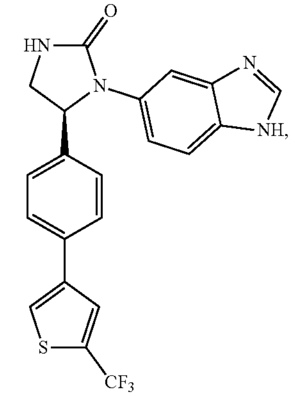
37
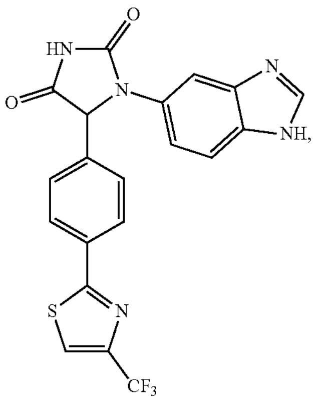
38
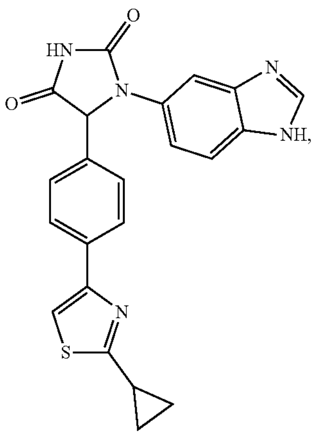
-continued
39
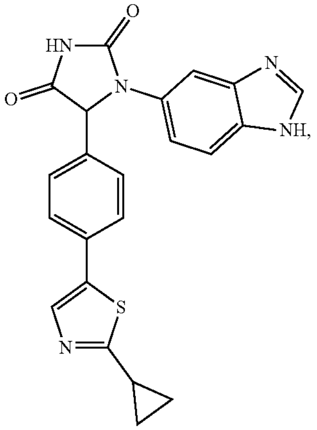
40
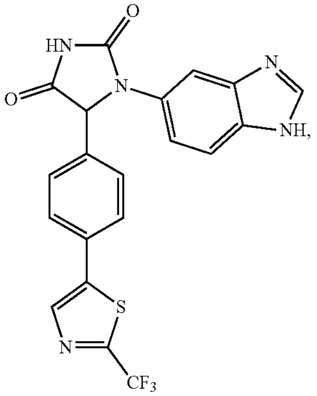
41
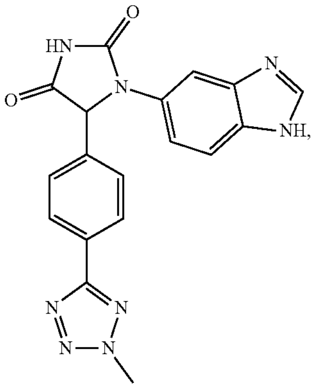
42
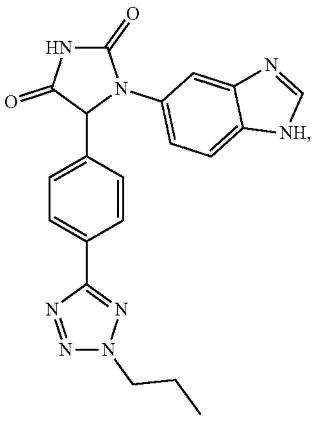

-continued
43
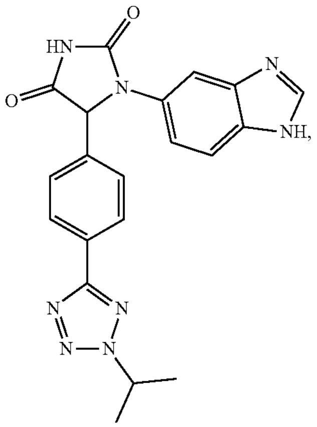
44
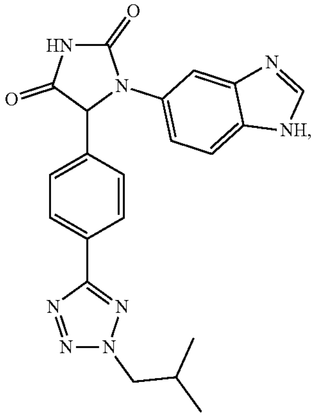
45
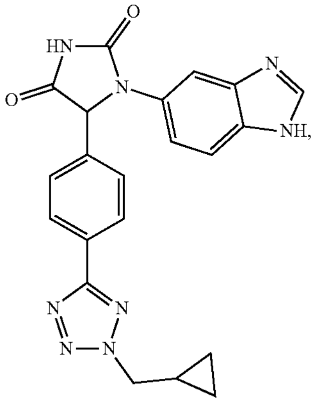
46
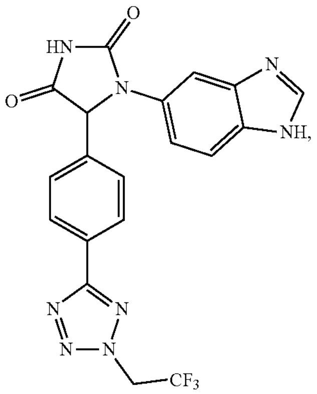
-continued
47
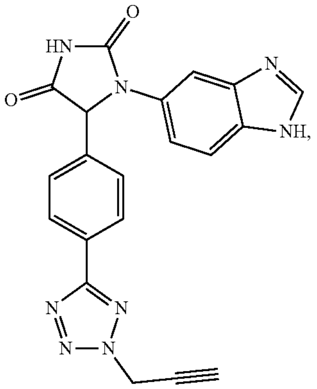
48
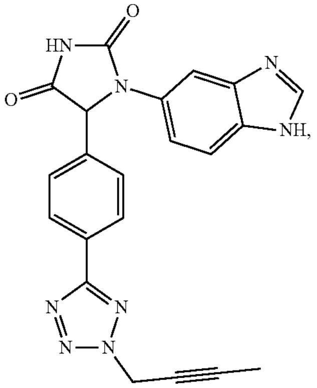
49
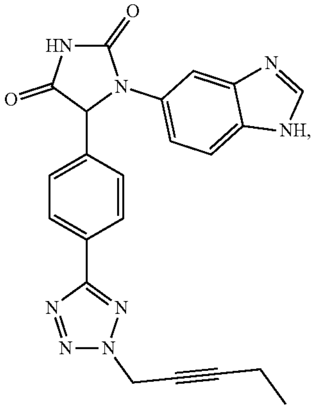
50
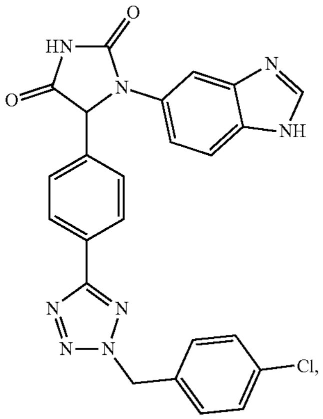

-continued
51
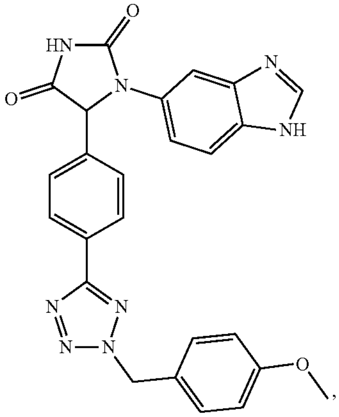
52
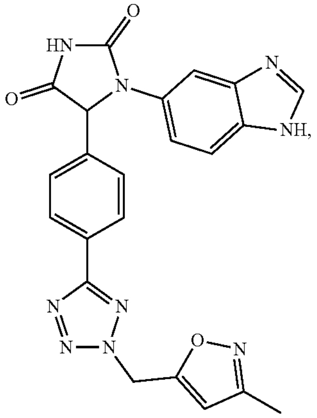
53
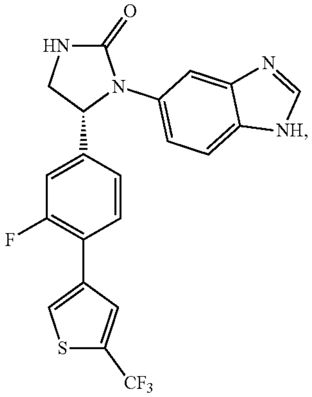
54
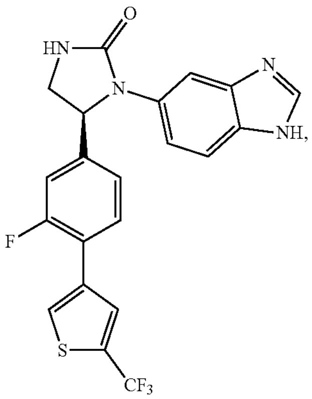
-continued
55
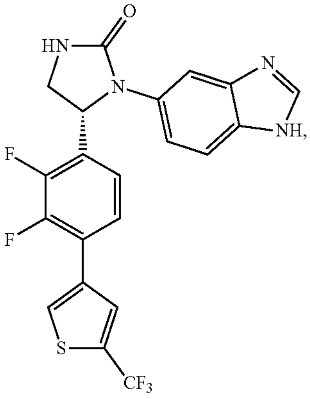
56
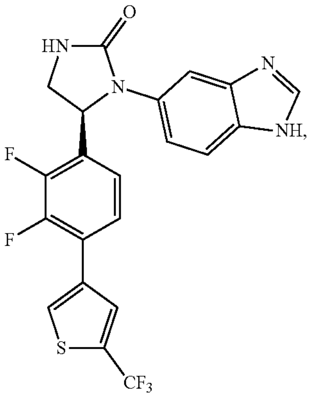
57
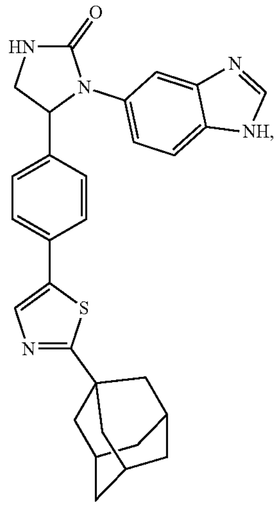

-continued
58
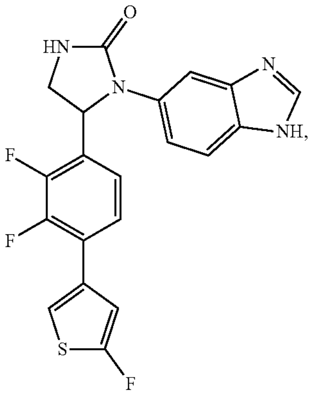
59
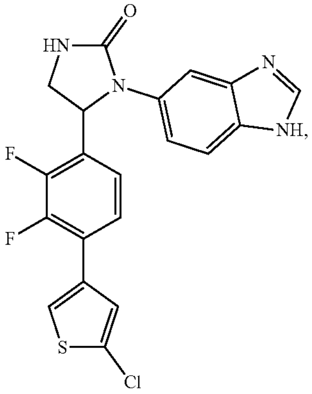
60
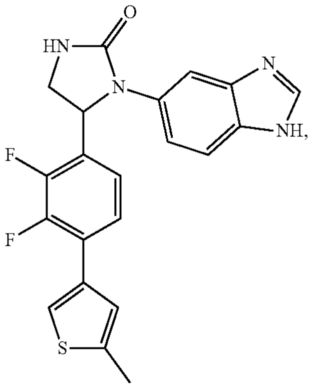
61
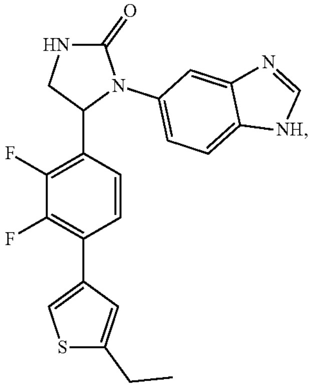
-continued
62
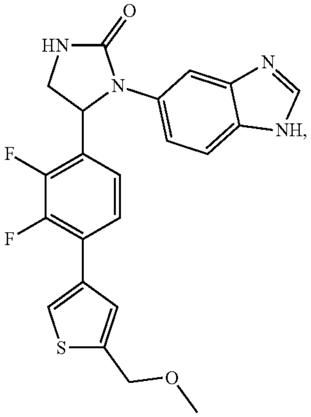
63
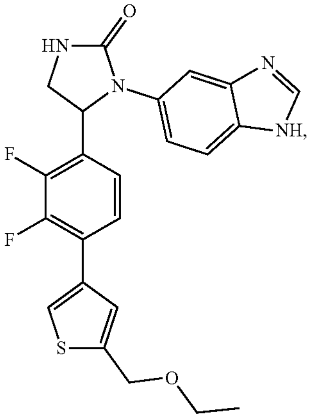
64
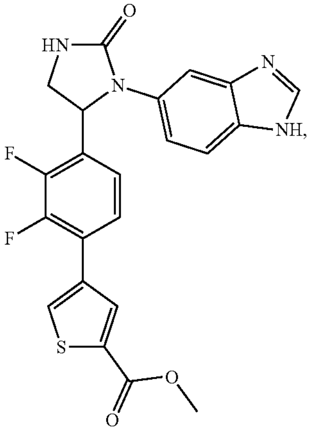
65
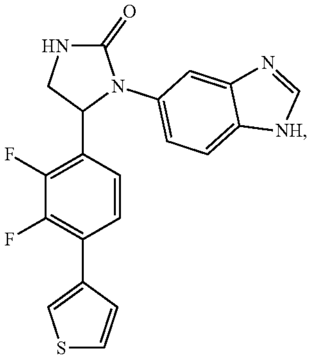

-continued
66
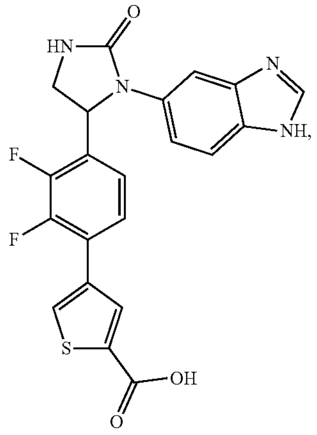
and
67
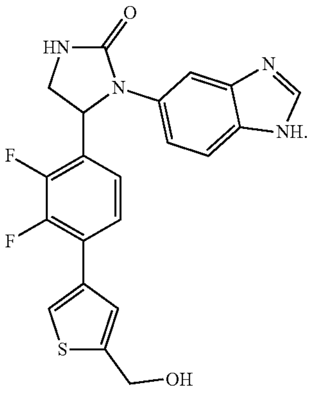
21. The compound of claim 20, wherein the compound is one of the following compounds:
9
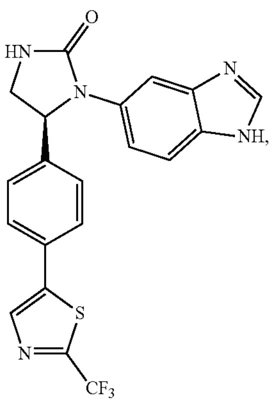
-continued
34
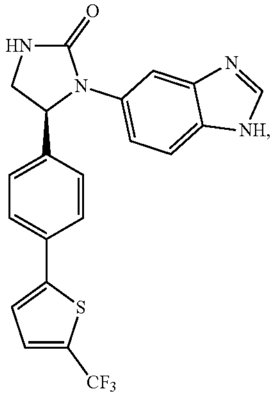
36
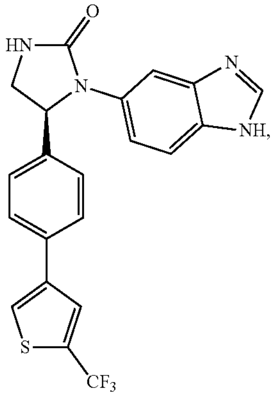
54
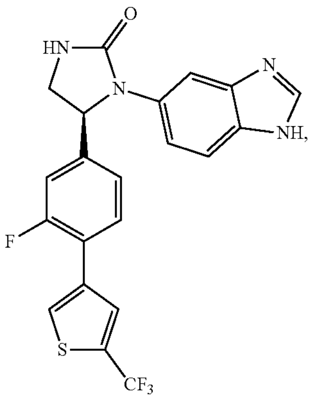
and
56
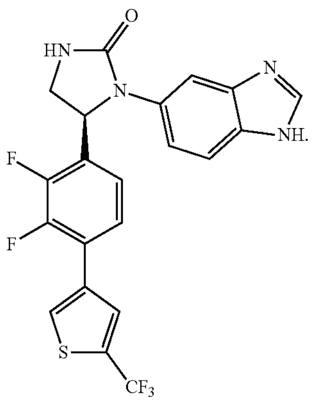

22. The compound of claim 1, wherein the compound is one of the following compounds:
68
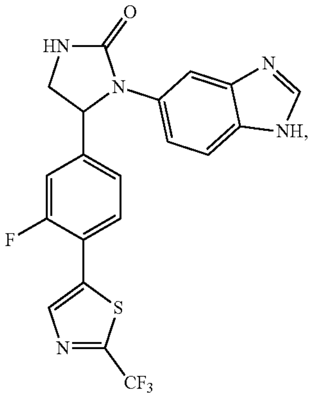
69
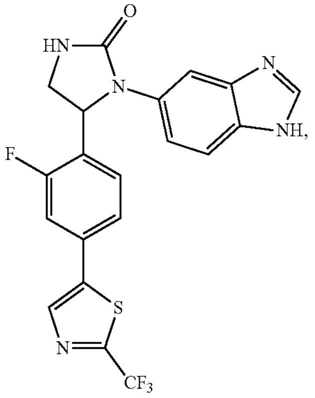
70
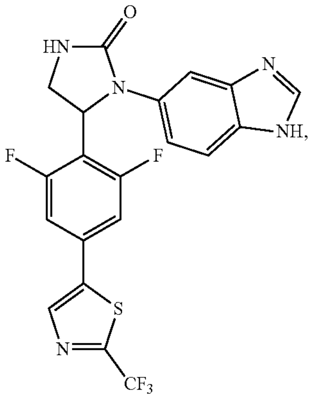
-continued
71
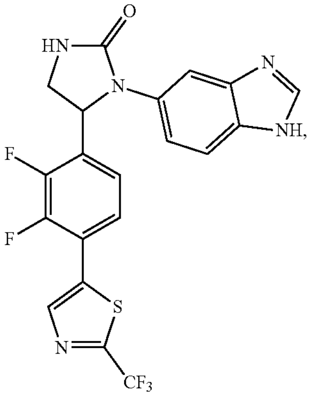
72
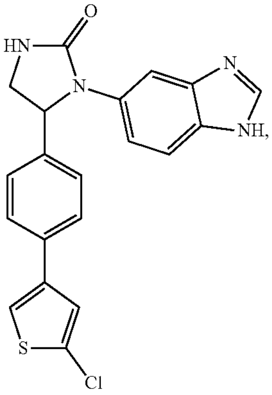
73
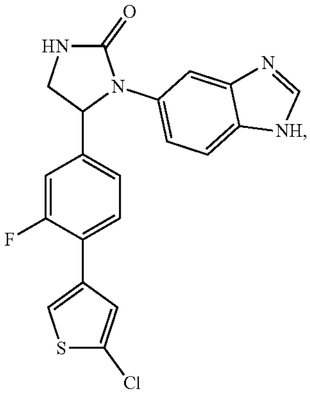
74
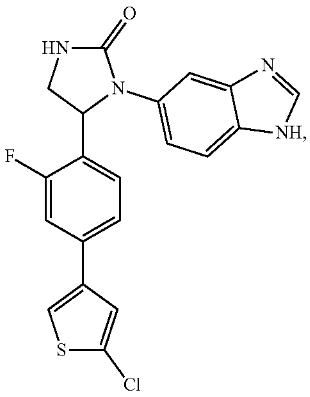

-continued
75
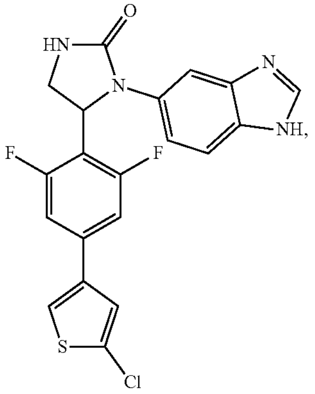
76
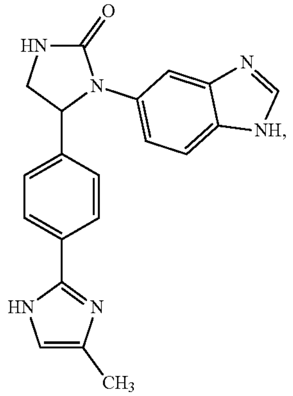
77
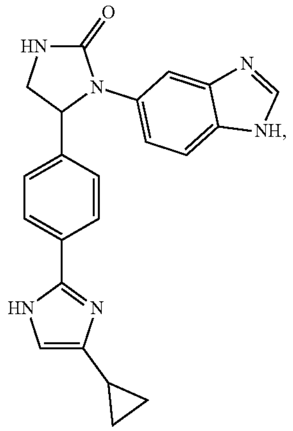
78
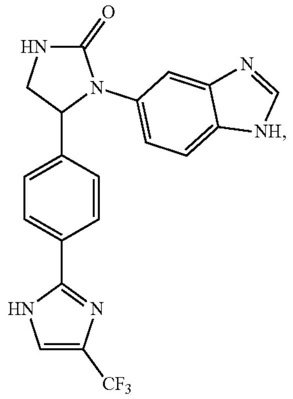
-continued
79
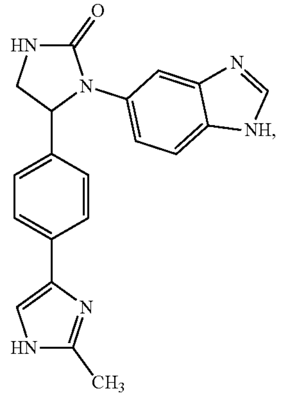
80
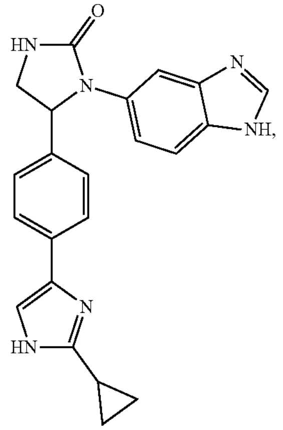
81
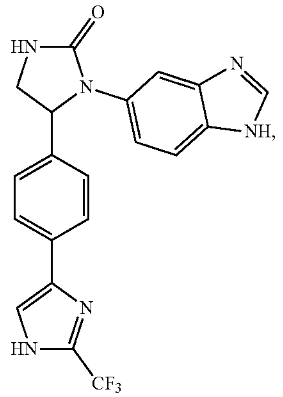
82
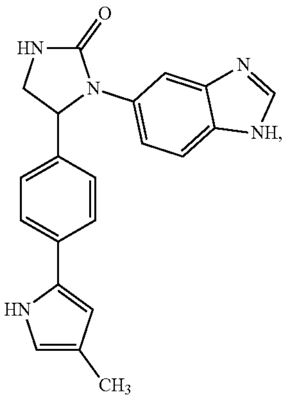

-continued
83
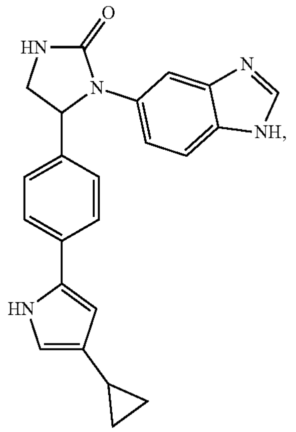
84
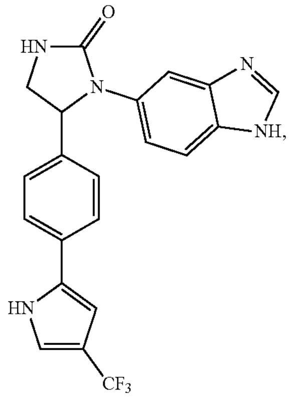
85
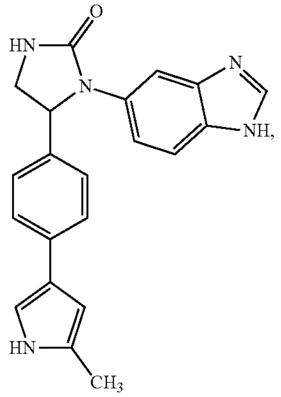
86
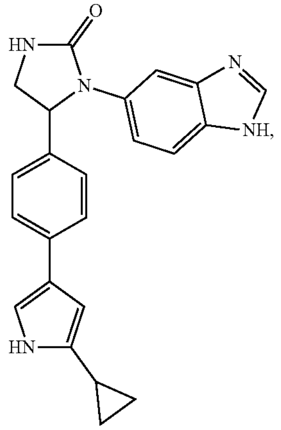
87
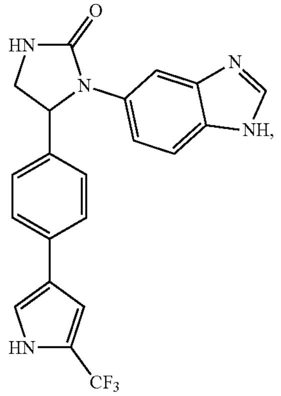
88
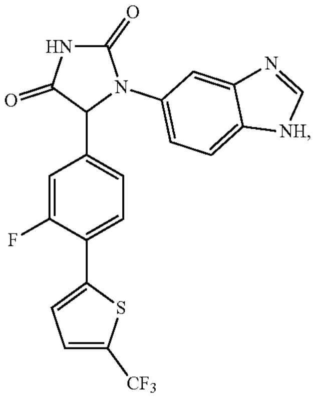
89
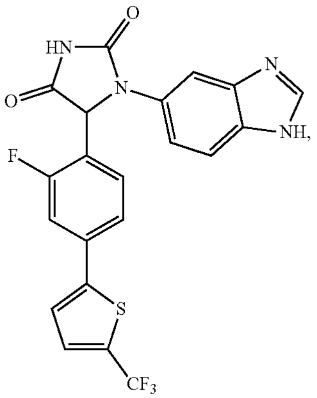

-continued
90
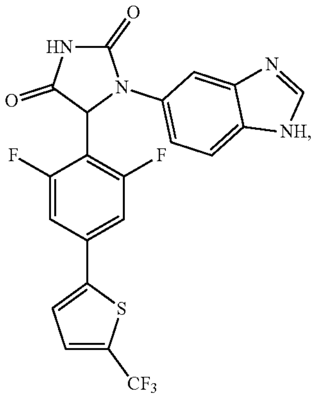
91
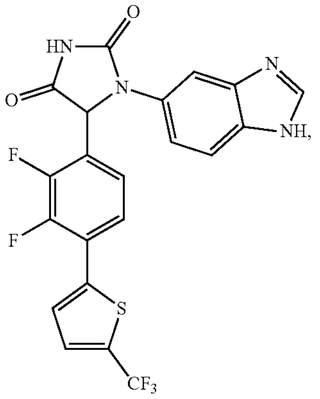
92
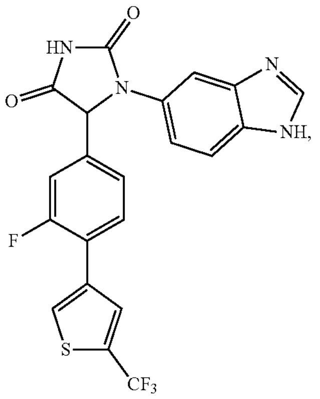
93
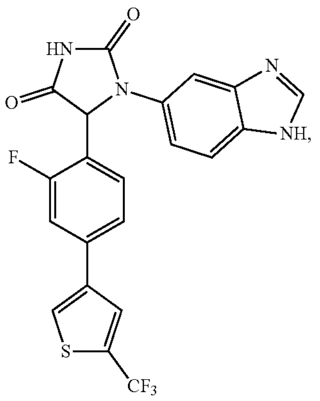
-continued
94
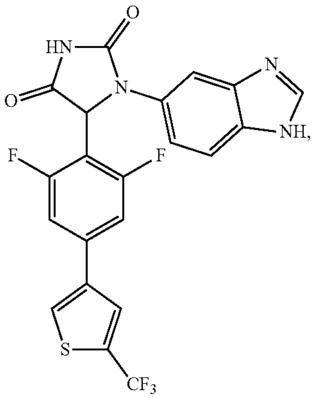
95
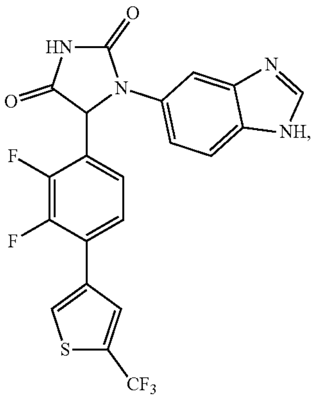
96
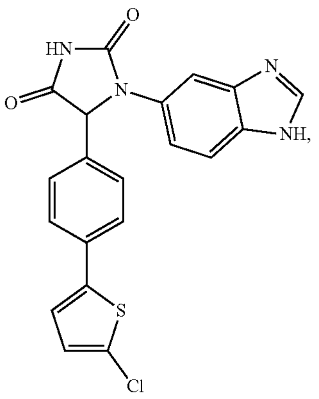
97
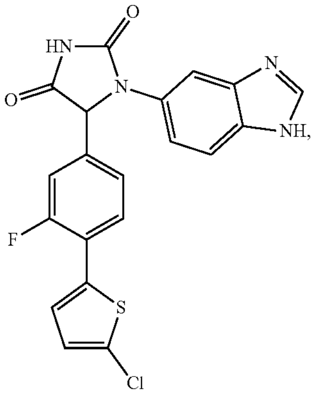

-continued
98
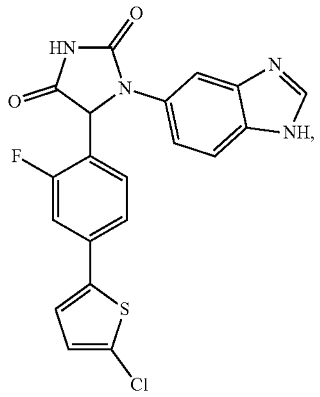
99
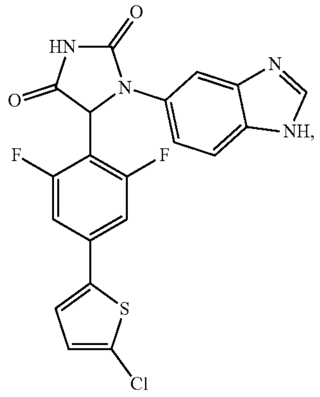
100
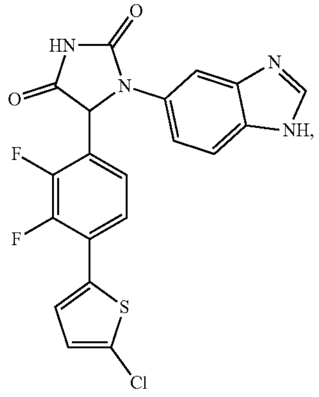
101
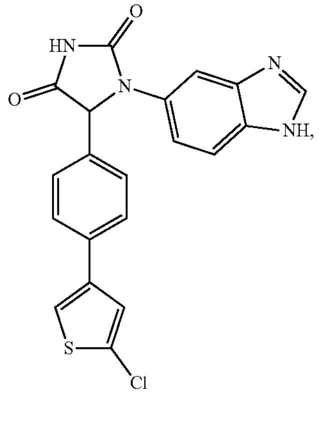
-continued
102
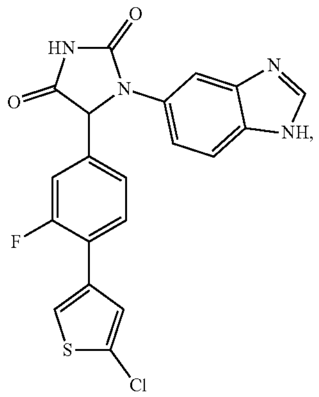
103
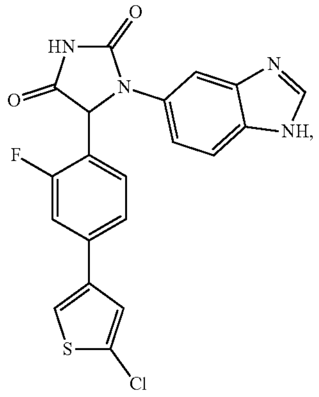
104
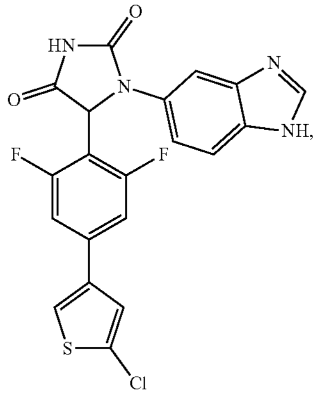
105
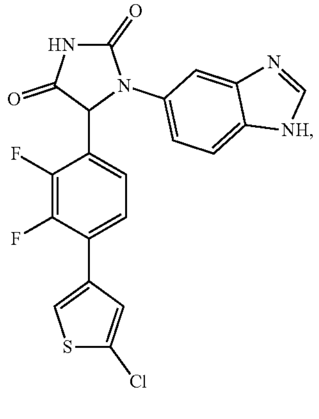

-continued
106
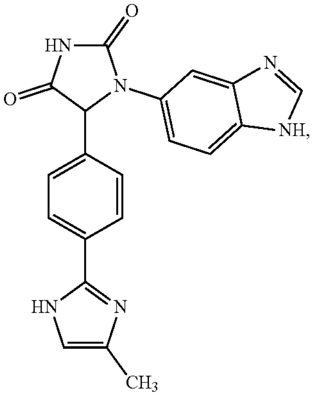
107
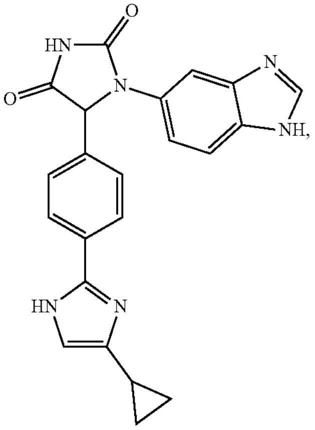
108
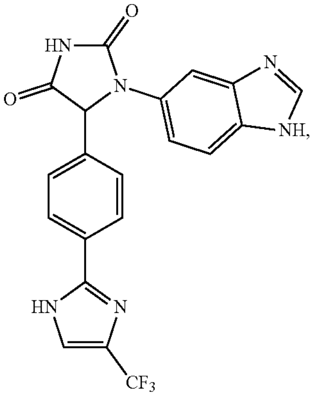
109
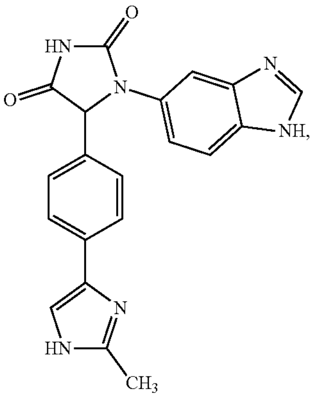
-continued
110
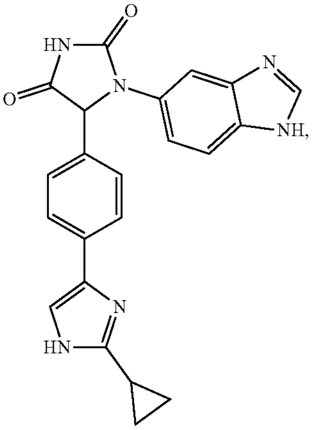
111
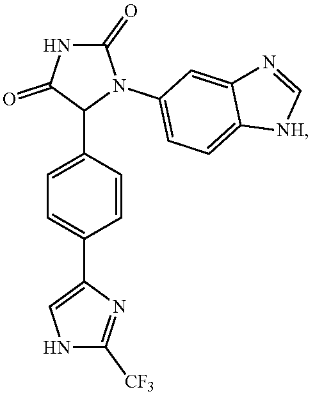
112
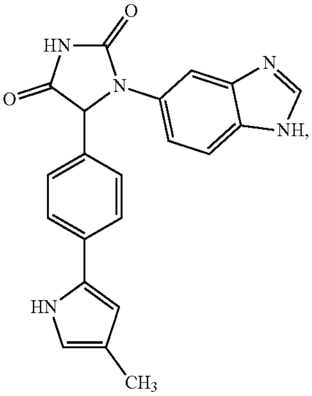

-continued
113
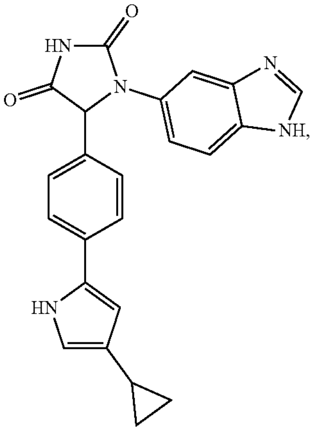
114
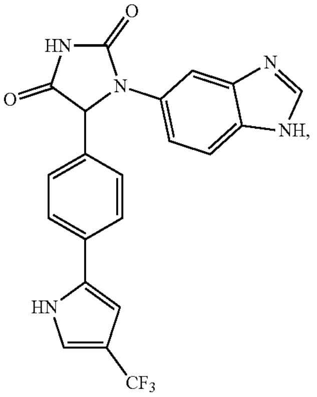
115
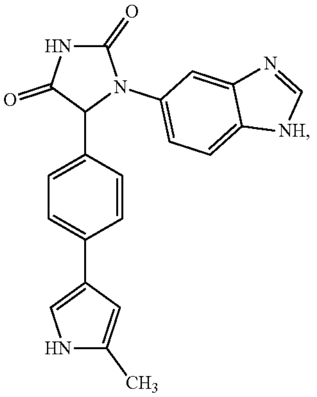
116
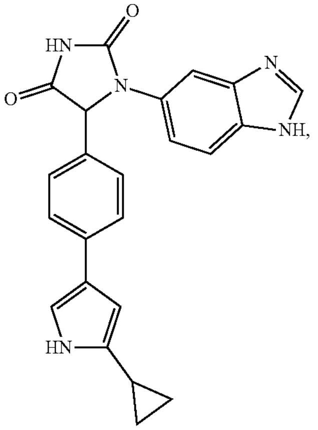
and
117
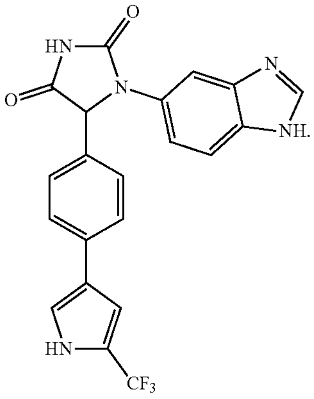
23. A pharmaceutical composition comprising a compound of claim 1 and a pharmaceutically acceptable carrier.
24. A method of treating Alzheimer's disease or Huntington's disease by administering to a subject in need thereof an effective amount of a compound of claim 1.
* * * * *